United States Patent [19]

Bayer et al.

[11] Patent Number: 6,130,247

[45] Date of Patent: Oct. 10, 2000

[54] PHENYLCARBAMATES, METHODS FOR PREPARING THEM AND AGENTS CONTAINING THEM

[76] Inventors: Herbert Bayer, D 3.4, 68159 Mannheim; Bernd Müller, Jean-Ganss-Str.21, 67227 Frankenthal; Ruth Müller, Von-Wieser-Str. 1, 67159 Friedelsheim; Hubert Sauter, Neckarpromenade 20, 68167 Mannheim; Thomas Grote, Breslauer Str. 6, 67105 Schifferstadt; Wassilios Grammenos, Borsigstr.5, 67063 Ludwigshafen; Reinhard Kirstgen, Erkenbrechtstr.23e, 67434 Neustadt; Klaus Oberdorf, Bienenstr.3, 69117 Heidelberg; Arne Ptock, Eichenstr. 23, 67067 Ludwigshafen; Norbert Götz, Schöfferstr.25, 67547 Worms; Michael Rack, Sandwingert 67, 69123 Heidelberg; Franz Röhl, Sebastian-Kneipp-Str.17, 67105 Schifferstadt; Eberhard Ammermann, Von-Gagern-Str.2, 64646 Heppenheim; Volker Harries, Immengärtenweg 29e, 67227 Frankenthal; Gisela Lorenz, Erlenweg 13, 67434 Hambach; Siegfried Strathmann, Donnersbergstr.9, 67117 Limburgerhof, all of Germany

[21] Appl. No.: 09/180,296

[22] PCT Filed: Apr. 25, 1997

[86] PCT No.: PCT/EP97/02126

§ 371 Date: Nov. 5, 1998

§ 102(e) Date: Nov. 5, 1998

[87] PCT Pub. No.: WO97/43252

PCT Pub. Date: Nov. 20, 1997

[30] Foreign Application Priority Data

May 10, 1996 [DE] Germany ............... 196 18 852

[51] Int. Cl.$^7$ ............. A01N 37/52; A01N 37/12; A01N 37/18; C07C 271/26
[52] U.S. Cl. ............. 514/508; 514/538; 514/542; 560/9; 560/29
[58] Field of Search ............. 560/9, 29; 514/508, 514/538, 542

[56] References Cited

FOREIGN PATENT DOCUMENTS

| 619 301 | 10/1994 | European Pat. Off. . |
|---|---|---|
| 44 41 674 | 5/1996 | Germany . |
| 93/15046 | 8/1993 | WIPO . |
| 96/16030 | 5/1996 | WIPO . |

*Primary Examiner*—Gary Geist
*Assistant Examiner*—Brian J. Davis

[57] ABSTRACT

The invention pertains to phenylcarbamates of formula (I), wherein X is a direct bond, O or $NR^a$; Z is O, S or $NR^{b-}$; $R^1$ is hydrogen, alkyl or alkyl halide; $R^2$ is substituted methyl or optionally substituted alkyl, alkenyl, alkinyl or cycloalkyl; $R^3$ is optionally substituted alkyl, alkenyl or alkinyl; $R^4$ is alkyl, alkenyl or alkinyl and, if X is $NR^a$, hydrogen also; $R^5$ is hydrogen or optionally substituted alkyl, alkenyl, alkinyl, alkyl carbonyl or alkoxy carbonyl. The invention also pertains to methods for their preparation and agents containing them.

(I)

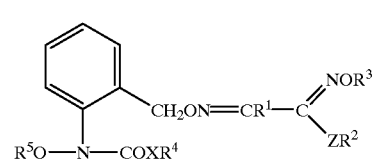

11 Claims, No Drawings

PHENYLCARBAMATES, METHODS FOR PREPARING THEM AND AGENTS CONTAINING THEM

The present invention relates to phenylcarbamates of the formula

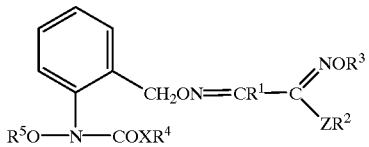

where

X is a direct bond, O or $NR^a$;
$R^a$ is hydrogen or alkyl;
Z is O, S or $NR^b$;
$R^b$ is hydrogen, $C_1$–$C_6$-alkyl, $C_3$–$C_6$-alkenyl or $C_3$–$C_6$-alkynyl;
$R^1$ is hydrogen, $C_1$–$C_6$-alkyl or $C_1$–$C_4$-haloalkyl; and
$R^2$ is $C_2$–$C_6$-alkyl, $C_3$–$C_6$-alkenyl or $C_3$–$C_6$-alkynyl, where these groups may be partially or completely halogenated and/or may carry from one to three of the following radicals:
cyano, nitro, amino, hydroxyl,
$C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfonyl, $C_1$–$C_6$-alkylsulfoxyl, $C_1$–$C_6$-alkylamino, di-$C_1$–$C_6$-alkylamino,
$C_3$–$C_6$-cycloalkyl, aryl, hetaryl or oxiranyl, where the cyclic radicals in turn may be partially or completely halogenated and/or may carry from one to three of the following groups: cyano, nitro, amino, aminocarbonyl, aminothiocarbonyl, $C_1$–$C_4$-alkyl, $C_1$–$C_4$-haloalkyl, $C_1$–$C_4$-alkylcarbonyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-haloalkylthio, $C_1$–$C_6$-alkylsulfonyl, $C_1$–$C_6$-alkylsulfoxyl, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_2$–$C_6$-alkenyloxy and phenyl;
methyl, which carries from one to three halogen atoms and/or carries one of the following radicals:
cyano, nitro,
$C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfonyl, $C_1$–$C_6$-alkylsulfoxyl, $C_1$–$C_6$-alkylamino, di-$C_1$–$C_6$-alkylamino,
$C_3$–$C_6$-cycloalkyl, aryl, hetaryl or oxiranyl, where the cyclic radicals in turn may be partially or completely halogenated and/or may carry from one to three of the following groups: cyano, nitro, amino, aminocarbonyl, aminothiocarbonyl, $C_1$–$C_4$-alkyl, $C_1$–$C_4$-haloalkyl, $C_1$–$C_4$-alkylcarbonyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-haloalkylthio, $C_1$–$C_6$-alkylsulfonyl, $C_1$–$C_6$-alkylsulfoxyl, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_2$–$C_6$-alkenyloxy and phenyl;
$C_3$–$C_6$-cycloalkyl, where these groups may be partially or completely halogenated and/or may carry from one to three of the following radicals:
cyano, nitro, amino, hydroxyl,
$C_1$–$C_4$-alkyl, $C_1$–$C_4$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfonyl, $C_1$–$C_6$-alkylsulfoxyl, $C_1$–$C_6$-alkylamino, di-$C_1$–$C_6$-alkylamino, $R^3$ is $C_1$–$C_6$-alkyl, $C_2$–$C_6$-alkenyl or $C_2$–$C_6$-alkynyl, where these groups may be partially or completely halogenated and/or may carry from one to three of the following radicals:
cyano, $C_1$–$C_3$-alkoxy,
oxiranyl or $C_3$–$C_6$-cycloalkyl, where the cyclic radicals in turn may be partially and/or completely halogenated and/or may carry from one to three $C_1$–$C_4$-alkyl groups; and
$R^4$ is alkyl, alkenyl or alkynyl, and, where X is $NR^a$, additionally hydrogen; and
$R^5$ is hydrogen or unsubstituted or substituted alkyl, alkenyl, alkynyl, alkylcarbonyl or alkoxycarbonyl.

The present invention furthermore relates to processes for the preparation of these compounds and to agents which contain them and are suitable for controlling animal pests and harmful fungi.

The literature discloses anilides for controlling animal pests and harmful fungi (WO-A93/15,046; German Application No. P 44 41 674.1).

It is an object of the present invention to provide compounds having improved activity compared with the above.

We have found that this object is achieved by the phenylcarmamates I defined at the outset.

We have also found processes for their preparation and agents which contain them and are suitable for controlling animal pests and harmful fungi.

The compounds I are obtainable in various ways by processes known per se in the literature. In the synthesis of the compounds I, it is in principle unimportant whether the group $N(OR^5)$—$COXR^4$ or the group —$CH_2ON=CR^1$—$C(ZR^2)=NOR^3$ is synthesized first. The various methods for synthesizing the $N(OR^5)$—$COXR^4$ group (denoted in some of the formulae below by the symbol # for short) are disclosed, for example, in the literature cited at the outset.

The group —$CH_2ON=CR^1$—$C(ZR^2)=NOR^3$ is synthesized in general by reacting a benzyl derivative of the formula II with a hydroxyimine of the formula III.

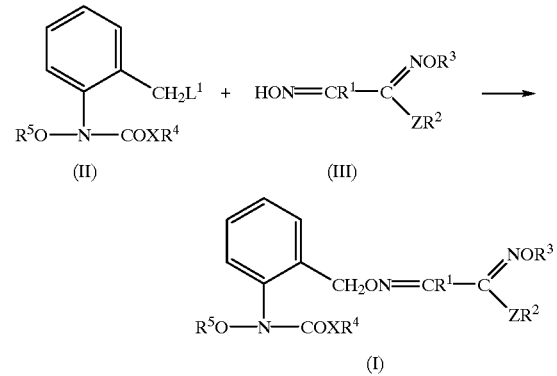

In the formula II, $L^1$ is a nucleophilically substitutable leaving group, for example halogen or sulfonate, preferably chlorine, bromine, iodine, mesylate, tosylate or triflate.

The reaction is carried out in a manner known per se in an inert organic solvent in the presence of a base (e.g. sodium hydride, potassium hydroxide, potassium carbonate or triethylamine) by the methods described in Houben-Weyl, Vol. E 14b, page 370 et seq., and Houben-Weyl, Vol. 10/1, page 1189 et seq.

The hydroxyimine III required is obtained, for example, by reacting a corresponding dihydroxyimine IV with a nucleophilically substituted reagent VIa.

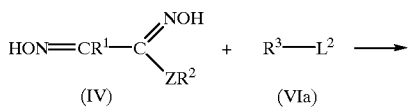 + 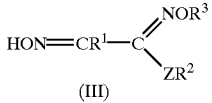

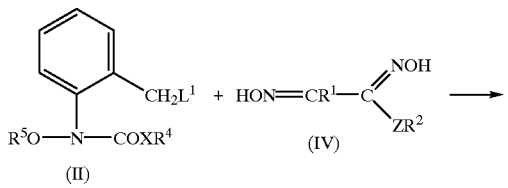

In the formula VIa, $L^2$ is a nucleophilically substitutable leaving group, for example halogen or sulfonate, preferably chlorine, bromine, iodine, mesylate, tosylate or triflate.

The reaction is carried out in a manner known per se in an inert organic solvent in the presence of a base (e.g. potassium carbonate, potassium hydroxide and sodium hydride, pyridine or triethylamine) by the methods described in Houben-Weyl, Vol. E 14b, page 307 et seq., page 370 et seq. and page 385 et seq.; Houben-Weyl, Vol. 10/4, page 55 et seq., page 180 et seq. and page 217 et seq.; Houben-Weyl, Vol. E 5, page 780 et seq.

The compounds IV are known (DE-A 26 21 102) or can be prepared by known methods.

Alternatively, the compounds I can also be obtained by first converting the benzyl derivative II with a dihydroxy-imine IV into a corresponding benzyl oxime V and then reacting V with a nucleophilically substituted reagent VIa to give I.

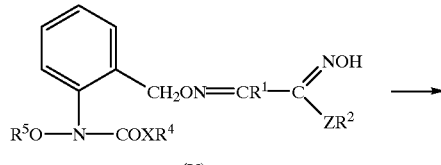

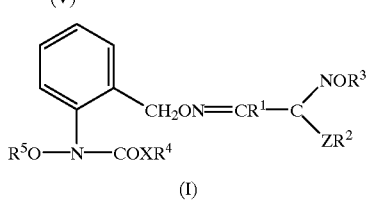

The reaction is carried out in a manner known per se in an inert organic solvent in the presence of a base (e.g. potassium carbonate, potassium hydroxide, sodium hydride, pyridine or triethylamine) by the methods described in Houben-Weyl, Vol. 10/1, page 1189 et seq.; Houben-Weyl, Vol. E 14b, page 307 et seq., page 370 et seq. and page 385 et seq.; Houben-Weyl, Vol. 10/4, page 55 et seq., page 180 et seq. and page 217 et seq.; Houben-Weyl, Vol. E 5, page 780 et seq.

In a further process, the compounds I can also be obtained by first converting the benzyl derivative II with a hydroxy-iminoester of the formula IVa into the benzyloxyiminoester Va and hydrolyzing Va to give the corresponding acid Vb. By reacting the acid Vb with a hydroxylamine of the formula IXa or its salt IXb, the corresponding hydroxamic acid Xa is obtained and can be converted into the corresponding hydroxamoyl halides Xb with conventional halogenating agents. The compounds I are obtained from the hydroxamoyl halides Xb by reaction with nucleophilic compounds XI.

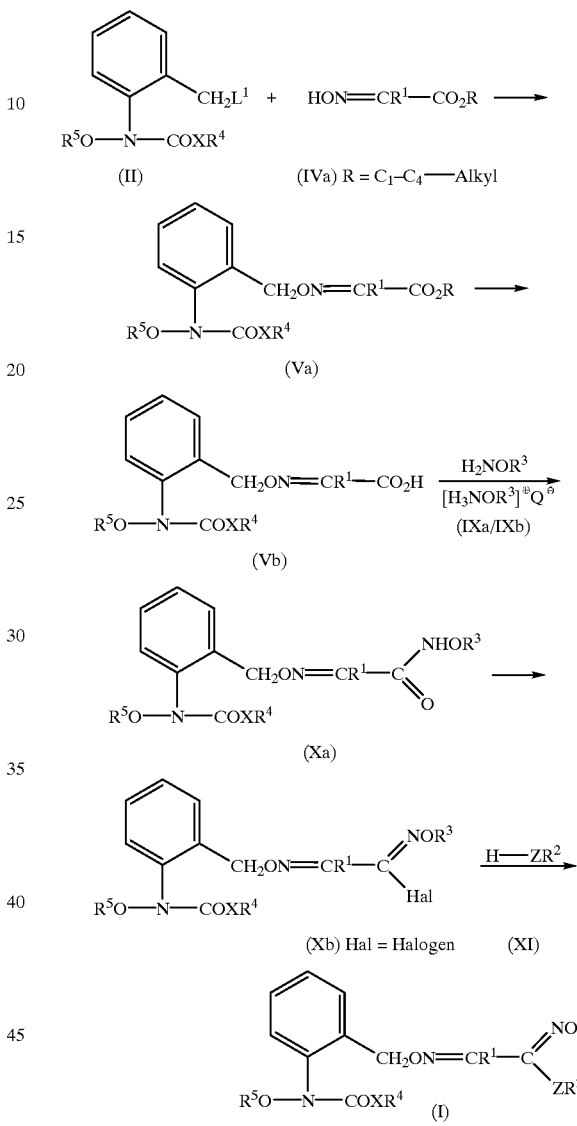

In the formulae IVa and Va, R is $C_1$–$C_4$-alkyl (in particular methyl, ethyl, isopropyl or tert-butyl); in the formula IXb, $Q^-$ is an anion of an inorganic acid (in particular a halide, such as chloride); in the formula Xb, Hal is halogen, such as chlorine, bromine or iodine.

The reaction of the benzyl derivative II with the hydroxy-iminoester IVa is carried out as described in general and in particular for the reaction of II with III.

The compounds IVa are known [J. Am. Chem. Soc. 100, (1978), 1857; Bull. Soc. Chim. Fr. 1975, 252; Bull. Soc. Chim. Fr. 31, (1904) 1054; U.S. Pat. No. 3,584,032] or can be obtained by the methods described there.

The hydrolysis of the ester Va to Vb is carried out similarly to methods known from the literature (cf. Houben-Weyl, Vol. E 5, page 223 et seq.) at from 0 to 150° C., preferably from 20 to 80° C., in the presence of an acid or base.

Suitable solvents are water, aliphatic hydrocarbons, such as pentane, hexane, cyclohexane and petroleum ether, aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, ketones, such as acetone, methyl ethyl ketone, diethyl ketone and tert-butyl methyl ketone, alcohols, such as methanol, ethanol, n-propanol, isopropanol, n-butanol and tert-butanol and dimethyl sulfoxide and dimethyl formamide, particularly preferably water, methanol and ethanol.

Mixtures of the stated solvents may also be used.

Suitable bases are in general inorganic compounds, such as alkali metal and alkaline earth metal hydroxides, e.g. lithium hydroxide, sodium hydroxide, potassium hydroxide and calcium hydroxide, alkali metal and alkaline earth metal carbonates, such as lithium carbonate and calcium carbonate, and alkali metal bicarbonates, such as sodium bicarbonate.

NaOH and KOH are particularly preferred.

The bases are used in general in equimolar amounts or in excess.

Acids and acidic catalysts used are acids, such as hydrofluoric acid, hydrochloric acid, hydrobromic acid, sulfuric acid and perchloric acid, Lewis acids, such as boron trifluoride, aluminum trichloride, iron(III) chloride, tin(IV) chloride, titanium(IV) chloride and zinc(II) chloride, and organic acids, such as formic acid, acetic acid, propionic acid, oxalic acid, citric acid and trifluoroacetic acid.

The acids are generally employed in catalytic amounts but may also be used in equimolar amounts, in excess or, if required, as solvents.

The starting materials are generally reacted with one another in equimolar amounts.

The reaction of the acid Vb with a hydroxylamine of the formula IXa or its salt IXb is usually carried out at from −10 to 120° C., preferably from 0 to 50° C., in the presence of an activating reagent by the methods described in Houben-Weyl Vol. E 5, page 1141 et seq.

Suitable solvents are aliphatic hydrocarbons, such as pentane, hexane, cyclohexane and petroleum ether, aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, ketones, such as acetone, methyl ethyl ketone, diethyl ketone and tert-butyl methyl ketone, alcohols, such as methanol, ethanol, n-propanol, isopropanol, n-butanol and tert-butanol, and dimethyl sulfoxide and dimethyl formamide, particularly preferably tetrahydrofuran.

Mixtures of the stated solvents may also be used.

Suitable activating reagents are acyl halide formers, such as phosgene, phosphorus tribromide, phosphorus trichloride, phosphorus pentachloride, phosphoryl chloride, thionyl chloride or oxalyl chloride; anhydride formers, such as ethyl chloroformate or methanesulfonyl chloride; carbodiimides such as N,N'-dicyclohexylcarbodiimide, or other conventional reagents, such as N,N'-carbonyldiimidazole or triphenylphosphine in carbon tetrachloride.

Thionyl chloride, oxalyl chloride and N,N'-carbonyldiimidazole are particularly preferred.

The activating reagents are used in general in equimolar amounts or excess.

In the subsequent halogenation of the hydroxamic acid Xa to the halides Xb, conventional halogenating agents (e.g. thionyl chloride, oxalyl chloride, phosphorus tribromide, phosphorus trichloride, phosphorus pentachloride, phosphoryl chloride, triphenyl phosphine and carbon tetrachloride or carbon tetrabromide) are used; the reaction is usually carried out at from −20° to 100° C., preferably from −10 to 80° C., by known methods [Houben-Weyl Vol. E5, page 631; J. Org. Chem. 36, (1971), 233; J. Org. Chem. 57, (1992), 3245].

Suitable solvents are aliphatic hydrocarbons, such as pentane, hexane, cyclohexane and petroleum ether, aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, ketones, such as acetone, methyl ethyl ketone, diethyl ketone and tert-butyl methyl ketone, alcohols, such as methanol, ethanol, n-propanol, isopropanol, n-butanol and tert-butanol, and dimethyl sulfoxide and dimethyl formamide, particularly preferably acetonitrile, toluene and tetrahydrofuran.

Mixtures of the stated solvents may also be used.

The starting materials are generally reacted with one another in equimolar amounts. Using the halogenating agent in excess or in less than stoichiometric amount, based on Xa, may be advantageous for the yield.

The resulting hydroxamoyl halides Xb are converted into the compounds I by reaction with nucleophilic compounds XI by generally known methods [Houben-weyl Vol. E 5, page 826 et seq. and page 1280 et seq.; J. Org. Chem. 36 (1971), 233; Collect. Czech. Chem. Commun. 48 (1983), 596; J. Org. Chem. 46 (1981), 3623], usually at from 0 to 150° C., preferably from 20 to 100° C., in the presence of a base.

Suitable solvents are water, aliphatic hydrocarbons, such as pentane, hexane, cyclohexane and petroleum ether, aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, ketones, such as acetone, methyl ethyl ketone, diethyl ketone and tert-butyl methyl ketone, alcohols, such as methanol, ethanol, n-propanol, isopropanol, n-butanol and tert-butanol, and dimethyl sulfoxide and dimethyl formamide, particularly preferably dimethyl formamide and tetrahydrofuran.

Mixtures of the stated solvents may also be used.

Suitable bases are in general inorganic compounds, such as alkali metal and alkaline earth metal hydroxides, e.g. lithium hydroxide, sodium hydroxide, potassium hydroxide and calcium hydroxide, alkali metal and alkaline earth metal oxides, such as lithium oxide, sodium oxide, calcium oxide and magnesium oxide, alkali metal and alkaline earth metal hydrides, such as lithium hydride, sodium hydride, potassium hydride and calcium hydride, alkali metal amides, such as lithium amide, sodium amide and potassium amide, alkali metal and alkaline earth metal carbonates, such as lithium carbonate and calcium carbonate, and alkali metal bicarbonates, such as sodium bicarbonate, organometallic compounds, in particular alkali metal alkyls, such as methyllithium, butyllithium and phenyllithium, alkali magnesium halides, such as methylmagnesium chloride, and alkali metal and alkaline earth metal alcoholates, such as sodium methylate, sodium ethylate, potassium ethylate, potassium tert-butylate and dimethoxymagnesium, in addition organic bases, for example tertiary amines, such as trimethylamine, triethylamine, triisopropylethylamine and N-methylpiperidine, pyridine, substituted pyridines, such as collidine, lutidine and 4-dimethylaminopyridine, and bicyclic amines.

Sodium hydride, potassium hydride, potassium carbonate, triethylamine and pyridine are particularly preferred.

The bases are generally used in equimolar amounts, in excess or, if required, as solvents.

The starting materials are generally reacted with one another in equimolar amounts. Using XI in excess, based on Xb, may be advantageous for the yield.

Compounds I in which Z is oxygen are particularly preferably obtained in the process described above by reacting the hydroxamic acids Xa directly with a compound VId in the presence of a base in an inert organic solvent [cf. Houben-Weyl Vol. E 5, page 826 et seq.; Aust. J. Chem. 27 (1974), 1341].

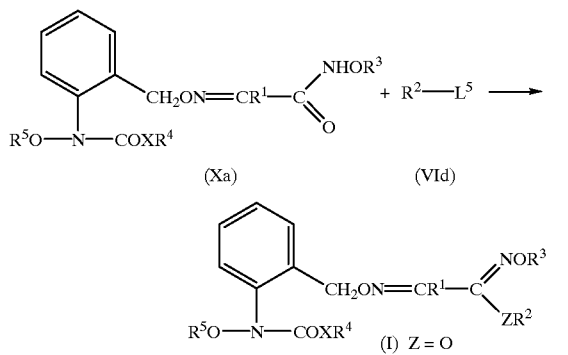

In the formula VId, $L^5$ is a nucleophilically substitutable leaving group, for example halogen or sulfonate, preferably chlorine, bromine, iodine, mesylate, tosylate or triflate.

The reaction is usually carried out at from 0 to 150° C., preferably from 20 to 180° C.

Suitable solvents are water, aliphatic hydrocarbons, such as pentane, hexane, cyclohexane and petroleum ether, aromatic hydrocarbons, such as toluene, o-, m- and p-xylene, halogenated hydrocarbons, such as methylene chloride, chloroform and chlorobenzene, ethers such as diethyl ether, diisopropyl ether, tert-butyl yl etheyl ether, dioxane, anisole and tetrahydrofuran, nitriles, such as acetonitrile and propionitrile, ketones, such as acetone, methyl ethyl ketone, diethyl ketone and tert-butyl methyl ketone, alcohols, such as methanol, ethanol, n-propanol, isopropanol, n-butanol and tert-butanol, and dimethyl sulfoxide and dimethyl formamide, particularly preferably dimethyl formamide and tetrahydrofuran.

Mixtures of the stated solvents may also be used.

Suitable bases are in general inorganic compounds, such as alkali metal and alkaline earth metal hydroxides, e.g. lithium hydroxide, sodium hydroxide, potassium hydroxide and calcium hydroxide, alkali metal and alkaline earth metal oxides, such as lithium oxide, sodium oxide, calcium oxide and magnesium oxide, alkali metal and alkaline earth metal hydrides, such as lithium hydride, sodium hydride, potassium hydride and calcium hydride, alkali metal amides, such as lithium amide, sodium amide and potassium amide, alkali metal and alkaline earth metal carbonates, such as lithium carbonate and calcium carbonate, and alkali metal bicarbonates, such as sodium bicarbonate, organometallic compounds, in particular alkali metal alkyls, such as methyllithium, butyllithium and phenyllithium, alkylmagnesium halides, such as methylmagnesium chloride, and alkali metal and alkaline earth metal alcoholates, such as sodium methylate, sodium ethylate, potassium ethylate, potassium tert-butylate and dimethoxymagnesium, in addition organic bases, for example tertiary amines, such as trimethylamine, triethylamine, triisopropyl ethylamine and N-methylpiperidine, pyridine, substituted pyridines, such as collidine, lutidine and 4-dimethylaminopyridine, and bicyclic amines.

Potassium carbonate, potassium hydroxide, sodium hydride, pyridine and triethylamine are particularly preferred.

The bases are used in general in equimolar amounts, in excess or, if required, as solvents.

A further possible method for the preparation of the compound I is the reaction of the benzyl derivative II with N-hydroxyphthalimide and subsequent hydrazinolysis to give the benzylhydroxylamine IIa and further reaction of IIa with a carbonyl compound XII.

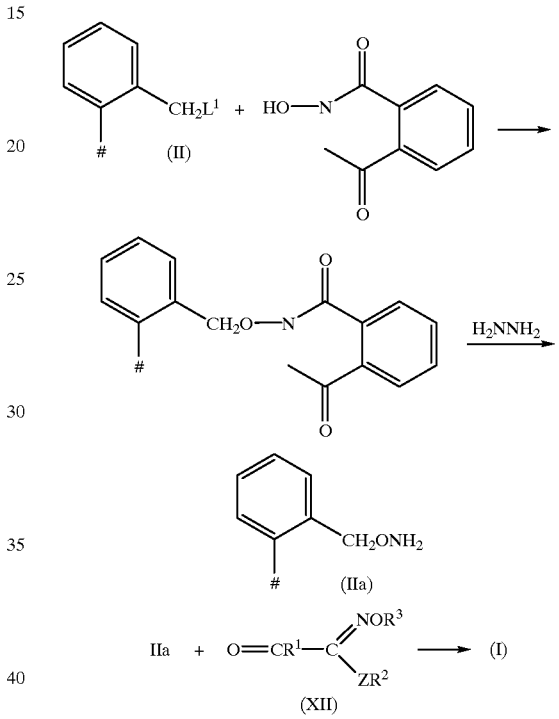

The reaction is carried out in a manner known per se in an inert organic solvent by the methods described in EP-A 463 488 and EP-A 585 751.

The carbonyl compounds XII required are obtained, for example, by reacting the corresponding hydroxyiminocarbonyl compounds XIIa with a nucleophilically substituted reagent VIa.

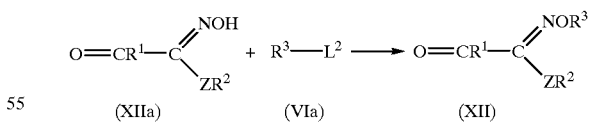

The reaction is carried out in a manner known per se in an inert organic solvent by the methods described in Houben-Weyl Vol. 10/4, page 217 et seq., Houbel-Weyl Vol. E 14b, page 370 et seq., or heterocycles 36 (1993), 1027.

The compounds XIIa are known (EP-A 056 161, EP-A 051 792, DE-A 21 11 459) or can be obtained by the processes described in the literature.

Accordingly, the compounds I can also be obtained by first converting the benzylhydroxylamine IIa with the hydroxyimino derivative XIIa into the corresponding benzyloxyimino derivative of the formula V and then reacting V with the nucleophilically substituted reagent VIa as described above to give I.

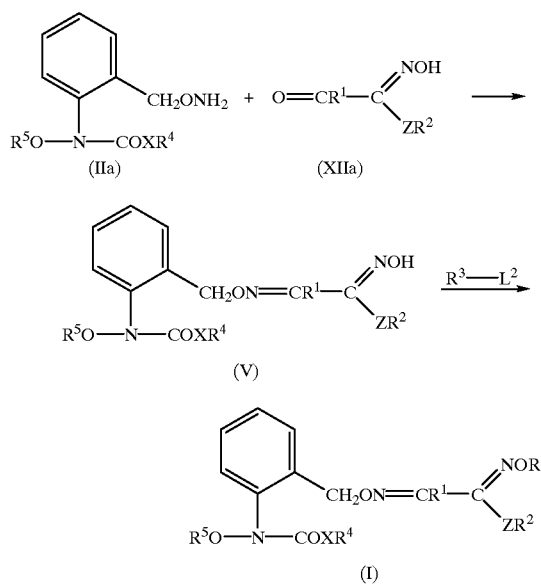

The compounds Va and Vb are also obtained, by processes similar to those described above, by reacting a benzylhydroxylamine of the formula IIa with an α-ketoester XIIIa or an α-keto acid XIIIb under the conditions described above.

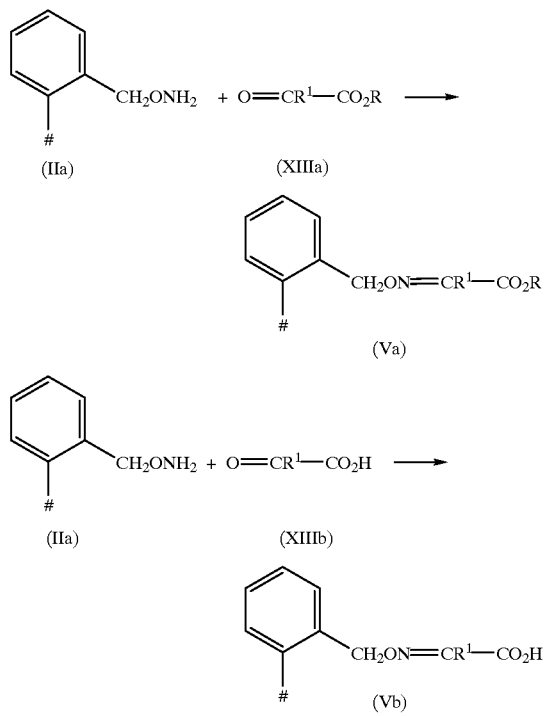

The compounds Xa and xb can be obtained in a similar manner by reacting a benzylhydroxylamino derivative of the formula IIa with an α-ketohydroxamic acid XIVa or an α-ketohydroxamyl halide XIVb.

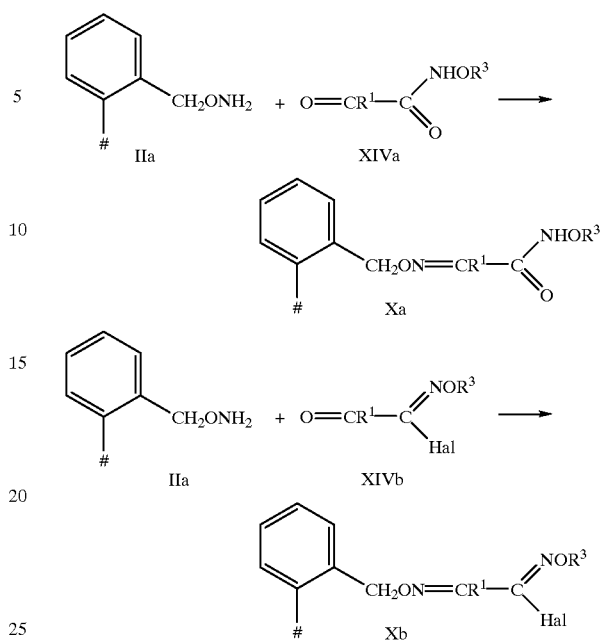

The compounds XIVb are known [Arch. Pharm. 310 (1977), 30 et seq.] or can be prepared by methods described in the literature.

The synthesis of the group —N(OR$^5$)—COXR$^4$ is known, for example, from the literature cited at the outset. For greater clarity, the CH$_2$ON=CR$^1$—C(ZR$^2$)=NOR$^3$ side chain or a suitable precursor of this group is denoted by * for short in the equations below.

1. Compounds I in which R$^5$ is hydrogen (I.a) are obtained in general by reducing a nitrobenzene of the formula VII to the corresponding hydroxylamine VIII and then converting VIII into I.a by reaction with an acylating agent of the formula VIb.

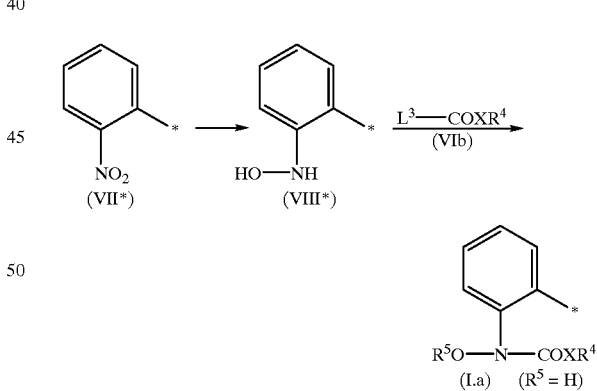

In the formula VIb, L$^3$ is, for example, halogen or aryloxy, in particular chlorine or phenoxy.

a) The reduction of VII and VII* to the hydroxylamine VIII and VIII*, respectively, is usually carried out at from −30 to 80° C., preferably from 0 to 60° C., in an inert organic solvent in the presence of a catalyst [cf. German Application No. 19 50 27 00.0].

b) The reaction of the hydroxylamines VIII or VIII* with VIb is usually carried out at from −20 to 60° C., preferably from 0 to 30° C., in an inert organic solvent in the presence of a base [cf. WO-A 93/15046].

Suitable solvents are aliphatic hydrocarbons, such as pentane, hexane, cyclohexane and petroleum ether, aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran, nitrites, such as acetonitrile and propionitrile, ketones, such as acetone, methyl ethyl ketone, diethyl ketone and tert-butyl methyl ketone, alcohols, such as methanol, ethanol, n-propanol, isopropanol, n-butanol and tert-butanol, and dimethyl sulfoxide and dimethylformamide, particularly preferably cyclohexane, toluene, methylene chloride, tert-butyl methyl ether and water. Mixtures of the stated solvents may also be used.

Suitable bases are in general inorganic compounds, such as alkali metal and alkaline earth metal hydroxides, e.g. lithium hydroxide, sodium hydroxide, potassium hydroxide and calcium hydroxide, alkali metal and alkaline earth metal oxides, such as lithium oxide, sodium oxide, calcium oxide and magnesium oxide, alkali metal and alkaline earth metal hydrides, such as lithium hydride, sodium hydride, potassium hydride and calcium hydride, alkali metal amides, such as lithium amide, sodium amide and potassium amide, alkali metal and alkaline earth metal carbonates, such as lithium carbonate and calcium carbonate, and alkali metal bicarbonates, such as sodium bicarbonate, organometallic compounds, in particular alkali metal alkyls, such as methyllithium butyllithium and phenyllithium, alkylmagnesium halides, such as methylmagnesium chloride, and alkali metal and alkaline earth metal alcoholates, such as sodium methylate, sodium ethylate, potassium ethylate, potassium tert-butylate and dimethoxymagnesium, in addition organic bases, for example tertiary amines, such as trimethylamine, triethylamine, triisopropylethylamine and N-methylpiperidine, pyridine, substituted pyridines, such as collidine, lutidine and 4-dimethylaminopyridine, and bicyclic amines. Potassium carbonate, sodium hydroxide and triethylamine are particularly preferred.

The bases are employed in general in catalytic amounts but may also be used in equimolar amounts, in excess, or, if required, as solvents.

2. The compounds I in which $R^5$ is not hydrogen (I.b) are obtained by reacting a compound of the formula I.a with a compound of the formula VIc in a manner known per se.

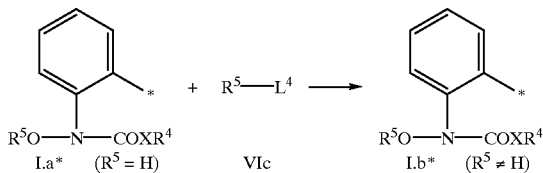

In the formula VIc, $L^4$ is, for example, halogen, mesylate, tosylate, carboxylate or sulfate, in particular chlorine, bromine, mesylate or $R^2$—$OSO_3$—.

This reaction is usually carried out at from −20 to 80° C., preferably from 0 to 60° C., in an inert organic solvent in the presence of a base [cf. WO-A 93/15,046].

Suitable solvents are aliphatic hydrocarbons, such as pentane, hexane, cyclohexane and petroleum ether, aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, ketones, such as acetone, methyl ethyl ketone, diethyl ketone and tert-butyl methyl ketone, alcohols, such as methanol, ethanol, n-propanol, isopropanol, n-butanol and tert-butanol and dimethyl sulfoxide and dimethylformamide, particularly preferably acetone, toluene, tert-butyl methyl ether, cyclohexane and water. Mixtures of the stated solvents may also be used.

Suitable bases are in general inorganic compounds, such as alkali metal and alkaline earth metal hydroxides, e.g. lithium hydroxide, sodium hydroxide, potassium hydroxide and calcium hydroxide, alkali metal and alkaline earth metal oxides, such as lithium oxide, sodium oxide, calcium oxide and magnesium oxide, alkali metal and alkaline earth metal hydrides such as lithium hydride, sodium hydride, potassium hydride and calcium hydride, alkali metal amides, such as lithium amide, sodium amide and potassium amide, alkali metal and alkaline earth metal carbonates, such as lithium carbonate and calcium carbonate, and alkali metal bicarbonates, such as sodium bicarbonate, organometallic compounds, in particular alkali metal alkyls, such as methyllithium, butyllithium and phenyllithium, alkylmagnesium halides, such as methylmagnesium chloride, and alkali metal and alkaline earth metal alcoholates, such as sodium methylate, sodium ethylate, potassium ethylate, potassium tert-butylate and dimethoxymagnesium, in addition organic bases, for example tertiary amines, such as trimethylamine, triethylamine, triisopropylethylamine and N-methylpiperidine, pyridine, substituted pyridines, such as collidine, lutidine and 4-dimethylaminopyridine, and bicyclic amines. Potassium carbonate, sodium hydroxide and triethylamine are particularly preferred.

The bases are employed in general in catalytic amounts but may also be used in equimolar amounts, in excess, or if required, as solvents.

In the equations above, the symbol * denotes the side chain or a suitable precursor. Suitable precursors are generally compounds in which * is $CH_3$ or $CH_2$—$L^1$ ($\equiv$ formula II).

The reaction mixtures are worked up in a conventional manner, for example by mixing with water, separation of the phases and, if required, chromatographic purification of the crude product. Some of the intermediates and end products are obtained in the form of colorless or slightly brownish, viscous oils, which are freed from volatile constituents or purified under reduced pressure and at moderately elevated temperatures. Where the intermediates and end products are obtained as solids, purification may also be effected by recrystallization or dispersing.

The compounds II are described in the literatur cited at the outset or can be synthesized by the processes described in the literature.

Owing to their C═N double bonds, the compounds I may be obtained in the preparation as E/Z isomer mixtures, which can be separated into the individual compounds in a conventional manner, for example by crystallization or chromatography.

With respect to the C═$NOR^3$ double bond, the cis isomers of the compounds I are preferred because of their activity (configuration based on the $OR^3$ group relative to the $ZR^2$ group).

With respect to the $CH_2ON$═$CR^1$ double bond, the cis isomers of the compounds I are preferred because of their activity (configuration based on the radicals $R^1$ relative to the $OCH_2$ group).

If isomer mixtures are formed in the synthesis, separation into the individual compounds is generally required but is not absolutely essential, since some of the individual isomers may be transformed into one another during working up for use or during use (for example under the action of light, acid or base). Corresponding transformations may also take place in the treated organism after application, for example in the treatment of plants, fungi and animal pests. In the definition of the compounds I which is stated at the outset, overall terms which are generally representative of the following groups were used:

halogen: fluorine, chlorine, bromine and iodine;

alkyl: saturated, straight-chain or branched hydrocarbon radicals of 1 to 6 carbon atoms, such as methyl, ethyl, propyl, 1-methyl-ethyl, butyl, 1-methylpropyl, 2-methylpropyl, 1,1-dimethylethyl, pentyl, 1-methylbutyl, 2-methylbutyl, 3-methylbutyl, 2,2-di-methylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-di-methylbutyl, 2,2-dimethylbutyl, 2,3-dimethylbutyl, 3,3-dimethyl-butyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

Alkylamino: straight-chain or branched alkyl of 1 to 6 carbon atoms (as stated above) which is linked to the skeleton via amino (—NH—);

Dialkylamino: amino which carries two independent, straight-chain or branched alkyl groups, each of 1 to 6 carbon atoms (as stated above);

Alkylaminocarbonyl: alkylamino (as stated above) which is linked to the skeleton via carbonyl (—CO—);

Dialkylaminocarbonyl: dialkylamino (as stated above) which is linked to the skeleton via carbonyl (—CO—);

Alkylcarbonyl: straight-chain or branched alkyl of 1 to 4 carbon atoms (as stated above) which is linked to the skeleton by a carbonyl (—CO—);

Alkylsulfonyl: straight-chain or branched alkyl of 1 to 6 carbon atoms (as stated above) which is linked to the skeleton by a sulfonyl (—SO$_2$—);

Alkylsulfoxyl: straight-chain or branched alkyl of 1 to 6 carbon toms (as stated above) which is linked to the skeleton by a sulfoxyl [—S(O)—];

Haloalkyl: straight-chain or branched alkyl of 1 to 4 carbon atoms (as stated above), where some or all of the hydrogen atoms in these groups may be replaced by halogen as stated above, for example C$_1$— or C$_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoro-ethyl, 2-chloro-2-fluoroethyl, 2-chlor-2,2-difluoroethyl, 2,2-dichloro-2-fluoroethyl, 2,2,2-trichloroethyl or pentafluoroethyl;

Alkoxy: straight-chain or branched alkyl of 1 to 6 carbon atoms (as stated above) which is linked to the skeleton via oxygen (—O—);

Alkoxycarbonyl: straight-chain or branched alkoxy of 1 to 6 carbon atoms (as stated above) which is linked to the skeleton via carbonyl (—CO—);

Haloalkoxy: straight-chain or branched haloalkyl of 1 to 6 carbon atoms (as stated above) which is linked to the skeleton via oxygen (—O—);

Alkylthio: straight-chain or branched alkyl of 1 to 6 carbon atoms (as stated above) which is linked to the skeleton via sulfur (—S—);

Haloalkylthio: straight-chain or branched haloalkyl of 1 to 6 carbon atoms (as stated above) which is linked to the skeleton via sulfur (—S—);

Alkenyl: unsaturated, straight-chain or branched hydrocarbon radicals of 2 or 3 to 6 carbon atoms, having a double bond in any desired position, for example C$_2$–C$_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

Alkenyloxy: straight-chain or branched alkenyl of 2 to 6 carbon atoms (as stated above) which is linked to the skeleton via oxygen;

Alkynyl: straight-chain or branched hydrocarbon groups of 2 to 6 carbon atoms having a triple bond in any desired position, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

Cycloalkyl: monocyclic alkyl groups having 3 to 6 carbon ring members, such as cyclopropyl, cyclobutyl, cyclopentyl and cyclohexyl;

Aryl: an aromatic monocyclic or polycyclic hydrocarbon radical, such as phenyl, naphthyl or anthracenyl;

Hetaryl: an aromatic, monocyclic or polycyclic radical, which, in addition to carbon, may also contain heteroatoms selected from the group consisting of oxygen, sulfur and nitrogen as ring members, for example 5-membered hetaryl containing from one to four nitrogen atoms or from one to three oxygen atoms and one sulfur or oxygen atom: Hetaryl groups which have a 5-membered ring and, in addition to carbon atoms, may contain from one to four nitrogen atoms or from one to three nitrogen atoms and one sulfur or oxygen atom as ring members, e.g. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2, 4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl;

6-membered hetaryl containing from one to three or from one to four nitrogen atoms: Hetaryl groups which have a 6-membered ring and, in addition to carbon atoms, may contain from one to three or from one to four nitrogen atoms as ring members, e.g. 2-pyridyl, 3-pyridyl, 4-pyridyl, 3-pyridazinyl, 4-pyridazinyl, 2-pyrimidinyl, 4-pyrimidinyl, 5-pyrimidinyl, 2-pyrazinyl, 1,3,5-triazin-2-yl or 1,2,4-triazin-3-yl.

The statement "partially or completely halogenated" is intended to express the fact that, in groups characterized in this manner, some or all of the hydrogen atoms (of the hydrocarbon groups) may be replaced by identical or different halogen atoms as stated above.

The statement "unsubstituted or substituted" in relation to the radicals stated for $R^5$ is intended to express the fact that the hydrocarbon groups may be partially or completely halogenated and/or may carry from one to three (in particular one) of the follow radicals: hydroxyl, cyano and $C_1$–$C_4$-alkoxy.

Because of their biological activity, compounds I in which X is oxygen are particularly preferred.

Compounds I in which X is NH are likewise preferred.

Compounds I in which X is a direct bond are also preferred.

Compounds I in which Z is oxygen are very particularly preferred.

Compounds I in which $R^1$ is $C_1$–$C_4$-alkyl, in particular methyl, are likewise preferred.

Compounds I in which $R^1$ is $C_1$–$C_4$-haloalkyl, in particular trifluoromethyl, are also preferred.

Moreover, compounds I in which Z is oxygen or sulfur are preferred.

Furthermore, compounds I in which Z is $NR^b$ are preferred, particularly preferred compounds I being those in which $R^b$ is hydrogen or $C_1$–$C_4$-alkyl (in particular hydrogen or methyl).

Compounds I in which $R^2$ is unsubstituted or substituted benzyl or alkyl, alkenyl or alkynyl, each of 2 to 6 carbon atoms, are like-wise preferred.

Other preferred compounds I are those in which $R^2$ is benzyl which may be partially or completely halogenated and/or may carry from one to three of the following radicals: cyano, $C_1$–$C_4$-alkyl, $C_1$–$C_4$-haloalkyl, $C_1$–$C_4$-alkylcarbonyl, $C_1$–$C_4$-alkoxy, $C_1$–$C_4$-haloalkoxy, $C_1$–$C_4$-alkoxycarbonyl and alkylthio.

Compounds I in which $R^2$ is $C_2$–$C_6$-alkyl are particularly preferred.

Compounds I in which $R^2$ is $C_3$–$C_6$-cycloalkyl are also preferred.

Compounds I in which $R^3$ is $C_1$–$C_6$-alkyl (preferably $C_1$–$C_4$-alkyl, in particular $C_1$- or $C_2$-alkyl) which may be partially or completely halogenated are likewise preferred.

Compounds I in which $R^3$ is $C_2$–$C_6$-alkenyl (preferably $C_3$–$C_6$-alkenyl, in particular $C_3$- or $C_4$-alkenyl) which may be partially or completely halogenated are also preferred.

Compounds I in which $R^3$ is $C_2$–$C_6$-alkynyl (preferably $C_3$–$C_6$-alkynyl, in particular $C_3$- or $C_4$-alkynyl) which may be partially or completely halogenated are furthermore preferred.

Compounds I in which $R^3$ is methyl are particularly preferred.

Compounds I in which $R^4$ is methyl are likewise preferred.

Furthermore, compounds I in which $R^4$ is ethyl are preferred.

Compounds I in which $R^5$ is hydrogen are likewise preferred.

Furthermore, compounds I in which $R^5$ is methyl are preferred.

Compounds I in which $R^5$ is ethyl are also preferred.

Compounds I in which $R^5$ is methoxymethyl, allyl or propargyl are also preferred.

Particularly with regard to their use, the compounds I listed in the tables below are preferred. Furthermore, considered by themselves independently of the combination in which they are mentioned, the groups stated in the tables as a substituent constitute a particularly preferred embodiment of the relevant substituent.

Table 1

Compounds of the formula I.A (X=O, $R^4$=$CH_3$, $R^5$=$CH_3$), in which $R^1$ is hydrogen, Z is oxygen and $R^3$ is methyl and $R^2$ for a compound corresponds in each case to a group in Table A.

Table 2

Compounds of the formula I.B (X=O, $R^4$=$CH_3$, $R^5$=H), in which $R^1$ is hydrogen, Z is oxygen and $R^3$ is methyl and $R^2$ for a compound corresponds in each case to a group in Table A.

Table 3

Compounds of the formula I.C (X=NH, $R^4$=$CH_3$, $R^5$=$CH_3$), in which $R^1$ is hydrogen, Z is oxygen and $R^3$ is methyl and $R^2$ for a compound corresponds in each case to a group in Table A.

Table 4

Compounds of the formula I.D (X=O, $R^4$=$CH_2CH_3$, $R^5$=$CH_3$), in which $R^1$ is hydrogen, Z is oxygen and $R^3$ is methyl and $R^2$ for a compound corresponds in each case to a group in Table A.

Table 5

Compounds of the formula I.A, in which $R^1$ is hydrogen, Z is sulfur and $R^3$ is methyl and $R^2$ for a compound corresponds in each case to a group in Table A.

Table 6

Compounds of the formula I.B, in which $R^1$ is hydrogen, Z is sulfur and $R^3$ is methyl and $R^2$ for a compound corresponds in each case to a group in Table A.

Table 7

Compounds of the formula I.C, in which $R^1$ is hydrogen, Z is sulfur and $R^3$ is methyl and $R^2$ for a compound corresponds in each case to a group in Table A.

Table 8

Compounds of the formula I.D, in which $R^1$ is hydrogen, Z is sulfur and $R^3$ is methyl and $R^2$ for a compound corresponds in each case to a group in Table A.

Table 9

Compounds of the formula I.A, in which $R^1$ is hydrogen, Z is NH and $R^3$ is methyl and $R^2$ for a compound corresponds in each case to a group in Table A.

Table 10

Compounds of the formula I.B, in which $R^1$ is hydrogen, Z is NH and $R^3$ is methyl and $R^2$ for a compound corresponds in each case to a group in Table A.

Table 11

Compounds of the formula I.C, in which $R^1$ is hydrogen, Z is NH and $R^3$ is methyl and $R^2$ for a compound corresponds in each case to a group in Table A.

Table 12

Compounds of the formula I.D, in which $R^1$ is hydrogen, Z is NH and $R^3$ is methyl and $R^2$ for a compound corresponds in each case to a group in Table A.

Table 13

Compounds of the formula I.A, in which $R^1$ is methyl, Z is oxygen and $R^3$ is methyl and $R^2$ for a compound corresponds in each case to a group in Table A.

Table 14

Compounds of the formula I.B, in which $R^1$ is methyl, Z is oxygen and $R^3$ is methyl and $R^2$ for a compound corresponds in each case to a group in Table A.

Table 15

Compounds of the formula I.C, in which $R^1$ is methyl, Z is oxygen and $R^3$ is methyl and $R^2$ for a compound corresponds in each case to a group in Table A.

Table 16

Compounds of the formula I.D, in which $R^1$ is methyl, Z is oxygen and $R^3$ is methyl and $R^2$ for a compound corresponds in each case to a group in Table A.

Table 17

Compounds of the formula I.A, in which $R^1$ is methyl, Z is sulfur and $R^3$ is methyl and $R^2$ for a compound corresponds in each case to a group in Table A.

Table 18

Compounds of the formula I.B, in which $R^1$ is methyl, Z is sulfur and $R^3$ is methyl and $R^2$ for a compound corresponds in each case to a group in Table A.

Table 19

Compounds of the formula I.C, in which $R^1$ is methyl, Z is sulfur and $R^3$ is methyl and $R^2$ for a compound corresponds in each case to a group in Table A.

Table 20

Compounds of the formula I.D, in which $R^1$ is methyl, Z is sulfur and $R^3$ is methyl and $R^2$ for a compound corresponds in each case to a group in Table A.

Table 21

Compounds of the formula I.A, in which $R^1$ is methyl, Z is NH and $R^3$ is methyl and $R^2$ for a compound corresponds in each case to a group in Table A.

Table 22

Compounds of the formula I.B, in which $R^1$ is methyl, Z is NH and $R^3$ is methyl and $R^2$ for a compound corresponds in each case to a group in Table A.

Table 23

Compounds of the formula I.C, in which $R^1$ is methyl, Z is NH and $R^3$ is methyl and $R^2$ for a compound corresponds in each case to a group in Table A.

Table 24

Compounds of the formula I.D, in which $R^1$ is methyl, Z is NH and $R^3$ is methyl and $R^2$ for a compound corresponds in each case to a group in Table A.

Table 25

Compounds of the formula I.A, in which $R^1$ is ethyl, Z is oxygen and $R^3$ is methyl and $R^2$ for a compound corresponds in each case to a group in Table A.

Table 26

Compounds of the formula I.B, in which $R^1$ is ethyl, Z is oxygen and $R^3$ is methyl and $R^2$ for a compound corresponds in each case to a group in Table A.

Table 27

Compounds of the formula I.A, in which $R^1$ is ethyl, Z is sulfur and $R^3$ is methyl and $R^2$ for a compound corresponds in each case to a group in Table A.

Table 28

Compounds of the formula I.B, in which $R^1$ is ethyl, Z is sulfur and $R^3$ is methyl and $R^2$ for a compound corresponds in each case to a group in Table A.

Table 29

Compounds of the formula I.A, in which $R^1$ is ethyl, Z is NH and $R^3$ is methyl and $R^2$ for a compound corresponds in each case to a group in Table A.

Table 30

Compounds of the formula I.B, in which $R^1$ is ethyl, Z is NH and $R^3$ is methyl and $R^2$ for a compound corresponds in each case to a group in Table A.

Table 31

Compounds of the formula I.A, in which $R^1$ is isopropyl, Z is oxygen and $R^3$ is methyl and $R^2$ for a compound corresponds in each case to a group in Table A.

Table 32

Compounds of the formula I.B, in which $R^1$ is isopropyl, Z is oxygen and $R^3$ is methyl and $R^2$ for a compound corresponds in each case to a group in Table A.

Table 33

Compounds of the formula I.A, in which $R^1$ is isopropyl, Z is sulfur and $R^3$ is methyl and $R^2$ for a compound corresponds in each case to a group in Table A.

Table 34

Compounds of the formula I.B, in which $R^1$ is isopropyl, Z is sulfur and $R^3$ is methyl and $R^2$ for a compound corresponds in each case to a group in Table A.

Table 35

Compounds of the formula I.A, in which $R^1$ is isopropyl, Z is NH and $R^3$ is methyl and $R^2$ for a compound corresponds in each case to a group in Table A.

Table 36

Compounds of the formula I.B, in which $R^1$ is isopropyl, Z is NH and $R^3$ is methyl and $R^2$ for a compound corresponds in each case to a group in Table A.

Table 37

Compounds of the formula I.A, in which $R^1$ is hydrogen, Z is oxygen and $R^3$ is ethyl and $R^2$ for a compound corresponds in each case to a group in Table A.

Table 38

Compounds of the formula I.B, in which $R^1$ is hydrogen, Z is oxygen and $R^3$ is ethyl and $R^2$ for a compound corresponds in each case to a group in Table A.

Table 39

Compounds of the formula I.A, in which $R^1$ is hydrogen, Z is sulfur and $R^3$ is ethyl and $R^2$ for a compound corresponds in each case to a group in Table A.

Table 40

Compounds of the formula I.B, in which $R^1$ is hydrogen, Z is sulfur and $R^3$ is ethyl and $R^2$ for a compound corresponds in each case to a group in Table A.

Table 41

Compounds of the formula I.A, in which $R^1$ is hydrogen, Z is NH and $R^3$ is ethyl and $R^2$ for a compound corresponds in each case to a group in Table A.

Table 42

Compounds of the formula I.B, in which $R^1$ is hydrogen, Z is NH and $R^3$ is ethyl and $R^2$ for a compound corresponds in each case to a group in Table A.

Table 43

Compounds of the formula I.A, in which $R^1$ is methyl, Z is oxygen and $R^3$ is ethyl and $R^2$ for a compound corresponds in each case to a group in Table A.

Table 44

Compounds of the formula I.B, in which $R^1$ is methyl, Z is oxygen and $R^3$ is ethyl and $R^2$ for a compound corresponds in each case to a group in Table A.

Table 45

Compounds of the formula I.A, in which $R^1$ is methyl, Z is sulfur and $R^3$ is ethyl and $R^2$ for a compound corresponds in each case to a group in Table A.

Table 46

Compounds of the formula I.B, in which $R^1$ is methyl, Z is sulfur and $R^3$ is ethyl and $R^2$ for a compound corresponds in each case to a group in Table A.

Table 47

Compounds of the formula I.A, in which $R^1$ is methyl, Z is NH and $R^3$ is ethyl and $R^2$ for a compound corresponds in each case to a group in Table A.

Table 48

Compounds of the formula I.B, in which $R^1$ is methyl, Z is NH and $R^3$ is ethyl and $R^2$ for a compound corresponds in each case to a group in Table A.

Table 49

Compounds of the formula I.A, in which $R^1$ is ethyl, Z is oxygen and $R^3$ is ethyl and $R^2$ for a compound corresponds in each case to a group in Table A.

Table 50

Compounds of the formula I.B, in which $R^1$ is ethyl, Z is oxygen and $R^3$ is ethyl and $R^2$ for a compound corresponds in each case to a group in Table A.

Table 51

Compounds of the formula I.A, in which $R^1$ is ethyl, Z is sulfur and $R^3$ is ethyl and $R^2$ for a compound corresponds in each case to a group in Table A.

Table 52

Compounds of the formula I.B, in which $R^1$ is ethyl, Z is sulfur and $R^3$ is ethyl and $R^2$ for a compound corresponds in each case to a group in Table A.

Table 53

Compounds of the formula I.A, in which $R^1$ is ethyl, Z is NH and $R^3$ is ethyl and $R^2$ for a compound corresponds in each case to a group in Table A.

Table 54

Compounds of the formula I.B, in which $R^1$ is ethyl, Z is NH and $R^3$ is ethyl and $R^2$ for a compound corresponds in each case to a group in Table A.

Table 55

Compounds of the formula I.A, in which $R^1$ is isopropyl, Z is oxygen and $R^3$ is ethyl and $R^2$ for a compound corresponds in each case to a group in Table A.

Table 56

Compounds of the formula I.B, in which $R^1$ is isopropyl, Z is oxygen and $R^3$ is ethyl and $R^2$ for a compound corresponds in each case to a group in Table A.

Table 57

Compounds of the formula I.A, in which $R^1$ is isopropyl, Z is sulfur and $R^3$ is ethyl and $R^2$ for a compound corresponds in each case to a group in Table A.

Table 58

Compounds of the formula I.B, in which $R^1$ is isopropyl, Z is sulfur and $R^3$ is ethyl and $R^2$ for a compound corresponds in each case to a group in Table A.

Table 59

Compounds of the formula I.A, in which $R^1$ is isopropyl, Z is NH and $R^3$ is ethyl and $R^2$ for a compound corresponds in each case to a group in Table A.

Table 60

Compounds of the formula I.B, in which $R^1$ is isopropyl, Z is NH and $R^3$ is ethyl and $R^2$ for a compound corresponds in each case to a group in Table A.

Table 61

Compounds of the formula I.A, in which $R^1$ is hydrogen, Z is oxygen and $R^3$ is propyl and $R^2$ for a compound corresponds in each case to a group in Table A.

Table 62

Compounds of the formula I.B, in which $R^1$ is hydrogen, Z is oxygen and $R^3$ is propyl and $R^2$ for a compound corresponds in each case to a group in Table A.

Table 63

Compounds of the formula I.A, in which $R^1$ is hydrogen, Z is sulfur and $R^3$ is propyl and $R^2$ for a compound corresponds in each case to a group in Table A.

Table 64

Compounds of the formula I.B, in which $R^1$ is hydrogen, Z is sulfur and $R^3$ is propyl and $R^2$ for a compound corresponds in each case to a group in Table A.

Table 65

Compounds of the formula I.A, in which $R^1$ is hydrogen, Z is NH and $R^3$ is propyl and $R^2$ for a compound corresponds in each case to a group in Table A.

Table 66

Compounds of the formula I.B, in which $R^1$ is hydrogen, Z is NH and $R^3$ is propyl and $R^2$ for a compound corresponds in each case to a group in Table A.

Table 67

Compounds of the formula I.A, in which $R^1$ is methyl, Z is oxygen and $R^3$ is propyl and $R^2$ for a compound corresponds in each case to a group in Table A.

Table 68

Compounds of the formula I.B, in which $R^1$ is methyl, Z is oxygen and $R^3$ is propyl and $R^2$ for a compound corresponds in each case to a group in Table A.

Table 69

Compounds of the formula I.A, in which $R^1$ is methyl, Z is sulfur and $R^3$ is propyl and $R^2$ for a compound corresponds in each case to a group in Table A.

Table 70

Compounds of the formula I.B, in which $R^1$ is methyl, Z is sulfur and $R^3$ is propyl and $R^2$ for a compound corresponds in each case to a group in Table A.

Table 71

Compounds of the formula I.A, in which $R^1$ is methyl, Z is NH and $R^3$ is propyl and $R^2$ for a compound corresponds in each case to a group in Table A.

Table 72

Compounds of the formula I.B, in which $R^1$ is methyl, Z is NH and $R^3$ is propyl and $R^2$ for a compound corresponds in each case to a group in Table A.

Table 73

Compounds of the formula I.A, in which $R^1$ is ethyl, Z is oxygen and $R^3$ is propyl and $R^2$ for a compound corresponds in each case to a group in Table A.

Table 74

Compounds of the formula I.B, in which $R^1$ is ethyl, Z is oxygen and $R^3$ is propyl and $R^2$ for a compound corresponds in each case to a group in Table A.

Table 75

Compounds of the formula I.A, in which $R^1$ is ethyl, Z is sulfur and $R^3$ is propyl and $R^2$ for a compound corresponds in each case to a group in Table A.

Table 76

Compounds of the formula I.B, in which $R^1$ is ethyl, Z is sulfur and $R^3$ is propyl and $R^2$ for a compound corresponds in each case to a group in Table A.

Table 77

Compounds of the formula I.A, in which $R^1$ is ethyl, Z is NH and $R^3$ is propyl and $R^2$ for a compound corresponds in each case to a group in Table A.

Table 78

Compounds of the formula I.B, in which $R^1$ is ethyl, Z is NH and $R^3$ is propyl and $R^2$ for a compound corresponds in each case to a group in Table A.

Table 79

Compounds of the formula I.A, in which $R^1$ is isopropyl, Z is oxygen and $R^3$ is propyl and $R^2$ for a compound corresponds in each case to a group in Table A.

Table 80

Compounds of the formula I.B, in which $R^1$ is isopropyl, Z is oxygen and $R^3$ is propyl and $R^2$ for a compound corresponds in each case to a group in Table A.

Table 81

Compounds of the formula I.A, in which $R^1$ is isopropyl, Z is sulfur and $R^3$ is propyl and $R^2$ for a compound corresponds in each case to a group in Table A.

Table 82

Compounds of the formula I.B, in which $R^1$ is isopropyl, Z is sulfur and $R^3$ is propyl and $R^2$ for a compound corresponds in each case to a group in Table A.

Table 83

Compounds of the formula I.A, in which $R^1$ is isopropyl, Z is NH and $R^3$ is propyl and $R^2$ for a compound corresponds in each case to a group in Table A

Table 84

Compounds of the formula I.B, in which $R^1$ is isopropyl, Z is NH and $R^3$ is propyl and $R^2$ for a compound corresponds in each case to a group in Table A.

Table 85

Compounds of the formula I.A, in which $R^1$ is hydrogen, Z is oxygen and $R^3$ is isopropyl and $R^2$ for a compound corresponds in each case to a group in Table A.

Table 86

Compounds of the formula I.B, in which $R^1$ is hydrogen, Z is oxygen and $R^3$ is isopropyl and $R^2$ for a compound corresponds in each case to a group in Table A.

Table 87

Compounds of the formula I.A, in which $R^1$ is hydrogen, Z is sulfur and $R^3$ is isopropyl and $R^2$ for a compound corresponds in each case to a group in Table A.

Table 88

Compounds of the formula I.B, in which $R^1$ is hydrogen, Z is sulfur and $R^3$ is isopropyl and $R^2$ for a compound corresponds in each case to a group in Table A.

Table 89

Compounds of the formula I.A, in which $R^1$ is hydrogen, Z is NH and $R^3$ is isopropyl and $R^2$ for a compound corresponds in each case to a group in Table A.

Table 90

Compounds of the formula I.B, in which $R^1$ is hydrogen, Z is NH and $R^3$ is isopropyl and $R^2$ for a compound corresponds in each case to a group in Table A.

Table 91

Compounds of the formula I.A, in which $R^1$ is methyl, Z is oxygen and $R^3$ is isopropyl and $R^2$ for a compound corresponds in each case to a group in Table A.

Table 92

Compounds of the formula I.B, in which $R^1$ is methyl, Z is oxygen and $R^3$ is isopropyl and $R^2$ for a compound corresponds in each case to a group in Table A.

Table 93

Compounds of the formula I.A, in which $R^1$ is methyl, Z is sulfur and $R^3$ is isopropyl and $R^2$ for a compound corresponds in each case to a group in Table A.

Table 94

Compounds of the formula I.B, in which $R^1$ is methyl, Z is sulfur and $R^3$ is isopropyl and $R^2$ for a compound corresponds in each case to a group in Table A.

Table 95

Compounds of the formula I.A, in which $R^1$ is methyl, Z is NH and $R^3$ is isopropyl and $R^2$ for a compound corresponds in each case to a group in Table A.

Table 96

Compounds of the formula I.B, in which $R^1$ is methyl, Z is NH and $R^3$ is isopropyl and $R^2$ for a compound corresponds in each case to a group in Table A.

Table 97

Compounds of the formula I.A, in which $R^1$ is ethyl, Z is oxygen and $R^3$ is isopropyl and $R^2$ for a compound corresponds in each case to a group in Table A.

Table 98

Compounds of the formula I.B, in which $R^1$ is ethyl, Z is oxygen and $R^3$ is isopropyl and $R^2$ for a compound corresponds in each case to a group in Table A.

Table 99

Compounds of the formula I.A, in which $R^1$ is ethyl, Z is sulfur and $R^3$ is isopropyl and $R^2$ for a compound corresponds in each case to a group in Table A.

Table 100

Compounds of the formula I.B, in which $R^1$ is ethyl, Z is sulfur and $R^3$ is isopropyl and $R^2$ for a compound corresponds in each case to a group in Table A.

Table 101

Compounds of the formula I.A, in which $R^1$ is ethyl, Z is NH and $R^3$ is isopropyl and $R^2$ for a compound corresponds in each case to a group in Table A.

Table 102

Compounds of the formula I.B, in which $R^1$ is ethyl, Z is NH and $R^3$ is isopropyl and $R^2$ for a compound corresponds in each case to a group in Table A.

Table 103

Compounds of the formula I.A, in which $R^1$ is isopropyl, Z is oxygen and $R^3$ is isopropyl and $R^2$ for a compound corresponds in each case to a group in Table A.

Table 104

Compounds of the formula I.B, in which $R^1$ is isopropyl, Z is oxygen and $R^3$ is isopropyl and $R^2$ for a compound corresponds in each case to a group in Table A.

Table 105

Compounds of the formula I.A, in which $R^1$ is isopropyl, Z is sulfur and $R^3$ is isopropyl and $R^2$ for a compound corresponds in each case to a group in Table A.

Table 106

Compounds of the formula I.B, in which $R^1$ is isopropyl, Z is sulfur and $R^3$ is isopropyl and $R^2$ for a compound corresponds in each case to a group in Table A.

Table 107

Compounds of the formula I.A, in which $R^1$ is isopropyl, Z is NH and $R^3$ is isopropyl and $R^2$ for a compound corresponds in each case to a group in Table A.

Table 108

Compounds of the formula I.B, in which $R^1$ is isopropyl, Z is NH and $R^3$ is isopropyl and $R^2$ for a compound corresponds in each case to a group in Table A.

Table 109

Compounds of the formula I.A, in which $R^1$ is hydrogen, Z is oxygen and $R^3$ is butyl and $R^2$ for a compound corresponds in each case to a group in Table A.

Table 110

Compounds of the formula I.B, in which $R^1$ is hydrogen, Z is oxygen and $R^3$ is butyl and $R^2$ for a compound corresponds in each case to a group in Table A.

Table 111

Compounds of the formula I.A, in which $R^1$ is hydrogen, Z is sulfur and $R^3$ is butyl and $R^2$ for a compound corresponds in each case to a group in Table A.

Table 112

Compounds of the formula I.B, in which $R^1$ is hydrogen, Z is sulfur and $R^3$ is butyl and $R^2$ for a compound corresponds in each case to a group in Table A.

Table 113

Compounds of the formula I.A, in which $R^1$ is hydrogen, Z is NH and $R^3$ is butyl and $R^2$ for a compound corresponds in each case to a group in Table A.

Table 114

Compounds of the formula I.B, in which $R^1$ is hydrogen, Z is NH and $R^3$ is butyl and $R^2$ for a compound corresponds in each case to a group in Table A.

Table 115

Compounds of the formula I.A, in which $R^1$ is methyl, Z is oxygen and $R^3$ is butyl and $R^2$ for a compound corresponds in each case to a group in Table A.

Table 116

Compounds of the formula I.B, in which $R^1$ is methyl, Z is oxygen and $R^3$ is butyl and $R^2$ for a compound corresponds in each case to a group in Table A.

Table 117

Compounds of the formula I.A, in which $R^1$ is methyl, Z is sulfur and $R^3$ is butyl and $R^2$ for a compound corresponds in each case to a group in Table A.

Table 118

Compounds of the formula I.B, in which $R^1$ is methyl, Z is sulfur and $R^3$ is butyl and $R^2$ for a compound corresponds in each case to a group in Table A.

Table 119

Compounds of the formula I.A, in which $R^1$ is methyl, Z is NH and $R^3$ is butyl and $R^2$ for a compound corresponds in each case to a group in Table A.

Table 120

Compounds of the formula I.B, in which $R^1$ is methyl, Z is NH and $R^3$ is butyl and $R^2$ for a compound corresponds in each case to a group in Table A.

Table 121

Compounds of the formula I.A, in which $R^1$ is ethyl, Z is oxygen and $R^3$ is butyl and $R^2$ for a compound corresponds in each case to a group in Table A.

Table 122

Compounds of the formula I.B, in which $R^1$ is ethyl, Z is oxygen and $R^3$ is butyl and $R^2$ for a compound corresponds in each case to a group in Table A.

Table 123

Compounds of the formula I.A, in which $R^1$ is ethyl, Z is sulfur and $R^3$ is butyl and $R^2$ for a compound corresponds in each case to a group in Table A.

Table 124

Compounds of the formula I.B, in which $R^1$ is ethyl, Z is sulfur and $R^3$ is butyl and $R^2$ for a compound corresponds in each case to a group in Table A.

Table 125

Compounds of the formula I.A, in which $R^1$ is ethyl, Z is NH and $R^3$ is butyl and $R^2$ for a compound corresponds in each case to a group in Table A.

Table 126

Compounds of the formula I.B, in which $R^1$ is ethyl, Z is NH and $R^3$ is butyl and $R^2$ for a compound corresponds in each case to a group in Table A.

Table 127

Compounds of the formula I.A, in which $R^1$ is isopropyl, Z is oxygen and $R^3$ is butyl and $R^2$ for a compound corresponds in each case to a group in Table A.

Table 128

Compounds of the formula I.B, in which $R^1$ is isopropyl, Z is oxygen and $R^3$ is butyl and $R^2$ for a compound corresponds in each case to a group in Table A.

Table 129

Compounds of the formula I.A, in which $R^1$ is isopropyl, Z is sulfur and $R^3$ is butyl and $R^2$ for a compound corresponds in each case to a group in Table A.

Table 130

Compounds of the formula I.B, in which $R^1$ is isopropyl, Z is sulfur and $R^3$ is butyl and $R^2$ for a compound corresponds in each case to a group in Table A.

Table 131

Compounds of the formula I.A, in which $R^1$ is isopropyl, Z is NH and $R^3$ is butyl and $R^2$ for a compound corresponds in each case to a group in Table A.

Table 132

Compounds of the formula I.B, in which $R^1$ is isopropyl, Z is NH and $R^3$ is butyl and $R^2$ for a compound corresponds in each case to a group in Table A.

Table 133

Compounds of the formula I.A, in which $R^1$ is hydrogen, Z is oxygen and $R^3$ is sec-butyl and $R^2$ for a compound corresponds in each case to a group in Table A.

Table 134

Compounds of the formula I.B, in which $R^1$ is hydrogen, Z is oxygen and $R^3$ is sec-butyl and $R^2$ for a compound corresponds in each case to a group in Table A.

Table 135

Compounds of the formula I.A, in which $R^1$ is hydrogen, Z is sulfur and $R^3$ is sec-butyl and $R^2$ for a compound corresponds in each case to a group in Table A.

Table 136

Compounds of the formula I.B, in which $R^1$ is hydrogen, Z is sulfur and $R^3$ is sec-butyl and $R^2$ for a compound corresponds in each case to a group in Table A.

Table 137

Compounds of the formula I.A, in which $R^1$ is hydrogen, Z is NH and $R^3$ is sec-butyl and $R^2$ for a compound corresponds in each case to a group in Table A.

Table 138

Compounds of the formula I.B, in which $R^1$ is hydrogen, Z is NH and $R^3$ is sec-butyl and $R^2$ for a compound corresponds in each case to a group in Table A.

Table 139

Compounds of the formula I.A, in which $R^1$ is methyl, Z is oxygen and $R^3$ is sec-butyl and $R^2$ for a compound corresponds in each case to a group in Table A.

Table 140

Compounds of the formula I.B, in which $R^1$ is methyl, Z is oxygen and $R^3$ is sec-butyl and $R^2$ for a compound corresponds in each case to a group in Table A.

Table 141

Compounds of the formula I.A, in which $R^1$ is methyl, Z is sulfur and $R^3$ is sec-butyl and $R^2$ for a compound corresponds in each case to a group in Table A.

Table 142

Compounds of the formula I.B, in which $R^1$ is methyl, Z is sulfur and $R^3$ is sec-butyl and $R^2$ for a compound corresponds in each case to a group in Table A.

Table 143

Compounds of the formula I.A, in which $R^1$ is methyl, Z is NH and $R^3$ is sec-butyl and $R^2$ for a compound corresponds in each case to a group in Table A.

Table 144

Compounds of the formula I.B, in which $R^1$ is methyl, Z is NH and $R^3$ is sec-butyl and $R^2$ for a compound corresponds in each case to a group in Table A.

Table 145

Compounds of the formula I.A, in which $R^1$ is ethyl, Z is oxygen and $R^3$ is sec-butyl and $R^2$ for a compound corresponds in each case to a group in Table A.

Table 146

Compounds of the formula I.B, in which $R^1$ is ethyl, Z is oxygen and $R^3$ is sec-butyl and $R^2$ for a compound corresponds in each case to a group in Table A.

Table 147

Compounds of the formula I.A, in which $R^1$ is ethyl, Z is sulfur and $R^3$ is sec-butyl and $R^2$ for a compound corresponds in each case to a group in Table A.

Table 148

Compounds of the formula I.B, in which $R^1$ is ethyl, Z is sulfur and $R^3$ is sec-butyl and $R^2$ for a compound corresponds in each case to a group in Table A.

Table 149

Compounds of the formula I.A, in which $R^1$ is ethyl, Z is NH and $R^3$ is sec-butyl and $R^2$ for a compound corresponds in each case to a group in Table A.

Table 150

Compounds of the formula I.B, in which $R^1$ is ethyl, Z is NH and $R^3$ is sec-butyl and $R^2$ for a compound corresponds in each case to a group in Table A.

Table 151

Compounds of the formula I.A, in which $R^1$ is isopropyl, Z is oxygen and $R^3$ is sec-butyl and $R^2$ for a compound corresponds in each case to a group in Table A.

Table 152

Compounds of the formula I.B, in which $R^1$ is isopropyl, Z is oxygen and $R^3$ is sec-butyl and $R^2$ for a compound corresponds in each case to a group in Table A.

Table 153

Compounds of the formula I.A, in which $R^1$ is isopropyl, Z is sulfur and $R^3$ is sec-butyl and $R^2$ for a compound corresponds in each case to a group in Table A.

Table 154

Compounds of the formula I.B, in which $R^1$ is isopropyl, Z is sulfur and $R^3$ is sec-butyl and $R^2$ for a compound corresponds in each case to a group in Table A.

Table 155

Compounds of the formula I.A, in which $R^1$ is isopropyl, Z is NH and $R^3$ is sec-butyl and $R^2$ for a compound corresponds in each case to a group in Table A.

Table 156

Compounds of the formula I.B, in which $R^1$ is isopropyl, Z is NH and $R^3$ is sec-butyl and $R^2$ for a compound corresponds in each case to a group in Table A.

Table 157

Compounds of the formula I.A, in which $R^1$ is hydrogen, Z is oxygen and $R^3$ is isobutyl and $R^2$ for a compound corresponds in each case to a group in Table A.

Table 158

Compounds of the formula I.B, in which $R^1$ is hydrogen, Z is oxygen and $R^3$ is isobutyl and $R^2$ for a compound corresponds in each case to a group in Table A.

Table 159

Compounds of the formula I.A, in which $R^1$ is hydrogen, Z is sulfur and $R^3$ is isobutyl and $R^2$ for a compound corresponds in each case to a group in Table A.

Table 160

Compounds of the formula I.B, in which $R^1$ is hydrogen, Z is sulfur and $R^3$ is isobutyl and $R^2$ for a compound corresponds in each case to a group in Table A.

Table 161

Compounds of the formula I.A, in which $R^1$ is hydrogen, Z is NH and $R^3$ is isobutyl and $R^2$ for a compound corresponds in each case to a group in Table A.

Table 162

Compounds of the formula I.B, in which $R^1$ is hydrogen, Z is NH and $R^3$ is isobutyl and $R^2$ for a compound corresponds in each case to a group in Table A.

Table 163

Compounds of the formula I.A, in which $R^1$ is methyl, Z is oxygen and $R^3$ is isobutyl and $R^2$ for a compound corresponds in each case to a group in Table A.

Table 164

Compounds of the formula I.B, in which $R^1$ is methyl, Z is oxygen and $R^3$ is isobutyl and $R^2$ for a compound corresponds in each case to a group in Table A.

Table 165

Compounds of the formula I.A, in which $R^1$ is methyl, Z is sulfur and $R^3$ is isobutyl and $R^2$ for a compound corresponds in each case to a group in Table A.

Table 166

Compounds of the formula I.B, in which $R^1$ is methyl, Z is sulfur and $R^3$ is isobutyl and $R^2$ for a compound corresponds in each case to a group in Table A.

Table 167

Compounds of the formula I.A, in which $R^1$ is methyl, Z is NH and $R^3$ is isobutyl and $R^2$ for a compound corresponds in each case to a group in Table A.

Table 168

Compounds of the formula I.B, in which $R^1$ is methyl, Z is NH and $R^3$ is isobutyl and $R^2$ for a compound corresponds in each case to a group in Table A.

Table 169

Compounds of the formula I.A, in which $R^1$ is ethyl, Z is oxygen and $R^3$ is isobutyl and $R^2$ for a compound corresponds in each case to a group in Table A.

Table 170

Compounds of the formula I.B, in which $R^1$ is ethyl, Z is oxygen and $R^3$ is isobutyl and $R^2$ for a compound corresponds in each case to a group in Table A.

Table 171

Compounds of the formula I.A, in which $R^1$ is ethyl, Z is sulfur and $R^3$ is isobutyl and $R^2$ for a compound corresponds in each case to a group in Table A.

Table 172

Compounds of the formula I.B, in which $R^1$ is ethyl, Z is sulfur and $R^3$ is isobutyl and $R^2$ for a compound corresponds in each case to a group in Table A.

Table 173

Compounds of the formula I.A, in which $R^1$ is ethyl, Z is NH and $R^3$ is isobutyl and $R^2$ for a compound corresponds in each case to a group in Table A.

Table 174

Compounds of the formula I.B, in which $R^1$ is ethyl, Z is NH and $R^3$ is isobutyl and $R^2$ for a compound corresponds in each case to a group in Table A.

Table 175

Compounds of the formula I.A, in which $R^1$ is isopropyl, Z is oxygen and $R^3$ is isobutyl and $R^2$ for a compound corresponds in each case to a group in Table A.

Table 176

Compounds of the formula I.B, in which $R^1$ is isopropyl, Z is oxygen and $R^3$ is isobutyl and $R^2$ for a compound corresponds in each case to a group in Table A.

Table 177

Compounds of the formula I.A, in which $R^1$ is isopropyl, Z is sulfur and $R^3$ is isobutyl and $R^2$ for a compound corresponds in each case to a group in Table A.

Table 178

Compounds of the formula I.B, in which $R^1$ is isopropyl, Z is sulfur and $R^3$ is isobutyl and $R^2$ for a compound corresponds in each case to a group in Table A.

Table 179

Compounds of the formula I.A, in which $R^1$ is isopropyl, Z is NH and $R^3$ is isobutyl and $R^2$ for a compound corresponds in each case to a group in Table A.

Table 180

Compounds of the formula I.B, in which $R^1$ is isopropyl, Z is NH and $R^3$ is isobutyl and $R^2$ for a compound corresponds in each case to a group in Table A.

Table 181

Compounds of the formula I.A, in which $R^1$ is hydrogen, Z is oxygen and $R^3$ is tert-butyl and $R^2$ for a compound corresponds in each case to a group in Table A.

Table 182

Compounds of the formula I.B, in which $R^1$ is hydrogen, Z is oxygen and $R^3$ is tert-butyl and $R^2$ for a compound corresponds in each case to a group in Table A.

Table 183

Compounds of the formula I.A, in which $R^1$ is hydrogen, Z is sulfur and $R^3$ is tert-butyl and $R^2$ for a compound corresponds in each case to a group in Table A.

Table 184

Compounds of the formula I.B, in which $R^1$ is hydrogen, Z is sulfur and $R^3$ is tert-butyl and $R^2$ for a compound corresponds in each case to a group in Table A.

Table 185

Compounds of the formula I.A, in which $R^1$ is hydrogen, Z is NH and $R^3$ is tert-butyl and $R^2$ for a compound corresponds in each case to a group in Table A.

Table 186

Compounds of the formula I.B, in which $R^1$ is hydrogen, Z is NH and $R^3$ is tert-butyl and $R^2$ for a compound corresponds in each case to a group in Table A.

Table 187

Compounds of the formula I.A, in which $R^1$ is methyl, Z is oxygen and $R^3$ is tert-butyl and $R^2$ for a compound corresponds in each case to a group in Table A.

Table 188

Compounds of the formula I.B, in which $R^1$ is methyl, Z is oxygen and $R^3$ is tert-butyl and $R^2$ for a compound corresponds in each case to a group in Table A.

Table 189

Compounds of the formula I.A, in which $R^1$ is methyl, Z is sulfur and $R^3$ is tert-butyl and $R^2$ for a compound corresponds in each case to a group in Table A.

Table 190

Compounds of the formula I.B, in which $R^1$ is methyl, Z is sulfur and $R^3$ is tert-butyl and $R^2$ for a compound corresponds in each case to a group in Table A.

Table 191

Compounds of the formula I.A, in which $R^1$ is methyl, Z is NH and $R^3$ is tert-butyl and $R^2$ for a compound corresponds in each case to a group in Table A.

Table 192

Compounds of the formula I.B, in which $R^1$ is methyl, Z is NH and $R^3$ is tert-butyl and $R^2$ for a compound corresponds in each case to a group in Table A.

Table 193

Compounds of the formula I.A, in which $R^1$ is ethyl, Z is oxygen and $R^3$ is tert-butyl and $R^2$ for a compound corresponds in each case to a group in Table A.

Table 194

Compounds of the formula I.B, in which $R^1$ is ethyl, Z is oxygen and $R^3$ is tert-butyl and $R^2$ for a compound corresponds in each case to a group in Table A.

Table 195

Compounds of the formula I.A, in which $R^1$ is ethyl, Z is sulfur and $R^3$ is tert-butyl and $R^2$ for a compound corresponds in each case to a group in Table A.

Table 196

Compounds of the formula I.B, in which $R^1$ is ethyl, Z is sulfur and $R^3$ is tert-butyl and $R^2$ for a compound corresponds in each case to a group in Table A.

Table 197

Compounds of the formula I.A, in which $R^1$ is ethyl, Z is NH and $R^3$ is tert-butyl and $R^2$ for a compound corresponds in each case to a group in Table A.

Table 198

Compounds of the formula I.B, in which $R^1$ is ethyl, Z is NH and $R^3$ is tert-butyl and $R^2$ for a compound corresponds in each case to a group in Table A.

Table 199

Compounds of the formula I.A, in which $R^1$ is isopropyl, Z is oxygen and $R^3$ is tert-butyl and $R^2$ for a compound corresponds in each case to a group in Table A.

Table 200

Compounds of the formula I.B, in which $R^1$ is isopropyl, Z is oxygen and $R^3$ is tert-butyl and $R^2$ for a compound corresponds in each case to a group in Table A.

Table 201

Compounds of the formula I.A, in which $R^1$ is isopropyl, Z is sulfur and $R^3$ is tert-butyl and $R^2$ for a compound corresponds in each case to a group in Table A.

Table 202

Compounds of the formula I.B, in which $R^1$ is isopropyl, Z is sulfur and $R^3$ is tert-butyl and $R^2$ for a compound corresponds in each case to a group in Table A.

Table 203

Compounds of the formula I.A, in which $R^1$ is isopropyl, Z is NH and $R^3$ is tert-butyl and $R^2$ for a compound corresponds in each case to a group in Table A.

Table 204

Compounds of the formula I.B, in which $R^1$ is isopropyl, Z is NH and $R^3$ is tert-butyl and $R^2$ for a compound corresponds in each case to a group in Table A.

Table 205

Compounds of the formula I.A, in which $R^1$ is hydrogen, Z is oxygen and $R^3$ is pentyl and $R^2$ for a compound corresponds in each case to a group in Table A.

Table 206

Compounds of the formula I.B, in which $R^1$ is hydrogen, Z is oxygen and $R^3$ is pentyl and $R^2$ for a compound corresponds in each case to a group in Table A.

Table 207

Compounds of the formula I.A, in which $R^1$ is hydrogen, Z is sulfur and $R^3$ is pentyl and $R^2$ for a compound corresponds in each case to a group in Table A.

Table 208

Compounds of the formula I.B, in which $R^1$ is hydrogen, Z is sulfur and $R^3$ is pentyl and $R^2$ for a compound corresponds in each case to a group in Table A.

Table 209

Compounds of the formula I.A, in which $R^1$ is hydrogen, Z is NH and $R^3$ is pentyl and $R^2$ for a compound corresponds in each case to a group in Table A.

Table 210

Compounds of the formula I.B, in which $R^1$ is hydrogen, Z is NH and $R^3$ is pentyl and $R^2$ for a compound corresponds in each case to a group in Table A.

Table 211

Compounds of the formula I.A, in which $R^1$ is methyl, Z is oxygen and $R^3$ is pentyl and $R^2$ for a compound corresponds in each case to a group in Table A.

Table 212

Compounds of the formula I.B, in which $R^1$ is methyl, Z is oxygen and $R^3$ is pentyl and $R^2$ for a compound corresponds in each case to a group in Table A.

Table 213

Compounds of the formula I.A, in which $R^1$ is methyl, Z is sulfur and $R^3$ is pentyl and $R^2$ for a compound corresponds in each case to a group in Table A.

Table 214

Compounds of the formula I.B, in which $R^1$ is methyl, Z is sulfur and $R^3$ is pentyl and $R^2$ for a compound corresponds in each case to a group in Table A.

Table 215

Compounds of the formula I.A, in which $R^1$ is methyl, Z is NH and $R^3$ is pentyl and $R^2$ for a compound corresponds in each case to a group in Table A.

Table 216

Compounds of the formula I.B, in which $R^1$ is methyl, Z is NH and $R^3$ is pentyl and $R^2$ for a compound corresponds in each case to a group in Table A.

Table 217

Compounds of the formula I.A, in which $R^1$ is ethyl, Z is oxygen and $R^3$ is pentyl and $R^2$ for a compound corresponds in each case to a group in Table A.

Table 218

Compounds of the formula I.B, in which $R^1$ is ethyl, Z is oxygen and $R^3$ is pentyl and $R^2$ for a compound corresponds in each case to a group in Table A.

Table 219

Compounds of the formula I.A, in which $R^1$ is ethyl, Z is sulfur and $R^3$ is pentyl and $R^2$ for a compound corresponds in each case to a group in Table A.

Table 220

Compounds of the formula I.B, in which $R^1$ is ethyl, Z is sulfur and $R^3$ is pentyl and $R^2$ for a compound corresponds in each case to a group in Table A.

Table 221

Compounds of the formula I.A, in which $R^1$ is ethyl, Z is NH and $R^3$ is pentyl and $R^2$ for a compound corresponds in each case to a group in Table A.

Table 222

Compounds of the formula I.B, in which $R^1$ is ethyl, Z is NH and $R^3$ is pentyl and $R^2$ for a compound corresponds in each case to a group in Table A.

Table 223

Compounds of the formula I.A, in which $R^1$ is isopropyl, Z is oxygen and $R^3$ is pentyl and $R^2$ for a compound corresponds in each case to a group in Table A.

Table 224

Compounds of the formula I.B, in which $R^1$ is isopropyl, Z is oxygen and $R^3$ is pentyl and $R^2$ for a compound corresponds in each case to a group in Table A.

Table 225

Compounds of the formula I.A, in which $R^1$ is isopropyl, Z is sulfur and $R^3$ is pentyl and $R^2$ for a compound corresponds in each case to a group in Table A.

Table 226

Compounds of the formula I.B, in which $R^1$ is isopropyl, Z is sulfur and $R^3$ is pentyl and $R^2$ for a compound corresponds in each case to a group in Table A.

Table 227

Compounds of the formula I.A, in which $R^1$ is isopropyl, Z is NH and $R^3$ is pentyl and $R^2$ for a compound corresponds in each case to a group in Table A.

Table 228

Compounds of the formula I.B, in which $R^1$ is isopropyl, Z is NH and $R^3$ is pentyl and $R^2$ for a compound corresponds in each case to a group in Table A.

Table 229

Compounds of the formula I.A, in which $R^1$ is hydrogen, Z is oxygen and $R^3$ is isopentyl and $R^2$ for a compound corresponds in each case to a group in Table A.

Table 230

Compounds of the formula I.B, in which $R^1$ is hydrogen, Z is oxygen and $R^3$ is isopentyl and $R^2$ for a compound corresponds in each case to a group in Table A.

Table 231

Compounds of the formula I.A, in which $R^1$ is hydrogen, Z is sulfur and $R^3$ is isopentyl and $R^2$ for a compound corresponds in each case to a group in Table A.

Table 232

Compounds of the formula I.B, in which $R^1$ is hydrogen, Z is sulfur and $R^3$ is isopentyl and $R^2$ for a compound corresponds in each case to a group in Table A.

Table 233

Compounds of the formula I.A, in which $R^1$ is hydrogen, Z is NH and $R^3$ is isopentyl and $R^2$ for a compound corresponds in each case to a group in Table A.

Table 234

Compounds of the formula I.B, in which $R^1$ is hydrogen, Z is NH and $R^3$ is isopentyl and $R^2$ for a compound corresponds in each case to a group in Table A.

Table 235

Compounds of the formula I.A, in which $R^1$ is methyl, Z is oxygen and $R^3$ is isopentyl and $R^2$ for a compound corresponds in each case to a group in Table A.

Table 236

Compounds of the formula I.B, in which $R^1$ is methyl, Z is oxygen and $R^3$ is isopentyl and $R^2$ for a compound corresponds in each case to a group in Table A.

Table 237

Compounds of the formula I.A, in which $R^1$ is methyl, Z is sulfur and $R^3$ is isopentyl and $R^2$ for a compound corresponds in each case to a group in Table A.

Table 238

Compounds of the formula I.B, in which $R^1$ is methyl, Z is sulfur and $R^3$ is isopentyl and $R^2$ for a compound corresponds in each case to a group in Table A.

Table 239

Compounds of the formula I.A, in which $R^1$ is methyl, Z is NH and $R^3$ is isopentyl and $R^2$ for a compound corresponds in each case to a group in Table A.

Table 240

Compounds of the formula I.B, in which $R^1$ is methyl, Z is NH and $R^3$ is isopentyl and $R^2$ for a compound corresponds in each case to a group in Table A.

Table 241

Compounds of the formula I.A, in which $R^1$ is ethyl, Z is oxygen and $R^3$ is isopentyl and $R^2$ for a compound corresponds in each case to a group in Table A.

Table 242

Compounds of the formula I.B, in which $R^1$ is ethyl, Z is oxygen and $R^3$ is isopentyl and $R^2$ for a compound corresponds in each case to a group in Table A.

Table 243

Compounds of the formula I.A, in which $R^1$ is ethyl, Z is sulfur and $R^3$ is isopentyl and $R^2$ for a compound corresponds in each case to a group in Table A.

Table 244

Compounds of the formula I.B, in which $R^1$ is ethyl, Z is sulfur and $R^3$ is isopentyl and $R^2$ for a compound corresponds in each case to a group in Table A.

Table 245

Compounds of the formula I.A, in which $R^1$ is ethyl, Z is NH and $R^3$ is isopentyl and $R^2$ for a compound corresponds in each case to a group in Table A.

Table 246

Compounds of the formula I.B, in which $R^1$ is ethyl, Z is NH and $R^3$ is isopentyl and $R^2$ for a compound corresponds in each case to a group in Table A.

Table 247

Compounds of the formula I.A, in which $R^1$ is isopropyl, Z is oxygen and $R^3$ is isopentyl and $R^2$ for a compound corresponds in each case to a group in Table A.

Table 248

Compounds of the formula I.B, in which $R^1$ is isopropyl, Z is oxygen and $R^3$ is isopentyl and $R^2$ for a compound corresponds in each case to a group in Table A.

Table 249

Compounds of the formula I.A, in which $R^1$ is isopropyl, Z is sulfur and $R^3$ is isopentyl and $R^2$ for a compound corresponds in each case to a group in Table A.

Table 250

Compounds of the formula I.13, in which $R^1$ is isopropyl, Z is sulfur and $R^3$ is isopentyl and $R^2$ for a compound corresponds in each case to a group in Table A.

Table 251

Compounds of the formula I.A, in which $R^1$ is isopropyl, Z is NH and $R^3$ is isopentyl and $R^2$ for a compound corresponds in each case to a group in Table A.

Table 252

Compounds of the formula I.B, in which $R^1$ is isopropyl, Z is NH and $R^3$ is isopentyl and $R^2$ for a compound corresponds in each case to a group in Table A.

Table 253

Compounds of the formula I.A, in which $R^1$ is hydrogen, Z is oxygen and $R^3$ is neopentyl and $R^2$ for a compound corresponds in each case to a group in Table A.

Table 254

Compounds of the formula I.B, in which $R^1$ is hydrogen, Z is oxygen and $R^3$ is neopentyl and $R^2$ for a compound corresponds in each case to a group in Table A.

Table 255

Compounds of the formula I.A, in which $R^1$ is hydrogen, Z is sulfur and $R^3$ is neopentyl and $R^2$ for a compound corresponds in each case to a group in Table A.

Table 256

Compounds of the formula I.B, in which $R^1$ is hydrogen, Z is sulfur and $R^3$ is neopentyl and $R^2$ for a compound corresponds in each case to a group in Table A.

Table 257

Compounds of the formula I.A, in which $R^1$ is hydrogen, Z is NH and $R^3$ is neopentyl and $R^2$ for a compound corresponds in each case to a group in Table A.

Table 258

Compounds of the formula I.B, in which $R^1$ is hydrogen, Z is NH and $R^3$ is neopentyl and $R^2$ for a compound corresponds in each case to a group in Table A.

Table 259

Compounds of the formula I.A, in which $R^1$ is methyl, Z is oxygen and $R^3$ is neopentyl and $R^2$ for a compound corresponds in each case to a group in Table A.

Table 260

Compounds of the formula I.B, in which $R^1$ is methyl, Z is oxygen and $R^3$ is neopentyl and $R^2$ for a compound corresponds in each case to a group in Table A.

Table 261

Compounds of the formula I.A, in which $R^1$ is methyl, Z is sulfur and $R^3$ is neopentyl and $R^2$ for a compound corresponds in each case to a group in Table A.

Table 262

Compounds of the formula I.B, in which $R^1$ is methyl, Z is sulfur and $R^3$ is neopentyl and $R^2$ for a compound corresponds in each case to a group in Table A.

Table 263

Compounds of the formula I.A, in which $R^1$ is methyl, Z is NH and $R^3$ is neopentyl and $R^2$ for a compound corresponds in each case to a group in Table A.

Table 264

Compounds of the formula I.B, in which $R^1$ is methyl, Z is NH and $R^3$ is neopentyl and $R^2$ for a compound corresponds in each case to a group in Table A.

Table 265

Compounds of the formula I.A, in which $R^1$ is ethyl, Z is oxygen and $R^3$ is neopentyl and $R^2$ for a compound corresponds in each case to a group in Table A.

Table 266

Compounds of the formula I.B, in which $R^1$ is ethyl, Z is oxygen and $R^3$ is neopentyl and $R^2$ for a compound corresponds in each case to a group in Table A.

Table 267

Compounds of the formula I.A, in which $R^1$ is ethyl, Z is sulfur and $R^3$ is neopentyl and $R^2$ for a compound corresponds in each case to a group in Table A.

Table 268

Compounds of the formula I.B, in which $R^1$ is ethyl, Z is sulfur and $R^3$ is neopentyl and $R^2$ for a compound corresponds in each case to a group in Table A.

Table 269

Compounds of the formula I.A, in which $R^1$ is ethyl, Z is NH and $R^3$ is neopentyl and $R^2$ for a compound corresponds in each case to a group in Table A.

Table 270

Compounds of the formula I.B, in which $R^1$ is ethyl, Z is NH and $R^3$ is neopentyl and $R^2$ for a compound corresponds in each case to a group in Table A.

Table 271

Compounds of the formula I.A, in which $R^1$ is isopropyl, Z is oxygen and $R^3$ is neopentyl and $R^2$ for a compound corresponds in each case to a group in Table A.

Table 272

Compounds of the formula I.B, in which $R^1$ is isopropyl, Z is oxygen and $R^3$ is neopentyl and $R^2$ for a compound corresponds in each case to a group in Table A.

Table 273

Compounds of the formula I.A, in which $R^1$ is isopropyl, Z is sulfur and $R^3$ is neopentyl and $R^2$ for a compound corresponds in each case to a group in Table A.

Table 274

Compounds of the formula I.B, in which $R^1$ is isopropyl, Z is sulfur and $R^3$ is neopentyl and $R^2$ for a compound corresponds in each case to a group in Table A.

Table 275

Compounds of the formula I.A, in which $R^1$ is isopropyl, Z is NH and $R^3$ is neopentyl and $R^2$ for a compound corresponds in each case to a group in Table A.

Table 276

Compounds of the formula I.B, in which $R^1$ is isopropyl, Z is NH and $R^3$ is neopentyl and $R^2$ for a compound corresponds in each case to a group in Table A.

Table 277

Compounds of the formula I.A, in which $R^1$ is hydrogen, Z is oxygen and $R^3$ is 2-methylbutyl and $R^2$ for a compound corresponds in each case to a group in Table A.

Table 278

Compounds of the formula I.B, in which $R^1$ is hydrogen, Z is oxygen and $R^3$ is 2-methylbutyl and $R^2$ for a compound corresponds in each case to a group in Table A.

Table 279

Compounds of the formula I.A, in which $R^1$ is hydrogen, Z is sulfur and $R^3$ is 2-methylbutyl and $R^2$ for a compound corresponds in each case to a group in Table A.

Table 280

Compounds of the formula I.B, in which $R^1$ is hydrogen, Z is sulfur and $R^3$ is 2-methylbutyl and $R^2$ for a compound corresponds in each case to a group in Table A.

Table 281

Compounds of the formula I.A, in which $R^1$ is hydrogen, Z is NH and $R^3$ is 2-methylbutyl and $R^2$ for a compound corresponds in each case to a group in Table A.

Table 282

Compounds of the formula I.B, in which $R^1$ is hydrogen, Z is NH and $R^3$ is 2-methylbutyl and $R^2$ for a compound corresponds in each case to a group in Table A.

Table 283

Compounds of the formula I.A, in which $R^1$ is methyl, Z is oxygen and $R^3$ is 2-methylbutyl and $R^2$ for a compound corresponds in each case to a group in Table A.

Table 284

Compounds of the formula I.B, in which $R^1$ is methyl, Z is oxygen and $R^3$ is 2-methylbutyl and $R^2$ for a compound corresponds in each case to a group in Table A.

Table 285

Compounds of the formula I.A, in which $R^1$ is methyl, Z is sulfur and $R^3$ is 2-methylbutyl and $R^2$ for a compound corresponds in each case to a group in Table A.

Table 286

Compounds of the formula I.B, in which $R^1$ is methyl, Z is sulfur and $R^3$ is 2-methylbutyl and $R^2$ for a compound corresponds in each case to a group in Table A.

Table 287

Compounds of the formula I.A, in which $R^1$ is methyl, Z is NH and $R^3$ is 2-methylbutyl and $R^2$ for a compound corresponds in each case to a group in Table A.

Table 288

Compounds of the formula I.B, in which $R^1$ is methyl, Z is NH and $R^3$ is 2-methylbutyl and $R^2$ for a compound corresponds in each case to a group in Table A.

Table 289

Compounds of the formula I.A, in which $R^1$ is ethyl, Z is oxygen and $R^3$ is 2-methylbutyl and $R^2$ for a compound corresponds in each case to a group in Table A.

Table 290

Compounds of the formula I.B, in which $R^1$ is ethyl, Z is oxygen and $R^3$ is 2-methylbutyl and $R^2$ for a compound corresponds in each case to a group in Table A.

Table 291

Compounds of the formula I.A, in which $R^1$ is ethyl, Z is sulfur and $R^3$ is 2-methylbutyl and $R^2$ for a compound corresponds in each case to a group in Table A.

Table 292

Compounds of the formula I.B, in which $R^1$ is ethyl, Z is sulfur and $R^3$ is 2-methylbutyl and $R^2$ for a compound corresponds in each case to a group in Table A.

Table 293

Compounds of the formula I.A, in which $R^1$ is ethyl, Z is NH and $R^3$ is 2-methylbutyl and $R^2$ for a compound corresponds in each case to a group in Table A.

Table 294

Compounds of the formula I.B, in which $R^1$ is ethyl, Z is NH and $R^3$ is 2-methylbutyl and $R^2$ for a compound corresponds in each case to a group in Table A.

Table 295

Compounds of the formula I.A, in which $R^1$ is isopropyl, Z is oxygen and $R^3$ is 2-methylbutyl and $R^2$ for a compound corresponds in each case to a group in Table A.

Table 296

Compounds of the formula I.B, in which $R^1$ is isopropyl, Z is oxygen and $R^3$ is 2-methylbutyl and $R^2$ for a compound corresponds in each case to a group in Table A.

Table 297

Compounds of the formula I.A, in which $R^1$ is isopropyl, Z is sulfur and $R^3$ is 2-methylbutyl and $R^2$ for a compound corresponds in each case to a group in Table A.

Table 298

Compounds of the formula I.B, in which $R^1$ is isopropyl, Z is sulfur and $R^3$ is 2-methylbutyl and $R^2$ for a compound corresponds in each case to a group in Table A.

Table 299

Compounds of the formula I.A, in which $R^1$ is isopropyl, Z is NH and $R^3$ is 2-methylbutyl and $R^2$ for a compound corresponds in each case to a group in Table A.

Table 300

Compounds of the formula I.B, in which $R^1$ is isopropyl, Z is NH and $R^3$ is 2-methylbutyl and $R^2$ for a compound corresponds in each case to a group in Table A.

Table 301

Compounds of the formula I.A, in which $R^1$ is hydrogen, Z is oxygen and $R^3$ is 1-methylbutyl and $R^2$ for a compound corresponds in each case to a group in Table A.

Table 302

Compounds of the formula I.B, in which $R^1$ is hydrogen, Z is oxygen and $R^3$ is 1-methylbutyl and $R^2$ for a compound corresponds in each case to a group in Table A.

Table 303

Compounds of the formula I.A, in which $R^1$ is hydrogen, Z is sulfur and $R^3$ is 1-methylbutyl and $R^2$ for a compound corresponds in each case to a group in Table A.

Table 304

Compounds of the formula I.B, in which $R^1$ is hydrogen, Z is sulfur and $R^3$ is 1-methylbutyl and $R^2$ for a compound corresponds in each case to a group in Table A.

Table 305

Compounds of the formula I.A, in which $R^1$ is hydrogen, Z is NH and $R^3$ is 1-methylbutyl and $R^2$ for a compound corresponds in each case to a group in Table A.

Table 306

Compounds of the formula I.B, in which $R^1$ is hydrogen, Z is NH and $R^3$ is 1-methylbutyl and $R^2$ for a compound corresponds in each case to a group in Table A.

Table 307

Compounds of the formula I.A, in which $R^1$ is methyl, Z is oxygen and $R^3$ 1-methylbutyl and $R^2$ for a compound corresponds in each case to a group in Table A.

Table 308

Compounds of the formula I.B, in which $R^1$ is methyl, Z is oxygen and $R^3$ 1-methylbutyl and $R^2$ for a compound corresponds in each case to a group in Table A.

Table 309

Compounds of the formula I.A, in which $R^1$ is methyl, Z is sulfur and $R^3$ is 1-methylbutyl and $R^2$ for a compound corresponds in each case to a group in Table A.

Table 310

Compounds of the formula I.B, in which $R^1$ is methyl, Z is sulfur and $R^3$ is 1-methylbutyl and $R^2$ for a compound corresponds in each case to a group in Table A.

Table 311

Compounds of the formula I.A, in which $R^1$ is methyl, Z is NH and $R^3$ is 1-methylbutyl and $R^2$ for a compound corresponds in each case to a group in Table A.

Table 312

Compounds of the formula I.B, in which $R^1$ is methyl, Z is NH and $R^3$ is 1-methylbutyl and $R^2$ for a compound corresponds in each case to a group in Table A.

Table 313

Compounds of the formula I.A, in which $R^1$ is ethyl, Z is oxygen and $R^3$ is 1-methylbutyl and $R^2$ for a compound corresponds in each case to a group in Table A.

Table 314

Compounds of the formula I.B, in which $R^1$ is ethyl, Z is oxygen and $R^3$ is 1-methylbutyl and $R^2$ for a compound corresponds in each case to a group in Table A.

Table 315

Compounds of the formula I.A, in which $R^1$ is ethyl, Z is sulfur and $R^3$ is 1-methylbutyl and $R^2$ for a compound corresponds in each case to a group in Table A.

Table 316

Compounds of the formula I.B, in which $R^1$ is ethyl, Z is sulfur and $R^3$ is 1-methylbutyl and $R^2$ for a compound corresponds in each case to a group in Table A.

Table 317

Compounds of the formula I.A, in which $R^1$ is ethyl, Z is NH and $R^3$ is 1-methylbutyl and $R^2$ for a compound corresponds in each case to a group in Table A.

Table 318

Compounds of the formula I.B, in which $R^1$ is ethyl, Z is NH and $R^3$ is 1-methylbutyl and $R^2$ for a compound corresponds in each case to a group in Table A.

Table 319

Compounds of the formula I.A, in which $R^1$ is isopropyl, Z is oxygen and $R^3$ is 1-methylbutyl and $R^2$ for a compound corresponds in each case to a group in Table A.

Table 320

Compounds of the formula I.B, in which $R^1$ is isopropyl, Z is oxygen and $R^3$ is 1-methylbutyl and $R^2$ for a compound corresponds in each case to a group in Table A.

Table 321

Compounds of the formula I.A, in which $R^1$ is isopropyl, Z is sulfur and $R^3$ is 1-methylbutyl and $R^2$ for a compound corresponds in each case to a group in Table A.

Table 322

Compounds of the formula I.B, in which $R^1$ is isopropyl, Z is sulfur and $R^3$ is 1-methylbutyl and $R^2$ for a compound corresponds in each case to a group in Table A.

Table 323

Compounds of the formula I.A, in which $R^1$ is isopropyl, Z is NH and $R^3$ is 1-methylbutyl and $R^2$ for a compound corresponds in each case to a group in Table A.

Table 324

Compounds of the formula I.B, in which $R^1$ is isopropyl, Z is NH and $R^3$ is 1-methylbutyl and $R^2$ for a compound corresponds in each case to a group in Table A.

Table 325

Compounds of the formula I.A, in which $R^1$ is hydrogen, Z is oxygen and $R^3$ is pentan-3-yl and $R^2$ for a compound corresponds in each case to a group in Table A.

Table 326

Compounds of the formula I.B, in which $R^1$ is hydrogen, Z is oxygen and $R^3$ is pentan-3-yl and $R^2$ for a compound corresponds in each case to a group in Table A.

Table 327

Compounds of the formula I.A, in which $R^1$ is hydrogen, Z is sulfur and $R^3$ is pentan-3-yl and $R^2$ for a compound corresponds in each case to a group in Table A.

Table 328

Compounds of the formula I.B, in which $R^1$ is hydrogen, Z is sulfur and $R^3$ is pentan-3-yl and $R^2$ for a compound corresponds in each case to a group in Table A.

Table 329

Compounds of the formula I.A, in which $R^1$ is hydrogen, Z is NH and $R^3$ is pentan-3-yl and $R^2$ for a compound corresponds in each case to a group in Table A.

Table 330

Compounds of the formula I.B, in which $R^1$ is hydrogen, Z is NH and $R^3$ is pentan-3-yl and $R^2$ for a compound corresponds in each case to a group in Table A.

Table 331

Compounds of the formula I.A, in which $R^1$ is methyl, Z is oxygen and $R^3$ is pentan-3-yl and $R^2$ for a compound corresponds in each case to a group in Table A.

Table 332

Compounds of the formula I.B, in which $R^1$ is methyl, Z is oxygen and $R^3$ is pentan-3-yl and $R^2$ for a compound corresponds in each case to a group in Table A.

Table 333

Compounds of the formula I.A, in which $R^1$ is methyl, Z is sulfur and $R^3$ is pentan-3-yl and $R^2$ for a compound corresponds in each case to a group in Table A.

Table 334

Compounds of the formula I.B, in which $R^1$ is methyl, Z is sulfur and $R^3$ is pentan-3-yl and $R^2$ for a compound corresponds in each case to a group in Table A.

Table 335

Compounds of the formula I.A, in which $R^1$ is methyl, Z is NH and $R^3$ is pentan-3-yl and $R^2$ for a compound corresponds in each case to a group in Table A.

Table 336

Compounds of the formula I.B, in which $R^1$ is methyl, Z is NH and $R^3$ is pentan-3-yl and $R^2$ for a compound corresponds in each case to a group in Table A.

Table 337

Compounds of the formula I.A, in which $R^1$ is ethyl, Z is oxygen and $R^3$ is pentan-3-yl and $R^2$ for a compound corresponds in each case to a group in Table A.

Table 338

Compounds of the formula I.B, in which $R^1$ is ethyl, Z is oxygen and $R^3$ is pentan-3-yl and $R^2$ for a compound corresponds in each case to a group in Table A.

Table 339

Compounds of the formula I.A, in which $R^1$ is ethyl, Z is sulfur and $R^3$ is pentan-3-yl and $R^2$ for a compound corresponds in each case to a group in Table A.

Table 340

Compounds of the formula I.B, in which $R^1$ is ethyl, Z is sulfur and $R^3$ is pentan-3-yl and $R^2$ for a compound corresponds in each case to a group in Table A.

Table 341

Compounds of the formula I.A, in which $R^1$ is ethyl, Z is NH and $R^3$ is pentan-3-yl and $R^2$ for a compound corresponds in each case to a group in Table A.

Table 342

Compounds of the formula I.B, in which $R^1$ is ethyl, Z is NH and $R^3$ is pentan-3-yl and $R^2$ for a compound corresponds in each case to a group in Table A.

Table 343

Compounds of the formula I.A, in which $R^1$ is isopropyl, Z is oxygen and $R^3$ is pentan-3-yl and $R^2$ for a compound corresponds in each case to a group in Table A.

Table 344

Compounds of the formula I.B, in which $R^1$ is isopropyl, Z is oxygen and $R^3$ is pentan-3-yl and $R^2$ for a compound corresponds in 40 each case to a group in Table A.

Table 345

Compounds of the formula I.A, in which $R^1$ is isopropyl, Z is sulfur and $R^3$ is pentan-3-yl and $R^2$ for a compound corresponds in each case to a group in Table A.

Table 346

Compounds of the formula I.B, in which $R^1$ is isopropyl, Z is sulfur and $R^3$ is pentan-3-yl and $R^2$ for a compound corresponds in each case to a group in Table A.

Table 347

Compounds of the formula I.A, in which $R^1$ is isopropyl, Z is NH and $R^3$ is pentan-3-yl and $R^2$ for a compound corresponds in each case to a group in Table A.

Table 348

Compounds of the formula I.B, in which $R^1$ is isopropyl, Z is NH and $R^3$ is pentan-3-yl and $R^2$ for a compound corresponds in each case to a group in Table A.

Table 349

Compounds of the formula I.A, in which $R^1$ is hydrogen, Z is oxygen and $R^3$ is 3-methylbut-2-yl and $R^2$ for a compound corresponds in each case to a group in Table A.

Table 350

Compounds of the formula I.B, in which $R^1$ is hydrogen, Z is oxygen and $R^3$ is 3-methylbut-2-yl and $R^2$ for a compound corresponds in each case to a group in Table A.

Table 351

Compounds of the formula I.A, in which $R^1$ is hydrogen, Z is sulfur and $R^3$ is 3-methylbut-2-yl and $R^2$ for a compound corresponds in each case to a group in Table A.

Table 352

Compounds of the formula I.B, in which $R^1$ is hydrogen, Z is sulfur and $R^3$ is 3-methylbut-2-yl and $R^2$ for a compound corresponds in each case to a group in Table A.

Table 353

Compounds of the formula I.A, in which $R^1$ is hydrogen, Z is NH and $R^3$ is 3-methylbut-2-yl and $R^2$ for a compound corresponds in each case to a group in Table A.

Table 354

Compounds of the formula I.B, in which $R^1$ is hydrogen, Z is NH and $R^3$ is 3-methylbut-2-yl and $R^2$ for a compound corresponds in each case to a group in Table A.

Table 355

Compounds of the formula I.A, in which $R^1$ is methyl, Z is oxygen and $R^3$ is 3-methylbut-2-yl and $R^2$ for a compound corresponds in each case to a group in Table A.

Table 356

Compounds of the formula I.B, in which $R^1$ is methyl, Z is oxygen and $R^3$ is 3-methylbut-2-yl and $R^2$ for a compound corresponds in each case to a group in Table A.

Table 357

Compounds of the formula I.A, in which $R^1$ is methyl, Z is sulfur and $R^3$ is 3-methylbut-2-yl and $R^2$ for a compound corresponds in each case to a group in Table A.

Table 358

Compounds of the formula I.B, in which $R^1$ is methyl, Z is sulfur and $R^3$ is 3-methylbut-2-yl and $R^2$ for a compound corresponds in each case to a group in Table A.

Table 359

Compounds of the formula I.A, in which $R^1$ is methyl, Z is NH and $R^3$ is 3-methylbut-2-yl and $R^2$ for a compound corresponds in each case to a group in Table A.

Table 360

Compounds of the formula I.B, in which $R^1$ is methyl, Z is NH and $R^3$ is 3-methylbut-2-yl and $R^2$ for a compound corresponds in each case to a group in Table A.

Table 361

Compounds of the formula I.A, in which $R^1$ is ethyl, Z is oxygen and $R^3$ is 3-methylbut-2-yl and $R^2$ for a compound corresponds in each case to a group in Table A.

Table 362

Compounds of the formula I.B, in which $R^1$ is ethyl, Z is oxygen and $R^3$ is 3-methylbut-2-yl and $R^2$ for a compound corresponds in each case to a group in Table A.

Table 363

Compounds of the formula I.A, in which $R^1$ is ethyl, Z is sulfur and $R^3$ is 3-methylbut-2-yl and $R^2$ for a compound corresponds in each case to a group in Table A.

Table 364

Compounds of the formula I.B, in which $R^1$ is ethyl, Z is sulfur and $R^3$ is 3-methylbut-2-yl and $R^2$ for a compound corresponds in each case to a group in Table A.

Table 365

Compounds of the formula I.A, in which $R^1$ is ethyl, Z is NH and $R^3$ is 3-methylbut-2-yl and $R^2$ for a compound corresponds in each case to a group in Table A.

Table 366

Compounds of the formula I.B, in which $R^1$ is ethyl, Z is NH and $R^3$ is 3-methylbut-2-yl and $R^2$ for a compound corresponds in each case to a group in Table A.

Table 367

Compounds of the formula I.A, in which $R^1$ is isopropyl, Z is oxygen and $R^3$ is 3-methylbut-2-yl and $R^2$ for a compound corresponds in each case to a group in Table A.

Table 368

Compounds of the formula I.B, in which $R^1$ is isopropyl, Z is oxygen and $R^3$ is 3-methylbut-2-yl and $R^2$ for a compound corresponds in each case to a group in Table A.

Table 369

Compounds of the formula I.A, in which $R^1$ is isopropyl, Z is sulfur and $R^3$ is 3-methylbut-2-yl and $R^2$ for a compound corresponds in each case to a group in Table A.

Table 370

Compounds of the formula I.B, in which $R^1$ is isopropyl, Z is sulfur and $R^3$ is 3-methylbut-2-yl and $R^2$ for a compound corresponds in each case to a group in Table A.

Table 371

Compounds of the formula I.A, in which $R^1$ is isopropyl, Z is NH and $R^3$ is 3-methylbut-2-yl and $R^2$ for a compound corresponds in each case to a group in Table A.

Table 372

Compounds of the formula I.B, in which $R^1$ is isopropyl, Z is NH and $R^3$ is 3-methylbut-2-yl and $R^2$ for a compound corresponds in each case to a group in Table A.

Table 373

Compounds of the formula I.A, in which $R^1$ is hydrogen, Z is oxygen and $R^3$ is 2-methylbut-2-yl and $R^2$ for a compound corresponds in each case to a group in Table A.

Table 374

Compounds of the formula I.B, in which $R^1$ is hydrogen, Z is oxygen and $R^3$ is 2-methylbut-2-yl and $R^2$ for a compound corresponds in each case to a group in Table A.

Table 375

Compounds of the formula I.A, in which $R^1$ is hydrogen, Z is sulfur and $R^3$ is 2-methylbut-2-yl and $R^2$ for a compound corresponds in each case to a group in Table A.

Table 376

Compounds of the formula I.B, in which $R^1$ is hydrogen, Z is sulfur and $R^3$ is 2-methylbut-2-yl and $R^2$ for a compound corresponds in each case to a group in Table A.

Table 377

Compounds of the formula I.A, in which $R^1$ is hydrogen, Z is NH and $R^3$ is 2-methylbut-2-yl and $R^2$ for a compound corresponds in each case to a group in Table A.

Table 378

Compounds of the formula I.B, in which $R^1$ is hydrogen, Z is NH and $R^3$ is 2-methylbut-2-yl and $R^2$ for a compound corresponds in each case to a group in Table A.

Table 379

Compounds of the formula I.A, in which $R^1$ is methyl, Z is oxygen and $R^3$ is 2-methylbut-2-yl and $R^2$ for a compound corresponds in each case to a group in Table A.

Table 380

Compounds of the formula I.B, in which $R^1$ is methyl, Z is oxygen and $R^3$ is 2-methylbut-2-yl and $R^2$ for a compound corresponds in each case to a group in Table A.

Table 381

Compounds of the formula I.A, in which $R^1$ is methyl, Z is sulfur and $R^3$ is 2-methylbut-2-yl and $R^2$ for a compound corresponds in each case to a group in Table A.

Table 382

Compounds of the formula I.B, in which $R^1$ is methyl, Z is sulfur and $R^3$ is 2-methylbut-2-yl and $R^2$ for a compound corresponds in each case to a group in Table A.

Table 383

Compounds of the formula I.A, in which $R^1$ is methyl, Z is NH and $R^3$ is 2-methylbut-2-yl and $R^2$ for a compound corresponds in each case to a group in Table A.

Table 384

Compounds of the formula I.B, in which $R^1$ is methyl, Z is NH and $R^3$ is 2-methylbut-2-yl and $R^2$ for a compound corresponds in each case to a group in Table A.

Table 385

Compounds of the formula I.A, in which $R^1$ is ethyl, Z is oxygen and $R^3$ is 2-methylbut-2-yl and $R^2$ for a compound corresponds in each case to a group in Table A.

Table 386

Compounds of the formula I.B, in which $R^1$ is ethyl, Z is oxygen and $R^3$ is 2-methylbut-2-yl and $R^2$ for a compound corresponds in each case to a group in Table A.

Table 387

Compounds of the formula I.A, in which $R^1$ is ethyl, Z is sulfur and $R^3$ is 2-methylbut-2-yl and $R^2$ for a compound corresponds in each case to a group in Table A.

Table 388

Compounds of the formula I.B, in which $R^1$ is ethyl, Z is sulfur and $R^3$ is 2-methylbut-2-yl and $R^2$ for a compound corresponds in each case to a group in Table A.

Table 389

Compounds of the formula I.A, in which $R^1$ is ethyl, Z is NH and $R^3$ is 2-methylbut-2-yl and $R^2$ for a compound corresponds in each case to a group in Table A.

Table 390

Compounds of the formula I.B, in which $R^1$ is ethyl, Z is NH and $R^3$ is 2-methylbut-2-yl and $R^2$ for a compound corresponds in each case to a group in Table A.

Table 391

Compounds of the formula I.A, in which $R^1$ is isopropyl, Z is oxygen and $R^3$ is 2-methylbut-2-yl and $R^2$ for a compound corresponds in each case to a group in Table A.

Table 392

Compounds of the formula I.B, in which $R^1$ is isopropyl, Z is oxygen and $R^3$ is 2-methylbut-2-yl and $R^2$ for a compound corresponds in each case to a group in Table A.

Table 393

Compounds of the formula I.A, in which $R^1$ is isopropyl, Z is sulfur and $R^3$ is 2-methylbut-2-yl and $R^2$ for a compound corresponds n each case to a group in Table A.

Table 394

Compounds of the formula I.B, in which $R^1$ is isopropyl, Z is sulfur and $R^3$ is 2-methylbut-2-yl and $R^2$ for a compound corresponds in each case to a group in Table A.

Table 395

Compounds of the formula I.A, in which $R^1$ is isopropyl, Z is NH and $R^3$ is 2-methylbut-2-yl and $R^2$ for a compound corresponds in each case to a group in Table A.

Table 396

Compounds of the formula I.B, in which $R^1$ is isopropyl, Z is NH and $R^3$ is 2-methylbut-2-yl and $R^2$ for a compound corresponds in each case to a group in Table A.

Table 397

Compounds of the formula I.A, in which $R^1$ is hydrogen, Z is oxygen and $R^3$ is hexyl and $R^2$ for a compound corresponds in each case to a group in Table A.

Table 398

Compounds of the formula I.B, in which $R^1$ is hydrogen, Z is oxygen and $R^3$ is hexyl and $R^2$ for a compound corresponds in each case to a group in Table A.

Table 399

Compounds of the formula I.A, in which $R^1$ is hydrogen, Z is sulfur and $R^3$ is hexyl and $R^2$ for a compound corresponds in each case to a group in Table A.

Table 400

Compounds of the formula I.B, in which $R^1$ is hydrogen, Z is sulfur and $R^3$ is hexyl and $R^2$ for a compound corresponds in each case to a group in Table A.

Table 401

Compounds of the formula I.A, in which $R^1$ is hydrogen, Z is NH and $R^3$ is hexyl and $R^2$ for a compound corresponds in each case to a group in Table A.

Table 402

Compounds of the formula I.B, in which $R^1$ is hydrogen, Z is NH and $R^3$ is hexyl and $R^2$ for a compound corresponds in each case to a group in Table A.

Table 403

Compounds of the formula I.A, in which $R^1$ is methyl, Z is oxygen and $R^3$ is hexyl and $R^2$ for a compound corresponds in each case to a group in Table A.

Table 404

Compounds of the formula I.B, in which $R^1$ is methyl, Z is oxygen and $R^3$ is hexyl and $R^2$ for a compound corresponds in each case to a group in Table A.

Table 405

Compounds of the formula I.A, in which $R^1$ is methyl, Z is sulfur and $R^3$ is hexyl and $R^2$ for a compound corresponds in each case to a group in Table A.

Table 406

Compounds of the formula I.B, in which $R^1$ is methyl, Z is sulfur and $R^3$ is hexyl and $R^2$ for a compound corresponds in each case to a group in Table A.

Table 407

Compounds of the formula I.A, in which $R^1$ is methyl, Z is NH and $R^3$ is hexyl and $R^2$ for a compound corresponds in each case to a group in Table A.

Table 408

Compounds of the formula I.B, in which $R^1$ is methyl, Z is NH and $R^3$ is hexyl and $R^2$ for a compound corresponds in each case to a group in Table A.

Table 409

Compounds of the formula I.A, in which $R^1$ is ethyl, Z is oxygen and $R^3$ is hexyl and $R^2$ for a compound corresponds in each case to a group in Table A.

Table 410

Compounds of the formula I.B, in which $R^1$ is ethyl, Z is oxygen and $R^3$ is hexyl and $R^2$ for a compound corresponds in each case to a group in Table A.

Table 411

Compounds of the formula I.A, in which $R^1$ is ethyl, Z is sulfur and $R^3$ is hexyl and $R^2$ for a compound corresponds in each case to a group in Table A.

Table 412

Compounds of the formula I.B, in which $R^1$ is ethyl, Z is sulfur and $R^3$ is hexyl and $R^2$ for a compound corresponds in each case to a group in Table A.

Table 413

Compounds of the formula I.A, in which $R^1$ is ethyl, Z is NH and $R^3$ is hexyl and $R^2$ for a compound corresponds in each case to a group in Table A.

Table 414

Compounds of the formula I.B, in which $R^1$ is ethyl, Z is NH and $R^3$ is hexyl and $R^2$ for a compound corresponds in each case to a group in Table A.

Table 415

Compounds of the formula I.A, in which $R^1$ is isopropyl, Z is oxygen and $R^3$ is hexyl and $R^2$ for a compound corresponds in each case to a group in Table A.

Table 416

Compounds of the formula I.B, in which $R^1$ is isopropyl, Z is oxygen and $R^3$ is hexyl and $R^2$ for a compound corresponds in each case to a group in Table A.

Table 417

Compounds of the formula I.A, in which $R^1$ is isopropyl, Z is sulfur and $R^3$ is hexyl and $R^2$ for a compound corresponds in each case to a group in Table A.

Table 418

Compounds of the formula I.B, in which $R^1$ is isopropyl, Z is sulfur and $R^3$ is hexyl and $R^2$ for a compound corresponds in each case to a group in Table A.

Table 419

Compounds of the formula I.A, in which $R^1$ is isopropyl, Z is NH and $R^3$ is hexyl and $R^2$ for a compound corresponds in each case to a group in Table A.

Table 420

Compounds of the formula I.B, in which $R^1$ is isopropyl, Z is NH and $R^3$ is hexyl and $R^2$ for a compound corresponds in each case to a group in Table A.

Table 421

Compounds of the formula I.A, in which $R^1$ is hydrogen, Z is oxygen and $R^3$ is 3,3-dimethylbutyl and $R^2$ for a compound corresponds in each case to a group in Table A.

Table 422

Compounds of the formula I.B, in which $R^1$ is hydrogen, Z is oxygen and $R^3$ is 3,3-dimethylbutyl and $R^2$ for a compound corresponds in each case to a group in Table A.

Table 423

Compounds of the formula I.A, in which $R^1$ is hydrogen, Z is sulfur and $R^3$ is 3,3-dimethylbutyl and $R^2$ for a compound corresponds in each case to a group in Table A.

Table 424

Compounds of the formula I.B, in which $R^1$ is hydrogen, Z is sulfur and $R^3$ is 3,3-dimethylbutyl and $R^2$ for a compound corresponds in each case to a group in Table A.

Table 425

Compounds of the formula I.A, in which $R^1$ is hydrogen, Z is NH and $R^3$ is 3,3-dimethylbutyl and $R^2$ for a compound corresponds in each case to a group in Table A.

Table 426

Compounds of the formula I.B, in which $R^1$ is hydrogen, Z is NH and $R^3$ is 3,3-dimethylbutyl and $R^2$ for a compound corresponds in each case to a group in Table A.

Table 427

Compounds of the formula I.A, in which $R^1$ is methyl, Z is oxygen and $R^3$ is 3,3-dimethylbutyl and $R^2$ for a compound corresponds in each case to a group in Table A.

Table 428

Compounds of the formula I.B, in which $R^1$ is methyl, Z is oxygen and $R^3$ is 3,3-dimethylbutyl and $R^2$ for a compound corresponds in each case to a group in Table A.

Table 429

Compounds of the formula I.A, in which $R^1$ is methyl, Z is sulfur and $R^3$ is 3,3-dimethylbutyl and $R^2$ for a compound corresponds in each case to a group in Table A.

Table 430

Compounds of the formula I.B, in which $R^1$ is methyl, Z is sulfur and $R^3$ is 3,3-dimethylbutyl and $R^2$ for a compound corresponds in each case to a group in Table A.

Table 431

Compounds of the formula I.A, in which $R^1$ is methyl, Z is NH and $R^3$ is 3,3-dimethylbutyl and $R^2$ for a compound corresponds in each case to a group in Table A.

Table 432

Compounds of the formula I.B, in which $R^1$ is methyl, Z is NH and $R^3$ is 3,3-dimethylbutyl and $R^2$ for a compound corresponds in each case to a group in Table A.

Table 433

Compounds of the formula I.A, in which $R^1$ is ethyl, Z is oxygen and $R^3$ is 3,3-dimethylbutyl and $R^2$ for a compound corresponds in each case to a group in Table A.

Table 434

Compounds of the formula I.B, in which $R^1$ is ethyl, Z is oxygen and $R^3$ is 3,3-dimethylbutyl and $R^2$ for a compound corresponds in each case to a group in Table A.

Table 435

Compounds of the formula I.A, in which $R^1$ is ethyl, Z is sulfur and $R^3$ is 3,3-dimethylbutyl and $R^2$ for a compound corresponds in each case to a group in Table A.

Table 436

Compounds of the formula I.B, in which $R^1$ is ethyl, Z is sulfur and $R^3$ is 3,3-dimethylbutyl and $R^2$ for a compound corresponds in each case to a group in Table A.

Table 437

Compounds of the formula I.A, in which $R^1$ is ethyl, Z is NH and $R^3$ is 3,3-dimethylbutyl and $R^2$ for a compound corresponds in each case to a group in Table A.

Table 438

Compounds of the formula I.B, in which $R^1$ is ethyl, Z is NH and $R^3$ is 3,3-dimethylbutyl and $R^2$ for a compound corresponds in each case to a group in Table A.

Table 439

Compounds of the formula I.A, in which $R^1$ is isopropyl, Z is oxygen and $R^3$ is 3,3-dimethylbutyl and $R^2$ for a compound corresponds in each case to a group in Table A.

Table 440

Compounds of the formula I.B, in which $R^1$ is isopropyl, Z is oxygen and $R^3$ is 3,3-dimethylbutyl and $R^2$ for a compound corresponds in each case to a group in Table A.

Table 441

Compounds of the formula I.A, in which $R^1$ is isopropyl, Z is sulfur and $R^3$ is 3,3-dimethylbutyl and $R^2$ for a compound corresponds in each case to a group in Table A.

Table 442

Compounds of the formula I.B, in which $R^1$ is isopropyl, Z is sulfur and $R^3$ is 3,3-dimethylbutyl and $R^2$ for a compound corresponds in each case to a group in Table A.

Table 443

Compounds of the formula I.A, in which $R^1$ is isopropyl, Z is NH and $R^3$ is 3,3-dimethylbutyl and $R^2$ for a compound corresponds in each case to a group in Table A.

Table 444

Compounds of the formula I.B, in which $R^1$ is isopropyl, Z is NH and $R^3$ is 3,3-dimethylbutyl and $R^2$ for a compound corresponds in each case to a group in Table A.

Table 445

Compounds of the formula I.A, in which $R^1$ is hydrogen, Z is oxygen and $R^3$ is 2-ethylbutyl and $R^2$ for a compound corresponds in each case to a group in Table A.

Table 446

Compounds of the formula I.B, in which $R^1$ is hydrogen, Z is oxygen and $R^3$ is 2-ethylbutyl and $R^2$ for a compound corresponds in each case to a group in Table A.

Table 447

Compounds of the formula I.A, in which $R^1$ is hydrogen, Z is sulfur and $R^3$ is 2-ethylbutyl and $R^2$ for a compound corresponds in each case to a group in Table A.

Table 448

Compounds of the formula I.B, in which $R^1$ is hydrogen, Z is sulfur and $R^3$ is 2-ethylbutyl and $R^2$ for a compound corresponds in each case to a group in Table A.

Table 449

Compounds of the formula I.A, in which $R^1$ is hydrogen, Z is NH and $R^3$ is 2-ethylbutyl and $R^2$ for a compound corresponds in each case to a group in Table A.

Table 450

Compounds of the formula I.B, in which $R^1$ is hydrogen, Z is NH and $R^3$ is 2-ethylbutyl and $R^2$ for a compound corresponds in each case to a group in Table A.

Table 451

Compounds of the formula I.A, in which $R^1$ is methyl, Z is oxygen and $R^3$ is 2-ethylbutyl and $R^2$ for a compound corresponds in each case to a group in Table A.

Table 452

Compounds of the formula I.B, in which $R^1$ is methyl, Z is oxygen and $R^3$ is 2-ethylbutyl and $R^2$ for a compound corresponds in each case to a group in Table A

Table 453

Compounds of the formula I.A, in which $R^1$ is methyl, Z is sulfur and $R^3$ is 2-ethylbutyl and $R^2$ for a compound corresponds in each case to a group in Table A

Table 454

Compounds of the formula I.B, in which $R^1$ is methyl, Z is sulfur and $R^3$ is 2-ethylbutyl and $R^2$ for a compound corresponds in each case to a group in Table A.

Table 455

Compounds of the formula I.A, in which $R^1$ is methyl, Z is NH and $R^3$ is 2-ethylbutyl and $R^2$ for a compound corresponds in each case to a group in Table A.

Table 456

Compounds of the formula I.B, in which $R^1$ is methyl, Z is NH and $R^3$ is 2-ethylbutyl and $R^2$ for a compound corresponds in each case to a group in Table A.

Table 457

Compounds of the formula I.A, in which $R^1$ is ethyl, Z is oxygen and $R^3$ is 2-ethylbutyl and $R^2$ for a compound corresponds in each case to a group in Table A.

Table 458

Compounds of the formula I.B, in which $R^1$ is ethyl, Z is oxygen and $R^3$ is 2-ethylbutyl and $R^2$ for a compound corresponds in each case to a group in Table A.

Table 459

Compounds of the formula I.A, in which $R^1$ is ethyl, Z is sulfur and $R^3$ is 2-ethylbutyl and $R^2$ for a compound corresponds in each case to a group in Table A.

Table 460

Compounds of the formula I.B, in which $R^1$ is ethyl, Z is sulfur and $R^3$ is 2-ethylbutyl and $R^2$ for a compound corresponds in each case to a group in Table A.

Table 461

Compounds of the formula I.A, in which $R^1$ is ethyl, Z is NH and $R^3$ is 2-ethylbutyl and $R^2$ for a compound corresponds in each case to a group in Table A.

Table 462

Compounds of the formula I.B, in which $R^1$ is ethyl, Z is NH and $R^3$ is 2-ethylbutyl and $R^2$ for a compound corresponds in each case to a group in Table A.

Table 463

Compounds of the formula I.A, in which $R^1$ is isopropyl, Z is oxygen and $R^3$ is 2-ethylbutyl and $R^2$ for a compound corresponds in each case to a group in Table A.

Table 464

Compounds of the formula I.B, in which $R^1$ is isopropyl, Z is oxygen and $R^3$ is 2-ethylbutyl and $R^2$ for a compound corresponds in each case to a group in Table A.

Table 465

Compounds of the formula I.A, in which $R^1$ is isopropyl, Z is sulfur and $R^3$ is 2-ethylbutyl and $R^2$ for a compound corresponds in each case to a group in Table A.

Table 466

Compounds of the formula I.B, in which $R^1$ is isopropyl, Z is sulfur and $R^3$ is 2-ethylbutyl and $R^2$ for a compound corresponds in each case to a group in Table A.

Table 467

Compounds of the formula I.A, in which $R^1$ is isopropyl, Z is NH and $R^3$ is 2-ethylbutyl and $R^2$ for a compound corresponds in each case to a group in Table A.

Table 468

Compounds of the formula I.B, in which $R^1$ is isopropyl, Z is NH and $R^3$ is 2-ethylbutyl and $R^2$ for a compound corresponds in each case to a group in Table A.

Table 469

Compounds of the formula I.A, in which $R^1$ is hydrogen, Z is oxygen and $R^3$ is 1-ethylbutyl and $R^2$ for a compound corresponds in each case to a group in Table A.

Table 470

Compounds of the formula I.B, in which $R^1$ is hydrogen, Z is oxygen and $R^3$ is 1-ethylbutyl and $R^2$ for a compound corresponds in each case to a group in Table A.

Table 471

Compounds of the formula I.A, in which $R^1$ is hydrogen, Z is sulfur and $R^3$ is 1-ethylbutyl and $R^2$ for a compound corresponds in each case to a group in Table A.

Table 472

Compounds of the formula I.B, in which $R^1$ is hydrogen, Z is sulfur and $R^3$ is 1-ethylbutyl and $R^2$ for a compound corresponds in each case to a group in Table A.

Table 473

Compounds of the formula I.A, in which $R^1$ is hydrogen, Z is NH and $R^3$ is 1-ethylbutyl and $R^2$ for a compound corresponds in each case to a group in Table A.

Table 474

Compounds of the formula I.B, in which $R^1$ is hydrogen, Z is NH and $R^3$ is 1-ethylbutyl and $R^2$ for a compound corresponds in each case to a group in Table A.

Table 475

Compounds of the formula I.A, in which $R^1$ is methyl, Z is oxygen and $R^3$ is 1-ethylbutyl and $R^2$ for a compound corresponds in each case to a group in Table A.

Table 476

Compounds of the formula I.B, in which $R^1$ is methyl, Z is oxygen and $R^3$ is 1-ethylbutyl and $R^2$ for a compound corresponds in each case to a group in Table A.

Table 477

Compounds of the formula I.A, in which $R^1$ is methyl, Z is sulfur and $R^3$ is 1-ethylbutyl and $R^2$ for a compound corresponds in each case to a group in Table A.

Table 478

Compounds of the formula I.B, in which $R^1$ is methyl, Z is sulfur and $R^3$ is 1-ethylbutyl and $R^2$ for a compound corresponds in each case to a group in Table A.

Table 479

Compounds of the formula I.A, in which $R^1$ is methyl, Z is NH and $R^3$ is 1-ethylbutyl and $R^2$ for a compound corresponds in each case to a group in Table A.

Table 480

Compounds of the formula I.B, in which $R^1$ is methyl, Z is NH and $R^3$ is 1-ethylbutyl and $R^2$ for a compound corresponds in each case to a group in Table A.

Table 481

Compounds of the formula I.A, in which $R^1$ is ethyl, Z is oxygen and $R^3$ is 1-ethylbutyl and $R^2$ for a compound corresponds in each case to a group in Table A.

Table 482

Compounds of the formula I.B, in which $R^1$ is ethyl, Z is oxygen and $R^3$ is 1-ethylbutyl and $R^2$ for a compound corresponds in each case to a group in Table A.

Table 483

Compounds of the formula I.A, in which $R^1$ is ethyl, Z is sulfur and $R^3$ is 1-ethylbutyl and $R^2$ for a compound corresponds in each case to a group in Table A.

Table 484

Compounds of the formula I.B, in which $R^1$ is ethyl, Z is sulfur and $R^3$ is 1-ethylbutyl and $R^2$ for a compound corresponds in each case to a group in Table A.

Table 485

Compounds of the formula I.A, in which $R^1$ is ethyl, Z is NH and $R^3$ is 1-ethylbutyl and $R^2$ for a compound corresponds in each case to a group in Table A.

Table 486

Compounds of the formula I.B, in which $R^1$ is ethyl, Z is NH and $R^3$ is 1-ethylbutyl and $R^2$ for a compound corresponds in each case to a group in Table A.

Table 487

Compounds of the formula I.A, in which $R^1$ is isopropyl, Z is oxygen and $R^3$ is 1-ethylbutyl and $R^2$ for a compound corresponds in each case to a group in Table A.

Table 488

Compounds of the formula I.B, in which $R^1$ is isopropyl, Z is oxygen and $R^3$ is 1-ethylbutyl and $R^2$ for a compound corresponds in each case to a group in Table A.

Table 489

Compounds of the formula I.A, in which $R^1$ is isopropyl, Z is sulfur and $R^3$ is 1-ethylbutyl and $R^2$ for a compound corresponds in each case to a group in Table A.

Table 490

Compounds of the formula I.B, in which $R^1$ is isopropyl, Z is sulfur and $R^3$ is 1-ethylbutyl and $R^2$ for a compound corresponds in each case to a group in Table A.

Table 491

Compounds of the formula I.A, in which $R^1$ is isopropyl, Z is NH and $R^3$ is 1-ethylbutyl and $R^2$ for a compound corresponds in each case to a group in Table A.

Table 492

Compounds of the formula I.B, in which $R^1$ is isopropyl, Z is NH and $R^3$ is 1-ethylbutyl and $R^2$ for a compound corresponds in each case to a group in Table A.

Table 493

Compounds of the formula I.A, in which $R^1$ is hydrogen, Z is oxygen and $R^3$ is 4-methylpentyl and $R^2$ for a compound corresponds in each case to a group in Table A.

Table 494

Compounds of the formula I.B, in which $R^1$ is hydrogen, Z is oxygen and $R^3$ is 4-methylpentyl and $R^2$ for a compound corresponds in each case to a group in Table A.

Table 495

Compounds of the formula I.A, in which $R^1$ is hydrogen, Z is sulfur and $R^3$ is 4-methylpentyl and $R^2$ for a compound corresponds in each case to a group in Table A.

Table 496

Compounds of the formula I.B, in which $R^1$ is hydrogen, Z is sulfur and $R^3$ is 4-methylpentyl and $R^2$ for a compound corresponds in each case to a group in Table A.

Table 497

Compounds of the formula I.A, in which $R^1$ is hydrogen, Z is NH and $R^3$ is 4-methylpentyl and $R^2$ for a compound corresponds in each case to a group in Table A.

Table 498

Compounds of the formula I.B, in which $R^1$ is hydrogen, Z is NH and $R^3$ is 4-methylpentyl and $R^2$ for a compound corresponds in each case to a group in Table A.

Table 499

Compounds of the formula I.A, in which $R^1$ is methyl, Z is oxygen and $R^3$ is 4-methylpentyl and $R^2$ for a compound corresponds in each case to a group in Table A.

Table 500

Compounds of the formula I.B, in which $R^1$ is methyl, Z is oxygen and $R^3$ is 4-methylpentyl and $R^2$ for a compound corresponds in each case to a group in Table A.

Table 501

Compounds of the formula I.A, in which $R^1$ is methyl, Z is sulfur and $R^3$ is 4-methylpentyl and $R^2$ for a compound corresponds in each case to a group in Table A.

Table 502

Compounds of the formula I.B, in which $R^1$ is methyl, Z is sulfur and $R^3$ is 4-methylpentyl and $R^2$ for a compound corresponds in each case to a group in Table A.

Table 503

Compounds of the formula I.A, in which $R^1$ is methyl, Z is NH and $R^3$ is 4-methylpentyl and $R^2$ for a compound corresponds in each case to a group in Table A.

Table 504

Compounds of the formula I.B, in which $R^1$ is methyl, Z is NH and $R^3$ is 4-methylpentyl and $R^2$ for a compound corresponds in each case to a group in Table A.

Table 505

Compounds of the formula I.A, in which $R^1$ is ethyl, Z is oxygen and $R^3$ is 4-methylpentyl and $R^2$ for a compound corresponds in each case to a group in Table A.

Table 506

Compounds of the formula I.B, in which $R^1$ is ethyl, Z is oxygen and $R^3$ is 4-methylpentyl and $R^2$ for a compound corresponds in each case to a group in Table A.

Table 507

Compounds of the formula I.A, in which $R^1$ is ethyl, Z is sulfur and $R^3$ is 4-methylpentyl and $R^2$ for a compound corresponds in each case to a group in Table A.

Table 508

Compounds of the formula I.B, in which $R^1$ is ethyl, Z is sulfur and $R^3$ is 4-methylpentyl and $R^2$ for a compound corresponds in each case to a group in Table A.

Table 509

Compounds of the formula I.A, in which $R^1$ is ethyl, Z is NH and $R^3$ is 4-methylpentyl and $R^2$ for a compound corresponds in each case to a group in Table A.

Table 510

Compounds of the formula I.B, in which $R^1$ is ethyl, Z is NH and $R^3$ is 4-methylpentyl and $R^2$ for a compound corresponds in each case to a group in Table A.

Table 511

Compounds of the formula I.A, in which $R^1$ is isopropyl, Z is oxygen and $R^3$ is 4-methylpentyl and $R^2$ for a compound corresponds in each case to a group in Table A.

Table 512

Compounds of the formula I.B, in which $R^1$ is isopropyl, Z is oxygen and $R^3$ is 4-methylpentyl and $R^2$ for a compound corresponds in each case to a group in Table A.

Table 513

Compounds of the formula I.A, in which $R^1$ is isopropyl, Z is sulfur and $R^3$ is 4-methylpentyl and $R^2$ for a compound corresponds in each case to a group in Table A.

Table 514

Compounds of the formula I.B, in which $R^1$ is isopropyl, Z is sulfur and $R^3$ is 4-methylpentyl and $R^2$ for a compound corresponds in each case to a group in Table A.

Table 515

Compounds of the formula I.A, in which $R^1$ is isopropyl, Z is NH and $R^3$ is 4-methylpentyl and $R^2$ for a compound corresponds in each case to a group in Table A.

Table 516

Compounds of the formula I.B, in which $R^1$ is isopropyl, Z is NH and $R^3$ is 4-methylpentyl and $R^2$ for a compound corresponds in each case to a group in Table A.

Table 517

Compounds of the formula I.A, in which $R^1$ is hydrogen, Z is oxygen and $R^3$ is cyclopropylmethyl and $R^2$ for a compound corresponds in each case to a group in Table A.

Table 518

Compounds of the formula I.B, in which $R^1$ is hydrogen, Z is oxygen and $R^3$ is cyclopropylmethyl and $R^2$ for a compound corresponds in each case to a group in Table A.

Table 519

Compounds of the formula I.A, in which $R^1$ is hydrogen, Z is sulfur and $R^3$ is cyclopropylmethyl and $R^2$ for a compound corresponds in each case to a group in Table A.

Table 520

Compounds of the formula I.B, in which $R^1$ is hydrogen, Z is sulfur and $R^3$ is cyclopropylmethyl and $R^2$ for a compound corresponds in each case to a group in Table A.

Table 521

Compounds of the formula I.A, in which $R^1$ is hydrogen, Z is NH and $R^3$ is cyclopropylmethyl and $R^2$ for a compound corresponds in each case to a group in Table A.

Table 522

Compounds of the formula I.B, in which $R^1$ is hydrogen, Z is NH and $R^3$ is cyclopropylmethyl and $R^2$ for a compound corresponds in each case to a group in Table A.

Table 523

Compounds of the formula I.A, in which $R^1$ is methyl, Z is oxygen and $R^3$ is cyclopropylmethyl and $R^2$ for a compound corresponds in each case to a group in Table A.

Table 524

Compounds of the formula I.B, in which $R^1$ is methyl, Z is oxygen and $R^3$ is cyclopropylmethyl and $R^2$ for a compound corresponds in each case to a group in Table A.

Table 525

Compounds of the formula I.A, in which $R^1$ is methyl, Z is sulfur and $R^3$ is cyclopropylmethyl and $R^2$ for a compound corresponds in each case to a group in Table A.

Table 526

Compounds of the formula I.B, in which $R^1$ is methyl, Z is sulfur and $R^3$ is cyclopropylmethyl and $R^2$ for a compound corresponds in each case to a group in Table A.

Table 527

Compounds of the formula I.A, in which $R^1$ is methyl, Z is NH and $R^3$ is cyclopropylmethyl and $R^2$ for a compound corresponds in each case to a group in Table A.

Table 528

Compounds of the formula I.B, in which $R^1$ is methyl, Z is NH and $R^3$ is cyclopropylmethyl and $R^2$ for a compound corresponds in each case to a group in Table A.

Table 529

Compounds of the formula I.A, in which $R^1$ is ethyl, Z is oxygen and $R^3$ is cyclopropylmethyl and $R^2$ for a compound corresponds in each case to a group in Table A.

Table 530

Compounds of the formula I.B, in which $R^1$ is ethyl, Z is oxygen and $R^3$ is cyclopropylmethyl and $R^2$ for a compound corresponds in each case to a group in Table A.

Table 531

Compounds of the formula I.A, in which $R^1$ is ethyl, Z is sulfur and $R^3$ is cyclopropylmethyl and $R^2$ for a compound corresponds in each case to a group in Table A.

Table 532

Compounds of the formula I.B, in which $R^1$ is ethyl, Z is sulfur and $R^3$ is cyclopropylmethyl and $R^2$ for a compound corresponds in each case to a group in Table A.

Table 533

Compounds of the formula I.A, in which $R^1$ is ethyl, Z is NH and $R^3$ is cyclopropylmethyl and $R^2$ for a compound corresponds in each case to a group in Table A.

Table 534

Compounds of the formula I.B, in which $R^1$ is ethyl, Z is NH and $R^3$ is cyclopropylmethyl and $R^2$ for a compound corresponds in each case to a group in Table A.

Table 535

Compounds of the formula I.A, in which $R^1$ is isopropyl, Z is oxygen and $R^3$ is cyclopropylmethyl and $R^2$ for a compound corresponds in each case to a group in Table A.

Table 536

Compounds of the formula I.B, in which $R^1$ is isopropyl, Z is oxygen and $R^3$ is cyclopropylmethyl and $R^2$ for a compound corresponds in each case to a group in Table A.

Table 537

Compounds of the formula I.A, in which $R^1$ is isopropyl, Z is sulfur and $R^3$ is cyclopropylmethyl and $R^2$ for a compound corresponds in each case to a group in Table A.

Table 538

Compounds of the formula I.B, in which $R^1$ is isopropyl, Z is sulfur and $R^3$ is cyclopropylmethyl and $R^2$ for a compound corresponds in each case to a group in Table A.

Table 539

Compounds of the formula I.A, in which $R^1$ is isopropyl, Z is NH and $R^3$ is cyclopropylmethyl and $R^2$ for a compound corresponds in each case to a group in Table A.

Table 540

Compounds of the formula I.B, in which $R^1$ is isopropyl, Z is NH and $R^3$ is cyclopropylmethyl and $R^2$ for a compound corresponds in each case to a group in Table A.

Table 541

Compounds of the formula I.A, in which $R^1$ is hydrogen, Z is oxygen and $R^3$ is cyclopentylmethyl and $R^2$ for a compound corresponds in each case to a group in Table A.

Table 542

Compounds of the formula I.B, in which $R^1$ is hydrogen, Z is oxygen and $R^3$ is cyclopentylmethyl and $R^2$ for a compound corresponds in each case to a group in Table A.

Table 543

Compounds of the formula I.A, in which $R^1$ is hydrogen, Z is sulfur and $R^3$ is cyclopentylmethyl and $R^2$ for a compound corresponds in each case to a group in Table A.

Table 544

Compounds of the formula I.B, in which $R^1$ is hydrogen, Z is sulfur and $R^3$ is cyclopentylmethyl and $R^2$ for a compound corresponds in each case to a group in Table A.

Table 545

Compounds of the formula I.A, in which $R^1$ is hydrogen, Z is NH and $R^3$ is cyclopentylmethyl and $R^2$ for a compound corresponds in each case to a group in Table A.

Table 546

Compounds of the formula I.B, in which $R^1$ is hydrogen, Z is NH and $R^3$ is cyclopentylmethyl and $R^2$ for a compound corresponds in each case to a group in Table A.

Table 547

Compounds of the formula I.A, in which $R^1$ is methyl, Z is oxygen and $R^3$ is cyclopentylmethyl and $R^2$ for a compound corresponds in each case to a group in Table A.

Table 548

Compounds of the formula I.B, in which $R^1$ is methyl, Z is oxygen and $R^3$ is cyclopentylmethyl and $R^2$ for a compound corresponds in each case to a group in Table A.

Table 549

Compounds of the formula I.A, in which $R^1$ is methyl, Z is sulfur and $R^3$ is cyclopentylmethyl and $R^2$ for a compound corresponds in each case to a group in Table A.

Table 550

Compounds of the formula I.B, in which $R^1$ is methyl, Z is sulfur and $R^3$ is cyclopentylmethyl and $R^2$ for a compound corresponds in each case to a group in Table A.

Table 551

Compounds of the formula I.A, in which $R^1$ is methyl, Z is NH and $R^3$ is cyclopentylmethyl and $R^2$ for a compound corresponds in each case to a group in Table A.

Table 552

Compounds of the formula I.B, in which $R^1$ is methyl, Z is NH and $R^3$ is cyclopentylmethyl and $R^2$ for a compound corresponds in each case to a group in Table A.

Table 553

Compounds of the formula I.A, in which $R^1$ is ethyl, Z is oxygen and $R^3$ is cyclopentylmethyl and $R^2$ for a compound corresponds in each case to a group in Table A.

Table 554

Compounds of the formula I.B, in which $R^1$ is ethyl, Z is oxygen and $R^3$ is cyclopentylmethyl and $R^2$ for a compound corresponds in each case to a group in Table A.

Table 555

Compounds of the formula I.A, in which $R^1$ is ethyl, Z is sulfur and $R^3$ is cyclopentylmethyl and $R^2$ for a compound corresponds in each case to a group in Table A.

Table 556

Compounds of the formula I.B, in which $R^1$ is ethyl, Z is sulfur and $R^3$ is cyclopentylmethyl and $R^2$ for a compound corresponds in each case to a group in Table A.

Table 557

Compounds of the formula I.A, in which $R^1$ is ethyl, Z is NH and $R^3$ is cyclopentylmethyl and $R^2$ for a compound corresponds in each case to a group in Table A.

Table 558

Compounds of the formula I.B, in which $R^1$ is ethyl, Z is NH and $R^3$ is cyclopentylmethyl and $R^2$ for a compound corresponds in each case to a group in Table A.

Table 559

Compounds of the formula I.A, in which $R^1$ is isopropyl, Z is oxygen and $R^3$ is cyclopentylmethyl and $R^2$ for a compound corresponds in each case to a group in Table A.

Table 560

Compounds of the formula I.B, in which $R^1$ is isopropyl, Z is oxygen and $R^3$ is cyclopentylmethyl and $R^2$ for a compound corresponds in each case to a group in Table A.

Table 561

Compounds of the formula I.A, in which $R^1$ is isopropyl, Z is sulfur and $R^3$ is cyclopentylmethyl and $R^2$ for a compound corresponds in each case to a group in Table A.

Table 562

Compounds of the formula I.B, in which $R^1$ is isopropyl, Z is sulfur and $R^3$ is cyclopentylmethyl and $R^2$ for a compound corresponds in each case to a group in Table A.

Table 563

Compounds of the formula I.A, in which $R^1$ is isopropyl, Z is NH and $R^3$ is cyclopentylmethyl and $R^2$ for a compound corresponds in each case to a group in Table A.

Table 564

Compounds of the formula I.B, in which $R^1$ is isopropyl, Z is NH and $R^3$ is cyclopentylmethyl and $R^2$ for a compound corresponds in each case to a group in Table A.

Table 565

Compounds of the formula I.A, in which $R^1$ is hydrogen, Z is oxygen and $R^3$ is cyclohexylmethyl and $R^2$ for a compound corresponds in each case to a group in Table A.

Table 566

Compounds of the formula I.B, in which $R^1$ is hydrogen, Z is oxygen and $R^3$ is cyclohexylmethyl and $R^2$ for a compound corresponds in each case to a group in Table A.

Table 567

Compounds of the formula I.A, in which $R^1$ is hydrogen, Z is sulfur and $R^3$ is cyclohexylmethyl and $R^2$ for a compound corresponds in each case to a group in Table A.

Table 568

Compounds of the formula I.B, in which $R^1$ is hydrogen, Z is sulfur and $R^3$ is cyclohexylmethyl and $R^2$ for a compound corresponds in each case to a group in Table A.

Table 569

Compounds of the formula I.A, in which $R^1$ is hydrogen, Z is NH and $R^3$ is cyclohexylmethyl and $R^2$ for a compound corresponds in each case to a group in Table A.

Table 570

Compounds of the formula I.B, in which $R^1$ is hydrogen, Z is NH and $R^3$ is cyclohexylmethyl and $R^2$ for a compound corresponds in each case to a group in Table A.

Table 571

Compounds of the formula I.A, in which $R^1$ is methyl, Z is oxygen and $R^3$ is cyclohexylmethyl and $R^2$ for a compound corresponds in each case to a group in Table A.

Table 572

Compounds of the formula I.B, in which $R^1$ is methyl, Z is oxygen and $R^3$ is cyclohexylmethyl and $R^2$ for a compound corresponds in each case to a group in Table A.

Table 573

Compounds of the formula I.A, in which $R^1$ is methyl, Z is sulfur and $R^3$ is cyclohexylmethyl and $R^2$ for a compound corresponds in each case to a group in Table A.

Table 574

Compounds of the formula I.B, in which $R^1$ is methyl, Z is sulfur and $R^3$ is cyclohexylmethyl and $R^2$ for a compound corresponds in each case to a group in Table A.

Table 575

Compounds of the formula I.A, in which $R^1$ is methyl, Z is NH and $R^3$ is cyclohexylmethyl and $R^2$ for a compound corresponds in each case to a group in Table A.

Table 576

Compounds of the formula I.B, in which $R^1$ is methyl, Z is NH and $R^3$ is cyclohexylmethyl and $R^2$ for a compound corresponds in each case to a group in Table A.

Table 577

Compounds of the formula I.A, in which $R^1$ is ethyl, Z is oxygen and $R^3$ is cyclohexylmethyl and $R^2$ for a compound corresponds in each case to a group in Table A.

Table 578

Compounds of the formula I.B, in which $R^1$ is ethyl, Z is oxygen and $R^3$ is cyclohexylmethyl and $R^2$ for a compound corresponds in each case to a group in Table A.

Table 579

Compounds of the formula I.A, in which $R^1$ is ethyl, Z is sulfur and $R^3$ is cyclohexylmethyl and $R^2$ for a compound corresponds in each case to a group in Table A.

Table 580

Compounds of the formula I.B, in which $R^1$ is ethyl, Z is sulfur and $R^3$ is cyclohexylmethyl and $R^2$ for a compound corresponds in each case to a group in Table A.

Table 581

Compounds of the formula I.A, in which $R^1$ is ethyl, Z is NH and $R^3$ is cyclohexylmethyl and $R^2$ for a compound corresponds in each case to a group in Table A.

Table 582

Compounds of the formula I.B, in which $R^1$ is ethyl, Z is NH and $R^3$ is cyclohexylmethyl and $R^2$ for a compound corresponds in each case to a group in Table A.

Table 583

Compounds of the formula I.A, in which $R^1$ is isopropyl, Z is oxygen and $R^3$ is cyclohexylmethyl and $R^2$ for a compound corresponds in each case to a group in Table A.

Table 584

Compounds of the formula I.B, in which $R^1$ is isopropyl, Z is oxygen and $R^3$ is cyclohexylmethyl and $R^2$ for a compound corresponds in each case to a group in Table A.

Table 585

Compounds of the formula I.A, in which $R^1$ is isopropyl, Z is sulfur and $R^3$ is cyclohexylmethyl and $R^2$ for a compound corresponds in each case to a group in Table A.

Table 586

Compounds of the formula I.B, in which $R^1$ is isopropyl, Z is sulfur and $R^3$ is cyclohexylmethyl and $R^2$ for a compound corresponds in each case to a group in Table A.

Table 587

Compounds of the formula I.A, in which $R^1$ is isopropyl, Z is NH and $R^3$ is cyclohexylmethyl and $R^2$ for a compound corresponds in each case to a group in Table A.

Table 588

Compounds of the formula I.B, in which $R^1$ is isopropyl, Z is NH and $R^3$ is cyclohexylmethyl and $R^2$ for a compound corresponds in each case to a group in Table A.

Table 589

Compounds of the formula I.A, in which $R^1$ is hydrogen, Z is oxygen and $R^3$ is 2-cyclopropylethyl and $R^2$ for a compound corresponds in each case to a group in Table A.

Table 590

Compounds of the formula I.B, in which $R^1$ is hydrogen, Z is oxygen and $R^3$ is 2-cyclopropylethyl and $R^2$ for a compound corresponds in each case to a group in Table A.

Table 591

Compounds of the formula I.A, in which $R^1$ is hydrogen, Z is sulfur and $R^3$ is 2-cyclopropylethyl and $R^2$ for a compound corresponds in each case to a group in Table A.

Table 592

Compounds of the formula I.B, in which $R^1$ is hydrogen, Z is sulfur and $R^3$ is 2-cyclopropylethyl and $R^2$ for a compound corresponds in each case to a group in Table A.

Table 593

Compounds of the formula I.A, in which $R^1$ is hydrogen, Z is NH and $R^3$ is 2-cyclopropylethyl and $R^2$ for a compound corresponds in each case to a group in Table A.

Table 594

Compounds of the formula I.B, in which $R^1$ is hydrogen, Z is NH and $R^3$ is 2-cyclopropylethyl and $R^2$ for a compound corresponds in each case to a group in Table A.

Table 595

Compounds of the formula I.A, in which $R^1$ is methyl, Z is oxygen and $R^3$ is 2-cyclopropylethyl and $R^2$ for a compound corresponds in each case to a group in Table A.

Table 596

Compounds of the formula I.B, in which $R^1$ is methyl, Z is oxygen and $R^3$ is 2-cyclopropylethyl and $R^2$ for a compound corresponds in each case to a group in Table A.

Table 597

Compounds of the formula I.A, in which $R^1$ is methyl, Z is sulfur and $R^3$ is 2-cyclopropylethyl and $R^2$ for a compound corresponds in each case to a group in Table A.

Table 598

Compounds of the formula I.B, in which $R^1$ is methyl, Z is sulfur and $R^3$ is 2-cyclopropylethyl and $R^2$ for a compound corresponds in each case to a group in Table A.

Table 599

Compounds of the formula I.A, in which $R^1$ is methyl, Z is NH and $R^3$ is 2-cyclopropylethyl and $R^2$ for a compound corresponds in each case to a group in Table A.

Table 600

Compounds of the formula I.B, in which $R^1$ is methyl, Z is NH and $R^3$ is 2-cyclopropylethyl and $R^2$ for a compound corresponds in each case to a group in Table A.

Table 601

Compounds of the formula I.A, in which $R^1$ is ethyl, Z is oxygen and $R^3$ is 2-cyclopropylethyl and $R^2$ for a compound corresponds in each case to a group in Table A.

Table 602

Compounds of the formula I.B, in which $R^1$ is ethyl, Z is oxygen and $R^3$ is 2-cyclopropylethyl and $R^2$ for a compound corresponds in each case to a group in Table A.

Table 603

Compounds of the formula I.A, in which $R^1$ is ethyl, Z is sulfur and $R^3$ is 2-cyclopropylethyl and $R^2$ for a compound corresponds in each case to a group in Table A.

Table 604

Compounds of the formula I.B, in which $R^1$ is ethyl, Z is sulfur and $R^3$ is 2-cyclopropylethyl and $R^2$ for a compound corresponds in each case to a group in Table A.

Table 605

Compounds of the formula I.A, in which $R^1$ is ethyl, Z is NH and $R^3$ is 2-cyclopropylethyl and $R^2$ for a compound corresponds in each case to a group in Table A.

Table 606

Compounds of the formula I.B, in which $R^1$ is ethyl, Z is NH and $R^3$ is 2-cyclopropylethyl and $R^2$ for a compound corresponds in each case to a group in Table A.

Table 607

Compounds of the formula I.A, in which $R^1$ is isopropyl, Z is oxygen and $R^3$ is 2-cyclopropylethyl and $R^2$ for a compound corresponds in each case to a group in Table A.

Table 608

Compounds of the formula I.B, in which $R^1$ is isopropyl, Z is oxygen and $R^3$ is 2-cyclopropylethyl and $R^2$ for a compound corresponds in each case to a group in Table A.

Table 609

Compounds of the formula I.A, in which $R^1$ is isopropyl, Z is sulfur and $R^3$ is 2-cyclopropylethyl and $R^2$ for a compound corresponds in each case to a group in Table A.

Table 610

Compounds of the formula I.B, in which $R^1$ is isopropyl, Z is sulfur and $R^3$ is 2-cyclopropylethyl and $R^2$ for a compound corresponds in each case to a group in Table A.

Table 611

Compounds of the formula I.A, in which $R^1$ is isopropyl, Z is NH and $R^3$ is 2-cyclopropylethyl and $R^2$ for a compound corresponds in each case to a group in Table A.

Table 612

Compounds of the formula I.B, in which $R^1$ is isopropyl, Z is NH and $R^3$ is 2-cyclopropylethyl and $R^2$ for a compound corresponds in each case to a group in Table A.

Table 613

Compounds of the formula I.A, in which $R^1$ is hydrogen, Z is oxygen and $R^3$ is 2-cyclopentylethyl and $R^2$ for a compound corresponds in each case to a group in Table A.

Table 614

Compounds of the formula I.B, in which $R^1$ is hydrogen, Z is oxygen and $R^3$ is 2-cyclopentylethyl and $R^2$ for a compound corresponds in each case to a group in Table A.

Table 615

Compounds of the formula I.A, in which $R^1$ is hydrogen, Z is sulfur and $R^3$ is 2-cyclopentylethyl and $R^2$ for a compound corresponds in each case to a group in Table A.

Table 616

Compounds of the formula I.B, in which $R^1$ is hydrogen, Z is sulfur and $R^3$ is 2-cyclopentylethyl and $R^2$ for a compound corresponds in each case to a group in Table A.

Table 617

Compounds of the formula I.A, in which $R^1$ is hydrogen, Z is NH and $R^3$ is 2-cyclopentylethyl and $R^2$ for a compound corresponds in each case to a group in Table A.

Table 618

Compounds of the formula I.B, in which $R^1$ is hydrogen, Z is NH and $R^3$ is 2-cyclopentylethyl and $R^2$ for a compound corresponds in each case to a group in Table A.

Table 619

Compounds of the formula I.A, in which $R^1$ is methyl, Z is oxygen and $R^3$ is 2-cyclopentylethyl and $R^2$ for a compound corresponds in each case to a group in Table A.

Table 620

Compounds of the formula I.B, in which $R^1$ is methyl, Z is oxygen and $R^3$ is 2-cyclopentylethyl and $R^2$ for a compound corresponds in each case to a group in Table A.

Table 621

Compounds of the formula I.A, in which $R^1$ is methyl, Z is sulfur and $R^3$ is 2-cyclopentylethyl and $R^2$ for a compound corresponds in each case to a group in Table A.

Table 622

Compounds of the formula I.B, in which $R^1$ is methyl, Z is sulfur and $R^3$ is 2-cyclopentylethyl and $R^2$ for a compound corresponds in each case to a group in Table A.

Table 623

Compounds of the formula I.A, in which $R^1$ is methyl, Z is NH and $R^3$ is 2-cyclopentylethyl and $R^2$ for a compound corresponds in each case to a group in Table A.

Table 624

Compounds of the formula I.B, in which $R^1$ is methyl, Z is NH and $R^3$ is 2-cyclopentylethyl and $R^2$ for a compound corresponds in each case to a group in Table A.

Table 625

Compounds of the formula I.A, in which $R^1$ is ethyl, Z is oxygen and $R^3$ is 2-cyclopentylethyl and $R^2$ for a compound corresponds in each case to a group in Table A.

Table 626

Compounds of the formula I.B, in which $R^1$ is ethyl, Z is oxygen and $R^3$ is 2-cyclopentylethyl and $R^2$ for a compound corresponds in each case to a group in Table A.

Table 627

Compounds of the formula I.A, in which $R^1$ is ethyl, Z is sulfur and $R^3$ is 2-cyclopentylethyl and $R^2$ for a compound corresponds in each case to a group in Table A.

Table 628

Compounds of the formula I.B, in which $R^1$ is ethyl, Z is sulfur and $R^3$ is 2-cyclopentylethyl and $R^2$ for a compound corresponds in each case to a group in Table A.

Table 629

Compounds of the formula I.A, in which $R^1$ is ethyl, Z is NH and $R^3$ is 2-cyclopentylethyl and $R^2$ for a compound corresponds in each case to a group in Table A.

Table 630

Compounds of the formula I.B, in which $R^1$ is ethyl, Z is NH and $R^3$ is 2-cyclopentylethyl and $R^2$ for a compound corresponds in each case to a group in Table A.

Table 631

Compounds of the formula I.A, in which $R^1$ is isopropyl, Z is oxygen and $R^3$ is 2-cyclopentylethyl and $R^2$ for a compound corresponds in each case to a group in Table A.

Table 632

Compounds of the formula I.B, in which $R^1$ is isopropyl, Z is oxygen and $R^3$ is 2-cyclopentylethyl and $R^2$ for a compound corresponds in each case to a group in Table A.

Table 633

Compounds of the formula I.A, in which $R^1$ is isopropyl, Z is sulfur and $R^3$ is 2-cyclopentylethyl and $R^2$ for a compound corresponds in each case to a group in Table A.

Table 634

Compounds of the formula I.B, in which $R^1$ is isopropyl, Z is sulfur and $R^3$ is 2-cyclopentylethyl and $R^2$ for a compound corresponds in each case to a group in Table A.

Table 635

Compounds of the formula I.A, in which $R^1$ is isopropyl, Z is NH and $R^3$ is 2-cyclopentylethyl and $R^2$ for a compound corresponds in each case to a group in Table A.

Table 636

Compounds of the formula I.B, in which $R^1$ is isopropyl, Z is NH and $R^3$ is 2-cyclopentylethyl and $R^2$ for a compound corresponds in each case to a group in Table A.

Table 637

Compounds of the formula I.A, in which $R^1$ is hydrogen, Z is oxygen and $R^3$ is 2-cyclohexylethyl and $R^2$ for a compound corresponds in each case to a group in Table A.

Table 638

Compounds of the formula I.B, in which $R^1$ is hydrogen, Z is oxygen and $R^3$ is 2-cyclohexylethyl and $R^2$ for a compound corresponds in each case to a group in Table A.

Table 639

Compounds of the formula I.A, in which $R^1$ is hydrogen, Z is sulfur and $R^3$ is 2-cyclohexylethyl and $R^2$ for a compound corresponds in each case to a group in Table A.

Table 640

Compounds of the formula I.B, in which $R^1$ is hydrogen, Z is sulfur and $R^3$ is 2-cyclohexylethyl and $R^2$ for a compound corresponds in each case to a group in Table A.

Table 641

Compounds of the formula I.A, in which $R^1$ is hydrogen, Z is NH and $R^3$ is 2-cyclohexylethyl and $R^2$ for a compound corresponds in each case to a group in Table A.

Table 642

Compounds of the formula I.B, in which $R^1$ is hydrogen, Z is NH and $R^3$ is 2-cyclohexylethyl and $R^2$ for a compound corresponds in each case to a group in Table A.

Table 643

Compounds of the formula I.A, in which $R^1$ is methyl, Z is oxygen and $R^3$ is 2-cyclohexylethyl and $R^2$ for a compound corresponds in each case to a group in Table A.

Table 644

Compounds of the formula I.B, in which $R^1$ is methyl, Z is oxygen and $R^3$ is 2-cyclohexylethyl and $R^2$ for a compound corresponds in each case to a group in Table A.

Table 645

Compounds of the formula I.A, in which $R^1$ is methyl, Z is sulfur and $R^3$ is 2-cyclohexylethyl and $R^2$ for a compound corresponds in each case to a group in Table A.

Table 646

Compounds of the formula I.B, in which $R^1$ is methyl, Z is sulfur and $R^3$ is 2-cyclohexylethyl and $R^2$ for a compound corresponds in each case to a group in Table A.

Table 647

Compounds of the formula I.A, in which $R^1$ is methyl, Z is NH and $R^3$ is 2-cyclohexylethyl and $R^2$ for a compound corresponds in each case to a group in Table A.

Table 648

Compounds of the formula I.B, in which $R^1$ is methyl, Z is NH and $R^3$ is 2-cyclohexylethyl and $R^2$ for a compound corresponds in each case to a group in Table A.

Table 649

Compounds of the formula I.A, in which $R^1$ is ethyl, Z is oxygen and $R^3$ is 2-cyclohexylethyl and $R^2$ for a compound corresponds in each case to a group in Table A.

Table 650

Compounds of the formula I.B, in which $R^1$ is ethyl, Z is oxygen and $R^3$ is 2-cyclohexylethyl and $R^2$ for a compound corresponds in each case to a group in Table A.

Table 651

Compounds of the formula I.A, in which $R^1$ is ethyl, Z is sulfur and $R^3$ is 2-cyclohexylethyl and $R^2$ for a compound corresponds in each case to a group in Table A.

Table 652

Compounds of the formula I.B, in which $R^1$ is ethyl, Z is sulfur and $R^3$ is 2-cyclohexylethyl and $R^2$ for a compound corresponds in each case to a group in Table A.

Table 653

Compounds of the formula I.A, in which $R^1$ is ethyl, Z is NH and $R^3$ is 2-cyclohexylethyl and $R^2$ for a compound corresponds in each case to a group in Table A.

Table 654

Compounds of the formula I.B, in which $R^1$ is ethyl, Z is NH and $R^3$ is 2-cyclohexylethyl and $R^2$ for a compound corresponds in each case to a group in Table A.

Table 655

Compounds of the formula I.A, in which $R^1$ is isopropyl, Z is oxygen and $R^3$ is 2-cyclohexylethyl and $R^2$ for a compound corresponds in each case to a group in Table A.

Table 656

Compounds of the formula I.B, in which $R^1$ is isopropyl, Z is oxygen and $R^3$ is 2-cyclohexylethyl and $R^2$ for a compound corresponds in each case to a group in Table A.

Table 657

Compounds of the formula I.A, in which $R^1$ is isopropyl, Z is sulfur and $R^3$ is 2-cyclohexylethyl and $R^2$ for a compound corresponds in each case to a group in Table A.

Table 658

Compounds of the formula I.B, in which $R^1$ is isopropyl, Z is sulfur and $R^3$ is 2-cyclohexylethyl and $R^2$ for a compound corresponds in each case to a group in Table A.

Table 659

Compounds of the formula I.A, in which $R^1$ is isopropyl, Z is NH and $R^3$ is 2-cyclohexylethyl and $R^2$ for a compound corresponds in each case to a group in Table A.

Table 660

Compounds of the formula I.B, in which $R^1$ is isopropyl, Z is NH and $R^3$ is 2-cyclohexylethyl and $R^2$ for a compound corresponds in each case to a group in Table A.

Table 661

Compounds of the formula I.A, in which $R^1$ is hydrogen, Z is oxygen and $R^3$ is difluoromethyl and $R^2$ for a compound corresponds in each case to a group in Table A.

Table 662

Compounds of the formula I.B, in which $R^1$ is hydrogen, Z is oxygen and $R^3$ is difluoromethyl and $R^2$ for a compound corresponds in each case to a group in Table A.

Table 663

Compounds of the formula I.A, in which $R^1$ is hydrogen, Z is sulfur and $R^3$ is difluoromethyl and $R^2$ for a compound corresponds in each case to a group in Table A.

Table 664

Compounds of the formula I.B, in which $R^1$ is hydrogen, Z is sulfur and $R^3$ is difluoromethyl and $R^2$ for a compound corresponds in each case to a group in Table A.

Table 665

Compounds of the formula I.A, in which $R^1$ is hydrogen, Z is NH and $R^3$ is difluoromethyl and $R^2$ for a compound corresponds in each case to a group in Table A.

Table 666

Compounds of the formula I.B, in which $R^1$ is hydrogen, Z is NH and $R^3$ is difluoromethyl and $R^2$ for a compound corresponds in each case to a group in Table A.

Table 667

Compounds of the formula I.A, in which $R^1$ is methyl, Z is oxygen and $R^3$ is difluoromethyl and $R^2$ for a compound corresponds in each case to a group in Table A.

Table 668

Compounds of the formula I.B, in which $R^1$ is methyl, Z is oxygen and $R^3$ is difluoromethyl and $R^2$ for a compound corresponds in each case to a group in Table A.

Table 669

Compounds of the formula I.A, in which $R^1$ is methyl, Z is sulfur and $R^3$ is difluoromethyl and $R^2$ for a compound corresponds in each case to a group in Table A.

Table 670

Compounds of the formula I.B, in which $R^1$ is methyl, Z is sulfur and $R^3$ is difluoromethyl and $R^2$ for a compound corresponds in each case to a group in Table A.

Table 671

Compounds of the formula I.A, in which $R^1$ is methyl, Z is NH and $R^3$ is difluoromethyl and $R^2$ for a compound corresponds in each case to a group in Table A.

Table 672

Compounds of the formula I.B, in which $R^1$ is methyl, Z is NH and $R^3$ is difluoromethyl and $R^2$ for a compound corresponds in each case to a group in Table A.

Table 673

Compounds of the formula I.A, in which $R^1$ is ethyl, Z is oxygen and $R^3$ is difluoromethyl and $R^2$ for a compound corresponds in each case to a group in Table A.

Table 674

Compounds of the formula I.B, in which $R^1$ is ethyl, Z is oxygen and $R^3$ is difluoromethyl and $R^2$ for a compound corresponds in each case to a group in Table A.

Table 675

Compounds of the formula I.A, in which $R^1$ is ethyl, Z is sulfur and $R^3$ is difluoromethyl and $R^2$ for a compound corresponds in each case to a group in Table A.

Table 676

Compounds of the formula I.B, in which $R^1$ is ethyl, Z is sulfur and $R^3$ is difluoromethyl and $R^2$ for a compound corresponds in each case to a group in Table A.

Table 677

Compounds of the formula I.A, in which $R^1$ is ethyl, Z is NH and $R^3$ is difluoromethyl and $R^2$ for a compound corresponds in each case to a group in Table A.

Table 678

Compounds of the formula I.B, in which $R^1$ is ethyl, Z is NH and $R^3$ is difluoromethyl and $R^2$ for a compound corresponds in each case to a group in Table A.

Table 679

Compounds of the formula I.A, in which $R^1$ is isopropyl, Z is oxygen and $R^3$ is difluoromethyl and $R^2$ for a compound corresponds in each case to a group in Table A.

Table 680

Compounds of the formula I.B, in which $R^1$ is isopropyl, Z is oxygen and $R^3$ is difluoromethyl and $R^2$ for a compound corresponds in each case to a group in Table A.

Table 681

Compounds of the formula I.A, in which $R^1$ is isopropyl, Z is sulfur and $R^3$ is difluoromethyl and $R^2$ for a compound corresponds in each case to a group in Table A.

Table 682

Compounds of the formula I.B, in which $R^1$ is isopropyl, Z is sulfur and $R^3$ is difluoromethyl and $R^2$ for a compound corresponds in each case to a group in Table A.

Table 683

Compounds of the formula I.A, in which $R^1$ is isopropyl, Z is NH and $R^3$ is difluoromethyl and $R^2$ for a compound corresponds in each case to a group in Table A.

Table 684

Compounds of the formula I.B, in which $R^1$ is isopropyl, Z is NH and $R^3$ is difluoromethyl and $R^2$ for a compound corresponds in each case to a group in Table A.

Table 685

Compounds of the formula I.A, in which $R^1$ is hydrogen, Z is oxygen and $R^3$ is 2-fluoroethyl and $R^2$ for a compound corresponds in each case to a group in Table A.

Table 686

Compounds of the formula I.B, in which $R^1$ is hydrogen, Z is oxygen and $R^3$ is 2-fluoroethyl and $R^2$ for a compound corresponds in each case to a group in Table A.

Table 687

Compounds of the formula I.A, in which $R^1$ is hydrogen, Z is sulfur and $R^3$ is 2-fluoroethyl and $R^2$ for a compound corresponds in each case to a group in Table A.

Table 688

Compounds of the formula I.B, in which $R^1$ is hydrogen, Z is sulfur and $R^3$ is 2-fluoroethyl and $R^2$ for a compound corresponds in each case to a group in Table A.

Table 689

Compounds of the formula I.A, in which $R^1$ is hydrogen, Z is NH and $R^3$ is 2-fluoroethyl and $R^2$ for a compound corresponds in each case to a group in Table A.

Table 690

Compounds of the formula I.B, in which $R^1$ is hydrogen, Z is NH and $R^3$ is 2-fluoroethyl and $R^2$ for a compound corresponds in each case to a group in Table A.

Table 691

Compounds of the formula I.A, in which $R^1$ is methyl, Z is oxygen and $R^3$ is 2-fluoroethyl and $R^2$ for a compound corresponds in each case to a group in Table A.

Table 692

Compounds of the formula I.B, in which $R^1$ is methyl, Z is oxygen and $R^3$ is 2-fluoroethyl and $R^2$ for a compound corresponds in each case to a group in Table A.

Table 693

Compounds of the formula I.A, in which $R^1$ is methyl, Z is sulfur and $R^3$ is 2-fluoroethyl and $R^2$ for a compound corresponds in each case to a group in Table A.

Table 694

Compounds of the formula I.B, in which $R^1$ is methyl, Z is sulfur and $R^3$ is 2-fluoroethyl and $R^2$ for a compound corresponds in each case to a group in Table A.

Table 695

Compounds of the formula I.A, in which $R^1$ is methyl, Z is NH and $R^3$ is 2-fluoroethyl and $R^2$ for a compound corresponds in each case to a group in Table A.

Table 696

Compounds of the formula I.B, in which $R^1$ is methyl, Z is NH and $R^3$ is 2-fluoroethyl and $R^2$ for a compound corresponds in each case to a group in Table A.

Table 697

Compounds of the formula I.A, in which $R^1$ is ethyl, Z is oxygen and $R^3$ is 2-fluoroethyl and $R^2$ for a compound corresponds in each case to a group in Table A.

Table 698

Compounds of the formula I.B, in which $R^1$ is ethyl, Z is oxygen and $R^3$ is 2-fluoroethyl and $R^2$ for a compound corresponds in each case to a group in Table A.

Table 699

Compounds of the formula I.A, in which $R^1$ is ethyl, Z is sulfur and $R^3$ is 2-fluoroethyl and $R^2$ for a compound corresponds in each case to a group in Table A.

Table 700

Compounds of the formula I.B, in which $R^1$ is ethyl, Z is sulfur and $R^3$ is 2-fluoroethyl and $R^2$ for a compound corresponds in each case to a group in Table A.

Table 701

Compounds of the formula I.A, in which $R^1$ is ethyl, Z is NH and $R^3$ is 2-fluoroethyl and $R^2$ for a compound corresponds in each case to a group in Table A.

Table 702

Compounds of the formula I.B, in which $R^1$ is ethyl, Z is NH and $R^3$ is 2-fluoroethyl and $R^2$ for a compound corresponds in each case to a group in Table A.

Table 703

Compounds of the formula I.A, in which $R^1$ is isopropyl, Z is oxygen and $R^3$ is 2-fluoroethyl and $R^2$ for a compound corresponds in each case to a group in Table A.

Table 704

Compounds of the formula I.B, in which $R^1$ is isopropyl, Z is oxygen and $R^3$ is 2-fluoroethyl and $R^2$ for a compound corresponds in each case to a group in Table A.

Table 705

Compounds of the formula I.A, in which $R^1$ is isopropyl, Z is sulfur and $R^3$ is 2-fluoroethyl and $R^2$ for a compound corresponds in each case to a group in Table A.

Table 706

Compounds of the formula I.B, in which $R^1$ is isopropyl, Z is sulfur and $R^3$ is 2-fluoroethyl and $R^2$ for a compound corresponds in each case to a group in Table A.

Table 707

Compounds of the formula I.A, in which $R^1$ is isopropyl, Z is NH and $R^3$ is 2-fluoroethyl and $R^2$ for a compound corresponds in each case to a group in Table A.

Table 708

Compounds of the formula I.B, in which $R^1$ is isopropyl, Z is NH and $R^3$ is 2-fluoroethyl and $R^2$ for a compound corresponds in each case to a group in Table A.

Table 709

Compounds of the formula I.A, in which $R^1$ is hydrogen, Z is oxygen and $R^3$ is 3-fluoropropyl and R2 for a compound corresponds in each case to a group in Table A.

Table 710

Compounds of the formula I.B, in which $R^1$ is hydrogen, Z is oxygen and $R^3$ is 3-fluoropropyl and $R^2$ for a compound corresponds in each case to a group in Table A.

Table 711

Compounds of the formula I.A, in which $R^1$ is hydrogen, Z is sulfur and $R^3$ is 3-fluoropropyl and $R^2$ for a compound corresponds in each case to a group in Table A.

Table 712

Compounds of the formula I.B, in which $R^1$ is hydrogen, Z is sulfur and $R^3$ is 3-fluoropropyl and $R^2$ for a compound corresponds in each case to a group in Table A.

Table 713

Compounds of the formula I.A, in which $R^1$ is hydrogen, Z is NH and $R^3$ is 3-fluoropropyl and $R^2$ for a compound corresponds in each case to a group in Table A.

Table 714

Compounds of the formula I.B, in which $R^1$ is hydrogen, Z is NH and $R^3$ is 3-fluoropropyl and $R^2$ for a compound corresponds in each case to a group in Table A.

Table 715

Compounds of the formula I.A, in which $R^1$ is methyl, Z is oxygen and $R^3$ is 3-fluoropropyl and $R^2$ for a compound corresponds in each case to a group in Table A.

Table 716

Compounds of the formula I.B, in which $R^1$ is methyl, Z is oxygen and $R^3$ is 3-fluoropropyl and $R^2$ for a compound corresponds in each case to a group in Table A.

Table 717

Compounds of the formula I.A, in which $R^1$ is methyl, Z is sulfur and $R^3$ is 3-fluoropropyl and $R^2$ for a compound corresponds in each case to a group in Table A.

Table 718

Compounds of the formula I.B, in which $R^1$ is methyl, Z is sulfur and $R^3$ is 3-fluoropropyl and $R^2$ for a compound corresponds in each case to a group in Table A.

Table 719

Compounds of the formula I.A, in which $R^1$ is methyl, Z is NH and $R^3$ is 3-fluoropropyl and $R^2$ for a compound corresponds in each case to a group in Table A.

Table 720

Compounds of the formula I.B, in which $R^1$ is methyl, Z is NH and $R^3$ is 3-fluoropropyl and $R^2$ for a compound corresponds in each case to a group in Table A.

Table 721

Compounds of the formula I.A, in which $R^1$ is ethyl, Z is oxygen and $R^3$ is 3-fluoropropyl and $R^2$ for a compound corresponds in each case to a group in Table A.

Table 722

Compounds of the formula I.B, in which $R^1$ is ethyl, Z is oxygen and $R^3$ is 3-fluoropropyl and $R^2$ for a compound corresponds in each case to a group in Table A.

Table 723

Compounds of the formula I.A, in which $R^1$ is ethyl, Z is sulfur and $R^3$ is 3-fluoropropyl and $R^2$ for a compound corresponds in each case to a group in Table A.

Table 724

Compounds of the formula I.B, in which $R^1$ is ethyl, Z is sulfur and $R^3$ is 3-fluoropropyl and $R^2$ for a compound corresponds in each case to a group in Table A.

Table 725

Compounds of the formula I.A, in which $R^1$ is ethyl, Z is NH and $R^3$ is 3-fluoropropyl and $R^2$ for a compound corresponds in each case to a group in Table A.

Table 726

Compounds of the formula I.B, in which $R^1$ is ethyl, Z is NH and $R^3$ is 3-fluoropropyl and $R^2$ for a compound corresponds in each case to a group in Table A.

Table 727

Compounds of the formula I.A, in which $R^1$ is isopropyl, Z is oxygen and $R^3$ is 3-fluoropropyl and $R^2$ for a compound corresponds in each case to a group in Table A.

Table 728

Compounds of the formula I.B, in which $R^1$ is isopropyl, Z is oxygen and $R^3$ is 3-fluoropropyl and $R^2$ for a compound corresponds in each case to a group in Table A.

Table 729

Compounds of the formula I.A, in which $R^1$ is isopropyl, Z is sulfur and $R^3$ is 3-fluoropropyl and $R^2$ for a compound corresponds in each case to a group in Table A.

Table 730

Compounds of the formula I.B, in which $R^1$ is isopropyl, Z is sulfur and $R^3$ is 3-fluoropropyl and $R^2$ for a compound corresponds in each case to a group in Table A.

Table 731

Compounds of the formula I.A, in which $R^1$ is isopropyl, Z is NH and $R^3$ is 3-fluoropropyl and $R^2$ for a compound corresponds in each case to a group in Table A.

Table 732

Compounds of the formula I.B, in which $R^1$ is isopropyl, Z is NH and $R^3$ is 3-fluoropropyl and $R^2$ for a compound corresponds in each case to a group in Table A.

Table 733

Compounds of the formula I.A, in which $R^1$ is hydrogen, Z is oxygen and $R^3$ is 2,2-difluoroethyl and $R^2$ for a compound corresponds in each case to a group in Table A.

Table 734

Compounds of the formula I.B, in which $R^1$ is hydrogen, Z is oxygen and $R^3$ is 2,2-difluoroethyl and $R^2$ for a compound corresponds in each case to a group in Table A.

Table 735

Compounds of the formula I.A, in which $R^1$ is hydrogen, Z is sulfur and $R^3$ is 2,2-difluoroethyl and $R^2$ for a compound corresponds in each case to a group in Table A.

Table 736

Compounds of the formula I.B, in which $R^1$ is hydrogen, Z is sulfur and $R^3$ is 2,2-difluoroethyl and $R^2$ for a compound corresponds in each case to a group in Table A.

Table 737

Compounds of the formula I.A, in which $R^1$ is hydrogen, Z is NH and $R^3$ is 2,2-difluoroethyl and $R^2$ for a compound corresponds in each case to a group in Table A.

Table 738

Compounds of the formula I.B, in which $R^1$ is hydrogen, Z is NH and $R^3$ is 2,2-difluoroethyl and $R^2$ for a compound corresponds in each case to a group in Table A.

Table 739

Compounds of the formula I.A, in which $R^1$ is methyl, Z is oxygen and $R^3$ is 2,2-difluoroethyl and $R^2$ for a compound corresponds in each case to a group in Table A.

Table 740

Compounds of the formula I.B, in which $R^1$ is methyl, Z is oxygen and $R^3$ is 2,2-difluoroethyl and $R^2$ for a compound corresponds in each case to a group in Table A.

Table 741

Compounds of the formula I.A, in which $R^1$ is methyl, Z is sulfur and $R^3$ is 2,2-difluoroethyl and $R^2$ for a compound corresponds in each case to a group in Table A.

Table 742

Compounds of the formula I.B, in which $R^1$ is methyl, Z is sulfur and $R^3$ is 2,2-difluoroethyl and $R^2$ for a compound corresponds in each case to a group in Table A.

Table 743

Compounds of the formula I.A, in which $R^1$ is methyl, Z is NH and $R^3$ is 2,2-difluoroethyl and $R^2$ for a compound corresponds in each case to a group in Table A.

Table 744

Compounds of the formula I.B, in which $R^1$ is methyl, Z is NH and $R^3$ is 2,2-difluoroethyl and $R^2$ for a compound corresponds in each case to a group in Table A.

Table 745

Compounds of the formula I.A, in which $R^1$ is ethyl, Z is oxygen and $R^3$ is 2,2-difluoroethyl and $R^2$ for a compound corresponds in each case to a group in Table A.

Table 746

Compounds of the formula I.B, in which $R^1$ is ethyl, Z is oxygen and $R^3$ is 2,2-difluoroethyl and $R^2$ for a compound corresponds in each case to a group in Table A.

Table 747

Compounds of the formula I.A, in which $R^1$ is ethyl, Z is sulfur and $R^3$ is 2,2-difluoroethyl and $R^2$ for a compound corresponds in each case to a group in Table A.

Table 748

Compounds of the formula I.B, in which $R^1$ is ethyl, Z is sulfur and $R^3$ is 2,2-difluoroethyl and $R^2$ for a compound corresponds in each case to a group in Table A.

Table 749

Compounds of the formula I.A, in which $R^1$ is ethyl, Z is NH and $R^3$ is 2,2-difluoroethyl and $R^2$ for a compound corresponds in each case to a group in Table A.

Table 750

Compounds of the formula I.B, in which $R^1$ is ethyl, Z is NH and $R^3$ is 2,2-difluoroethyl and $R^2$ for a compound corresponds in each case to a group in Table A.

Table 751

Compounds of the formula I.A, in which $R^1$ is isopropyl, Z is oxygen and $R^3$ is 2,2-difluoroethyl and $R^2$ for a compound corresponds in each case to a group in Table A.

Table 752

Compounds of the formula I.B, in which $R^1$ is isopropyl, Z is oxygen and $R^3$ is 2,2-difluoroethyl and $R^2$ for a compound corresponds in each case to a group in Table A.

Table 753

Compounds of the formula I.A, in which $R^1$ is isopropyl, Z is sulfur and $R^3$ is 2,2-difluoroethyl and $R^2$ for a compound corresponds in each case to a group in Table A.

Table 754

Compounds of the formula I.B, in which $R^1$ is isopropyl, Z is sulfur and $R^3$ is 2,2-difluoroethyl and $R^2$ for a compound corresponds in each case to a group in Table A.

Table 755

Compounds of the formula I.A, in which $R^1$ is isopropyl, Z is NH and $R^3$ is 2,2-difluoroethyl and $R^2$ for a compound corresponds in each case to a group in Table A.

Table 756

Compounds of the formula I.B, in which $R^1$ is isopropyl, Z is NH and $R^3$ is 2,2-difluoroethyl and $R^2$ for a compound corresponds in each case to a group in Table A.

Table 757

Compounds of the formula I.A, in which $R^1$ is hydrogen, Z is oxygen and $R^3$ is 2,2,2-trifluoroethyl and $R^2$ for a compound corresponds in each case to a group in Table A.

Table 758

Compounds of the formula I.B, in which $R^1$ is hydrogen, Z is oxygen and $R^3$ is 2,2,2-trifluoroethyl and $R^2$ for a compound corresponds in each case to a group in Table A.

Table 759

Compounds of the formula I.A, in which $R^1$ is hydrogen, Z is sulfur and $R^3$ is 2,2,2-trifluoroethyl and $R^2$ for a compound corresponds in each case to a group in Table A.

Table 760

Compounds of the formula I.B, in which $R^1$ is hydrogen, Z is sulfur and $R^3$ is 2,2,2-trifluoroethyl and $R^2$ for a compound corresponds in each case to a group in Table A.

Table 761

Compounds of the formula I.A, in which $R^1$ is hydrogen, Z is NH and $R^3$ is 2,2,2-trifluoroethyl and $R^2$ for a compound corresponds in each case to a group in Table A.

Table 762

Compounds of the formula I.B, in which $R^1$ is hydrogen, Z is NH and $R^3$ is 2,2,2-trifluoroethyl and $R^2$ for a compound corresponds in each case to a group in Table A.

Table 763

Compounds of the formula I.A, in which $R^1$ is methyl, Z is oxygen and $R^3$ is 2,2,2-trifluoroethyl and $R^2$ for a compound corresponds in each case to a group in Table A.

Table 764

Compounds of the formula I.B, in which $R^1$ is methyl, Z is oxygen and $R^3$ is 2,2,2-trifluoroethyl and $R^2$ for a compound corresponds in each case to a group in Table A.

Table 765

Compounds of the formula I.A, in which $R^1$ is methyl, Z is sulfur and $R^3$ is 2,2,2-trifluoroethyl and $R^2$ for a compound corresponds in each case to a group in Table A.

Table 766

Compounds of the formula I.B, in which $R^1$ is methyl, Z is sulfur and $R^3$ is 2,2,2-trifluoroethyl and $R^2$ for a compound corresponds in each case to a group in Table A.

Table 767

Compounds of the formula I.A, in which $R^1$ is methyl, Z is NH and $R^3$ is 2,2,2-trifluoroethyl and $R^2$ for a compound corresponds in each case to a group in Table A.

Table 768

Compounds of the formula I.B, in which $R^1$ is methyl, Z is NH and $R^3$ is 2,2,2-trifluoroethyl and $R^2$ for a compound corresponds in each case to a group in Table A.

Table 769

Compounds of the formula I.A, in which $R^1$ and $R^3$ is oxygen and $R^3$ is 2,2,2-trifluoroethyl and $R^2$ for a compound corresponds in each case to a group in Table A.

Table 770

Compounds of the formula I.B, in which $R^1$ is ethyl, Z is oxygen and $R^3$ is 2,2,2-trifluoroethyl and $R^2$ for a compound corresponds in each case to a group in Table A.

Table 771

Compounds of the formula I.A, in which $R^1$ is ethyl, Z is sulfur and $R^3$ is 2,2,2-trifluoroethyl and $R^2$ for a compound corresponds in each case to a group in Table A.

Table 772

Compounds of the formula I.B, in which $R^1$ is ethyl, Z is sulfur and $R^3$ is 2,2,2-trifluoroethyl and $R^2$ for a compound corresponds in each case to a group in Table A.

Table 773

Compounds of the formula I.A, in which $R^1$ is ethyl, Z is NH and $R^3$ is 2,2,2-trifluoroethyl and $R^2$ for a compound corresponds in each case to a group in Table A.

Table 774

Compounds of the formula I.B, in which $R^1$ is ethyl, Z is NH and $R^3$ is 2,2,2-trifluoroethyl and $R^2$ for a compound corresponds in each case to a group in Table A.

Table 775

Compounds of the formula I.A, in which $R^1$ is isopropyl, Z is oxygen and $R^3$ is 2,2,2-trifluoroethyl and $R^2$ for a compound corresponds in each case to a group in Table A.

Table 776

Compounds of the formula I.B, in which $R^1$ is isopropyl, Z is oxygen and $R^3$ is 2,2,2-trifluoroethyl and $R^2$ for a compound corresponds in each case to a group in Table A.

Table 777

Compounds of the formula I.A, in which $R^1$ is isopropyl, Z is sulfur and $R^3$ is 2,2,2-trifluoroethyl and $R^2$ for a compound corresponds in each case to a group in Table A.

Table 778

Compounds of the formula I.B, in which $R^1$ is isopropyl, Z is sulfur and $R^3$ is 2,2,2-trifluoroethyl and $R^2$ for a compound corresponds in each case to a group in Table A.

Table 779

Compounds of the formula I.A, in which $R^1$ is isopropyl, Z is NH and $R^3$ is 2,2,2-trifluoroethyl and $R^2$ for a compound corresponds in each case to a group in Table A.

Table 780

Compounds of the formula I.B, in which $R^1$ is isopropyl, Z is NH and $R^3$ is 2,2,2-trifluoroethyl and $R^2$ for a compound corresponds in each case to a group in Table A.

Table 781

Compounds of the formula I.A, in which $R^1$ is hydrogen, Z is oxygen and $R^3$ is 2-bromoethyl and $R^2$ for a compound corresponds in each case to a group in Table A.

Table 782

Compounds of the formula I.B, in which $R^1$ is hydrogen, Z is oxygen and $R^3$ is 2-bromoethyl and $R^2$ for a compound corresponds in each case to a group in Table A.

Table 783

Compounds of the formula I.A, in which $R^1$ is hydrogen, Z is sulfur and $R^3$ is 2-bromoethyl and $R^2$ for a compound corresponds in each case to a group in Table A.

Table 784

Compounds of the formula I.B, in which $R^1$ is hydrogen, Z is sulfur and $R^3$ is 2-bromoethyl and $R^2$ for a compound corresponds in each case to a group in Table A.

Table 785

Compounds of the formula I.A, in which $R^1$ is hydrogen, Z is NH and $R^3$ is 2-bromoethyl and $R^2$ for a compound corresponds in each case to a group in Table A.

Table 786

Compounds of the formula I.B, in which $R^1$ is hydrogen, Z is NH and $R^3$ is 2-bromoethyl and $R^2$ for a compound corresponds in each case to a group in Table A.

Table 787

Compounds of the formula I.A, in which $R^1$ is methyl, Z is oxygen and $R^3$ is 2-bromoethyl and $R^2$ for a compound corresponds in each case to a group in Table A.

Table 788

Compounds of the formula I.B, in which $R^1$ is methyl, Z is oxygen and $R^3$ is 2-bromoethyl and $R^2$ for a compound corresponds in each case to a group in Table A.

Table 789

Compounds of the formula I.A, in which $R^1$ is methyl, Z is sulfur and $R^3$ is 2-bromoethyl and $R^2$ for a compound corresponds in each case to a group in Table A.

Table 790

Compounds of the formula I.B, in which $R^1$ is methyl, Z is sulfur and $R^3$ is 2-bromoethyl and $R^2$ for a compound corresponds in each case to a group in Table A.

Table 791

Compounds of the formula I.A, in which $R^1$ is methyl, Z is NH and $R^3$ is 2-bromoethyl and $R^2$ for a compound corresponds in each case to a group in Table A.

Table 792

Compounds of the formula I.B, in which $R^1$ is methyl, Z is NH and $R^3$ is 2-bromoethyl and $R^2$ for a compound corresponds in each case to a group in Table A.

Table 793

Compounds of the formula I.A, in which $R^1$ is ethyl, Z is oxygen and $R^3$ is 2-bromoethyl and $R^2$ for a compound corresponds in each case to a group in Table A.

Table 794

Compounds of the formula I.B, in which $R^1$ is ethyl, Z is oxygen and $R^3$ is 2-bromoethyl and $R^2$ for a compound corresponds in each case to a group in Table A.

Table 795

Compounds of the formula I.A, in which $R^1$ is ethyl, Z is sulfur and $R^3$ is 2-bromoethyl and $R^2$ for a compound corresponds in each case to a group in Table A.

Table 796

Compounds of the formula I.B, in which $R^1$ is ethyl, Z is sulfur and $R^3$ is 2-bromoethyl and $R^2$ for a compound corresponds in each case to a group in Table A.

Table 797

Compounds of the formula I.A, in which $R^1$ is ethyl, Z is NH and $R^3$ is 2-bromoethyl and $R^2$ for a compound corresponds in each case to a group in Table A.

Table 798

Compounds of the formula I.B, in which $R^1$ is ethyl, Z is NH and $R^3$ is 2-bromoethyl and $R^2$ for a compound corresponds in each case to a group in Table A.

Table 799

Compounds of the formula I.A, in which $R^1$ is isopropyl, Z is oxygen and $R^3$ is 2-bromoethyl and $R^2$ for a compound corresponds in each case to a group in Table A.

Table 800

Compounds of the formula I.B, in which $R^1$ is isopropyl, Z is oxygen and $R^3$ is 2-bromoethyl and $R^2$ for a compound corresponds in each case to a group in Table A.

Table 801

Compounds of the formula I.A, in which $R^1$ is isopropyl, Z is sulfur and $R^3$ is 2-bromoethyl and $R^2$ for a compound corresponds in each case to a group in Table A.

Table 802

Compounds of the formula I.B, in which $R^1$ is isopropyl, Z is sulfur and $R^3$ is 2-bromoethyl and $R^2$ for a compound corresponds in each case to a group in Table A.

Table 803

Compounds of the formula I.A, in which $R^1$ is isopropyl, Z is NH and $R^3$ is 2-bromoethyl and $R^2$ for a compound corresponds in each case to a group in Table A.

Table 804

Compounds of the formula I.B, in which $R^1$ is isopropyl, Z is NH and $R^3$ is 2-bromoethyl and $R^2$ for a compound corresponds in each case to a group in Table A.

Table 805

Compounds of the formula I.A, in which $R^1$ is hydrogen, Z is oxygen and $R^3$ is 3-bromopropyl and $R^2$ for a compound corresponds in each case to a group in Table A.

Table 806

Compounds of the formula I.B, in which $R^1$ is hydrogen, Z is oxygen and $R^3$ is 3-bromopropyl and $R^2$ for a compound corresponds in each case to a group in Table A.

Table 807

Compounds of the formula I.A, in which $R^1$ is hydrogen, Z is sulfur and $R^3$ is 3-bromopropyl and $R^2$ for a compound corresponds in each case to a group in Table A.

Table 808

Compounds of the formula I.B, in which $R^1$ is hydrogen, Z is sulfur and $R^3$ is 3-bromopropyl and $R^2$ for a compound corresponds in each case to a group in Table A.

Table 809

Compounds of the formula I.A, in which $R^1$ is hydrogen, Z is NH and $R^3$ is 3-bromopropyl and $R^2$ for a compound corresponds in each case to a group in Table A.

Table 810

Compounds of the formula I.B, in which $R^1$ is hydrogen, Z is NH and $R^3$ is 3-bromopropyl and $R^2$ for a compound corresponds in each case to a group in Table A.

Table 811

Compounds of the formula I.A, in which $R^1$ is methyl, Z is oxygen and $R^3$ is 3-bromopropyl and $R^2$ for a compound corresponds in each case to a group in Table A.

Table 812

Compounds of the formula I.B, in which $R^1$ is methyl, Z is oxygen and $R^3$ is 3-bromopropyl and $R^2$ for a compound corresponds in each case to a group in Table A.

Table 813

Compounds of the formula I.A, in which $R^1$ is methyl, Z is sulfur and $R^3$ is 3-bromopropyl and $R^2$ for a compound corresponds in each case to a group in Table A.

Table 814

Compounds of the formula I.B, in which $R^1$ is methyl, Z is sulfur and $R^3$ is 3-bromopropyl and $R^2$ for a compound corresponds in each case to a group in Table A.

Table 815

Compounds of the formula I.A, in which $R^1$ is methyl, Z is NH and $R^3$ is 3-bromopropyl and $R^2$ for a compound corresponds in each case to a group in Table A.

Table 816

Compounds of the formula I.B, in which $R^1$ is methyl, Z is NH and $R^3$ is 3-bromopropyl and $R^2$ for a compound corresponds in each case to a group in Table A.

Table 817

Compounds of the formula I.A, in which $R^1$ is ethyl, Z is oxygen and $R^3$ is 3-bromopropyl and $R^2$ for a compound corresponds in each case to a group in Table A.

Table 818

Compounds of the formula I.B, in which $R^1$ is ethyl, Z is oxygen and $R^3$ is 3-bromopropyl and $R^2$ for a compound corresponds in each case to a group in Table A.

Table 819

Compounds of the formula I.A, in which $R^1$ is ethyl, Z is sulfur and $R^3$ is 3-bromopropyl and $R^2$ for a compound corresponds in each case to a group in Table A.

Table 820

Compounds of the formula I.B, in which $R^1$ is ethyl, Z is sulfur and $R^3$ is 3-bromopropyl and $R^2$ for a compound corresponds in each case to a group in Table A.

Table 821

Compounds of the formula I.A, in which $R^1$ is ethyl, Z is NH and $R^3$ is 3-bromopropyl and $R^2$ for a compound corresponds in each case to a group in Table A.

Table 822

Compounds of the formula I.B, in which $R^1$ is ethyl, Z is NH and $R^3$ is 3-bromopropyl and $R^2$ for a compound corresponds in each case to a group in Table A.

Table 823

Compounds of the formula I.A, in which $R^1$ is isopropyl, Z is oxygen and $R^3$ is 3-bromopropyl and $R^2$ for a compound corresponds in each case to a group in Table A.

Table 824

Compounds of the formula I.B, in which $R^1$ is isopropyl, Z is oxygen and $R^3$ is 3-bromopropyl and $R^2$ for a compound corresponds in each case to a group in Table A.

Table 825

Compounds of the formula I.A, in which $R^1$ is isopropyl, Z is sulfur and $R^3$ is 3-bromopropyl and $R^2$ for a compound corresponds in each case to a group in Table A.

Table 826

Compounds of the formula I.B, in which $R^1$ is isopropyl, Z is sulfur and $R^3$ is 3-bromopropyl and $R^2$ for a compound corresponds in each case to a group in Table A.

Table 827

Compounds of the formula I.A, in which $R^1$ is isopropyl, Z is NH and $R^3$ is 3-bromopropyl and $R^2$ for a compound corresponds in each case to a group in Table A.

Table 828

Compounds of the formula I.B, in which $R^1$ is isopropyl, Z is NH and $R^3$ is 3-bromopropyl and $R^2$ for a compound corresponds in each case to a group in Table A.

Table 829

Compounds of the formula I.A, in which $R^1$ is hydrogen, Z is oxygen and $R^3$ is 4-bromobutyl and $R^2$ for a compound corresponds in each case to a group in Table A.

Table 830

Compounds of the formula I.B, in which $R^1$ is hydrogen, Z is oxygen and $R^3$ is 4-bromobutyl and $R^2$ for a compound corresponds in each case to a group in Table A.

Table 831

Compounds of the formula I.A, in which $R^1$ is hydrogen, Z is sulfur and $R^3$ is 4-bromobutyl and $R^2$ for a compound corresponds in each case to a group in Table A.

Table 832

Compounds of the formula I.B, in which $R^1$ is hydrogen, Z is sulfur and $R^3$ is 4-bromobutyl and $R^2$ for a compound corresponds in each case to a group in Table A.

Table 833

Compounds of the formula I.A, in which $R^1$ is hydrogen, Z is NH and $R^3$ is 4-bromobutyl and $R^2$ for a compound corresponds in each case to a group in Table A.

Table 834

Compounds of the formula I.B, in which $R^1$ is hydrogen, Z is NH and $R^3$ is 4-bromobutyl and $R^2$ for a compound corresponds in each case to a group in Table A.

Table 835

Compounds of the formula I.A, in which $R^1$ is methyl, Z is oxygen and $R^3$ is 4-bromobutyl and $R^2$ for a compound corresponds in each case to a group in Table A.

Table 836

Compounds of the formula I.B, in which $R^1$ is methyl, Z is oxygen and $R^3$ is 4-bromobutyl and $R^2$ for a compound corresponds in each case to a group in Table A.

Table 837

Compounds of the formula I.A, in which $R^1$ is methyl, Z is sulfur and $R^3$ is 4-bromobutyl and $R^2$ for a compound corresponds in each case to a group in Table A.

Table 838

Compounds of the formula I.B, in which $R^1$ is methyl, Z is sulfur and $R^3$ is 4-bromobutyl and $R^2$ for a compound corresponds in each case to a group in Table A.

Table 839

Compounds of the formula I.A, in which $R^1$ is methyl, Z is NH and $R^3$ is 4-bromobutyl and $R^2$ for a compound corresponds in each case to a group in Table A.

Table 840

Compounds of the formula I.B, in which $R^1$ is methyl, Z is NH and $R^3$ is 4-bromobutyl and $R^2$ for a compound corresponds in each case to a group in Table A.

Table 841

Compounds of the formula I.A, in which $R^1$ is ethyl, Z is oxygen and $R^3$ is 4-bromobutyl and $R^2$ for a compound corresponds in each case to a group in Table A.

Table 842

Compounds of the formula I.B, in which $R^1$ is ethyl, Z is oxygen and $R^3$ is 4-bromobutyl and $R^2$ for a compound corresponds in each case to a group in Table A.

Table 843

Compounds of the formula I.A, in which $R^1$ is ethyl, Z is sulfur and $R^3$ is 4-bromobutyl and $R^2$ for a compound corresponds in each case to a group in Table A.

Table 844

Compounds of the formula I.B, in which $R^1$ is ethyl, Z is sulfur and $R^3$ is 4-bromobutyl and $R^2$ for a compound corresponds in each case to a group in Table A.

Table 845

Compounds of the formula I.A, in which $R^1$ is ethyl, Z is NH and $R^3$ is 4-bromobutyl and $R^2$ for a compound corresponds in each case to a group in Table A.

Table 846

Compounds of the formula I.B, in which $R^1$ is ethyl, Z is NH and $R^3$ is 4-bromobutyl and $R^2$ for a compound corresponds in each case to a group in Table A.

Table 847

Compounds of the formula I.A, in which $R^1$ is isopropyl, Z is oxygen and $R^3$ is 4-bromobutyl and $R^2$ for a compound corresponds in each case to a group in Table A.

Table 848

Compounds of the formula I.B, in which $R^1$ is isopropyl, Z is oxygen and $R^3$ is 4-bromobutyl and $R^2$ for a compound corresponds in each case to a group in Table A.

Table 849

Compounds of the formula I.A, in which $R^1$ is isopropyl, Z is sulfur and $R^3$ is 4-bromobutyl and $R^2$ for a compound corresponds in each case to a group in Table A.

Table 850

Compounds of the formula I.B, in which $R^1$ is isopropyl, Z is sulfur and $R^3$ is 4-bromobutyl and $R^2$ for a compound corresponds in each case to a group in Table A.

Table 851

Compounds of the formula I.A, in which $R^1$ is isopropyl, Z is NH and $R^3$ is 4-bromobutyl and $R^2$ for a compound corresponds in each case to a group in Table A.

Table 852

Compounds of the formula I.B, in which $R^1$ is isopropyl, Z is NH and $R^3$ is 4-bromobutyl and $R^2$ for a compound corresponds in each case to a group in Table A.

Table 853

Compounds of the formula I.A, in which $R^1$ is hydrogen, Z is oxygen and $R^3$ is 2-iodoethyl and $R^2$ for a compound corresponds in each case to a group in Table A.

Table 854

Compounds of the formula I.B, in which $R^1$ is hydrogen, Z is oxygen and $R^3$ is 2-iodoethyl and $R^2$ for a compound corresponds in each case to a group in Table A.

Table 855

Compounds of the formula I.A, in which $R^1$ is hydrogen, Z is sulfur and $R^3$ is 2-iodoethyl and $R^2$ for a compound corresponds in each case to a group in Table A.

Table 856

Compounds of the formula I.B, in which $R^1$ is hydrogen, Z is sulfur and $R^3$ is 2-iodoethyl and $R^2$ for a compound corresponds in each case to a group in Table A.

Table 857

Compounds of the formula I.A, in which $R^1$ is hydrogen, Z is NH and $R^3$ is 2-iodoethyl and $R^2$ for a compound corresponds in each case to a group in Table A.

Table 858

Compounds of the formula I.B, in which $R^1$ is hydrogen, Z is NH and $R^3$ is 2-iodoethyl and $R^2$ for a compound corresponds in each case to a group in Table A.

Table 859

Compounds of the formula I.A, in which $R^1$ is methyl, Z is oxygen and $R^3$ is 2-iodoethyl and $R^2$ for a compound corresponds in each case to a group in Table A.

Table 860

Compounds of the formula I.B, in which $R^1$ is methyl, Z is oxygen and $R^3$ is 2-iodoethyl and $R^2$ for a compound corresponds in each case to a group in Table A.

Table 861

Compounds of the formula I.A, in which $R^1$ is methyl, Z is sulfur and $R^3$ is 2-iodoethyl and $R^2$ for a compound corresponds in each case to a group in Table A.

Table 862

Compounds of the formula I.B, in which $R^1$ is methyl, Z is sulfur and $R^3$ is 2-iodoethyl and $R^2$ for a compound corresponds in each case to a group in Table A.

Table 863

Compounds of the formula I.A, in which $R^1$ is methyl, Z is NH and $R^3$ is 2-iodoethyl and $R^2$ for a compound corresponds in each case to a group in Table A.

Table 864

Compounds of the formula I.B, in which $R^1$ is methyl, Z is NH and $R^3$ is 2-iodoethyl and $R^2$ for a compound corresponds in each case to a group in Table A.

Table 865

Compounds of the formula I.A, in which $R^1$ is ethyl, Z is oxygen and $R^3$ is 2-iodoethyl and $R^2$ for a compound corresponds in each case to a group in Table A.

Table 866

Compounds of the formula I.B, in which $R^1$ is ethyl, Z is oxygen and $R^3$ is 2-iodoethyl and $R^2$ for a compound corresponds in each case to a group in Table A.

Table 867

Compounds of the formula I.A, in which $R^1$ is ethyl, Z is sulfur and $R^3$ is 2-iodoethyl and $R^2$ for a compound corresponds in each case to a group in Table A.

Table 868
Compounds of the formula I.B, in which $R^1$ is ethyl, Z is sulfur and $R^3$ is 2-iodoethyl and $R^2$ for a compound corresponds in each case to a group in Table A.

Table 869
Compounds of the formula I.A, in which $R^1$ is ethyl, Z is NH and $R^3$ is 2-iodoethyl and $R^2$ for a compound corresponds in each case to a group in Table A.

Table 870
Compounds of the formula I.B, in which $R^1$ is ethyl, Z is NH and $R^3$ is 2-iodoethyl and $R^2$ for a compound corresponds in each case to a group in Table A.

Table 871
Compounds of the formula I.A, in which $R^1$ is isopropyl, Z is oxygen and $R^3$ is 2-iodoethyl and $R^2$ for a compound corresponds in each case to a group in Table A.

Table 872
Compounds of the formula I.B, in which $R^1$ is isopropyl, Z is oxygen and $R^3$ is 2-iodoethyl and $R^2$ for a compound corresponds in each case to a group in Table A.

Table 873
Compounds of the formula I.A, in which $R^1$ is isopropyl, Z is sulfur and $R^3$ is 2-iodoethyl and $R^2$ for a compound corresponds in each case to a group in Table A.

Table 874
Compounds of the formula I.B, in which $R^1$ is isopropyl, Z is sulfur and $R^3$ is 2-iodoethyl and $R^2$ for a compound corresponds in each case to a group in Table A.

Table 875
Compounds of the formula I.A, in which $R^1$ is isopropyl, Z is NH and $R^3$ is 2-iodoethyl and $R^2$ for a compound corresponds in each case to a group in Table A.

Table 876
Compounds of the formula I.B, in which $R^1$ is isopropyl, Z is NH and $R^3$ is 2-iodoethyl and $R^2$ for a compound corresponds in each case to a group in Table A.

Table 877
Compounds of the formula I.A, in which $R^1$ is hydrogen, Z is oxygen and $R^3$ is 2-chloroethyl and $R^2$ for a compound corresponds in each case to a group in Table A.

Table 878
Compounds of the formula I.B, in which $R^1$ is hydrogen, Z is oxygen and $R^3$ is 2-chloroethyl and $R^2$ for a compound corresponds in each case to a group in Table A.

Table 879
Compounds of the formula I.A, in which $R^1$ is hydrogen, Z is sulfur and $R^3$ is 2-chloroethyl and $R^2$ for a compound corresponds in each case to a group in Table A.

Table 880
Compounds of the formula I.B, in which $R^1$ is hydrogen, Z is sulfur and $R^3$ is 2-chloroethyl and $R^2$ for a compound corresponds in each case to a group in Table A.

Table 881
Compounds of the formula I.A, in which $R^1$ is hydrogen, Z is NH and $R^3$ is 2-chloroethyl and $R^2$ for a compound corresponds in each case to a group in Table A.

Table 882
Compounds of the formula I.B, in which $R^1$ is hydrogen, Z is NH and $R^3$ is 2-chloroethyl and $R^2$ for a compound corresponds in each case to a group in Table A.

Table 883
Compounds of the formula I.A, in which $R^1$ is methyl, Z is oxygen and $R^3$ is 2-chloroethyl and $R^2$ for a compound corresponds in each case to a group in Table A.

Table 884
Compounds of the formula I.B, in which $R^1$ is methyl, Z is oxygen and $R^3$ is 2-chloroethyl and $R^2$ for a compound corresponds in each case to a group in Table A.

Table 885
Compounds of the formula I.A, in which $R^1$ is methyl, Z is sulfur and $R^3$ is 2-chloroethyl and $R^2$ for a compound corresponds in each case to a group in Table A.

Table 886
Compounds of the formula I.B, in which $R^1$ is methyl, Z is sulfur and $R^3$ is 2-chloroethyl and $R^2$ for a compound corresponds in each case to a group in Table A.

Table 887
Compounds of the formula I.A, in which $R^1$ is methyl, Z is NH and $R^3$ is 2-chloroethyl and $R^2$ for a compound corresponds in each case to a group in Table A.

Table 888
Compounds of the formula I.B, in which $R^1$ is methyl, Z is NH and $R^3$ is 2-chloroethyl and $R^2$ for a compound corresponds in each case to a group in Table A.

Table 889
Compounds of the formula I.A, in which $R^1$ is ethyl, Z is oxygen and $R^3$ is 2-chloroethyl and $R^2$ for a compound corresponds in each case to a group in Table A.

Table 890
Compounds of the formula I.B, in which $R^1$ is ethyl, Z is oxygen and $R^3$ is 2-chloroethyl and $R^2$ for a compound corresponds in each case to a group in Table A.

Table 891
Compounds of the formula I.A, in which $R^1$ is ethyl, Z is sulfur and $R^3$ is 2-chloroethyl and $R^2$ for a compound corresponds in each case to a group in Table A.

Table 892
Compounds of the formula I.B, in which $R^1$ is ethyl, Z is sulfur and $R^3$ is 2-chloroethyl and $R^2$ for a compound corresponds in each case to a group in Table A.

Table 893
Compounds of the formula I.A, in which $R^1$ is ethyl, Z is NH and $R^3$ is 2-chloroethyl and $R^2$ for a compound corresponds in each case to a group in Table A.

Table 894

Compounds of the formula I.B, in which $R^1$ is ethyl, Z is NH and $R^3$ is 2-chloroethyl and $R^2$ for a compound corresponds in each case to a group in Table A.

Table 895

Compounds of the formula I.A, in which $R^1$ is isopropyl, Z is oxygen and $R^3$ is 2-chloroethyl and $R^2$ for a compound corresponds in each case to a group in Table A.

Table 896

Compounds of the formula I.B, in which $R^1$ is isopropyl, Z is oxygen and $R^3$ is 2-chloroethyl and $R^2$ for a compound corresponds in each case to a group in Table A.

Table 897

Compounds of the formula I.A, in which $R^1$ is isopropyl, Z is sulfur and $R^3$ is 2-chloroethyl and $R^2$ for a compound corresponds in each case to a group in Table A.

Table 898

Compounds of the formula I.B, in which $R^1$ is isopropyl, Z is sulfur and $R^3$ is 2-chloroethyl and $R^2$ for a compound corresponds in each case to a group in Table A.

Table 899

Compounds of the formula I.A, in which $R^1$ is isopropyl, Z is NH and $R^3$ is 2-chloroethyl and $R^2$ for a compound corresponds in each case to a group in Table A.

Table 900

Compounds of the formula I.B, in which $R^1$ is isopropyl, Z is NH and $R^3$ is 2-chloroethyl and $R^2$ for a compound corresponds in each case to a group in Table A.

Table 901

Compounds of the formula I.A, in which $R^1$ is hydrogen, Z is oxygen and $R^3$ is 3-chloropropyl and $R^2$ for a compound corresponds in each case to a group in Table A.

Table 902

Compounds of the formula I.B, in which $R^1$ is hydrogen, Z is oxygen and $R^3$ is 3-chloropropyl and $R^2$ for a compound corresponds in each case to a group in Table A.

Table 903

Compounds of the formula I.A, in which $R^1$ is hydrogen, Z is sulfur and $R^3$ is 3-chloropropyl and $R^2$ for a compound corresponds in each case to a group in Table A.

Table 904

Compounds of the formula I.B, in which $R^1$ is hydrogen, Z is sulfur and $R^3$ is 3-chloropropyl and $R^2$ for a compound corresponds in each case to a group in Table A.

Table 905

Compounds of the formula I.A, in which $R^1$ is hydrogen, Z is NH and $R^3$ is 3-chloropropyl and $R^2$ for a compound corresponds in each case to a group in Table A.

Table 906

Compounds of the formula I.B, in which $R^1$ is hydrogen, Z is NH and $R^3$ is 3-chloropropyl and $R^2$ for a compound corresponds in each case to a group in Table A.

Table 907

Compounds of the formula I.A, in which $R^1$ is methyl, Z is oxygen and $R^3$ is 3-chloropropyl and $R^2$ for a compound corresponds in each case to a group in Table A.

Table 908

Compounds of the formula I.B, in which $R^1$ is methyl, Z is oxygen and $R^3$ is 3-chloropropyl and $R^2$ for a compound corresponds in each case to a group in Table A.

Table 909

Compounds of the formula I.A, in which $R^1$ is methyl, Z is sulfur and $R^3$ is 3-chloropropyl and $R^2$ for a compound corresponds in each case to a group in Table A.

Table 910

Compounds of the formula I.B, in which $R^1$ is methyl, Z is sulfur and $R^3$ is 3-chloropropyl and $R^2$ for a compound corresponds in each case to a group in Table A.

Table 911

Compounds of the formula I.A, in which $R^1$ is methyl, Z is NH and $R^3$ is 3-chloropropyl and $R^2$ for a compound corresponds in each case to a group in Table A.

Table 912

Compounds of the formula I.B, in which $R^1$ is methyl, Z is NH and $R^3$ is 3-chloropropyl and $R^2$ for a compound corresponds in each case to a group in Table A.

Table 913

Compounds of the formula I.A, in which $R^1$ is ethyl, Z is oxygen and $R^3$ is 3-chloropropyl and $R^2$ for a compound corresponds in each case to a group in Table A.

Table 914

Compounds of the formula I.B, in which $R^1$ is ethyl, Z is oxygen and $R^3$ is 3-chloropropyl and $R^2$ for a compound corresponds in each case to a group in Table A.

Table 915

Compounds of the formula I.A, in which $R^1$ is ethyl, Z is sulfur and $R^3$ is 3-chloropropyl and $R^2$ for a compound corresponds in each case to a group in Table A.

Table 916

Compounds of the formula I.B, in which $R^1$ is ethyl, Z is sulfur and $R^3$ is 3-chloropropyl and $R^2$ for a compound corresponds in each case to a group in Table A.

Table 917

Compounds of the formula I.A, in which $R^1$ is ethyl, Z is NH and $R^3$ is 3-chloropropyl and $R^2$ for a compound corresponds in each case to a group in Table A.

Table 918

Compounds of the formula I.B, in which $R^1$ is ethyl, Z is NH and $R^3$ is 3-chloropropyl and $R^2$ for a compound corresponds in each case to a group in Table A.

Table 919

Compounds of the formula I.A, in which $R^1$ is isopropyl, Z is oxygen and $R^3$ is 3-chloropropyl and $R^2$ for a compound corresponds in each case to a group in Table A.

Table 920

Compounds of the formula I.B, in which $R^1$ is isopropyl, Z is oxygen and $R^3$ is 3-chloropropyl and $R^2$ for a compound corresponds in each case to a group in Table A.

Table 921

Compounds of the formula I.A, in which $R^1$ is isopropyl, Z is sulfur and $R^3$ is 3-chloropropyl and $R^2$ for a compound corresponds in each case to a group in Table A.

Table 922

Compounds of the formula I.B, in which $R^1$ is isopropyl, Z is sulfur and $R^3$ is 3-chloropropyl and $R^2$ for a compound corresponds in each case to a group in Table A.

Table 923

Compounds of the formula I.A, in which $R^1$ is isopropyl, Z is NH and $R^3$ is 3-chloropropyl and $R^2$ for a compound corresponds in each case to a group in Table A.

Table 924

Compounds of the formula I.B, in which $R^1$ is isopropyl, Z is NH and $R^3$ is 3-chloropropyl and $R^2$ for a compound corresponds in each case to a group in Table A.

Table 925

Compounds of the formula I.A, in which $R^1$ is hydrogen, Z is oxygen and $R^3$ is 4-chlorobutyl and $R^2$ for a compound corresponds in each case to a group in Table A.

Table 926

Compounds of the formula I.B, in which $R^1$ is hydrogen, Z is oxygen and $R^3$ is 4-chlorobutyl and $R^2$ for a compound corresponds in each case to a group in Table A.

Table 927

Compounds of the formula I.A, in which $R^1$ is hydrogen, Z is sulfur and $R^3$ is 4-chlorobutyl and $R^2$ for a compound corresponds in each case to a group in Table A.

Table 928

Compounds of the formula I.B, in which $R^1$ is hydrogen, Z is sulfur and $R^3$ is 4-chlorobutyl and $R^2$ for a compound corresponds in each case to a group in Table A.

Table 929

Compounds of the formula I.A, in which $R^1$ is hydrogen, Z is NH and $R^3$ is 4-chlorobutyl and $R^2$ for a compound corresponds in each case to a group in Table A.

Table 930

Compounds of the formula I.B, in which $R^1$ is hydrogen, Z is NH and $R^3$ is 4-chlorobutyl and $R^2$ for a compound corresponds in each case to a group in Table A.

Table 931

Compounds of the formula I.A, in which $R^1$ is methyl, Z is oxygen and $R^3$ is 4-chlorobutyl and $R^2$ for a compound corresponds in each case to a group in Table A.

Table 932

Compounds of the formula I.B, in which $R^1$ is methyl, Z is oxygen and $R^3$ is 4-chlorobutyl and $R^2$ for a compound corresponds in each case to a group in Table A.

Table 933

Compounds of the formula I.A, in which $R^1$ is methyl, Z is sulfur and $R^3$ is 4-chlorobutyl and $R^2$ for a compound corresponds in each case to a group in Table A.

Table 934

Compounds of the formula I.B, in which $R^1$ is methyl, Z is sulfur and $R^3$ is 4-chlorobutyl and $R^2$ for a compound corresponds in each case to a group in Table A.

Table 935

Compounds of the formula I.A, in which $R^1$ is methyl, Z is NH and $R^3$ is 4-chlorobutyl and $R^2$ for a compound corresponds in each case to a group in Table A.

Table 936

Compounds of the formula I.B, in which $R^1$ is methyl, Z is NH and $R^3$ is 4-chlorobutyl and $R^2$ for a compound corresponds in each case to a group in Table A.

Table 937

Compounds of the formula I.A, in which $R^1$ is ethyl, Z is oxygen and $R^3$ is 4-chlorobutyl and $R^2$ for a compound corresponds in each case to a group in Table A.

Table 938

Compounds of the formula I.B, in which $R^1$ is ethyl, Z is oxygen and $R^3$ is 4-chlorobutyl and $R^2$ for a compound corresponds in each case to a group in Table A.

Table 939

Compounds of the formula I.A, in which $R^1$ is ethyl, Z is sulfur and $R^3$ is 4-chlorobutyl and $R^2$ for a compound corresponds in each case to a group in Table A.

Table 940

Compounds of the formula I.B, in which $R^1$ is ethyl, Z is sulfur and $R^3$ is 4-chlorobutyl and $R^2$ for a compound corresponds in each case to a group in Table A.

Table 941

Compounds of the formula I.A, in which $R^1$ is ethyl, Z is NH and $R^3$ is 4-chlorobutyl and $R^2$ for a compound corresponds in each case to a group in Table A.

Table 942

Compounds of the formula I.B, in which $R^1$ is ethyl, Z is NH and $R^3$ is 4-chlorobutyl and $R^2$ for a compound corresponds in each case to a group in Table A.

Table 943

Compounds of the formula I.A, in which $R^1$ is isopropyl, Z is oxygen and $R^3$ is 4-chlorobutyl and $R^2$ for a compound corresponds in each case to a group in Table A.

Table 944

Compounds of the formula I.B, in which $R^1$ is isopropyl, Z is oxygen and $R^3$ is 4-chlorobutyl and $R^2$ for a compound corresponds in each case to a group in Table A.

Table 945

Compounds of the formula I.A, in which $R^1$ is isopropyl, Z is sulfur and $R^3$ is 4-chlorobutyl and $R^2$ for a compound corresponds in each case to a group in Table A.

Table 946

Compounds of the formula I.B, in which $R^1$ is isopropyl, Z is sulfur and $R^3$ is 4-chlorobutyl and $R^2$ for a compound corresponds in each case to a group in Table A.

Table 947

Compounds of the formula I.A, in which $R^1$ is isopropyl, Z is NH and $R^3$ is 4-chlorobutyl and $R^2$ for a compound corresponds in each case to a group in Table A.

Table 948

Compounds of the formula I.B, in which $R^1$ is isopropyl, Z is NH and $R^3$ is 4-chlorobutyl and $R^2$ for a compound corresponds in each case to a group in Table A.

Table 949

Compounds of the formula I.A, in which $R^1$ is hydrogen, Z is oxygen and $R^3$ is cyanomethyl and $R^2$ for a compound corresponds in each case to a group in Table A.

Table 950

Compounds of the formula I.B, in which $R^1$ is hydrogen, Z is oxygen and $R^3$ is cyanomethyl and $R^2$ for a compound corresponds in each case to a group in Table A.

Table 951

Compounds of the formula I.A, in which $R^1$ is hydrogen, Z is sulfur and $R^3$ is cyanomethyl and $R^2$ for a compound corresponds in each case to a group in Table A.

Table 952

Compounds of the formula I.B, in which $R^1$ is hydrogen, Z is sulfur and $R^3$ is cyanomethyl and $R^2$ for a compound corresponds in each case to a group in Table A.

Table 953

Compounds of the formula I.A, in which $R^1$ is hydrogen, Z is NH and $R^3$ is cyanomethyl and $R^2$ for a compound corresponds in each case to a group in Table A.

Table 954

Compounds of the formula I.B, in which $R^1$ is hydrogen, Z is NH and $R^3$ is cyanomethyl and $R^2$ for a compound corresponds in each case to a group in Table A.

Table 955

Compounds of the formula I.A, in which $R^1$ is methyl, Z is oxygen and $R^3$ is cyanomethyl and $R^2$ for a compound corresponds in each case to a group in Table A.

Table 956

Compounds of the formula I.B, in which $R^1$ is methyl, Z is oxygen and $R^3$ is cyanomethyl and $R^2$ for a compound corresponds in each case to a group in Table A.

Table 957

Compounds of the formula I.A, in which $R^1$ is methyl, Z is sulfur and $R^3$ is cyanomethyl and $R^2$ for a compound corresponds in each case to a group in Table A.

Table 958

Compounds of the formula I.B, in which $R^1$ is methyl, Z is sulfur and $R^3$ is cyanomethyl and $R^2$ for a compound corresponds in each case to a group in Table A.

Table 959

Compounds of the formula I.A, in which $R^1$ is methyl, Z is NH and $R^3$ is cyanomethyl and $R^2$ for a compound corresponds in each case to a group in Table A.

Table 960

Compounds of the formula I.B, in which $R^1$ is methyl, Z is NH and $R^3$ is cyanomethyl and $R^2$ for a compound corresponds in each case to a group in Table A.

Table 961

Compounds of the formula I.A, in which $R^1$ is ethyl, Z is oxygen and $R^3$ is cyanomethyl and $R^2$ for a compound corresponds in each case to a group in Table A.

Table 962

Compounds of the formula I.B, in which $R^1$ is ethyl, Z is oxygen and $R^3$ is cyanomethyl and $R^2$ for a compound corresponds in each case to a group in Table A.

Table 963

Compounds of the formula I.A, in which $R^1$ is ethyl, Z is sulfur and $R^3$ is cyanomethyl and $R^2$ for a compound corresponds in each case to a group in Table A.

Table 964

Compounds of the formula I.B, in which $R^1$ is ethyl, Z is sulfur and $R^3$ is cyanomethyl and $R^2$ for a compound corresponds in each case to a group in Table A.

Table 965

Compounds of the formula I.A, in which $R^1$ is ethyl, Z is NH and $R^3$ is cyanomethyl and $R^2$ for a compound corresponds in each case to a group in Table A.

Table 966

Compounds of the formula I.B, in which $R^1$ is ethyl, Z is NH and $R^3$ is cyanomethyl and $R^2$ for a compound corresponds in each case to a group in Table A.

Table 967

Compounds of the formula I.A, in which $R^1$ is isopropyl, Z is oxygen and $R^3$ is cyanomethyl and $R^2$ for a compound corresponds in each case to a group in Table A.

Table 968

Compounds of the formula I.B, in which $R^1$ is isopropyl, Z is oxygen and $R^3$ is cyanomethyl and $R^2$ for a compound corresponds in each case to a group in Table A.

Table 969

Compounds of the formula I.A, in which $R^1$ is isopropyl, Z is sulfur and $R^3$ is cyanomethyl and $R^2$ for a compound corresponds in each case to a group in Table A.

Table 970

Compounds of the formula I.B, in which $R^1$ is isopropyl, Z is sulfur and $R^3$ is cyanomethyl and $R^2$ for a compound corresponds in each case to a group in Table A.

Table 971

Compounds of the formula I.A, in which $R^1$ is isopropyl, Z is NH and $R^3$ is cyanomethyl and $R^2$ for a compound corresponds in each case to a group in Table A.

Table 972

Compounds of the formula I.B, in which $R^1$ is isopropyl, Z is NH and $R^3$ is cyanomethyl and $R^2$ for a compound corresponds in each case to a group in Table A.

Table 973

Compounds of the formula I.A, in which $R^1$ is hydrogen, Z is oxygen and $R^3$ is 2-cyanoethyl and $R^2$ for a compound corresponds in each case to a group in Table A.

Table 974

Compounds of the formula I.B, in which $R^1$ is hydrogen, Z is oxygen and $R^3$ is 2-cyanoethyl and $R^2$ for a compound corresponds in each case to a group in Table A.

Table 975

Compounds of the formula I.A, in which $R^1$ is hydrogen, Z is sulfur and $R^3$ is 2-cyanoethyl and $R^2$ for a compound corresponds in each case to a group in Table A.

Table 976

Compounds of the formula I.B, in which $R^1$ is hydrogen, Z is sulfur and $R^3$ is 2-cyanoethyl and $R^2$ for a compound corresponds in each case to a group in Table A.

Table 977

Compounds of the formula I.A, in which $R^1$ is hydrogen, Z is NH and $R^3$ is 2-cyanoethyl and $R^2$ for a compound corresponds in each case to a group in Table A.

Table 978

Compounds of the formula I.B, in which $R^1$ is hydrogen, Z is NH and $R^3$ is 2-cyanoethyl and $R^2$ for a compound corresponds in each case to a group in Table A.

Table 979

Compounds of the formula I.A, in which $R^1$ is methyl, Z is oxygen and $R^3$ is 2-cyanoethyl and $R^2$ for a compound corresponds in each case to a group in Table A.

Table 980

Compounds of the formula I.B, in which $R^1$ is methyl, Z is oxygen and $R^3$ is 2-cyanoethyl and $R^2$ for a compound corresponds in each case to a group in Table A.

Table 981

Compounds of the formula I.A, in which $R^1$ is methyl, Z is sulfur and $R^3$ is 2-cyanoethyl and $R^2$ for a compound corresponds in each case to a group in Table A.

Table 982

Compounds of the formula I.B, in which $R^1$ is methyl, Z is sulfur and $R^3$ is 2-cyanoethyl and $R^2$ for a compound corresponds in each case to a group in Table A.

Table 983

Compounds of the formula I.A, in which $R^1$ is methyl, Z is NH and $R^3$ is 2-cyanoethyl and $R^2$ for a compound corresponds in each case to a group in Table A.

Table 984

Compounds of the formula I.B, in which $R^1$ is methyl, Z is NH and $R^3$ is 2-cyanoethyl and $R^2$ for a compound corresponds in each case to a group in Table A.

Table 985

Compounds of the formula I.A, in which $R^1$ is ethyl, Z is oxygen and $R^3$ is 2-cyanoethyl and $R^2$ for a compound corresponds in each case to a group in Table A.

Table 986

Compounds of the formula I.B, in which $R^1$ is ethyl, Z is oxygen and $R^3$ is 2-cyanoethyl and $R^2$ for a compound corresponds in each case to a group in Table A.

Table 987

Compounds of the formula I.A, in which $R^1$ is ethyl, Z is sulfur and $R^3$ is 2-cyanoethyl and $R^2$ for a compound corresponds in each case to a group in Table A.

Table 988

Compounds of the formula I.B, in which $R^1$ is ethyl, Z is sulfur and $R^3$ is 2-cyanoethyl and $R^2$ for a compound corresponds in each case to a group in Table A.

Table 989

Compounds of the formula I.A, in which $R^1$ is ethyl, Z is NH and $R^3$ is 2-cyanoethyl and $R^2$ for a compound corresponds in each case to a group in Table A.

Table 990

Compounds of the formula I.B, in which $R^1$ is ethyl, Z is NH and $R^3$ is 2-cyanoethyl and $R^2$ for a compound corresponds in each case to a group in Table A.

Table 991

Compounds of the formula I.A, in which $R^1$ is isopropyl, Z is oxygen and $R^3$ is 2-cyanoethyl and $R^2$ for a compound corresponds in each case to a group in Table A.

Table 992

Compounds of the formula I.B, in which $R^1$ is isopropyl, Z is oxygen and $R^3$ is 2-cyanoethyl and $R^2$ for a compound corresponds in each case to a group in Table A.

Table 993

Compounds of the formula I.A, in which $R^1$ is isopropyl, Z is sulfur and $R^3$ is 2-cyanoethyl and $R^2$ for a compound corresponds in each case to a group in Table A.

Table 994

Compounds of the formula I.B, in which $R^1$ is isopropyl, Z is sulfur and $R^3$ is 2-cyanoethyl and $R^2$ for a compound corresponds in each case to a group in Table A.

Table 995

Compounds of the formula I.A, in which $R^1$ is isopropyl, Z is NH and $R^3$ is 2-cyanoethyl and $R^2$ for a compound corresponds in each case to a group in Table A.

Table 996

Compounds of the formula I.B, in which $R^1$ is isopropyl, Z is NH and $R^3$ is 2-cyanoethyl and $R^2$ for a compound corresponds in each case to a group in Table A.

Table 997

Compounds of the formula I.A, in which $R^1$ is hydrogen, Z is oxygen and $R^3$ is 3-cyanopropyl and $R^2$ for a compound corresponds in each case to a group in Table A.

Table 998

Compounds of the formula I.B, in which $R^1$ is hydrogen, Z is oxygen and $R^3$ is 3-cyanopropyl and $R^2$ for a compound corresponds in each case to a group in Table A.

Table 999

Compounds of the formula I.A, in which $R^1$ is hydrogen, Z is sulfur and $R^3$ is 3-cyanopropyl and $R^2$ for a compound corresponds in each case to a group in Table A.

Table 1000

Compounds of the formula I.B, in which $R^1$ is hydrogen, Z is sulfur and $R^3$ is 3-cyanopropyl and $R^2$ for a compound corresponds in each case to a group in Table A.

Table 1001

Compounds of the formula I.A, in which $R^1$ is hydrogen, Z is NH and $R^3$ is 3-cyanopropyl and $R^2$ for a compound corresponds in each case to a group in Table A.

Table 1002

Compounds of the formula I.B, in which $R^1$ is hydrogen, Z is NH and $R^3$ is 3-cyanopropyl and $R^2$ for a compound corresponds in each case to a group in Table A.

Table 1003

Compounds of the formula I.A, in which $R^1$ is methyl, Z is oxygen and $R^3$ is 3-cyanopropyl and $R^2$ for a compound corresponds in each case to a group in Table A.

Table 1004

Compounds of the formula I.B, in which $R^1$ is methyl, Z is oxygen and $R^3$ is 3-cyanopropyl and $R^2$ for a compound corresponds in each case to a group in Table A.

Table 1005

Compounds of the formula I.A, in which $R^1$ is methyl, Z is sulfur and $R^3$ is 3-cyanopropyl and $R^2$ for a compound corresponds in each case to a group in Table A.

Table 1006

Compounds of the formula I.B, in which $R^1$ is methyl, Z is sulfur and $R^3$ is 3-cyanopropyl and $R^2$ for a compound corresponds in each case to a group in Table A.

Table 1007

Compounds of the formula I.A, in which $R^1$ is methyl, Z is NH and $R^3$ is 3-cyanopropyl and $R^2$ for a compound corresponds in each case to a group in Table A.

Table 1008

Compounds of the formula I.B, in which $R^1$ is methyl, Z is NH and $R^3$ is 3-cyanopropyl and $R^2$ for a compound corresponds in each case to a group in Table A.

Table 1009

Compounds of the formula I.A, in which $R^1$ is ethyl, Z is oxygen and $R^3$ is 3-cyanopropyl and $R^2$ for a compound corresponds in each case to a group in Table A.

Table 1010

Compounds of the formula I.B, in which $R^1$ is ethyl, Z is oxygen and $R^3$ is 3-cyanopropyl and $R^2$ for a compound corresponds in each case to a group in Table A.

Table 1011

Compounds of the formula I.A, in which $R^1$ is ethyl, Z is sulfur and $R^3$ is 3-cyanopropyl and $R^2$ for a compound corresponds in each case to a group in Table A.

Table 1012

Compounds of the formula I.B, in which $R^1$ is ethyl, Z is sulfur and $R^3$ is 3-cyanopropyl and $R^2$ for a compound corresponds in each case to a group in Table A.

Table 1013

Compounds of the formula I.A, in which $R^1$ is ethyl, Z is NH and $R^3$ is 3-cyanopropyl and $R^2$ for a compound corresponds in each case to a group in Table A.

Table 1014

Compounds of the formula I.B, in which $R^1$ is ethyl, Z is NH and $R^3$ is 3-cyanopropyl and $R^2$ for a compound corresponds in each case to a group in Table A.

Table 1015

Compounds of the formula I.A, in which $R^1$ is isopropyl, Z is oxygen and $R^3$ is 3-cyanopropyl and $R^2$ for a compound corresponds in each case to a group in Table A.

Table 1016

Compounds of the formula I.B, in which $R^1$ is isopropyl, Z is oxygen and $R^3$ is 3-cyanopropyl and $R^2$ for a compound corresponds in each case to a group in Table A.

Table 1017

Compounds of the formula I.A, in which $R^1$ is isopropyl, Z is sulfur and $R^3$ is 3-cyanopropyl and $R^2$ for a compound corresponds in each case to a group in Table A.

Table 1018

Compounds of the formula I.B, in which $R^1$ is isopropyl, Z is sulfur and $R^3$ is 3-cyanopropyl and $R^2$ for a compound corresponds in each case to a group in Table A.

Table 1019

Compounds of the formula I.A, in which $R^1$ is isopropyl, Z is NH and $R^3$ is 3-cyanopropyl and $R^2$ for a compound corresponds in each case to a group in Table A.

Table 1020

Compounds of the formula I.B, in which $R^1$ is isopropyl, Z is NH and $R^3$ is 3-cyanopropyl and $R^2$ for a compound corresponds in each case to a group in Table A.

Table 1021

Compounds of the formula I.A, in which $R^1$ is hydrogen, Z is oxygen and $R^3$ is 4-cyanobutyl and $R^2$ for a compound corresponds in each case to a group in Table A.

Table 1022

Compounds of the formula I.B, in which $R^1$ is hydrogen, Z is oxygen and $R^3$ is 4-cyanobutyl and $R^2$ for a compound corresponds in each case to a group in Table A.

Table 1023

Compounds of the formula I.A, in which $R^1$ is hydrogen, Z is sulfur and $R^3$ is 4-cyanobutyl and $R^2$ for a compound corresponds in each case to a group in Table A.

Table 1024

Compounds of the formula I.B, in which $R^1$ is hydrogen, Z is sulfur and $R^3$ is 4-cyanobutyl and $R^2$ for a compound corresponds in each case to a group in Table A.

Table 1025

Compounds of the formula I.A, in which $R^1$ is hydrogen, Z is NH and $R^3$ is 4-cyanobutyl and $R^2$ for a compound corresponds in each case to a group in Table A.

Table 1026

Compounds of the formula I.B, in which $R^1$ is hydrogen, Z is NH and $R^3$ is 4-cyanobutyl and $R^2$ for a compound corresponds in each case to a group in Table A.

Table 1027

Compounds of the formula I.A, in which $R^1$ is methyl, Z is oxygen and $R^3$ is 4-cyanobutyl and $R^2$ for a compound corresponds in each case to a group in Table A.

Table 1028

Compounds of the formula I.B, in which $R^1$ is methyl, Z is oxygen and $R^3$ is 4-cyanobutyl and $R^2$ for a compound corresponds in each case to a group in Table A.

Table 1029

Compounds of the formula I.A, in which $R^1$ is methyl, Z is sulfur and $R^3$ is 4-cyanobutyl and $R^2$ for a compound corresponds in each case to a group in Table A.

Table 1030

Compounds of the formula I.B, in which $R^1$ is methyl, Z is sulfur and $R^3$ is 4-cyanobutyl and $R^2$ for a compound corresponds in each case to a group in Table A.

Table 1031

Compounds of the formula I.A, in which $R^1$ is methyl, Z is NH and $R^3$ is 4-cyanobutyl and $R^2$ for a compound corresponds in each case to a group in Table A.

Table 1032

Compounds of the formula I.B, in which $R^1$ is methyl, Z is NH and $R^3$ is 4-cyanobutyl and $R^2$ for a compound corresponds in each case to a group in Table A.

Table 1033

Compounds of the formula I.A, in which $R^1$ is ethyl, Z is oxygen and $R^3$ is 4-cyanobutyl and $R^2$ for a compound corresponds in each case to a group in Table A.

Table 1034

Compounds of the formula I.B, in which $R^1$ is ethyl, Z is oxygen and $R^3$ is 4-cyanobutyl and $R^2$ for a compound corresponds in each case to a group in Table A.

Table 1035

Compounds of the formula I.A, in which $R^1$ is ethyl, Z is sulfur and $R^3$ is 4-cyanobutyl and $R^2$ for a compound corresponds in each case to a group in Table A.

Table 1036

Compounds of the formula I.B, in which $R^1$ is ethyl, Z is sulfur and $R^3$ is 4-cyanobutyl and $R^2$ for a compound corresponds in each case to a group in Table A.

Table 1037

Compounds of the formula I.A, in which $R^1$ is ethyl, Z is NH and $R^3$ is 4-cyanobutyl and $R^2$ for a compound corresponds in each case to a group in Table A.

Table 1038

Compounds of the formula I.B, in which $R^1$ is ethyl, Z is NH and $R^3$ is 4-cyanobutyl and $R^2$ for a compound corresponds in each case to a group in Table A.

Table 1039

Compounds of the formula I.A, in which $R^1$ is isopropyl, Z is oxygen and $R^3$ is 4-cyanobutyl and $R^2$ for a compound corresponds in each case to a group in Table A.

Table 1040

Compounds of the formula I.B, in which $R^1$ is isopropyl, Z is oxygen and $R^3$ is 4-cyanobutyl and $R^2$ for a compound corresponds in each case to a group in Table A.

Table 1041

Compounds of the formula I.A, in which $R^1$ is isopropyl, Z is sulfur and $R^3$ is 4-cyanobutyl and $R^2$ for a compound corresponds in each case to a group in Table A.

Table 1042

Compounds of the formula I.B, in which $R^1$ is isopropyl, Z is sulfur and $R^3$ is 4-cyanobutyl and $R^2$ for a compound corresponds in each case to a group in Table A.

Table 1043

Compounds of the formula I.A, in which $R^1$ is isopropyl, Z is NH and $R^3$ is 4-cyanobutyl and $R^2$ for a compound corresponds in each case to a group in Table A.

Table 1044

Compounds of the formula I.B, in which $R^1$ is isopropyl, Z is NH and $R^3$ is 4-cyanobutyl and $R^2$ for a compound corresponds in each case to a group in Table A.

Table 1045

Compounds of the formula I.A, in which $R^1$ is hydrogen, Z is oxygen and $R^3$ is 2-methoxyethyl and $R^2$ for a compound corresponds in each case to a group in Table A.

Table 1046

Compounds of the formula I.B, in which $R^1$ is hydrogen, Z is oxygen and $R^3$ is 2-methoxyethyl and $R^2$ for a compound corresponds in each case to a group in Table A.

Table 1047

Compounds of the formula I.A, in which $R^1$ is hydrogen, Z is sulfur and $R^3$ is 2-methoxyethyl and $R^2$ for a compound corresponds in each case to a group in Table A.

Table 1048

Compounds of the formula I.B, in which $R^1$ is hydrogen, Z is sulfur and $R^3$ is 2-methoxyethyl and $R^2$ for a compound corresponds in each case to a group in Table A.

Table 1049

Compounds of the formula I.A, in which $R^1$ is hydrogen, Z is NH and $R^3$ is 2-methoxyethyl and $R^2$ for a compound corresponds in each case to a group in Table A.

Table 1050

Compounds of the formula I.B, in which $R^1$ is hydrogen, Z is NH and $R^3$ is 2-methoxyethyl and $R^2$ for a compound corresponds in each case to a group in Table A.

Table 1051

Compounds of the formula I.A, in which $R^1$ is methyl, Z is oxygen and $R^3$ is 2-methoxyethyl and $R^2$ for a compound corresponds in each case to a group in Table A.

Table 1052

Compounds of the formula I.B, in which $R^1$ is methyl, Z is oxygen and $R^3$ is 2-methoxyethyl and $R^2$ for a compound corresponds in each case to a group in Table A.

Table 1053

Compounds of the formula I.A, in which $R^1$ is methyl, Z is sulfur and $R^3$ is 2-methoxyethyl and $R^2$ for a compound corresponds in each case to a group in Table A.

Table 1054

Compounds of the formula I.B, in which $R^1$ is methyl, Z is sulfur and $R^3$ is 2-methoxyethyl and $R^2$ for a compound corresponds in each case to a group in Table A.

Table 1055

Compounds of the formula I.A, in which $R^1$ is methyl, Z is NH and $R^3$ is 2-methoxyethyl and $R^2$ for a compound corresponds in each case to a group in Table A.

Table 1056

Compounds of the formula I.B, in which $R^1$ is methyl, Z is NH and $R^3$ is 2-methoxyethyl and $R^2$ for a compound corresponds in each case to a group in Table A.

Table 1057

Compounds of the formula I.A, in which $R^1$ is ethyl, Z is oxygen and $R^3$ is 2-methoxyethyl and $R^2$ for a compound corresponds in each case to a group in Table A.

Table 1058

Compounds of the formula I.B, in which $R^1$ is ethyl, Z is oxygen and $R^3$ is 2-methoxyethyl and $R^2$ for a compound corresponds in each case to a group in Table A.

Table 1059

Compounds of the formula I.A, in which $R^1$ is ethyl, Z is sulfur and $R^3$ is 2-methoxyethyl and $R^2$ for a compound corresponds in each case to a group in Table A.

Table 1060

Compounds of the formula I.B, in which $R^1$ is ethyl, Z is sulfur and $R^3$ is 2-methoxyethyl and $R^2$ for a compound corresponds in each case to a group in Table A.

Table 1061

Compounds of the formula I.A, in which $R^1$ is ethyl, Z is NH and $R^3$ is 2-methoxyethyl and $R^2$ for a compound corresponds in each case to a group in Table A.

Table 1062

Compounds of the formula I.B, in which $R^1$ is ethyl, Z is NH and $R^3$ is 2-methoxyethyl and $R^2$ for a compound corresponds in each case to a group in Table A.

Table 1063

Compounds of the formula I.A, in which $R^1$ is isopropyl, Z is oxygen and $R^3$ is 2-methoxyethyl and $R^2$ for a compound corresponds in each case to a group in Table A.

Table 1064

Compounds of the formula I.B, in which $R^1$ is isopropyl, Z is oxygen and $R^3$ is 2-methoxyethyl and $R^2$ for a compound corresponds in each case to a group in Table A.

Table 1065

Compounds of the formula I.A, in which $R^1$ is isopropyl, Z is sulfur and $R^3$ is 2-methoxyethyl and $R^2$ for a compound corresponds in each case to a group in Table A.

Table 1066

Compounds of the formula I.B, in which $R^1$ is isopropyl, Z is sulfur and $R^3$ is 2-methoxyethyl and $R^2$ for a compound corresponds in each case to a group in Table A.

Table 1067

Compounds of the formula I.A, in which $R^1$ is isopropyl, Z is NH and $R^3$ is 2-methoxyethyl and $R^2$ for a compound corresponds in each case to a group in Table A.

Table 1068

Compounds of the formula I.B, in which $R^1$ is isopropyl, Z is NH and $R^3$ is 2-methoxyethyl and $R^2$ for a compound corresponds in each case to a group in Table A.

Table 1069

Compounds of the formula I.A, in which $R^1$ is hydrogen, Z is oxygen and $R^3$ is 2-ethoxyethyl and $R^2$ for a compound corresponds in each case to a group in Table A.

Table 1070

Compounds of the formula I.B, in which $R^1$ is hydrogen, Z is oxygen and $R^3$ is 2-ethoxyethyl and $R^2$ for a compound corresponds in each case to a group in Table A.

Table 1071

Compounds of the formula I.A, in which $R^1$ is hydrogen, Z is sulfur and $R^3$ is 2-ethoxyethyl and $R^2$ for a compound corresponds in each case to a group in Table A.

Table 1072

Compounds of the formula I.B, in which $R^1$ is hydrogen, Z is sulfur and $R^3$ is 2-ethoxyethyl and $R^2$ for a compound corresponds in each case to a group in Table A.

Table 1073

Compounds of the formula I.A, in which $R^1$ is hydrogen, Z is NH and $R^3$ is 2-ethoxyethyl and $R^2$ for a compound corresponds in each case to a group in Table A.

Table 1074

Compounds of the formula I.B, in which $R^1$ is hydrogen, Z is NH and $R^3$ is 2-ethoxyethyl and $R^2$ for a compound corresponds in each case to a group in Table A.

Table 1075

Compounds of the formula I.A, in which $R^1$ is methyl, Z is oxygen and $R^3$ is 2-ethoxyethyl and $R^2$ for a compound corresponds in each case to a group in Table A.

Table 1076

Compounds of the formula I.B, in which $R^1$ is methyl, Z is oxygen and $R^3$ is 2-ethoxyethyl and $R^2$ for a compound corresponds in each case to a group in Table A.

Table 1077

Compounds of the formula I.A, in which $R^1$ is methyl, Z is sulfur and $R^3$ is 2-ethoxyethyl and $R^2$ for a compound corresponds in each case to a group in Table A.

Table 1078

Compounds of the formula I.B, in which $R^1$ is methyl, Z is sulfur and $R^3$ is 2-ethoxyethyl and $R^2$ for a compound corresponds in each case to a group in Table A.

Table 1079

Compounds of the formula I.A, in which $R^1$ is methyl, Z is NH and $R^3$ is 2-ethoxyethyl and $R^2$ for a compound corresponds in each case to a group in Table A.

Table 1080

Compounds of the formula I.B, in which $R^1$ is methyl, Z is NH and $R^3$ is 2-ethoxyethyl and $R^2$ for a compound corresponds in each case to a group in Table A.

Table 1081

Compounds of the formula I.A, in which $R^1$ is ethyl, Z is oxygen and $R^3$ is 2-ethoxyethyl and $R^2$ for a compound corresponds in each case to a group in Table A.

Table 1082

Compounds of the formula I.B, in which $R^1$ is ethyl, Z is oxygen and $R^3$ is 2-ethoxyethyl and $R^2$ for a compound corresponds in each case to a group in Table A.

Table 1083

Compounds of the formula I.A, in which $R^1$ is ethyl, Z is sulfur and $R^3$ is 2-ethoxyethyl and $R^2$ for a compound corresponds in each case to a group in Table A.

Table 1084

Compounds of the formula I.B, in which $R^1$ is ethyl, Z is sulfur and $R^3$ is 2-ethoxyethyl and $R^2$ for a compound corresponds in each case to a group in Table A.

Table 1085

Compounds of the formula I.A, in which $R^1$ is ethyl, Z is NH and $R^3$ is 2-ethoxyethyl and $R^2$ for a compound corresponds in each case to a group in Table A.

Table 1086

Compounds of the formula I.B, in which $R^1$ is ethyl, Z is NH and $R^3$ is 2-ethoxyethyl and $R^2$ for a compound corresponds in each case to a group in Table A.

Table 1087

Compounds of the formula I.A, in which $R^1$ is isopropyl, Z is oxygen and $R^3$ is 2-ethoxyethyl and $R^2$ for a compound corresponds in each case to a group in Table A.

Table 1088

Compounds of the formula I.B, in which $R^1$ is isopropyl, Z is oxygen and $R^3$ is 2-ethoxyethyl and $R^2$ for a compound corresponds in each case to a group in Table A.

Table 1089

Compounds of the formula I.A, in which $R^1$ is isopropyl, Z is sulfur and $R^3$ is 2-ethoxyethyl and $R^2$ for a compound corresponds in each case to a group in Table A.

Table 1090

Compounds of the formula I.B, in which $R^1$ is isopropyl, Z is sulfur and $R^3$ is 2-ethoxyethyl and $R^2$ for a compound corresponds in each case to a group in Table A.

Table 1091

Compounds of the formula I.A, in which $R^1$ is isopropyl, Z is NH and $R^3$ is 2-ethoxyethyl and $R^2$ for a compound corresponds in each case to a group in Table A.

Table 1092

Compounds of the formula I.B, in which $R^1$ is isopropyl, Z is NH and $R^3$ is 2-ethoxyethyl and $R^2$ for a compound corresponds in each case to a group in Table A.

Table 1093

Compounds of the formula I.A, in which $R^1$ is hydrogen, Z is oxygen and $R^3$ is 2-isopropoxyethyl and $R^2$ for a compound corresponds in each case to a group in Table A.

Table 1094

Compounds of the formula I.B, in which $R^1$ is hydrogen, Z is oxygen and $R^3$ is 2-isopropoxyethyl and $R^2$ for a compound corresponds in each case to a group in Table A.

Table 1095

Compounds of the formula I.A, in which $R^1$ is hydrogen, Z is sulfur and $R^3$ is 2-isopropoxyethyl and $R^2$ for a compound corresponds in each case to a group in Table A.

Table 1096

Compounds of the formula I.B, in which $R^1$ is hydrogen, Z is sulfur and $R^3$ is 2-isopropoxyethyl and $R^2$ for a compound corresponds in each case to a group in Table A.

Table 1097

Compounds of the formula I.A, in which $R^1$ is hydrogen, Z is NH and $R^3$ is 2-isopropoxyethyl and $R^2$ for a compound corresponds in each case to a group in Table A.

Table 1098

Compounds of the formula I.B, in which $R^1$ is hydrogen, Z is NH and $R^3$ is 2-isopropoxyethyl and $R^2$ for a compound corresponds in each case to a group in Table A.

Table 1099

Compounds of the formula I.A, in which $R^1$ is methyl, Z is oxygen and $R^3$ is 2-isopropoxyethyl and $R^2$ for a compound corresponds in each case to a group in Table A.

Table 1100

Compounds of the formula I.B, in which $R^1$ is methyl, Z is oxygen and $R^3$ is 2-isopropoxyethyl and $R^2$ for a compound corresponds in each case to a group in Table A.

Table 1101

Compounds of the formula I.A, in which $R^1$ is methyl, Z is sulfur and $R^3$ is 2-isopropoxyethyl and $R^2$ for a compound corresponds in each case to a group in Table A.

Table 2203

Compounds of the formula I.B, in which $R^1$ is methyl, Z is sulfur and $R^3$ is 2-isopropoxyethyl and $R^2$ for a compound corresponds in each case to a group in Table A.

Table 2204

Compounds of the formula I.A, in which $R^1$ is methyl, Z is NH and $R^3$ is 2-isopropoxyethyl and $R^2$ for a compound corresponds in each case to a group in Table A.

Table 2205

Compounds of the formula I.B, in which $R^1$ is methyl, Z is NH and $R^3$ is 2-isopropoxyethyl and $R^2$ for a compound corresponds in each case to a group in Table A.

Table 2206

Compounds of the formula I.A, in which $R^1$ is ethyl, Z is oxygen and $R^3$ is 2-isopropoxyethyl and $R^2$ for a compound corresponds in each case to a group in Table A.

Table 2207

Compounds of the formula I.B, in which $R^1$ is ethyl, Z is oxygen and $R^3$ is 2-isopropoxyethyl and $R^2$ for a compound corresponds in each case to a group in Table A.

Table 2208

Compounds of the formula I.A, in which $R^1$ is ethyl, Z is sulfur and $R^3$ is 2-isopropoxyethyl and $R^2$ for a compound corresponds in each case to a group in Table A.

Table 2209

Compounds of the formula I.B, in which $R^1$ is ethyl, Z is sulfur and $R^3$ is 2-isopropoxyethyl and $R^2$ for a compound corresponds in each case to a group in Table A.

Table 2210

Compounds of the formula I.A, in which $R^1$ is ethyl, Z is NH and $R^3$ is 2-isopropoxyethyl and $R^2$ for a compound corresponds in each case to a group in Table A.

Table 2211

Compounds of the formula I.B, in which $R^1$ is ethyl, Z is NH and $R^3$ is 2-isopropoxyethyl and $R^2$ for a compound corresponds in each case to a group in Table A.

Table 2212

Compounds of the formula I.A, in which $R^1$ is isopropyl, Z is oxygen and $R^3$ is 2-isopropoxyethyl and $R^2$ for a compound corresponds in each case to a group in Table A.

Table 2213

Compounds of the formula I.B, in which $R^1$ is isopropyl, Z is oxygen and $R^3$ is 2-isopropoxyethyl and $R^2$ for a compound corresponds in each case to a group in Table A.

Table 2214

Compounds of the formula I.A, in which $R^1$ is isopropyl, Z is sulfur and $R^3$ is 2-isopropoxyethyl and $R^2$ for a compound corresponds in each case to a group in Table A.

Table 2215

Compounds of the formula I.B, in which $R^1$ is isopropyl, Z is sulfur and $R^3$ is 2-isopropoxyethyl and $R^2$ for a compound corresponds in each case to a group in Table A.

Table 2216

Compounds of the formula I.A, in which $R^1$ is isopropyl, Z is NH and $R^3$ is 2-isopropoxyethyl and $R^2$ for a compound corresponds in each case to a group in Table A.

Table 2217

Compounds of the formula I.B, in which $R^1$ is isopropyl, Z is NH and $R^3$ is 2-isopropoxyethyl and $R^2$ for a compound corresponds in each case to a group in Table A.

Table 2218

Compounds of the formula I.A, in which $R^1$ is hydrogen, Z is oxygen and $R^3$ is 3-methoxypropyl and $R^2$ for a compound corresponds in each case to a group in Table A.

Table 2219

Compounds of the formula I.B, in which $R^1$ is hydrogen, Z is oxygen and $R^3$ is 3-methoxypropyl and $R^2$ for a compound corresponds in each case to a group in Table A.

Table 2220

Compounds of the formula I.A, in which $R^1$ is hydrogen, Z is sulfur and $R^3$ is 3-methoxypropyl and $R^2$ for a compound corresponds in each case to a group in Table A.

Table 2221

Compounds of the formula I.B, in which $R^1$ is hydrogen, Z is sulfur and $R^3$ is 3-methoxypropyl and $R^2$ for a compound corresponds in each case to a group in Table A.

Table 2222

Compounds of the formula I.A, in which $R^1$ is hydrogen, Z is NH and $R^3$ is 3-methoxypropyl and $R^2$ for a compound corresponds in each case to a group in Table A.

Table 2223

Compounds of the formula I.B, in which $R^1$ is hydrogen, Z is NH and $R^3$ is 3-methoxypropyl and $R^2$ for a compound corresponds in each case to a group in Table A.

Table 2224

Compounds of the formula I.A, in which $R^1$ is methyl, Z is oxygen and $R^3$ is 3-methoxypropyl and $R^2$ for a compound corresponds in each case to a group in Table A.

Table 2225

Compounds of the formula I.B, in which $R^1$ is methyl, Z is oxygen and $R^3$ is 3-methoxypropyl and $R^2$ for a compound corresponds in each case to a group in Table A.

Table 2226

Compounds of the formula I.A, in which $R^1$ is methyl, Z is sulfur and $R^3$ is 3-methoxypropyl and $R^2$ for a compound corresponds in each case to a group in Table A.

Table 2227

Compounds of the formula I.B, in which $R^1$ is methyl, Z is sulfur and $R^3$ is 3-methoxypropyl and $R^2$ for a compound corresponds in each case to a group in Table A.

Table 2228

Compounds of the formula I.A, in which $R^1$ is methyl, Z is NH and $R^3$ is 3-methoxypropyl and $R^2$ for a compound corresponds in each case to a group in Table A.

Table 2229

Compounds of the formula I.B, in which $R^1$ is methyl, Z is NH and $R^3$ is 3-methoxypropyl and $R^2$ for a compound corresponds in each case to a group in Table A.

Table 2230

Compounds of the formula I.A, in which $R^1$ is ethyl, Z is oxygen and $R^3$ is 3-methoxypropyl and $R^2$ for a compound corresponds in each case to a group in Table A.

Table 2231

Compounds of the formula I.B, in which $R^1$ is ethyl, Z is oxygen and $R^3$ is 3-methoxypropyl and $R^2$ for a compound corresponds in each case to a group in Table A.

Table 2232

Compounds of the formula I.A, in which $R^1$ is ethyl, Z is sulfur and $R^3$ is 3-methoxypropyl and $R^2$ for a compound corresponds in each case to a group in Table A.

Table 2233

Compounds of the formula I.B, in which $R^1$ is ethyl, Z is sulfur and $R^3$ is 3-methoxypropyl and $R^2$ for a compound corresponds in each case to a group in Table A.

Table 2234

Compounds of the formula I.A, in which $R^1$ is ethyl, Z is NH and $R^3$ is 3-methoxypropyl and $R^2$ for a compound corresponds in each case to a group in Table A.

Table 2235

Compounds of the formula I.B, in which $R^1$ is ethyl, Z is NH and $R^3$ is 3-methoxypropyl and $R^2$ for a compound corresponds in each case to a group in Table A.

Table 2236

Compounds of the formula I.A, in which $R^1$ is isopropyl, Z is oxygen and $R^3$ is 3-methoxypropyl and $R^2$ for a compound corresponds in each case to a group in Table A.

Table 2237

Compounds of the formula I.B, in which $R^1$ is isopropyl, Z is oxygen and $R^3$ is 3-methoxypropyl and $R^2$ for a compound corresponds in each case to a group in Table A.

Table 2238

Compounds of the formula I.A, in which $R^1$ is isopropyl, Z is sulfur and $R^3$ is 3-methoxypropyl and $R^2$ for a compound corresponds in each case to a group in Table A.

Table 2239

Compounds of the formula I.B, in which $R^1$ is isopropyl, Z is sulfur and $R^3$ is 3-methoxypropyl and $R^2$ for a compound corresponds in each case to a group in Table A.

Table 2240

Compounds of the formula I.A, in which $R^1$ is isopropyl, Z is NH and $R^3$ is 3-methoxypropyl and $R^2$ for a compound corresponds in each case to a group in Table A.

Table 2241

Compounds of the formula I.B, in which $R^1$ is isopropyl, Z is NH and $R^3$ is 3-methoxypropyl and $R^2$ for a compound corresponds in each case to a group in Table A.

Table 2242

Compounds of the formula I.A, in which $R^1$ is hydrogen, Z is oxygen and $R^3$ is 3-ethoxypropyl and $R^2$ for a compound corresponds in each case to a group in Table A.

Table 2243

Compounds of the formula I.B, in which $R^1$ is hydrogen, Z is oxygen and $R^3$ is 3-ethoxypropyl and $R^2$ for a compound corresponds in each case to a group in Table A.

Table 2244

Compounds of the formula I.A, in which $R^1$ is hydrogen, Z is sulfur and $R^3$ is 3-ethoxypropyl and $R^2$ for a compound corresponds in each case to a group in Table A.

Table 2245

Compounds of the formula I.B, in which $R^1$ is hydrogen, Z is sulfur and $R^3$ is 3-ethoxypropyl and $R^2$ for a compound corresponds in each case to a group in Table A.

Table 2246

Compounds of the formula I.A, in which $R^1$ is hydrogen, Z is NH and $R^3$ is 3-ethoxypropyl and $R^2$ for a compound corresponds in each case to a group in Table A.

Table 2247

Compounds of the formula I.B, in which $R^1$ is hydrogen, Z is NH and $R^3$ is 3-ethoxypropyl and $R^2$ for a compound corresponds in each case to a group in Table A.

Table 2248

Compounds of the formula I.A, in which $R^1$ is methyl, Z is oxygen and $R^3$ is 3-ethoxypropyl and $R^2$ for a compound corresponds in each case to a group in Table A.

Table 2249

Compounds of the formula I.B, in which $R^1$ is methyl, Z is oxygen and $R^3$ is 3-ethoxypropyl and $R^2$ for a compound corresponds in each case to a group in Table A.

Table 2250

Compounds of the formula I.A, in which $R^1$ is methyl, Z is sulfur and $R^3$ is 3-ethoxypropyl and $R^2$ for a compound corresponds in each case to a group in Table A.

Table 2251

Compounds of the formula I.B, in which $R^1$ is methyl, Z is sulfur and $R^3$ is 3-ethoxypropyl and $R^2$ for a compound corresponds in each case to a group in Table A.

Table 2252

Compounds of the formula I.A, in which $R^1$ is methyl, Z is NH and $R^3$ is 3-ethoxypropyl and $R^2$ for a compound corresponds in each case to a group in Table A.

Table 2253

Compounds of the formula I.B, in which $R^1$ is methyl, Z is NH and $R^3$ is 3-ethoxypropyl and $R^2$ for a compound corresponds in each case to a group in Table A.

Table 2254

Compounds of the formula I.A, in which $R^1$ is ethyl, Z is oxygen and $R^3$ is 3-ethoxypropyl and $R^2$ for a compound corresponds in each case to a group in Table A.

Table 2255

Compounds of the formula I.B, in which $R^1$ is ethyl, Z is oxygen and $R^3$ is 3-ethoxypropyl and $R^2$ for a compound corresponds in each case to a group in Table A.

Table 2256

Compounds of the formula I.A, in which $R^1$ is ethyl, Z is sulfur and $R^3$ is 3-ethoxypropyl and $R^2$ for a compound corresponds in each case to a group in Table A.

Table 2257

Compounds of the formula I.B, in which $R^1$ is ethyl, Z is sulfur and $R^3$ is 3-ethoxypropyl and $R^2$ for a compound corresponds in each case to a group in Table A.

Table 2258

Compounds of the formula I.A, in which $R^1$ is ethyl, Z is NH and $R^3$ is 3-ethoxypropyl and $R^2$ for a compound corresponds in each case to a group in Table A.

Table 2259

Compounds of the formula I.B, in which $R^1$ is ethyl, Z is NH and $R^3$ is 3-ethoxypropyl and $R^2$ for a compound corresponds in each case to a group in Table A.

Table 2260

Compounds of the formula I.A, in which $R^1$ is isopropyl, Z is oxygen and $R^3$ is 3-ethoxypropyl and $R^2$ for a compound corresponds in each case to a group in Table A.

Table 2261

Compounds of the formula I.B, in which $R^1$ is isopropyl, Z is oxygen and $R^3$ is 3-ethoxypropyl and $R^2$ for a compound corresponds in each case to a group in Table A.

Table 2262

Compounds of the formula I.A, in which $R^1$ is isopropyl, Z is sulfur and $R^3$ is 3-ethoxypropyl and $R^2$ for a compound corresponds in each case to a group in Table A.

Table 2263

Compounds of the formula I.B, in which $R^1$ is isopropyl, Z is sulfur and $R^3$ is 3-ethoxypropyl and $R^2$ for a compound corresponds in each case to a group in Table A.

Table 2264

Compounds of the formula I.A, in which $R^1$ is isopropyl, Z is NH and $R^3$ is 3-ethoxypropyl and $R^2$ for a compound corresponds in each case to a group in Table A.

Table 2265

Compounds of the formula I.B, in which $R^1$ is isopropyl, Z is NH and $R^3$ is 3-ethoxypropyl and $R^2$ for a compound corresponds in each case to a group in Table A.

Table 2266

Compounds of the formula I.A, in which $R^1$ is hydrogen, Z is oxygen and $R^3$ is 3-isopropoxypropyl and $R^2$ for a compound corresponds in each case to a group in Table A.

Table 2267

Compounds of the formula I.B, in which $R^1$ is hydrogen, Z is oxygen and $R^3$ is 3-isopropoxypropyl and $R^2$ for a compound corresponds in each case to a group in Table A.

Table 2268

Compounds of the formula I.A, in which $R^1$ is hydrogen, Z is sulfur and $R^3$ is 3-isopropoxypropyl and $R^2$ for a compound corresponds in each case to a group in Table A.

Table 2269

Compounds of the formula I.B, in which $R^1$ is hydrogen, Z is sulfur and $R^3$ is 3-isopropoxypropyl and $R^2$ for a compound corresponds in each case to a group in Table A.

Table 2270

Compounds of the formula I.A, in which $R^1$ is hydrogen, Z is NH and $R^3$ is 3-isopropoxypropyl and $R^2$ for a compound corresponds in each case to a group in Table A.

Table 2271

Compounds of the formula I.B, in which $R^1$ is hydrogen, Z is NH and $R^3$ is 3-isopropoxypropyl and $R^2$ for a compound corresponds in each case to a group in Table A.

Table 2272

Compounds of the formula I.A, in which $R^1$ is methyl, Z is oxygen and $R^3$ is 3-isopropoxypropyl and $R^2$ for a compound corresponds in each case to a group in Table A.

Table 2273

Compounds of the formula I.B, in which $R^1$ is methyl, Z is oxygen and $R^3$ is 3-isopropoxypropyl and $R^2$ for a compound corresponds in each case to a group in Table A.

Table 2274

Compounds of the formula I.A, in which $R^1$ is methyl, Z is sulfur and $R^3$ is 3-isopropoxypropyl and $R^2$ for a compound corresponds in each case to a group in Table A.

Table 2275

Compounds of the formula I.B, in which $R^1$ is methyl, Z is sulfur and $R^3$ is 3-isopropoxypropyl and $R^2$ for a compound corresponds in each case to a group in Table A.

Table 2276

Compounds of the formula I.A, in which $R^1$ is methyl, Z is NH and $R^3$ is 3-isopropoxypropyl and $R^2$ for a compound corresponds in each case to a group in Table A.

Table 2277

Compounds of the formula I.B, in which $R^1$ is methyl, Z is NH and $R^3$ is 3-isopropoxypropyl and $R^2$ for a compound corresponds in each case to a group in Table A.

Table 2278

Compounds of the formula I.A, in which $R^1$ is ethyl, Z is oxygen and $R^3$ is 3-isopropoxypropyl and $R^2$ for a compound corresponds in each case to a group in Table A.

Table 2279

Compounds of the formula I.B, in which $R^1$ is ethyl, Z is oxygen and $R^3$ is 3-isopropoxypropyl and $R^2$ for a compound corresponds in each case to a group in Table A.

Table 2280

Compounds of the formula I.A, in which $R^1$ is ethyl, Z is sulfur and $R^3$ is 3-isopropoxypropyl and $R^2$ for a compound corresponds in each case to a group in Table A.

Table 2281

Compounds of the formula I.B, in which $R^1$ is ethyl, Z is sulfur and $R^3$ is 3-isopropoxypropyl and $R^2$ for a compound corresponds in each case to a group in Table A.

Table 2282

Compounds of the formula I.A, in which $R^1$ is ethyl, Z is NH and $R^3$ is 3-isopropoxypropyl and $R^2$ for a compound corresponds in each case to a group in Table A.

Table 2283

Compounds of the formula I.B, in which $R^1$ is ethyl, Z is NH and $R^3$ is 3-isopropoxypropyl and $R^2$ for a compound corresponds in each case to a group in Table A.

Table 2284

Compounds of the formula I.A, in which $R^1$ is isopropyl, Z is oxygen and $R^3$ is 3-isopropoxypropyl and $R^2$ for a compound corresponds in each case to a group in Table A.

Table 2285

Compounds of the formula I.B, in which $R^1$ is isopropyl, Z is oxygen and $R^3$ is 3-isopropoxypropyl and $R^2$ for a compound corresponds in each case to a group in Table A.

Table 2286

Compounds of the formula I.A, in which $R^1$ is isopropyl, Z is sulfur and $R^3$ is 3-isopropoxypropyl and $R^2$ for a compound corresponds in each case to a group in Table A.

Table 2287

Compounds of the formula I.B, in which $R^1$ is isopropyl, Z is sulfur and $R^3$ is 3-isopropoxypropyl and $R^2$ for a compound corresponds in each case to a group in Table A.

Table 2288

Compounds of the formula I.A, in which $R^1$ is isopropyl, Z is NH and $R^3$ is 3-isopropoxypropyl and $R^2$ for a compound corresponds in each case to a group in Table A.

Table 2289

Compounds of the formula I.B, in which $R^1$ is isopropyl, Z is NH and $R^3$ is 3-isopropoxypropyl and $R^2$ for a compound corresponds in each case to a group in Table A.

Table 2290

Compounds of the formula I.A, in which $R^1$ is hydrogen, Z is oxygen and $R^3$ is 4-methoxybutyl and $R^2$ for a compound corresponds in each case to a group in Table A.

Table 2291

Compounds of the formula I.B, in which $R^1$ is hydrogen, Z is oxygen and $R^3$ is 4-methoxybutyl and $R^2$ for a compound corresponds in each case to a group in Table A.

Table 2292

Compounds of the formula I.A, in which $R^1$ is hydrogen, Z is sulfur and $R^3$ is 4-methoxybutyl and $R^2$ for a compound corresponds in each case to a group in Table A.

Table 2293

Compounds of the formula I.B, in which $R^1$ is hydrogen, Z is sulfur and $R^3$ is 4-methoxybutyl and $R^2$ for a compound corresponds in each case to a group in Table A.

Table 2294

Compounds of the formula I.A, in which $R^1$ is hydrogen, Z is NH and $R^3$ is 4-methoxybutyl and $R^2$ for a compound corresponds in each case to a group in Table A.

Table 2295

Compounds of the formula I.B, in which $R^1$ is hydrogen, Z is NH and $R^3$ is 4-methoxybutyl and $R^2$ for a compound corresponds in each case to a group in Table A.

Table 2296

Compounds of the formula I.A, in which $R^1$ is methyl, Z is oxygen and $R^3$ is 4-methoxybutyl and $R^2$ for a compound corresponds in each case to a group in Table A.

Table 2297

Compounds of the formula I.B, in which $R^1$ is methyl, Z is oxygen and $R^3$ is 4-methoxybutyl and $R^2$ for a compound corresponds in each case to a group in Table A.

Table 2298

Compounds of the formula I.A, in which $R^1$ is methyl, Z is sulfur and $R^3$ is 4-methoxybutyl and $R^2$ for a compound corresponds in each case to a group in Table A.

Table 2299

Compounds of the formula I.B, in which $R^1$ is methyl, Z is sulfur and $R^3$ is 4-methoxybutyl and $R^2$ for a compound corresponds in each case to a group in Table A.

Table 2300

Compounds of the formula I.A, in which $R^1$ is methyl, Z is NH and $R^3$ is 4-methoxybutyl and $R^2$ for a compound corresponds in each case to a group in Table A.

Table 2301

Compounds of the formula I.B, in which $R^1$ is methyl, Z is NH and $R^3$ is 4-methoxybutyl and $R^2$ for a compound corresponds in each case to a group in Table A.

Table 2302

Compounds of the formula I.A, in which $R^1$ is ethyl, Z is oxygen and $R^3$ is 4-methoxybutyl and $R^2$ for a compound corresponds in each case to a group in Table A.

Table 2303

Compounds of the formula I.B, in which $R^1$ is ethyl, Z is oxygen and $R^3$ is 4-methoxybutyl and $R^2$ for a compound corresponds in each case to a group in Table A.

Table 2304

Compounds of the formula I.A, in which $R^1$ is ethyl, Z is sulfur and $R^3$ is 4-methoxybutyl and $R^2$ for a compound corresponds in each case to a group in Table A.

Table 2305

Compounds of the formula I.B, in which $R^1$ is ethyl, Z is sulfur and $R^3$ is 4-methoxybutyl and $R^2$ for a compound corresponds in each case to a group in Table A.

Table 2306

Compounds of the formula I.A, in which $R^1$ is ethyl, Z is NH and $R^3$ is 4-methoxybutyl and $R^2$ for a compound corresponds in each case to a group in Table A.

Table 2307

Compounds of the formula I.B, in which $R^1$ is ethyl, Z is NH and $R^3$ is 4-methoxybutyl and $R^2$ for a compound corresponds in each case to a group in Table A.

Table 2308

Compounds of the formula I.A, in which $R^1$ is isopropyl, Z is oxygen and $R^3$ is 4-methoxybutyl and $R^2$ for a compound corresponds in each case to a group in Table A.

Table 2309

Compounds of the formula I.B, in which $R^1$ is isopropyl, Z is oxygen and $R^3$ is 4-methoxybutyl and $R^2$ for a compound corresponds in each case to a group in Table A.

Table 2310

Compounds of the formula I.A, in which $R^1$ is isopropyl, Z is sulfur and $R^3$ is 4-methoxybutyl and $R^2$ for a compound corresponds in each case to a group in Table A.

Table 2311

Compounds of the formula I.B, in which $R^1$ is isopropyl, Z is sulfur and $R^3$ is 4-methoxybutyl and $R^2$ for a compound corresponds in each case to a group in Table A.

Table 2312

Compounds of the formula I.A, in which $R^1$ is isopropyl, Z is NH and $R^3$ is 4-methoxybutyl and $R^2$ for a compound corresponds in each case to a group in Table A.

Table 2313

Compounds of the formula I.B, in which $R^1$ is isopropyl, Z is NH and $R^3$ is 4-methoxybutyl and $R^2$ for a compound corresponds in each case to a group in Table A.

Table 2314

Compounds of the formula I.A, in which $R^1$ is hydrogen, Z is oxygen and $R^3$ is 4-ethoxybutyl and $R^2$ for a compound corresponds in each case to a group in Table A.

Table 2315

Compounds of the formula I.B, in which $R^1$ is hydrogen, Z is oxygen and $R^3$ is 4-ethoxybutyl and $R^2$ for a compound corresponds in each case to a group in Table A.

Table 2316

Compounds of the formula I.A, in which $R^1$ is hydrogen, Z is sulfur and $R^3$ is 4-ethoxybutyl and $R^2$ for a compound corresponds in each case to a group in Table A.

Table 2317

Compounds of the formula I.B, in which $R^1$ is hydrogen, Z is sulfur and $R^3$ is 4-ethoxybutyl and $R^2$ for a compound corresponds in each case to a group in Table A.

Table 2318

Compounds of the formula I.A, in which $R^1$ is hydrogen, Z is NH and $R^3$ is 4-ethoxybutyl and $R^2$ for a compound corresponds in each case to a group in Table A.

Table 2319

Compounds of the formula I.B, in which $R^1$ is hydrogen, Z is NH and $R^3$ is 4-ethoxybutyl and $R^2$ for a compound corresponds in each case to a group in Table A.

Table 2320

Compounds of the formula I.A, in which $R^1$ is methyl, Z is oxygen and $R^3$ is 4-ethoxybutyl and $R^2$ for a compound corresponds in each case to a group in Table A.

Table 2321

Compounds of the formula I.B, in which $R^1$ is methyl, Z is oxygen and $R^3$ is 4-ethoxybutyl and $R^2$ for a compound corresponds in each case to a group in Table A.

Table 2322

Compounds of the formula I.A, in which $R^1$ is methyl, Z is sulfur and $R^3$ is 4-ethoxybutyl and $R^2$ for a compound corresponds in each case to a group in Table A.

Table 2323

Compounds of the formula I.B, in which $R^1$ is methyl, Z is sulfur and $R^3$ is 4-ethoxybutyl and $R^2$ for a compound corresponds in each case to a group in Table A.

Table 2324

Compounds of the formula I.A, in which $R^1$ is methyl, Z is NH and $R^3$ is 4-ethoxybutyl and $R^2$ for a compound corresponds in each case to a group in Table A.

Table 2325

Compounds of the formula I.B, in which $R^1$ is methyl, Z is NH and $R^3$ is 4-ethoxybutyl and $R^2$ for a compound corresponds in each case to a group in Table A.

Table 2326

Compounds of the formula I.A, in which $R^1$ is ethyl, Z is oxygen and $R^3$ is 4-ethoxybutyl and $R^2$ for a compound corresponds in each case to a group in Table A.

Table 2327

Compounds of the formula I.B, in which $R^1$ is ethyl, Z is oxygen and $R^3$ is 4-ethoxybutyl and $R^2$ for a compound corresponds in each case to a group in Table A.

Table 2328

Compounds of the formula I.A, in which $R^1$ is ethyl, Z is sulfur and $R^3$ is 4-ethoxybutyl and $R^2$ for a compound corresponds in each case to a group in Table A.

Table 2329

Compounds of the formula I.B, in which $R^1$ is ethyl, Z is sulfur and $R^3$ is 4-ethoxybutyl and $R^2$ for a compound corresponds in each case to a group in Table A.

Table 2330

Compounds of the formula I.A, in which $R^1$ is ethyl, Z is NH and $R^3$ is 4-ethoxybutyl and $R^2$ for a compound corresponds in each case to a group in Table A.

Table 2331

Compounds of the formula I.B, in which $R^1$ is ethyl, Z is NH and $R^3$ is 4-ethoxybutyl and $R^2$ for a compound corresponds in each case to a group in Table A.

Table 2332

Compounds of the formula I.A, in which $R^1$ is isopropyl, Z is oxygen and $R^3$ is 4-ethoxybutyl and $R^2$ for a compound corresponds in each case to a group in Table A.

Table 2333

Compounds of the formula I.B, in which $R^1$ is isopropyl, Z is oxygen and $R^3$ is 4-ethoxybutyl and $R^2$ for a compound corresponds in each case to a group in Table A.

Table 2334

Compounds of the formula I.A, in which $R^1$ is isopropyl, Z is sulfur and $R^3$ is 4-ethoxybutyl and $R^2$ for a compound corresponds in each case to a group in Table A.

Table 2335

Compounds of the formula I.B, in which $R^1$ is isopropyl, Z is sulfur and $R^3$ is 4-ethoxybutyl and $R^2$ for a compound corresponds in each case to a group in Table A.

Table 2336

Compounds of the formula I.A, in which $R^1$ is isopropyl, Z is NH and $R^3$ is 4-ethoxybutyl and $R^2$ for a compound corresponds in each case to a group in Table A.

Table 2337

Compounds of the formula I.B, in which $R^1$ is isopropyl, Z is NH and $R^3$ is 4-ethoxybutyl and $R^2$ for a compound corresponds in each case to a group in Table A.

Table 2338

Compounds of the formula I.A, in which $R^1$ is hydrogen, Z is oxygen and $R^3$ is 4-isopropoxybutyl and $R^2$ for a compound corresponds in each case to a group in Table A.

Table 2339

Compounds of the formula I.B, in which $R^1$ is hydrogen, Z is oxygen and $R^3$ is 4-isopropoxybutyl and $R^2$ for a compound corresponds in each case to a group in Table A.

Table 2340

Compounds of the formula I.A, in which $R^1$ is hydrogen, Z is sulfur and $R^3$ is 4-isopropoxybutyl and $R^2$ for a compound corresponds in each case to a group in Table A.

Table 2341

Compounds of the formula I.B, in which $R^1$ is hydrogen, Z is sulfur and $R^3$ is 4-isopropoxybutyl and $R^2$ for a compound corresponds in each case to a group in Table A.

Table 2342

Compounds of the formula I.A, in which $R^1$ is hydrogen, Z is NH and $R^3$ is 4-isopropoxybutyl and $R^2$ for a compound corresponds in each case to a group in Table A.

Table 2343

Compounds of the formula I.B, in which $R^1$ is hydrogen, Z is NH and $R^3$ is 4-isopropoxybutyl and $R^2$ for a compound corresponds in each case to a group in Table A.

Table 2344

Compounds of the formula I.A, in which $R^1$ is methyl, Z is oxygen and $R^3$ is 4-isopropoxybutyl and $R^2$ for a compound corresponds in each case to a group in Table A.

Table 2345

Compounds of the formula I.B, in which $R^1$ is methyl, Z is oxygen and $R^3$ is 4-isopropoxybutyl and $R^2$ for a compound corresponds in each case to a group in Table A.

Table 2346

Compounds of the formula I.A, in which $R^1$ is methyl, Z is sulfur and $R^3$ is 4-isopropoxybutyl and $R^2$ for a compound corresponds in each case to a group in Table A.

Table 2347

Compounds of the formula I.B, in which $R^1$ is methyl, Z is sulfur and $R^3$ is 4-isopropoxybutyl and $R^2$ for a compound corresponds in each case to a group in Table A.

Table 2348

Compounds of the formula I.A, in which $R^1$ is methyl, Z is NH and $R^3$ is 4-isopropoxybutyl and $R^2$ for a compound corresponds in each case to a group in Table A.

Table 2349

Compounds of the formula I.B, in which $R^1$ is methyl, Z is NH and $R^3$ is 4-isopropoxybutyl and $R^2$ for a compound corresponds in each case to a group in Table A.

Table 2350

Compounds of the formula I.A, in which $R^1$ is ethyl, Z is oxygen and $R^3$ is 4-isopropoxybutyl and $R^2$ for a compound corresponds in each case to a group in Table A.

Table 2351

Compounds of the formula I.B, in which $R^1$ is ethyl, Z is oxygen and $R^3$ is 4-isopropoxybutyl and $R^2$ for a compound corresponds in each case to a group in Table A.

Table 2352

Compounds of the formula I.A, in which $R^1$ is ethyl, Z is sulfur and $R^3$ is 4-isopropoxybutyl and $R^2$ for a compound corresponds in each case to a group in Table A.

Table 2353

Compounds of the formula I.B, in which $R^1$ is ethyl, Z is sulfur and $R^3$ is 4-isopropoxybutyl and $R^2$ for a compound corresponds in each case to a group in Table A.

Table 2354

Compounds of the formula I.A, in which $R^1$ is ethyl, Z is NH and $R^3$ is 4-isopropoxybutyl and $R^2$ for a compound corresponds in each case to a group in Table A.

Table 2355

Compounds of the formula I.B, in which $R^1$ is ethyl, Z is NH and $R^3$ is 4-isopropoxybutyl and $R^2$ for a compound corresponds in each case to a group in Table A.

Table 2356

Compounds of the formula I.A, in which $R^1$ is isopropyl, Z is oxygen and $R^3$ is 4-isopropoxybutyl and $R^2$ for a compound corresponds in each case to a group in Table A.

Table 2357

Compounds of the formula I.B, in which $R^1$ is isopropyl, Z is oxygen and $R^3$ is 4-isopropoxybutyl and $R^2$ for a compound corresponds in each case to a group in Table A.

Table 2358

Compounds of the formula I.A, in which $R^1$ is isopropyl, Z is sulfur and $R^3$ is 4-isopropoxybutyl and $R^2$ for a compound corresponds in each case to a group in Table A.

Table 2359

Compounds of the formula I.B, in which $R^1$ is isopropyl, Z is sulfur and $R^3$ is 4-isopropoxybutyl and $R^2$ for a compound corresponds in each case to a group in Table A.

Table 2360

Compounds of the formula I.A, in which $R^1$ is isopropyl, Z is NH and $R^3$ is 4-isopropoxybutyl and $R^2$ for a compound corresponds in each case to a group in Table A.

Table 2361

Compounds of the formula I.B, in which $R^1$ is isopropyl, Z is NH and $R^3$ is 4-isopropoxybutyl and $R^2$ for a compound corresponds in each case to a group in Table A.

Table 2362

Compounds of the formula I.A, in which $R^1$ is hydrogen, Z is oxygen and $R^3$ is prop-2-enyl and $R^2$ for a compound corresponds in each case to a group in Table A.

Table 2363

Compounds of the formula I.B, in which $R^1$ is hydrogen, Z is oxygen and $R^3$ is prop-2-enyl and $R^2$ for a compound corresponds in each case to a group in Table A.

Table 2364

Compounds of the formula I.A, in which $R^1$ is hydrogen, Z is sulfur and $R^3$ is prop-2-enyl and $R^2$ for a compound corresponds in each case to a group in Table A.

Table 2365

Compounds of the formula I.B, in which $R^1$ is hydrogen, Z is sulfur and $R^3$ is prop-2-enyl and $R^2$ for a compound corresponds in each case to a group in Table A.

Table 2366

Compounds of the formula I.A, in which $R^1$ is hydrogen, Z is NH and $R^3$ is prop-2-enyl and $R^2$ for a compound corresponds in each case to a group in Table A.

Table 2367

Compounds of the formula I.B, in which $R^1$ is hydrogen, Z is NH and $R^3$ is prop-2-enyl and $R^2$ for a compound corresponds in each case to a group in Table A.

Table 2368

Compounds of the formula I.A, in which $R^1$ is methyl, Z is oxygen and $R^3$ is prop-2-enyl and $R^2$ for a compound corresponds in each case to a group in Table A.

Table 2369

Compounds of the formula I.B, in which $R^1$ is methyl, Z is oxygen and $R^3$ is prop-2-enyl and $R^2$ for a compound corresponds in each case to a group in Table A.

Table 2370

Compounds of the formula I.A, in which $R^1$ is methyl, Z is sulfur and $R^3$ is prop-2-enyl and $R^2$ for a compound corresponds in each case to a group in Table A.

Table 2371

Compounds of the formula I.B, in which $R^1$ is methyl, Z is sulfur and $R^3$ is prop-2-enyl and $R^2$ for a compound corresponds in each case to a group in Table A.

Table 2372

Compounds of the formula I.A, in which $R^1$ is methyl, Z is NH and $R^3$ is prop-2-enyl and $R^2$ for a compound corresponds in each case to a group in Table A.

Table 2373

Compounds of the formula I.B, in which $R^1$ is methyl, Z is NH and $R^3$ is prop-2-enyl and $R^2$ for a compound corresponds in each case to a group in Table A.

Table 2374

Compounds of the formula I.A, in which $R^1$ is ethyl, Z is oxygen and $R^3$ is prop-2-enyl and $R^2$ for a compound corresponds in each case to a group in Table A.

Table 2375

Compounds of the formula I.B, in which $R^1$ is ethyl, Z is oxygen and $R^3$ is prop-2-enyl and $R^2$ for a compound corresponds in each case to a group in Table A.

Table 2376

Compounds of the formula I.A, in which $R^1$ is ethyl, Z is sulfur and $R^3$ is prop-2-enyl and $R^2$ for a compound corresponds in each case to a group in Table A.

Table 2377

Compounds of the formula I.B, in which $R^1$ is ethyl, Z is sulfur and $R^3$ is prop-2-enyl and $R^2$ for a compound corresponds in each case to a group in Table A.

Table 2378

Compounds of the formula I.A, in which $R^1$ is ethyl, Z is NH and $R^3$ is prop-2-enyl and $R^2$ for a compound corresponds in each case to a group in Table A.

Table 2379

Compounds of the formula I.B, in which $R^1$ is ethyl, Z is NH and $R^3$ is prop-2-enyl and $R^2$ for a compound corresponds in each case to a group in Table A.

Table 2380

Compounds of the formula I.A, in which $R^1$ is isopropyl, Z is oxygen and $R^3$ is prop-2-enyl and $R^2$ for a compound corresponds in each case to a group in Table A.

Table 2381

Compounds of the formula I.B, in which $R^1$ is isopropyl, Z is oxygen and $R^3$ is prop-2-enyl and $R^2$ for a compound corresponds in each case to a group in Table A.

Table 2382

Compounds of the formula I.A, in which $R^1$ is isopropyl, Z is sulfur and $R^3$ is prop-2-enyl and $R^2$ for a compound corresponds in each case to a group in Table A.

Table 2383

Compounds of the formula I.B, in which $R^1$ is isopropyl, Z is sulfur and $R^3$ is prop-2-enyl and $R^2$ for a compound corresponds in each case to a group in Table A.

Table 2384

Compounds of the formula I.A, in which $R^1$ is isopropyl, Z is NH and $R^3$ is prop-2-enyl and $R^2$ for a compound corresponds in each case to a group in Table A.

Table 2385

Compounds of the formula I.B, in which $R^1$ is isopropyl, Z is NH and $R^3$ is prop-2-enyl and $R^2$ for a compound corresponds in each case to a group in Table A.

Table 2386

Compounds of the formula I.A, in which $R^1$ is hydrogen, Z is oxygen and $R^3$ is cis-but-2-enyl and $R^2$ for a compound corresponds in each case to a group in Table A.

Table 2387

Compounds of the formula I.B, in which $R^1$ is hydrogen, Z is oxygen and $R^3$ is cis-but-2-enyl and $R^2$ for a compound corresponds in each case to a group in Table A.

Table 2388

Compounds of the formula I.A, in which $R^1$ is hydrogen, Z is sulfur and $R^3$ is cis-but-2-enyl and $R^2$ for a compound corresponds in each case to a group in Table A.

Table 2389

Compounds of the formula I.B, in which $R^1$ is hydrogen, Z is sulfur and $R^3$ is cis-but-2-enyl and $R^2$ for a compound corresponds in each case to a group in Table A.

Table 2390

Compounds of the formula I.A, in which $R^1$ is hydrogen, Z is NH and $R^3$ is cis-but-2-enyl and $R^2$ for a compound corresponds in each case to a group in Table A.

Table 2391

Compounds of the formula I.B, in which $R^1$ is hydrogen, Z is NH and $R^3$ is cis-but-2-enyl and $R^2$ for a compound corresponds in each case to a group in Table A.

Table 2392

Compounds of the formula I.A, in which $R^1$ is methyl, Z is oxygen and $R^3$ is cis-but-2-enyl and $R^2$ for a compound corresponds in each case to a group in Table A.

Table 2393

Compounds of the formula I.B, in which $R^1$ is methyl, Z is oxygen and $R^3$ is cis-but-2-enyl and $R^2$ for a compound corresponds in each case to a group in Table A.

Table 2394

Compounds of the formula I.A, in which $R^1$ is methyl, Z is sulfur and $R^3$ is cis-but-2-enyl and $R^2$ for a compound corresponds in each case to a group in Table A.

Table 2395

Compounds of the formula I.B, in which $R^1$ is methyl, Z is sulfur and $R^3$ is cis-but-2-enyl and $R^2$ for a compound corresponds in each case to a group in Table A.

Table 2396

Compounds of the formula I.A, in which $R^1$ is methyl, Z is NH and $R^3$ is cis-but-2-enyl and $R^2$ for a compound corresponds in each case to a group in Table A.

Table 2397

Compounds of the formula I.B, in which $R^1$ is methyl, Z is NH and $R^3$ is cis-but-2-enyl and $R^2$ for a compound corresponds in each case to a group in Table A.

Table 2398

Compounds of the formula I.A, in which $R^1$ is ethyl, Z is oxygen and $R^3$ is cis-but-2-enyl and $R^2$ for a compound corresponds in each case to a group in Table A.

Table 2399

Compounds of the formula I.B, in which $R^1$ is ethyl, Z is oxygen and $R^3$ is cis-but-2-enyl and $R^2$ for a compound corresponds in each case to a group in Table A.

Table 2400

Compounds of the formula I.A, in which $R^1$ is ethyl, Z is sulfur and $R^3$ is cis-but-2-enyl and $R^2$ for a compound corresponds in each case to a group in Table A.

Table 2401

Compounds of the formula I.B, in which $R^1$ is ethyl, Z is sulfur and $R^3$ is cis-but-2-enyl and $R^2$ for a compound corresponds in each case to a group in Table A.

Table 2402

Compounds of the formula I.A, in which $R^1$ is ethyl, Z is NH and $R^3$ is cis-but-2-enyl and $R^2$ for a compound corresponds in each case to a group in Table A.

Table 2403

Compounds of the formula I.B, in which $R^1$ is ethyl, Z is NH and $R^3$ is cis-but-2-enyl and $R^2$ for a compound corresponds in each case to a group in Table A.

Table 2404

Compounds of the formula I.A, in which $R^1$ is isopropyl, Z is oxygen and $R^3$ is cis-but-2-enyl and $R^2$ for a compound corresponds in each case to a group in Table A.

Table 2405

Compounds of the formula I.B, in which $R^1$ is isopropyl, Z is oxygen and $R^3$ is cis-but-2-enyl and $R^2$ for a compound corresponds in each case to a group in Table A.

Table 2406

Compounds of the formula I.A, in which $R^1$ is isopropyl, Z is sulfur and $R^3$ is cis-but-2-enyl and $R^2$ for a compound corresponds in each case to a group in Table A.

Table 2407

Compounds of the formula I.B, in which $R^1$ is isopropyl, Z is sulfur and $R^3$ is cis-but-2-enyl and $R^2$ for a compound corresponds in each case to a group in Table A.

Table 2408

Compounds of the formula I.A, in which $R^1$ is isopropyl, Z is NH and $R^3$ is cis-but-2-enyl and $R^2$ for a compound corresponds in each case to a group in Table A.

Table 2409

Compounds of the formula I.B, in which $R^1$ is isopropyl, Z is NH and $R^3$ is cis-but-2-enyl and $R^2$ for a compound corresponds in each case to a group in Table A.

Table 2410

Compounds of the formula I.A, in which $R^1$ is hydrogen, Z is oxygen and $R^3$ is trans-but-2-enyl and $R^2$ for a compound corresponds in each case to a group in Table A.

Table 2411

Compounds of the formula I.B, in which $R^1$ is hydrogen, Z is oxygen and $R^3$ is trans-but-2-enyl and $R^2$ for a compound corresponds in each case to a group in Table A.

Table 2412

Compounds of the formula I.A, in which $R^1$ is hydrogen, Z is sulfur and $R^3$ is trans-but-2-enyl and $R^2$ for a compound corresponds in each case to a group in Table A.

Table 2413

Compounds of the formula I.B, in which $R^1$ is hydrogen, Z is sulfur and $R^3$ is trans-but-2-enyl and $R^2$ for a compound corresponds in each case to a group in Table A.

Table 2414

Compounds of the formula I.A, in which $R^1$ is hydrogen, Z is NH and $R^3$ is trans-but-2-enyl and $R^2$ for a compound corresponds in each case to a group in Table A.

Table 2415

Compounds of the formula I.B, in which $R^1$ is hydrogen, Z is NH and $R^3$ is trans-but-2-enyl and $R^2$ for a compound corresponds in each case to a group in Table A.

Table 2416

Compounds of the formula I.A, in which $R^1$ is methyl, Z is oxygen and $R^3$ is trans-but-2-enyl and $R^2$ for a compound corresponds in each case to a group in Table A.

Table 2417

Compounds of the formula I.B, in which $R^1$ is methyl, Z is oxygen and $R^3$ is trans-but-2-enyl and $R^2$ for a compound corresponds in each case to a group in Table A.

Table 2418

Compounds of the formula I.A, in which $R^1$ is methyl, Z is sulfur and $R^3$ is trans-but-2-enyl and $R^2$ for a compound corresponds in each case to a group in Table A.

Table 2419

Compounds of the formula I.B, in which $R^1$ is methyl, Z is sulfur and $R^3$ is trans-but-2-enyl and $R^2$ for a compound corresponds in each case to a group in Table A.

Table 2420

Compounds of the formula I.A, in which $R^1$ is methyl, Z is NH and $R^3$ is trans-but-2-enyl and $R^2$ for a compound corresponds in each case to a group in Table A.

Table 2421

Compounds of the formula I.B, in which $R^1$ is methyl, Z is NH and $R^3$ is trans-but-2-enyl and $R^2$ for a compound corresponds in each case to a group in Table A.

Table 2422

Compounds of the formula I.A, in which $R^1$ is ethyl, Z is oxygen and $R^3$ is trans-but-2-enyl and $R^2$ for a compound corresponds in each case to a group in Table A.

Table 2423

Compounds of the formula I.B, in which $R^1$ is ethyl, Z is oxygen and $R^3$ is trans-but-2-enyl and $R^2$ for a compound corresponds in each case to a group in Table A.

Table 2424

Compounds of the formula I.A, in which $R^1$ is ethyl, Z is sulfur and $R^3$ is trans-but-2-enyl and $R^2$ for a compound corresponds in each case to a group in Table A.

Table 2425

Compounds of the formula I.B, in which $R^1$ is ethyl, Z is sulfur and $R^3$ is trans-but-2-enyl and $R^2$ for a compound corresponds in each case to a group in Table A.

Table 2426

Compounds of the formula I.A, in which $R^1$ is ethyl, Z is NH and $R^3$ is trans-but-2-enyl and $R^2$ for a compound corresponds in each case to a group in Table A.

Table 2427

Compounds of the formula I.B, in which $R^1$ is ethyl, Z is NH and $R^3$ is trans-but-2-enyl and $R^2$ for a compound corresponds in each case to a group in Table A.

Table 2428

Compounds of the formula I.A, in which $R^1$ is isopropyl, Z is oxygen and $R^3$ is trans-but-2-enyl and $R^2$ for a compound corresponds in each case to a group in Table A.

Table 2429

Compounds of the formula I.B, in which $R^1$ is isopropyl, Z is oxygen and $R^3$ is trans-but-2-enyl and $R^2$ for a compound corresponds in each case to a group in Table A.

Table 2430

Compounds of the formula I.A, in which $R^1$ is isopropyl, Z is sulfur and $R^3$ is trans-but-2-enyl and $R^2$ for a compound corresponds in each case to a group in Table A.

Table 2431

Compounds of the formula I.B, in which $R^1$ is isopropyl, Z is sulfur and $R^3$ is trans-but-2-enyl and $R^2$ for a compound corresponds in each case to a group in Table A.

Table 2432

Compounds of the formula I.A, in which $R^1$ is isopropyl, Z is NH and $R^3$ is trans-but-2-enyl and $R^2$ for a compound corresponds in each case to a group in Table A.

Table 2433

Compounds of the formula I.B, in which $R^1$ is isopropyl, Z is NH and $R^3$ is trans-but-2-enyl and $R^2$ for a compound corresponds in each case to a group in Table A.

Table 2434

Compounds of the formula I.A, in which $R^1$ is hydrogen, Z is oxygen and $R^3$ is 3-methylbut-2-enyl and $R^2$ for a compound corresponds in each case to a group in Table A.

Table 2435

Compounds of the formula I.B, in which $R^1$ is hydrogen, Z is oxygen and $R^3$ is 3-methylbut-2-enyl and $R^2$ for a compound corresponds in each case to a group in Table A.

Table 2436

Compounds of the formula I.A, in which $R^1$ is hydrogen, Z is sulfur and $R^3$ is 3-methylbut-2-enyl and $R^2$ for a compound corresponds in each case to a group in Table A.

Table 2437

Compounds of the formula I.B, in which $R^1$ is hydrogen, Z is sulfur and $R^3$ is 3-methylbut-2-enyl and $R^2$ for a compound corresponds in each case to a group in Table A.

Table 2438

Compounds of the formula I.A, in which $R^1$ is hydrogen, Z is NH and $R^3$ is 3-methylbut-2-enyl and $R^2$ for a compound corresponds in each case to a group in Table A.

Table 2439

Compounds of the formula I.B, in which $R^1$ is hydrogen, Z is NH and $R^3$ is 3-methylbut-2-enyl and $R^2$ for a compound corresponds in each case to a group in Table A.

Table 2440

Compounds of the formula I.A, in which $R^1$ is methyl, Z is oxygen and $R^3$ is 3-methylbut-2-enyl and $R^2$ for a compound corresponds in each case to a group in Table A.

Table 2441

Compounds of the formula I.B, in which $R^1$ is methyl, Z is oxygen and $R^3$ is 3-methylbut-2-enyl and $R^2$ for a compound corresponds in each case to a group in Table A.

Table 2442

Compounds of the formula I.A, in which $R^1$ is methyl, Z is sulfur and $R^3$ is 3-methylbut-2-enyl and $R^2$ for a compound corresponds in each case to a group in Table A.

Table 2443

Compounds of the formula I.B, in which $R^1$ is methyl, Z is sulfur and $R^3$ is 3-methylbut-2-enyl and $R^2$ for a compound corresponds in each case to a group in Table A.

Table 2444

Compounds of the formula I.A, in which $R^1$ is methyl, Z is NH and $R^3$ is 3-methylbut-2-enyl and $R^2$ for a compound corresponds in each case to a group in Table A.

Table 2445

Compounds of the formula I.B, in which $R^1$ is methyl, Z is NH and $R^3$ is 3-methylbut-2-enyl and $R^2$ for a compound corresponds in each case to a group in Table A.

Table 2446

Compounds of the formula I.A, in which $R^1$ is ethyl, Z is oxygen and $R^3$ is 3-methylbut-2-enyl and $R^2$ for a compound corresponds in each case to a group in Table A.

Table 2447

Compounds of the formula I.B, in which $R^1$ is ethyl, Z is oxygen and $R^3$ is 3-methylbut-2-enyl and $R^2$ for a compound corresponds in each case to a group in Table A.

Table 2448

Compounds of the formula I.A, in which $R^1$ is ethyl, Z is sulfur and $R^3$ is 3-methylbut-2-enyl and $R^2$ for a compound corresponds in each case to a group in Table A.

Table 2449

Compounds of the formula I.B, in which $R^1$ is ethyl, Z is sulfur and $R^3$ is 3-methylbut-2-enyl and $R^2$ for a compound corresponds in each case to a group in Table A.

Table 2450

Compounds of the formula I.A, in which $R^1$ is ethyl, Z is NH and $R^3$ is 3-methylbut-2-enyl and $R^2$ for a compound corresponds in each case to a group in Table A.

Table 2451

Compounds of the formula I.B, in which $R^1$ is ethyl, Z is NH and $R^3$ is 3-methylbut-2-enyl and $R^2$ for a compound corresponds in each case to a group in Table A.

Table 2452

Compounds of the formula I.A, in which $R^1$ is isopropyl, Z is oxygen and $R^3$ is 3-methylbut-2-enyl and $R^2$ for a compound corresponds in each case to a group in Table A.

Table 2453

Compounds of the formula I.B, in which $R^1$ is isopropyl, Z is oxygen and $R^3$ is 3-methylbut-2-enyl and $R^2$ for a compound corresponds in each case to a group in Table A.

Table 2454

Compounds of the formula I.A, in which $R^1$ is isopropyl, Z is sulfur and $R^3$ is 3-methylbut-2-enyl and $R^2$ for a compound corresponds in each case to a group in Table A.

Table 2455

Compounds of the formula I.B, in which $R^1$ is isopropyl, Z is sulfur and $R^3$ is 3-methylbut-2-enyl and $R^2$ for a compound corresponds in each case to a group in Table A.

Table 2456

Compounds of the formula I.A, in which $R^1$ is isopropyl, Z is NH and $R^3$ is 3-methylbut-2-enyl and $R^2$ for a compound corresponds in each case to a group in Table A.

Table 2457

Compounds of the formula I.B, in which $R^1$ is isopropyl, Z is NH and $R^3$ is 3-methylbut-2-enyl and $R^2$ for a compound corresponds in each case to a group in Table A.

Table 2458

Compounds of the formula I.A, in which $R^1$ is hydrogen, Z is oxygen and $R^3$ is 2-methylprop-2-enyl and $R^2$ for a compound corresponds in each case to a group in Table A.

Table 2459

Compounds of the formula I.B, in which $R^1$ is hydrogen, Z is oxygen and $R^3$ is 2-methylprop-2-enyl and $R^2$ for a compound corresponds in each case to a group in Table A.

Table 2460

Compounds of the formula I.A, in which $R^1$ is hydrogen, Z is sulfur and $R^3$ is 2-methylprop-2-enyl and $R^2$ for a compound corresponds in each case to a group in Table A.

Table 2461

Compounds of the formula I.B, in which $R^1$ is hydrogen, Z is sulfur and $R^3$ is 2-methylprop-2-enyl and $R^2$ for a compound corresponds in each case to a group in Table A.

Table 2462

Compounds of the formula I.A, in which $R^1$ is hydrogen, Z is NH and $R^3$ is 2-methylprop-2-enyl and $R^2$ for a compound corresponds in each case to a group in Table A.

Table 2463

Compounds of the formula I.B, in which $R^1$ is hydrogen, Z is NH and $R^3$ is 2-methylprop-2-enyl and $R^2$ for a compound corresponds in each case to a group in Table A.

Table 2464

Compounds of the formula I.A, in which $R^1$ is methyl, Z is oxygen and $R^3$ is 2-methylprop-2-enyl and $R^2$ for a compound corresponds in each case to a group in Table A.

Table 2465

Compounds of the formula I.B, in which $R^1$ is methyl, Z is oxygen and $R^3$ is 2-methylprop-2-enyl and $R^2$ for a compound corresponds in each case to a group in Table A.

Table 2466

Compounds of the formula I.A, in which $R^1$ is methyl, Z is sulfur and $R^3$ is 2-methylprop-2-enyl and $R^2$ for a compound corresponds in each case to a group in Table A.

Table 2467

Compounds of the formula I.B, in which $R^1$ is methyl, Z is sulfur and $R^3$ is 2-methylprop-2-enyl and $R^2$ for a compound corresponds in each case to a group in Table A.

Table 2468

Compounds of the formula I.A, in which $R^1$ is methyl, Z is NH and $R^3$ is 2-methylprop-2-enyl and $R^2$ for a compound corresponds in each case to a group in Table A.

Table 2469

Compounds of the formula I.B, in which $R^1$ is methyl, Z is NH and $R^3$ is 2-methylprop-2-enyl and $R^2$ for a compound corresponds in each case to a group in Table A.

Table 2470

Compounds of the formula I.A, in which $R^1$ is ethyl, Z is oxygen and $R^3$ is 2-methylprop-2-enyl and $R^2$ for a compound corresponds in each case to a group in Table A.

Table 2471

Compounds of the formula I.B, in which $R^1$ is ethyl, Z is oxygen and $R^3$ is 2-methylprop-2-enyl and $R^2$ for a compound corresponds in each case to a group in Table A.

Table 2472

Compounds of the formula I.A, in which $R^1$ is ethyl, Z is sulfur and $R^3$ is 2-methylprop-2-enyl and $R^2$ for a compound corresponds in each case to a group in Table A.

Table 2473

Compounds of the formula I.B, in which $R^1$ is ethyl, Z is sulfur and $R^3$ is 2-methylprop-2-enyl and $R^2$ for a compound corresponds in each case to a group in Table A.

Table 2474

Compounds of the formula I.A, in which $R^1$ is ethyl, Z is NH and $R^3$ is 2-methylprop-2-enyl and $R^2$ for a compound corresponds in each case to a group in Table A.

Table 2475

Compounds of the formula I.B, in which $R^1$ is ethyl, Z is NH and $R^3$ is 2-methylprop-2-enyl and $R^2$ for a compound corresponds in each case to a group in Table A.

Table 2476

Compounds of the formula I.A, in which $R^1$ is isopropyl, Z is oxygen and $R^3$ is 2-methylprop-2-enyl and $R^2$ for a compound corresponds in each case to a group in Table A.

Table 2477

Compounds of the formula I.B, in which $R^1$ is isopropyl, Z is oxygen and $R^3$ is 2-methylprop-2-enyl and $R^2$ for a compound corresponds in each case to a group in Table A.

Table 2478

Compounds of the formula I.A, in which $R^1$ is isopropyl, Z is sulfur and $R^3$ is 2-methylprop-2-enyl and $R^2$ for a compound corresponds in each case to a group in Table A.

Table 2479

Compounds of the formula I.B, in which $R^1$ is isopropyl, Z is sulfur and $R^3$ is 2-methylprop-2-enyl and $R^2$ for a compound corresponds in each case to a group in Table A.

Table 2480

Compounds of the formula I.A, in which $R^1$ is isopropyl, Z is NH and $R^3$ is 2-methylprop-2-enyl and $R^2$ for a compound corresponds in each case to a group in Table A.

Table 2481

Compounds of the formula I.B, in which $R^1$ is isopropyl, Z is NH and $R^3$ is 2-methylprop-2-enyl and $R^2$ for a compound corresponds in each case to a group in Table A.

Table 2482

Compounds of the formula I.A, in which $R^1$ is hydrogen, Z is oxygen and $R^3$ is but-3-enyl and $R^2$ for a compound corresponds in each case to a group in Table A.

Table 2483

Compounds of the formula I.B, in which $R^1$ is hydrogen, Z is oxygen and $R^3$ is but-3-enyl and $R^2$ for a compound corresponds in each case to a group in Table A.

Table 2484

Compounds of the formula I.A, in which $R^1$ is hydrogen, Z is sulfur and $R^3$ is but-3-enyl and $R^2$ for a compound corresponds in each case to a group in Table A.

Table 2485

Compounds of the formula I.B, in which $R^1$ is hydrogen, Z is sulfur and $R^3$ is but-3-enyl and $R^2$ for a compound corresponds in each case to a group in Table A.

Table 2486

Compounds of the formula I.A, in which $R^1$ is hydrogen, Z is NH and $R^3$ is but-3-enyl and $R^2$ for a compound corresponds in each case to a group in Table A.

Table 2487

Compounds of the formula I.B, in which $R^1$ is hydrogen, Z is NH and $R^3$ is but-3-enyl and $R^2$ for a compound corresponds in each case to a group in Table A.

Table 2488

Compounds of the formula I.A, in which $R^1$ is methyl, Z is oxygen and $R^3$ is but-3-enyl and $R^2$ for a compound corresponds in each case to a group in Table A.

Table 2489

Compounds of the formula I.B, in which $R^1$ is methyl, Z is oxygen and $R^3$ is but-3-enyl and $R^2$ for a compound corresponds in each case to a group in Table A.

Table 2490

Compounds of the formula I.A, in which $R^1$ is methyl, Z is sulfur and $R^3$ is but-3-enyl and $R^2$ for a compound corresponds in each case to a group in Table A.

Table 2491

Compounds of the formula I.B, in which $R^1$ is methyl, Z is sulfur and $R^3$ is but-3-enyl and $R^2$ for a compound corresponds in each case to a group in Table A.

Table 2492

Compounds of the formula I.A, in which $R^1$ is methyl, Z is NH and $R^3$ is but-3-enyl and $R^2$ for a compound corresponds in each case to a group in Table A.

Table 2493

Compounds of the formula I.B, in which $R^1$ is methyl, Z is NH and $R^3$ is but-3-enyl and $R^2$ for a compound corresponds in each case to a group in Table A.

Table 2494

Compounds of the formula I.A, in which $R^1$ is ethyl, Z is oxygen and $R^3$ is but-3-enyl and $R^2$ for a compound corresponds in each case to a group in Table A.

Table 2495

Compounds of the formula I.B, in which $R^1$ is ethyl, Z is oxygen and $R^3$ is but-3-enyl and $R^2$ for a compound corresponds in each case to a group in Table A.

Table 2496

Compounds of the formula I.A, in which $R^1$ is ethyl, Z is sulfur and $R^3$ is but-3-enyl and $R^2$ for a compound corresponds in each case to a group in Table A.

Table 2497

Compounds of the formula I.B, in which $R^1$ is ethyl, Z is sulfur and $R^3$ is but-3-enyl and $R^2$ for a compound corresponds in each case to a group in Table A.

Table 2498

Compounds of the formula I.A, in which $R^1$ is ethyl, Z is NH and $R^3$ is but-3-enyl and $R^2$ for a compound corresponds in each case to a group in Table A.

Table 2499

Compounds of the formula I.B, in which $R^1$ is ethyl, Z is NH and $R^3$ is but-3-enyl and $R^2$ for a compound corresponds in each case to a group in Table A.

Table 2500

Compounds of the formula I.A, in which $R^1$ is isopropyl, Z is oxygen and $R^3$ is but-3-enyl and $R^2$ for a compound corresponds in each case to a group in Table A.

Table 2501

Compounds of the formula I.B, in which $R^1$ is isopropyl, Z is oxygen and $R^3$ is but-3-enyl and $R^2$ for a compound corresponds in each case to a group in Table A.

Table 2502

Compounds of the formula I.A, in which $R^1$ is isopropyl, Z is sulfur and $R^3$ is but-3-enyl and $R^2$ for a compound corresponds in each case to a group in Table A.

Table 2503

Compounds of the formula I.B, in which $R^1$ is isopropyl, Z is sulfur and $R^3$ is but-3-enyl and $R^2$ for a compound corresponds in each case to a group in Table A.

Table 2504

Compounds of the formula I.A, in which $R^1$ is isopropyl, Z is NH and $R^3$ is but-3-enyl and $R^2$ for a compound corresponds in each case to a group in Table A.

Table 2505

Compounds of the formula I.B, in which $R^1$ is isopropyl, Z is NH and $R^3$ is but-3-enyl and $R^2$ for a compound corresponds in each case to a group in Table A.

Table 2506

Compounds of the formula I.A, in which $R^1$ is hydrogen, Z is oxygen and $R^3$ is cis-3-chloroprop-2-enyl and $R^2$ for a compound corresponds in each case to a group in Table A.

Table 2507

Compounds of the formula I.B, in which $R^1$ is hydrogen, Z is oxygen and $R^3$ is cis-3-chloroprop-2-enyl and $R^2$ for a compound corresponds in each case to a group in Table A.

Table 2508

Compounds of the formula I.A, in which $R^1$ is hydrogen, Z is sulfur and $R^3$ is cis-3-chloroprop-2-enyl and $R^2$ for a compound corresponds in each case to a group in Table A.

Table 2509

Compounds of the formula I.B, in which $R^1$ is hydrogen, Z is sulfur and $R^3$ is cis-3-chloroprop-2-enyl and $R^2$ for a compound corresponds in each case to a group in Table A.

Table 2510

Compounds of the formula I.A, in which $R^1$ is hydrogen, Z is NH and $R^3$ is cis-3-chloroprop-2-enyl and $R^2$ for a compound corresponds in each case to a group in Table A.

Table 2511

Compounds of the formula I.B, in which $R^1$ is hydrogen, Z is NH and $R^3$ is cis-3-chloroprop-2-enyl and $R^2$ for a compound corresponds in each case to a group in Table A.

Table 2512

Compounds of the formula I.A, in which $R^1$ is methyl, Z is oxygen and $R^3$ is cis-3-chloroprop-2-enyl and $R^2$ for a compound corresponds in each case to a group in Table A.

Table 2513

Compounds of the formula I.B, in which $R^1$ is methyl, Z is oxygen and $R^3$ is cis-3-chloroprop-2-enyl and $R^2$ for a compound corresponds in each case to a group in Table A.

Table 2514

Compounds of the formula I.A, in which $R^1$ is methyl, Z is sulfur and $R^3$ is cis-3-chloroprop-2-enyl and $R^2$ for a compound corresponds in each case to a group in Table A.

Table 2515

Compounds of the formula I.B, in which $R^1$ is methyl, Z is sulfur and $R^3$ is cis-3-chloroprop-2-enyl and $R^2$ for a compound corresponds in each case to a group in Table A.

Table 2516

Compounds of the formula I.A, in which $R^1$ is methyl, Z is NH and $R^3$ is cis-3-chloroprop-2-enyl and $R^2$ for a compound corresponds in each case to a group in Table A.

Table 2517

Compounds of the formula I.B, in which $R^1$ is methyl, Z is NH and $R^3$ is cis-3-chloroprop-2-enyl and $R^2$ for a compound corresponds in each case to a group in Table A.

Table 2518

Compounds of the formula I.A, in which $R^1$ is ethyl, Z is oxygen and $R^3$ is cis-3-chloroprop-2-enyl and $R^2$ for a compound corresponds in each case to a group in Table A.

Table 2519

Compounds of the formula I.B, in which $R^1$ is ethyl, Z is oxygen and $R^3$ is cis-3-chloroprop-2-enyl and $R^2$ for a compound corresponds in each case to a group in Table A.

Table 2520

Compounds of the formula I.A, in which $R^1$ is ethyl, Z is sulfur and $R^3$ is cis-3-chloroprop-2-enyl and $R^2$ for a compound corresponds in each case to a group in Table A.

Table 2521

Compounds of the formula I.B, in which $R^1$ is ethyl, Z is sulfur and $R^3$ is cis-3-chloroprop-2-enyl and $R^2$ for a compound corresponds in each case to a group in Table A.

Table 2522

Compounds of the formula I.A, in which $R^1$ is ethyl, Z is NH and $R^3$ is cis-3-chloroprop-2-enyl and $R^2$ for a compound corresponds in each case to a group in Table A.

Table 2523

Compounds of the formula I.B, in which $R^1$ is ethyl, Z is NH and $R^3$ is cis-3-chloroprop-2-enyl and $R^2$ for a compound corresponds in each case to a group in Table A.

Table 2524

Compounds of the formula I.A, in which $R^1$ is isopropyl, Z is oxygen and $R^3$ is cis-3-chloroprop-2-enyl and $R^2$ for a compound corresponds in each case to a group in Table A.

Table 2525

Compounds of the formula I.B, in which $R^1$ is isopropyl, Z is oxygen and $R^3$ is cis-3-chloroprop-2-enyl and $R^2$ for a compound corresponds in each case to a group in Table A.

Table 2526

Compounds of the formula I.A, in which $R^1$ is isopropyl, Z is sulfur and $R^3$ is cis-3-chloroprop-2-enyl and $R^2$ for a compound corresponds in each case to a group in Table A.

Table 2527

Compounds of the formula I.B, in which $R^1$ is isopropyl, Z is sulfur and $R^3$ is cis-3-chloroprop-2-enyl and $R^2$ for a compound corresponds in each case to a group in Table A.

Table 2528

Compounds of the formula I.A, in which $R^1$ is isopropyl, Z is NH and $R^3$ is cis-3-chloroprop-2-enyl and $R^2$ for a compound corresponds in each case to a group in Table A.

Table 2529

Compounds of the formula I.B, in which $R^1$ is isopropyl, Z is NH and $R^3$ is cis-3-chloroprop-2-enyl and $R^2$ for a compound corresponds in each case to a group in Table A.

Table 2530

Compounds of the formula I.A, in which $R^1$ is hydrogen, Z is oxygen and $R^3$ is trans-3-chloroprop-2-enyl and $R^2$ for a compound corresponds in each case to a group in Table A.

Table 2531

Compounds of the formula I.B, in which $R^1$ is hydrogen, Z is oxygen and $R^3$ is trans-3-chloroprop-2-enyl and $R^2$ for a compound corresponds in each case to a group in Table A.

Table 2532

Compounds of the formula I.A, in which $R^1$ is hydrogen, Z is sulfur and $R^3$ is trans-3-chloroprop-2-enyl and $R^2$ for a compound corresponds in each case to a group in Table A.

Table 2533

Compounds of the formula I.B, in which $R^1$ is hydrogen, Z is sulfur and $R^3$ is trans-3-chloroprop-2-enyl and $R^2$ for a compound corresponds in each case to a group in Table A.

Table 2534

Compounds of the formula I.A, in which $R^1$ is hydrogen, Z is NH and $R^3$ is trans-3-chloroprop-2-enyl and $R^2$ for a compound corresponds in each case to a group in Table A.

Table 2535

Compounds of the formula I.B, in which $R^1$ is hydrogen, Z is NH and $R^3$ is trans-3-chloroprop-2-enyl and $R^2$ for a compound corresponds in each case to a group in Table A.

Table 2536

Compounds of the formula I.A, in which $R^1$ is methyl, Z is oxygen and $R^3$ is trans-3-chloroprop-2-enyl and $R^2$ for a compound corresponds in each case to a group in Table A.

Table 2537

Compounds of the formula I.B, in which $R^1$ is methyl, Z is oxygen and $R^3$ is trans-3-chloroprop-2-enyl and $R^2$ for a compound corresponds in each case to a group in Table A.

Table 2538

Compounds of the formula I.A, in which $R^1$ is methyl, Z is sulfur and $R^3$ is trans-3-chloroprop-2-enyl and $R^2$ for a compound corresponds in each case to a group in Table A.

Table 2539

Compounds of the formula I.B, in which $R^1$ is methyl, Z is sulfur and $R^3$ is trans-3-chloroprop-2-enyl and $R^2$ for a compound corresponds in each case to a group in Table A.

Table 2540

Compounds of the formula I.A, in which $R^1$ is methyl, Z is NH and $R^3$ is trans-3-chloroprop-2-enyl and $R^2$ for a compound corresponds in each case to a group in Table A.

Table 2541

Compounds of the formula I.B, in which $R^1$ is methyl, Z is NH and $R^3$ is trans-3-chloroprop-2-enyl and $R^2$ for a compound corresponds in each case to a group in Table A.

Table 2542

Compounds of the formula I.A, in which $R^1$ is ethyl, Z is oxygen and $R^3$ is trans-3-chloroprop-2-enyl and $R^2$ for a compound corresponds in each case to a group in Table A.

Table 2543

Compounds of the formula I.B, in which $R^1$ is ethyl, Z is oxygen and $R^3$ is trans-3-chloroprop-2-enyl and $R^2$ for a compound corresponds in each case to a group in Table A.

Table 2544

Compounds of the formula I.A, in which $R^1$ is ethyl, Z is sulfur and $R^3$ is trans-3-chloroprop-2-enyl and $R^2$ for a compound corresponds in each case to a group in Table A.

Table 2545

Compounds of the formula I.B, in which $R^1$ is ethyl, Z is sulfur and $R^3$ is trans-3-chloroprop-2-enyl and $R^2$ for a compound corresponds in each case to a group in Table A.

Table 2546

Compounds of the formula I.A, in which $R^1$ is ethyl, Z is NH and $R^3$ is trans-3-chloroprop-2-enyl and $R^2$ for a compound corresponds in each case to a group in Table A.

Table 2547

Compounds of the formula I.B, in which $R^1$ is ethyl, Z is NH and $R^3$ is trans-3-chloroprop-2-enyl and $R^2$ for a compound corresponds in each case to a group in Table A.

Table 2548

Compounds of the formula I.A, in which $R^1$ is isopropyl, Z is oxygen and $R^3$ is trans-3-chloroprop-2-enyl and $R^2$ for a compound corresponds in each case to a group in Table A.

Table 2549

Compounds of the formula I.B, in which $R^1$ is isopropyl, Z is oxygen and $R^3$ is trans-3-chloroprop-2-enyl and $R^2$ for a compound corresponds in each case to a group in Table A.

Table 2550

Compounds of the formula I.A, in which $R^1$ is isopropyl, Z is sulfur and $R^3$ is trans-3-chloroprop-2-enyl and $R^2$ for a compound corresponds in each case to a group in Table A.

Table 2551

Compounds of the formula I.B, in which $R^1$ is isopropyl, Z is sulfur and $R^3$ is trans-3-chloroprop-2-enyl and $R^2$ for a compound corresponds in each case to a group in Table A.

Table 2552

Compounds of the formula I.A, in which $R^1$ is isopropyl, Z is NH and $R^3$ is trans-3-chloroprop-2-enyl and $R^2$ for a compound corresponds in each case to a group in Table A.

Table 2553

Compounds of the formula I.B, in which $R^1$ is isopropyl, Z is NH and $R^3$ is trans-3-chloroprop-2-enyl and $R^2$ for a compound corresponds in each case to a group in Table A.

Table 2554

Compounds of the formula I.A, in which $R^1$ is hydrogen, Z is oxygen and $R^3$ is 2-chloroprop-2-enyl and $R^2$ for a compound corresponds in each case to a group in Table A.

Table 2555

Compounds of the formula I.B, in which $R^1$ is hydrogen, Z is oxygen and $R^3$ is 2-chloroprop-2-enyl and $R^2$ for a compound corresponds in each case to a group in Table A.

Table 2556

Compounds of the formula I.A, in which $R^1$ is hydrogen, Z is sulfur and $R^3$ is 2-chloroprop-2-enyl and $R^2$ for a compound corresponds in each case to a group in Table A.

Table 2557

Compounds of the formula I.B, in which $R^1$ is hydrogen, Z is sulfur and $R^3$ is 2-chloroprop-2-enyl and $R^2$ for a compound corresponds in each case to a group in Table A.

Table 2558

Compounds of the formula I.A, in which $R^1$ is hydrogen, Z is NH and $R^3$ is 2-chloroprop-2-enyl and $R^2$ for a compound corresponds in each case to a group in Table A.

Table 2559

Compounds of the formula I.B, in which $R^1$ is hydrogen, Z is NH and $R^3$ is 2-chloroprop-2-enyl and $R^2$ for a compound corresponds in each case to a group in Table A.

Table 2560

Compounds of the formula I.A, in which $R^1$ is methyl, Z is oxygen and $R^3$ is 2-chloroprop-2-enyl and $R^2$ for a compound corresponds in each case to a group in Table A.

Table 2561

Compounds of the formula I.B, in which $R^1$ is methyl, Z is oxygen and $R^3$ is 2-chloroprop-2-enyl and $R^2$ for a compound corresponds in each case to a group in Table A.

Table 2562

Compounds of the formula I.A, in which $R^1$ is methyl, Z is sulfur and $R^3$ is 2-chloroprop-2-enyl and $R^2$ for a compound corresponds in each case to a group in Table A.

Table 2563

Compounds of the formula I.B, in which $R^1$ is methyl, Z is sulfur and $R^3$ is 2-chloroprop-2-enyl and $R^2$ for a compound corresponds in each case to a group in Table A.

Table 2564

Compounds of the formula I.A, in which $R^1$ is methyl, Z is NH and $R^3$ is 2-chloroprop-2-enyl and $R^2$ for a compound corresponds in each case to a group in Table A.

Table 2565

Compounds of the formula I.B, in which $R^1$ is methyl, Z is NH and $R^3$ is 2-chloroprop-2-enyl and $R^2$ for a compound corresponds in each case to a group in Table A.

Table 2566

Compounds of the formula I.A, in which $R^1$ is ethyl, Z is oxygen and $R^3$ is 2-chloroprop-2-enyl and $R^2$ for a compound corresponds in each case to a group in Table A.

Table 2567

Compounds of the formula I.B, in which $R^1$ is ethyl, Z is oxygen and $R^3$ is 2-chloroprop-2-enyl and $R^2$ for a compound corresponds in each case to a group in Table A.

Table 2568

Compounds of the formula I.A, in which $R^1$ is ethyl, Z is sulfur and $R^3$ is 2-chloroprop-2-enyl and $R^2$ for a compound corresponds in each case to a group in Table A.

Table 2569

Compounds of the formula I.B, in which $R^1$ is ethyl, Z is sulfur and $R^3$ is 2-chloroprop-2-enyl and $R^2$ for a compound corresponds in each case to a group in Table A.

Table 2570

Compounds of the formula I.A, in which $R^1$ is ethyl, Z is NH and $R^3$ is 2-chloroprop-2-enyl and $R^2$ for a compound corresponds in each case to a group in Table A.

Table 2571

Compounds of the formula I.B, in which $R^1$ is ethyl, Z is NH and $R^3$ is 2-chloroprop-2-enyl and $R^2$ for a compound corresponds in each case to a group in Table A.

Table 2572

Compounds of the formula I.A, in which $R^1$ is isopropyl, Z is oxygen and $R^3$ is 2-chloroprop-2-enyl and $R^2$ for a compound corresponds in each case to a group in Table A.

Table 2573

Compounds of the formula I.B, in which $R^1$ is isopropyl, Z is oxygen and $R^3$ is 2-chloroprop-2-enyl and $R^2$ for a compound corresponds in each case to a group in Table A.

Table 2574

Compounds of the formula I.A, in which $R^1$ is isopropyl, Z is sulfur and $R^3$ is 2-chloroprop-2-enyl and $R^2$ for a compound corresponds in each case to a group in Table A.

Table 2575

Compounds of the formula I.B, in which $R^1$ is isopropyl, Z is sulfur and $R^3$ is 2-chloroprop-2-enyl and $R^2$ for a compound corresponds in each case to a group in Table A.

Table 2576

Compounds of the formula I.A, in which $R^1$ is isopropyl, Z is NH and $R^3$ is 2-chloroprop-2-enyl and $R^2$ for a compound corresponds in each case to a group in Table A.

Table 2577

Compounds of the formula I.B, in which $R^1$ is isopropyl, Z is NH and $R^3$ is 2-chloroprop-2-enyl and $R^2$ for a compound corresponds in each case to a group in Table A.

Table 2578

Compounds of the formula I.A, in which $R^1$ is hydrogen, Z is oxygen and $R^3$ is 3,3-dichloroprop-2-enyl and $R^2$ for a compound corresponds in each case to a group in Table A.

Table 2579

Compounds of the formula I.B, in which $R^1$ is hydrogen, Z is oxygen and $R^3$ is 3,3-dichloroprop-2-enyl and $R^2$ for a compound corresponds in each case to a group in Table A.

Table 2580

Compounds of the formula I.A, in which $R^1$ is hydrogen, Z is sulfur and $R^3$ is 3,3-dichloroprop-2-enyl and $R^2$ for a compound corresponds in each case to a group in Table A.

Table 2581

Compounds of the formula I.B, in which $R^1$ is hydrogen, Z is sulfur and $R^3$ is 3,3-dichloroprop-2-enyl and $R^2$ for a compound corresponds in each case to a group in Table A.

Table 2582

Compounds of the formula I.A, in which $R^1$ is hydrogen, Z is NH and $R^3$ is 3,3-dichloroprop-2-enyl and $R^2$ for a compound corresponds in each case to a group in Table A.

Table 2583

Compounds of the formula I.B, in which $R^1$ is hydrogen, Z is NH and $R^3$ is 3,3-dichloroprop-2-enyl and $R^2$ for a compound corresponds in each case to a group in Table A.

Table 2584

Compounds of the formula I.A, in which $R^1$ is methyl, Z is oxygen and $R^3$ is 3,3-dichloroprop-2-enyl and $R^2$ for a compound corresponds in each case to a group in Table A.

Table 2585

Compounds of the formula I.B, in which $R^1$ is methyl, Z is oxygen and $R^3$ is 3,3-dichloroprop-2-enyl and $R^2$ for a compound corresponds in each case to a group in Table A.

Table 2586

Compounds of the formula I.A, in which $R^1$ is methyl, Z is sulfur and $R^3$ is 3,3-dichloroprop-2-enyl and $R^2$ for a compound corresponds in each case to a group in Table A.

Table 2587

Compounds of the formula I.B, in which $R^1$ is methyl, Z is sulfur and $R^3$ is 3,3-dichloroprop-2-enyl and $R^2$ for a compound corresponds in each case to a group in Table A.

Table 2588

Compounds of the formula I.A, in which $R^1$ is methyl, Z is NH and $R^3$ is 3,3-dichloroprop-2-enyl and $R^2$ for a compound corresponds in each case to a group in Table A.

Table 2589

Compounds of the formula I.B, in which $R^1$ is methyl, Z is NH and $R^3$ is 3,3-dichloroprop-2-enyl and $R^2$ for a compound corresponds in each case to a group in Table A.

Table 2590

Compounds of the formula I.A, in which $R^1$ is ethyl, Z is oxygen and $R^3$ is 3,3-dichloroprop-2-enyl and $R^2$ for a compound corresponds in each case to a group in Table A.

Table 2591

Compounds of the formula I.B, in which $R^1$ is ethyl, Z is oxygen and $R^3$ is 3,3-dichloroprop-2-enyl and $R^2$ for a compound corresponds in each case to a group in Table A.

Table 2592

Compounds of the formula I.A, in which $R^1$ is ethyl, Z is sulfur and $R^3$ is 3,3-dichloroprop-2-enyl and $R^2$ for a compound corresponds in each case to a group in Table A.

Table 2593

Compounds of the formula I.B, in which $R^1$ is ethyl, Z is sulfur and $R^3$ is 3,3-dichloroprop-2-enyl and $R^2$ for a compound corresponds in each case to a group in Table A.

Table 2594

Compounds of the formula I.A, in which $R^1$ is ethyl, Z is NH and $R^3$ is 3,3-dichloroprop-2-enyl and $R^2$ for a compound corresponds in each case to a group in Table A.

Table 2595

Compounds of the formula I.B, in which $R^1$ is ethyl, Z is NH and $R^3$ is 3,3-dichloroprop-2-enyl and $R^2$ for a compound corresponds in each case to a group in Table A.

Table 2596

Compounds of the formula I.A, in which $R^1$ is isopropyl, Z is oxygen and $R^3$ is 3,3-dichloroprop-2-enyl and $R^2$ for a compound corresponds in each case to a group in Table A.

Table 2597

Compounds of the formula I.B, in which $R^1$ is isopropyl, Z is oxygen and $R^3$ is 3,3-dichloroprop-2-enyl and $R^2$ for a compound corresponds in each case to a group in Table A.

Table 2598

Compounds of the formula I.A, in which $R^1$ is isopropyl, Z is sulfur and $R^3$ is 3,3-dichloroprop-2-enyl and $R^2$ for a compound corresponds in each case to a group in Table A.

Table 2599

Compounds of the formula I.B, in which $R^1$ is isopropyl, Z is sulfur and $R^3$ is 3,3-dichloroprop-2-enyl and $R^2$ for a compound corresponds in each case to a group in Table A.

Table 2600

Compounds of the formula I.A, in which $R^1$ is isopropyl, Z is NH and $R^3$ is 3,3-dichloroprop-2-enyl and $R^2$ for a compound corresponds in each case to a group in Table A.

Table 2601

Compounds of the formula I.B, in which $R^1$ is isopropyl, Z is NH and $R^3$ is 3,3-dichloroprop-2-enyl and $R^2$ for a compound corresponds in each case to a group in Table A.

Table 2602

Compounds of the formula I.A, in which $R^1$ is hydrogen, Z is oxygen and $R^3$ is 2,3,3-trichloroprop-2-enyl and $R^2$ for a compound corresponds in each case to a group in Table A.

Table 2603

Compounds of the formula I.B, in which $R^1$ is hydrogen, Z is oxygen and $R^3$ is 2,3,3-trichloroprop-2-enyl and $R^2$ for a compound corresponds in each case to a group in Table A.

Table 2604

Compounds of the formula I.A, in which $R^1$ is hydrogen, Z is sulfur and $R^3$ is 2,3,3-trichloroprop-2-enyl and $R^2$ for a compound corresponds in each case to a group in Table A.

Table 2605

Compounds of the formula I.B, in which $R^1$ is hydrogen, Z is sulfur and $R^3$ is 2,3,3-trichloroprop-2-enyl and $R^2$ for a compound corresponds in each case to a group in Table A.

Table 2606

Compounds of the formula I.A, in which $R^1$ is hydrogen, Z is NH and $R^3$ is 2,3,3-trichloroprop-2-enyl and $R^2$ for a compound corresponds in each case to a group in Table A.

Table 2607

Compounds of the formula I.B, in which $R^1$ is hydrogen, Z is NH and $R^3$ is 2,3,3-trichloroprop-2-enyl and $R^2$ for a compound corresponds in each case to a group in Table A.

Table 2608

Compounds of the formula I.A, in which $R^1$ is methyl, Z is oxygen and $R^3$ is 2,3,3-trichloroprop-2-enyl and $R^2$ for a compound corresponds in each case to a group in Table A.

Table 2609

Compounds of the formula I.B, in which $R^1$ is methyl, Z is oxygen and $R^3$ is 2,3,3-trichloroprop-2-enyl and $R^2$ for a compound corresponds in each case to a group in Table A.

Table 2610

Compounds of the formula I.A, in which $R^1$ is methyl, Z is sulfur and $R^3$ is 2,3,3-trichloroprop-2-enyl and $R^2$ for a compound corresponds in each case to a group in Table A.

Table 2611

Compounds of the formula I.B, in which $R^1$ is methyl, Z is sulfur and $R^3$ is 2,3,3-trichloroprop-2-enyl and $R^2$ for a compound corresponds in each case to a group in Table A.

Table 2612

Compounds of the formula I.A, in which $R^1$ is methyl, Z is NH and $R^3$ is 2,3,3-trichloroprop-2-enyl and $R^2$ for a compound corresponds in each case to a group in Table A.

Table 2613

Compounds of the formula I.B, in which $R^1$ is methyl, Z is NH and $R^3$ is 2,3,3-trichloroprop-2-enyl and $R^2$ for a compound corresponds in each case to a group in Table A.

Table 2614

Compounds of the formula I.A, in which $R^1$ is ethyl, Z is oxygen and $R^3$ is 2,3,3-trichloroprop-2-enyl and $R^2$ for a compound corresponds in each case to a group in Table A.

Table 2615

Compounds of the formula I.B, in which $R^1$ is ethyl, Z is oxygen and $R^3$ is 2,3,3-trichloroprop-2-enyl and $R^2$ for a compound corresponds in each case to a group in Table A.

Table 2616

Compounds of the formula I.A, in which $R^1$ is ethyl, Z is sulfur and $R^3$ is 2,3,3-trichloroprop-2-enyl and $R^2$ for a compound corresponds in each case to a group in Table A.

Table 2617

Compounds of the formula I.B, in which $R^1$ is ethyl, Z is sulfur and $R^3$ is 2,3,3-trichloroprop-2-enyl and $R^2$ for a compound corresponds in each case to a group in Table A.

Table 2618

Compounds of the formula I.A, in which $R^1$ is ethyl, Z is NH and $R^3$ is 2,3,3-trichloroprop-2-enyl and $R^2$ for a compound corresponds in each case to a group in Table A.

Table 2619

Compounds of the formula I.B, in which $R^1$ is ethyl, Z is NH and $R^3$ is 2,3,3-trichloroprop-2-enyl and $R^2$ for a compound corresponds in each case to a group in Table A.

Table 2620

Compounds of the formula I.A, in which $R^1$ is isopropyl, Z is oxygen and $R^3$ is 2,3,3-trichloroprop-2-enyl and $R^2$ for a compound corresponds in each case to a group in Table A.

Table 2621

Compounds of the formula I.B, in which $R^1$ is isopropyl, Z is oxygen and $R^3$ is 2,3,3-trichloroprop-2-enyl and $R^2$ for a compound corresponds in each case to a group in Table A.

Table 2622

Compounds of the formula I.A, in which $R^1$ is isopropyl, Z is sulfur and $R^3$ is 2,3,3-trichloroprop-2-enyl and $R^2$ for a compound corresponds in each case to a group in Table A.

Table 2623

Compounds of the formula I.B, in which $R^1$ is isopropyl, Z is sulfur and $R^3$ is 2,3,3-trichloroprop-2-enyl and $R^2$ for a compound corresponds in each case to a group in Table A.

Table 2624

Compounds of the formula I.A, in which $R^1$ is isopropyl, Z is NH and $R^3$ is 2,3,3-trichloroprop-2-enyl and $R^2$ for a compound corresponds in each case to a group in Table A.

Table 2625

Compounds of the formula I.B, in which $R^1$ is isopropyl, Z is NH and $R^3$ is 2,3,3-trichloroprop-2-enyl and $R^2$ for a compound corresponds in each case to a group in Table A.

Table 2626

Compounds of the formula I.A, in which $R^1$ is hydrogen, Z is oxygen and $R^3$ is cis-2,3-dichloroprop-2-enyl and $R^2$ for a compound corresponds in each case to a group in Table A.

Table 2627

Compounds of the formula I.B, in which $R^1$ is hydrogen, Z is oxygen and $R^3$ is cis-2,3-dichloroprop-2-enyl and $R^2$ for a compound corresponds in each case to a group in Table A.

Table 2628

Compounds of the formula I.A, in which $R^1$ is hydrogen, Z is sulfur and $R^3$ is cis-2,3-dichloroprop-2-enyl and $R^2$ for a compound corresponds in each case to a group in Table A.

Table 2629

Compounds of the formula I.B, in which $R^1$ is hydrogen, Z is sulfur and $R^3$ is cis-2,3-dichloroprop-2-enyl and $R^2$ for a compound corresponds in each case to a group in Table A.

Table 2630

Compounds of the formula I.A, in which $R^1$ is hydrogen, Z is NH and $R^3$ is cis-2,3-dichloroprop-2-enyl and $R^2$ for a compound corresponds in each case to a group in Table A.

Table 2631

Compounds of the formula I.B, in which $R^1$ is hydrogen, Z is NH and $R^3$ is cis-2,3-dichloroprop-2-enyl and $R^2$ for a compound corresponds in each case to a group in Table A.

Table 2632

Compounds of the formula I.A, in which $R^1$ is methyl, Z is oxygen and $R^3$ is cis-2,3-dichloroprop-2-enyl and $R^2$ for a compound corresponds in each case to a group in Table A.

Table 2633

Compounds of the formula I.B, in which $R^1$ is methyl, Z is oxygen and $R^3$ is cis-2,3-dichloroprop-2-enyl and $R^2$ for a compound corresponds in each case to a group in Table A.

Table 2634

Compounds of the formula I.A, in which $R^1$ is methyl, Z is sulfur and $R^3$ is cis-2,3-dichloroprop-2-enyl and $R^2$ for a compound corresponds in each case to a group in Table A.

Table 2635

Compounds of the formula I.B, in which $R^1$ is methyl, Z is sulfur and $R^3$ is cis-2,3-dichloroprop-2-enyl and $R^2$ for a compound corresponds in each case to a group in Table A.

Table 2636

Compounds of the formula I.A, in which $R^1$ is methyl, Z is NH and $R^3$ is cis-2,3-dichloroprop-2-enyl and $R^2$ for a compound corresponds in each case to a group in Table A.

Table 2637

Compounds of the formula I.B, in which $R^1$ is methyl, Z is NH and $R^3$ is cis-2,3-dichloroprop-2-enyl and $R^2$ for a compound corresponds in each case to a group in Table A.

Table 2638

Compounds of the formula I.A, in which $R^1$ is ethyl, Z is oxygen and $R^3$ is cis-2,3-dichloroprop-2-enyl and $R^2$ for a compound corresponds in each case to a group in Table A.

Table 2639

Compounds of the formula I.B, in which $R^1$ is ethyl, Z is oxygen and $R^3$ is cis-2,3-dichloroprop-2-enyl and $R^2$ for a compound corresponds in each case to a group in Table A.

Table 2640

Compounds of the formula I.A, in which $R^1$ is ethyl, Z is sulfur and $R^3$ is cis-2,3-dichloroprop-2-enyl and $R^2$ for a compound corresponds in each case to a group in Table A.

Table 2641

Compounds of the formula I.B, in which $R^1$ is ethyl, Z is sulfur and $R^3$ is cis-2,3-dichloroprop-2-enyl and $R^2$ for a compound corresponds in each case to a group in Table A.

Table 2642

Compounds of the formula I.A, in which $R^1$ is ethyl, Z is NH and $R^3$ is cis-2,3-dichloroprop-2-enyl and $R^2$ for a compound corresponds in each case to a group in Table A.

Table 2643

Compounds of the formula I.B, in which $R^1$ is ethyl, Z is NH and $R^3$ is cis-2,3-dichloroprop-2-enyl and $R^2$ for a compound corresponds in each case to a group in Table A.

Table 2644

Compounds of the formula I.A, in which $R^1$ is isopropyl, Z is oxygen and $R^3$ is cis-2,3-dichloroprop-2-enyl and $R^2$ for a compound corresponds in each case to a group in Table A.

Table 2645

Compounds of the formula I.B, in which $R^1$ is isopropyl, Z is oxygen and $R^3$ is cis-2,3-dichloroprop-2-enyl and $R^2$ for a compound corresponds in each case to a group in Table A.

Table 2646

Compounds of the formula I.A, in which $R^1$ is isopropyl, Z is sulfur and $R^3$ is cis-2,3-dichloroprop-2-enyl and $R^2$ for a compound corresponds in each case to a group in Table A.

Table 2647

Compounds of the formula I.B, in which $R^1$ is isopropyl, Z is sulfur and $R^3$ is cis-2,3-dichloroprop-2-enyl and $R^2$ for a compound corresponds in each case to a group in Table A.

Table 2648

Compounds of the formula I.A, in which $R^1$ is isopropyl, Z is NH and $R^3$ is cis-2,3-dichloroprop-2-enyl and $R^2$ for a compound corresponds in each case to a group in Table A.

Table 2649

Compounds of the formula I.B, in which $R^1$ is isopropyl, Z is NH and $R^3$ is cis-2,3-dichloroprop-2-enyl and $R^2$ for a compound corresponds in each case to a group in Table A.

Table 2650

Compounds of the formula I.A, in which $R^1$ is hydrogen, Z is oxygen and $R^3$ is trans-2,3-dichloroprop-2-enyl and $R^2$ for a compound corresponds in each case to a group in Table A.

Table 2651

Compounds of the formula I.B, in which $R^1$ is hydrogen, Z is oxygen and $R^3$ is trans-2,3-dichloroprop-2-enyl and $R^2$ for a compound corresponds in each case to a group in Table A.

Table 2652

Compounds of the formula I.A, in which $R^1$ is hydrogen, Z is sulfur and $R^3$ is trans-2,3-dichloroprop-2-enyl and $R^2$ for a compound corresponds in each case to a group in Table A.

Table 2653

Compounds of the formula I.B, in which $R^1$ is hydrogen, Z is sulfur and $R^3$ is trans-2,3-dichloroprop-2-enyl and $R^2$ for a compound corresponds in each case to a group in Table A.

Table 2654

Compounds of the formula I.A, in which $R^1$ is hydrogen, Z is NH and $R^3$ is trans-2,3-dichloroprop-2-enyl and $R^2$ for a compound corresponds in each case to a group in Table A.

Table 2655

Compounds of the formula I.B, in which $R^1$ is hydrogen, Z is NH and $R^3$ is trans-2,3-dichloroprop-2-enyl and $R^2$ for a compound corresponds in each case to a group in Table A.

Table 2656

Compounds of the formula I.A, in which $R^1$ is methyl, Z is oxygen and $R^3$ is trans-2,3-dichloroprop-2-enyl and $R^2$ for a compound corresponds in each case to a group in Table A.

Table 2657

Compounds of the formula I.B, in which $R^1$ is methyl, Z is oxygen and $R^3$ is trans-2,3-dichloroprop-2-enyl and $R^2$ for a compound corresponds in each case to a group in Table A.

Table 2658

Compounds of the formula I.A, in which $R^1$ is methyl, Z is sulfur and $R^3$ is trans-2,3-dichloroprop-2-enyl and $R^2$ for a compound corresponds in each case to a group in Table A.

Table 2659

Compounds of the formula I.B, in which $R^1$ is methyl, Z is sulfur and $R^3$ is trans-2,3-dichloroprop-2-enyl and $R^2$ for a compound corresponds in each case to a group in Table A.

Table 2660

Compounds of the formula I.A, in which $R^1$ is methyl, Z is NH and $R^3$ is trans-2,3-dichloroprop-2-enyl and $R^2$ for a compound corresponds in each case to a group in Table A.

Table 2661

Compounds of the formula I.B, in which $R^1$ is methyl, Z is NH and $R^3$ is trans-2,3-dichloroprop-2-enyl and $R^2$ for a compound corresponds in each case to a group in Table A.

Table 2662

Compounds of the formula I.A, in which $R^1$ is ethyl, Z is oxygen and $R^3$ is trans-2,3-dichloroprop-2-enyl and $R^2$ for a compound corresponds in each case to a group in Table A.

Table 2663

Compounds of the formula I.B, in which $R^1$ is ethyl, Z is oxygen and $R^3$ is trans-2,3-dichloroprop-2-enyl and $R^2$ for a compound corresponds in each case to a group in Table A.

Table 2664

Compounds of the formula I.A, in which $R^1$ is ethyl, Z is sulfur and $R^3$ is trans-2,3-dichloroprop-2-enyl and $R^2$ for a compound corresponds in each case to a group in Table A.

Table 2665

Compounds of the formula I.B, in which $R^1$ is ethyl, Z is sulfur and $R^3$ is trans-2,3-dichloroprop-2-enyl and $R^2$ for a compound corresponds in each case to a group in Table A.

Table 2666

Compounds of the formula I.A, in which $R^1$ is ethyl, Z is NH and $R^3$ is trans-2,3-dichloroprop-2-enyl and $R^2$ for a compound corresponds in each case to a group in Table A.

Table 2667

Compounds of the formula I.B, in which $R^1$ is ethyl, Z is NH and $R^3$ is trans-2,3-dichloroprop-2-enyl and $R^2$ for a compound corresponds in each case to a group in Table A.

Table 2668

Compounds of the formula I.A, in which $R^1$ is isopropyl, Z is oxygen and $R^3$ is trans-2,3-dichloroprop-2-enyl and $R^2$ for a compound corresponds in each case to a group in Table A.

Table 2669

Compounds of the formula I.B, in which $R^1$ is isopropyl, Z is oxygen and $R^3$ is trans-2,3-dichloroprop-2-enyl and $R^2$ for a compound corresponds in each case to a group in Table A.

Table 2670

Compounds of the formula I.A, in which $R^1$ is isopropyl, Z is sulfur and $R^3$ is trans-2,3-dichloroprop-2-enyl and $R^2$ for a compound corresponds in each case to a group in Table A.

Table 2671

Compounds of the formula I.B, in which $R^1$ is isopropyl, Z is sulfur and $R^3$ is trans-2,3-dichloroprop-2-enyl and $R^2$ for a compound corresponds in each case to a group in Table A.

Table 2672

Compounds of the formula I.A, in which $R^1$ is isopropyl, Z is NH and $R^3$ is trans-2,3-dichloroprop-2-enyl and $R^2$ for a compound corresponds in each case to a group in Table A.

Table 2673

Compounds of the formula I.B, in which $R^1$ is isopropyl, Z is NH and $R^3$ is trans-2,3-dichloroprop-2-enyl and $R^2$ for a compound corresponds in each case to a group in Table A.

Table 2674

Compounds of the formula I.A, in which $R^1$ is hydrogen, Z is oxygen and $R^3$ is cis-3-bromoprop-2-enyl and $R^2$ for a compound corresponds in each case to a group in Table A.

Table 2675

Compounds of the formula I.B, in which $R^1$ is hydrogen, Z is oxygen and $R^3$ is cis-3-bromoprop-2-enyl and $R^2$ for a compound corresponds in each case to a group in Table A.

Table 2676

Compounds of the formula I.A, in which $R^1$ is hydrogen, Z is sulfur and $R^3$ is cis-3-bromoprop-2-enyl and $R^2$ for a compound corresponds in each case to a group in Table A.

Table 2677

Compounds of the formula I.B, in which $R^1$ is hydrogen, Z is sulfur and $R^3$ is cis-3-bromoprop-2-enyl and $R^2$ for a compound corresponds in each case to a group in Table A.

Table 2678

Compounds of the formula I.A, in which $R^1$ is hydrogen, Z is NH and $R^3$ is cis-3-bromoprop-2-enyl and $R^2$ for a compound corresponds in each case to a group in Table A.

Table 2679

Compounds of the formula I.B, in which $R^1$ is hydrogen, Z is NH and $R^3$ is cis-3-bromoprop-2-enyl and $R^2$ for a compound corresponds in each case to a group in Table A.

Table 2680

Compounds of the formula I.A, in which $R^1$ is methyl, Z is oxygen and $R^3$ is cis-3-bromoprop-2-enyl and $R^2$ for a compound corresponds in each case to a group in Table A.

Table 2681

Compounds of the formula I.B, in which $R^1$ is methyl, Z is oxygen and $R^3$ is cis-3-bromoprop-2-enyl and $R^2$ for a compound corresponds in each case to a group in Table A.

Table 2682

Compounds of the formula I.A, in which $R^1$ is methyl, Z is sulfur and $R^3$ is cis-3-bromoprop-2-enyl and $R^2$ for a compound corresponds in each case to a group in Table A.

Table 2683

Compounds of the formula I.B, in which $R^1$ is methyl, Z is sulfur and $R^3$ is cis-3-bromoprop-2-enyl and $R^2$ for a compound corresponds in each case to a group in Table A.

Table 2684

Compounds of the formula I.A, in which $R^1$ is methyl, Z is NH and $R^3$ is cis-3-bromoprop-2-enyl and $R^2$ for a compound corresponds in each case to a group in Table A.

Table 2685

Compounds of the formula I.B, in which $R^1$ is methyl, Z is NH and $R^3$ is cis-3-bromoprop-2-enyl and $R^2$ for a compound corresponds in each case to a group in Table A.

Table 2686

Compounds of the formula I.A, in which $R^1$ is ethyl, Z is oxygen and $R^3$ is cis-3-bromoprop-2-enyl and $R^2$ for a compound corresponds in each case to a group in Table A.

Table 2687

Compounds of the formula I.B, in which $R^1$ is ethyl, Z is oxygen and $R^3$ is cis-3-bromoprop-2-enyl and $R^2$ for a compound corresponds in each case to a group in Table A.

Table 2688

Compounds of the formula I.A, in which $R^1$ is ethyl, Z is sulfur and $R^3$ is cis-3-bromoprop-2-enyl and $R^2$ for a compound corresponds in each case to a group in Table A.

Table 2689

Compounds of the formula I.B, in which $R^1$ is ethyl, Z is sulfur and $R^3$ is cis-3-bromoprop-2-enyl and $R^2$ for a compound corresponds in each case to a group in Table A.

Table 2690

Compounds of the formula I.A, in which $R^1$ is ethyl, Z is NH and $R^3$ is cis-3-bromoprop-2-enyl and $R^2$ for a compound corresponds in each case to a group in Table A.

Table 2691

Compounds of the formula I.B, in which $R^1$ is ethyl, Z is NH and $R^3$ is cis-3-bromoprop-2-enyl and $R^2$ for a compound corresponds in each case to a group in Table A.

Table 2692

Compounds of the formula I.A, in which $R^1$ is isopropyl, Z is oxygen and $R^3$ is cis-3-bromoprop-2-enyl and $R^2$ for a compound corresponds in each case to a group in Table A.

Table 2693

Compounds of the formula I.B, in which $R^1$ is isopropyl, Z is oxygen and $R^3$ is cis-3-bromoprop-2-enyl and $R^2$ for a compound corresponds in each case to a group in Table A.

Table 2694

Compounds of the formula I.A, in which $R^1$ is isopropyl, Z is sulfur and $R^3$ is cis-3-bromoprop-2-enyl and $R^2$ for a compound corresponds in each case to a group in Table A.

Table 2695

Compounds of the formula I.B, in which $R^1$ is isopropyl, Z is sulfur and $R^3$ is cis-3-bromoprop-2-enyl and $R^2$ for a compound corresponds in each case to a group in Table A.

Table 2696

Compounds of the formula I.A, in which $R^1$ is isopropyl, Z is NH and $R^3$ is cis-3-bromoprop-2-enyl and $R^2$ for a compound corresponds in each case to a group in Table A.

Table 2697

Compounds of the formula I.B, in which $R^1$ is isopropyl, Z is NH and $R^3$ is cis-3-bromoprop-2-enyl and $R^2$ for a compound corresponds in each case to a group in Table A.

Table 2698

Compounds of the formula I.A, in which $R^1$ is hydrogen, Z is oxygen and $R^3$ is trans-3-bromoprop-2-enyl and $R^2$ for a compound corresponds in each case to a group in Table A.

Table 2699

Compounds of the formula I.B, in which $R^1$ is hydrogen, Z is oxygen and $R^3$ is trans-3-bromoprop-2-enyl and $R^2$ for a compound corresponds in each case to a group in Table A.

Table 2700

Compounds of the formula I.A, in which $R^1$ is hydrogen, Z is sulfur and $R^3$ is trans-3-bromoprop-2-enyl and $R^2$ for a compound corresponds in each case to a group in Table A.

Table 2701

Compounds of the formula I.B, in which $R^1$ is hydrogen, Z is sulfur and $R^3$ is trans-3-bromoprop-2-enyl and $R^2$ for a compound corresponds in each case to a group in Table A.

Table 2702

Compounds of the formula I.A, in which $R^1$ is hydrogen, Z is NH and $R^3$ is trans-3-bromoprop-2-enyl and $R^2$ for a compound corresponds in each case to a group in Table A.

Table 2703

Compounds of the formula I.B, in which $R^1$ is hydrogen, Z is NH and $R^3$ is trans-3-bromoprop-2-enyl and $R^2$ for a compound corresponds in each case to a group in Table A.

Table 2704

Compounds of the formula I.A, in which $R^1$ is methyl, Z is oxygen and $R^3$ is trans-3-bromoprop-2-enyl and $R^2$ for a compound corresponds in each case to a group in Table A.

Table 2705

Compounds of the formula I.B, in which $R^1$ is methyl, Z is oxygen and $R^3$ is trans-3-bromoprop-2-enyl and $R^2$ for a compound corresponds in each case to a group in Table A.

Table 2706

Compounds of the formula I.A, in which $R^1$ is methyl, Z is sulfur and $R^3$ is trans-3-bromoprop-2-enyl and $R^2$ for a compound corresponds in each case to a group in Table A.

Table 2707

Compounds of the formula I.B, in which $R^1$ is methyl, Z is sulfur and $R^3$ is trans-3-bromoprop-2-enyl and $R^2$ for a compound corresponds in each case to a group in Table A.

Table 2708

Compounds of the formula I.A, in which $R^1$ is methyl, Z is NH and $R^3$ is trans-3-bromoprop-2-enyl and $R^2$ for a compound corresponds in each case to a group in Table A.

Table 2709

Compounds of the formula I.B, in which $R^1$ is methyl, Z is NH and $R^3$ is trans-3-bromoprop-2-enyl and $R^2$ for a compound corresponds in each case to a group in Table A.

Table 2710

Compounds of the formula I.A, in which $R^1$ is ethyl, Z is oxygen and $R^3$ is trans-3-bromoprop-2-enyl and $R^2$ for a compound corresponds in each case to a group in Table A.

Table 2711

Compounds of the formula I.B, in which $R^1$ is ethyl, Z is oxygen and $R^3$ is trans-3-bromoprop-2-enyl and $R^2$ for a compound corresponds in each case to a group in Table A.

Table 2712

Compounds of the formula I.A, in which $R^1$ is ethyl, Z is sulfur and $R^3$ is trans-3-bromoprop-2-enyl and $R^2$ for a compound corresponds in each case to a group in Table A.

Table 2713

Compounds of the formula I.B, in which $R^1$ is ethyl, Z is sulfur and $R^3$ is trans-3-bromoprop-2-enyl and $R^2$ for a compound corresponds in each case to a group in Table A.

Table 2714

Compounds of the formula I.A, in which $R^1$ is ethyl, Z is NH and $R^3$ is trans-3-bromoprop-2-enyl and $R^2$ for a compound corresponds in each case to a group in Table A.

Table 2715

Compounds of the formula I.B, in which $R^1$ is ethyl, Z is NH and $R^3$ is trans-3-bromoprop-2-enyl and $R^2$ for a compound corresponds in each case to a group in Table A.

Table 2716

Compounds of the formula I.A, in which $R^1$ is isopropyl, Z is oxygen and $R^3$ is trans-3-bromoprop-2-enyl and $R^2$ for a compound corresponds in each case to a group in Table A.

Table 2717

Compounds of the formula I.B, in which $R^1$ is isopropyl, Z is oxygen and $R^3$ is trans-3-bromoprop-2-enyl and $R^2$ for a compound corresponds in each case to a group in Table A.

Table 2718

Compounds of the formula I.A, in which $R^1$ is isopropyl, Z is sulfur and $R^3$ is trans-3-bromoprop-2-enyl and $R^2$ for a compound corresponds in each case to a group in Table A.

Table 2719

Compounds of the formula I.B, in which $R^1$ is isopropyl, Z is sulfur and $R^3$ is trans-3-bromoprop-2-enyl and $R^2$ for a compound corresponds in each case to a group in Table A.

Table 2720

Compounds of the formula I.A, in which $R^1$ is isopropyl, Z is NH and $R^3$ is trans-3-bromoprop-2-enyl and $R^2$ for a compound corresponds in each case to a group in Table A.

Table 2721

Compounds of the formula I.B, in which $R^1$ is isopropyl, Z is NH and $R^3$ is trans-3-bromoprop-2-enyl and $R^2$ for a compound corresponds in each case to a group in Table A.

Table 2722

Compounds of the formula I.A, in which $R^1$ is hydrogen, Z is oxygen and $R^3$ is 2-bromoprop-2-enyl and $R^2$ for a compound corresponds in each case to a group in Table A.

Table 2723

Compounds of the formula I.B, in which $R^1$ is hydrogen, Z is oxygen and $R^3$ is 2-bromoprop-2-enyl and $R^2$ for a compound corresponds in each case to a group in Table A.

Table 2724

Compounds of the formula I.A, in which $R^1$ is hydrogen, Z is sulfur and $R^3$ is 2-bromoprop-2-enyl and $R^2$ for a compound corresponds in each case to a group in Table A.

Table 2725

Compounds of the formula I.B, in which $R^1$ is hydrogen, Z is sulfur and $R^3$ is 2-bromoprop-2-enyl and $R^2$ for a compound corresponds in each case to a group in Table A.

Table 2726

Compounds of the formula I.A, in which $R^1$ is hydrogen, Z is NH and $R^3$ is 2-bromoprop-2-enyl and $R^2$ for a compound corresponds in each case to a group in Table A.

Table 2727

Compounds of the formula I.B, in which $R^1$ is hydrogen, Z is NH and $R^3$ is 2-bromoprop-2-enyl and $R^2$ for a compound corresponds in each case to a group in Table A.

Table 2728

Compounds of the formula I.A, in which $R^1$ is methyl, Z is oxygen and $R^3$ is 2-bromoprop-2-enyl and $R^2$ for a compound corresponds in each case to a group in Table A.

Table 2729

Compounds of the formula I.B, in which $R^1$ is methyl, Z is oxygen and $R^3$ is 2-bromoprop-2-enyl and $R^2$ for a compound corresponds in each case to a group in Table A.

Table 2730

Compounds of the formula I.A, in which $R^1$ is methyl, Z is sulfur and $R^3$ is 2-bromoprop-2-enyl and $R^2$ for a compound corresponds in each case to a group in Table A.

Table 2731

Compounds of the formula I.B, in which $R^1$ is methyl, Z is sulfur and $R^3$ is 2-bromoprop-2-enyl and $R^2$ for a compound corresponds in each case to a group in Table A.

Table 2732

Compounds of the formula I.A, in which $R^1$ is methyl, Z is NH and $R^3$ is 2-bromoprop-2-enyl and $R^2$ for a compound corresponds in each case to a group in Table A.

Table 2733

Compounds of the formula I.B, in which $R^1$ is methyl, Z is NH and $R^3$ is 2-bromoprop-2-enyl and $R^2$ for a compound corresponds in each case to a group in Table A.

Table 2734

Compounds of the formula I.A, in which $R^1$ is ethyl, Z is oxygen and $R^3$ is 2-bromoprop-2-enyl and $R^2$ for a compound corresponds in each case to a group in Table A.

Table 2735

Compounds of the formula I.B, in which $R^1$ is ethyl, Z is oxygen and $R^3$ is 2-bromoprop-2-enyl and $R^2$ for a compound corresponds in each case to a group in Table A.

Table 2736

Compounds of the formula I.A, in which $R^1$ is ethyl, Z is sulfur and $R^3$ is 2-bromoprop-2-enyl and $R^2$ for a compound corresponds in each case to a group in Table A.

Table 2737

Compounds of the formula I.B, in which $R^1$ is ethyl, Z is sulfur and $R^3$ is 2-bromoprop-2-enyl and $R^2$ for a compound corresponds in each case to a group in Table A.

Table 2738

Compounds of the formula I.A, in which $R^1$ is ethyl, Z is NH and $R^3$ is 2-bromoprop-2-enyl and $R^2$ for a compound corresponds in each case to a group in Table A.

Table 2739

Compounds of the formula I.B, in which $R^1$ is ethyl, Z is NH and $R^3$ is 2-bromoprop-2-enyl and $R^2$ for a compound corresponds in each case to a group in Table A.

Table 2740

Compounds of the formula I.A, in which $R^1$ is isopropyl, Z is oxygen and $R^3$ is 2-bromoprop-2-enyl and $R^2$ for a compound corresponds in each case to a group in Table A.

Table 2741

Compounds of the formula I.B, in which $R^1$ is isopropyl, Z is oxygen and $R^3$ is 2-bromoprop-2-enyl and $R^2$ for a compound corresponds in each case to a group in Table A.

Table 2742

Compounds of the formula I.A, in which $R^1$ is isopropyl, Z is sulfur and $R^3$ is 2-bromoprop-2-enyl and $R^2$ for a compound corresponds in each case to a group in Table A.

Table 2743

Compounds of the formula I.B, in which $R^1$ is isopropyl, Z is sulfur and $R^3$ is 2-bromoprop-2-enyl and $R^2$ for a compound corresponds in each case to a group in Table A.

Table 2744

Compounds of the formula I.A, in which $R^1$ is isopropyl, Z is NH and $R^3$ is 2-bromoprop-2-enyl and $R^2$ for a compound corresponds in each case to a group in Table A.

Table 2745

Compounds of the formula I.B, in which $R^1$ is isopropyl, Z is NH and $R^3$ is 2-bromoprop-2-enyl and $R^2$ for a compound corresponds in each case to a group in Table A.

Table 2746

Compounds of the formula I.A, in which $R^1$ is hydrogen, Z is oxygen and $R^3$ is 3,3-dibromoprop-2-enyl and $R^2$ for a compound corresponds in each case to a group in Table A.

Table 2747

Compounds of the formula I.B, in which $R^1$ is hydrogen, Z is oxygen and $R^3$ is 3,3-dibromoprop-2-enyl and $R^2$ for a compound corresponds in each case to a group in Table A.

Table 2748

Compounds of the formula I.A, in which $R^1$ is hydrogen, Z is sulfur and $R^3$ is 3,3-dibromoprop-2-enyl and $R^2$ for a compound corresponds in each case to a group in Table A.

Table 2749

Compounds of the formula I.B, in which $R^1$ is hydrogen, Z is sulfur and $R^3$ is 3,3-dibromoprop-2-enyl and $R^2$ for a compound corresponds in each case to a group in Table A.

Table 2750

Compounds of the formula I.A, in which $R^1$ is hydrogen, Z is NH and $R^3$ is 3,3-dibromoprop-2-enyl and $R^2$ for a compound corresponds in each case to a group in Table A.

Table 2751

Compounds of the formula I.B, in which $R^1$ is hydrogen, Z is NH and $R^3$ is 3,3-dibromoprop-2-enyl and $R^2$ for a compound corresponds in each case to a group in Table A.

Table 2752

Compounds of the formula I.A, in which $R^1$ is methyl, Z is oxygen and $R^3$ is 3,3-dibromoprop-2-enyl and $R^2$ for a compound corresponds in each case to a group in Table A.

Table 2753

Compounds of the formula I.B, in which $R^1$ is methyl, Z is oxygen and $R^3$ is 3,3-dibromoprop-2-enyl and $R^2$ for a compound corresponds in each case to a group in Table A.

Table 2754

Compounds of the formula I.A, in which $R^1$ is methyl, Z is sulfur and $R^3$ is 3,3-dibromoprop-2-enyl and $R^2$ for a compound corresponds in each case to a group in Table A.

Table 2755

Compounds of the formula I.B, in which $R^1$ is methyl, Z is sulfur and $R^3$ is 3,3-dibromoprop-2-enyl and $R^2$ for a compound corresponds in each case to a group in Table A.

Table 2756

Compounds of the formula I.A, in which $R^1$ is methyl, Z is NH and $R^3$ is 3,3-dibromoprop-2-enyl and $R^2$ for a compound corresponds in each case to a group in Table A.

Table 2757

Compounds of the formula I.B, in which $R^1$ is methyl, Z is NH and $R^3$ is 3,3-dibromoprop-2-enyl and $R^2$ for a compound corresponds in each case to a group in Table A.

Table 2758

Compounds of the formula I.A, in which $R^1$ is ethyl, Z is oxygen and $R^3$ is 3,3-dibromoprop-2-enyl and $R^2$ for a compound corresponds in each case to a group in Table A.

Table 2759

Compounds of the formula I.B, in which $R^1$ is ethyl, Z is oxygen and $R^3$ is 3,3-dibromoprop-2-enyl and $R^2$ for a compound corresponds in each case to a group in Table A.

Table 2760

Compounds of the formula I.A, in which $R^1$ is ethyl, Z is sulfur and $R^3$ is 3,3-dibromoprop-2-enyl and $R^2$ for a compound corresponds in each case to a group in Table A.

Table 2761

Compounds of the formula I.B, in which $R^1$ is ethyl, Z is sulfur and $R^3$ is 3,3-dibromoprop-2-enyl and $R^2$ for a compound corresponds in each case to a group in Table A.

Table 2762

Compounds of the formula I.A, in which $R^1$ is ethyl, Z is NH and $R^3$ is 3,3-dibromoprop-2-enyl and $R^2$ for a compound corresponds in each case to a group in Table A.

Table 2763

Compounds of the formula I.B, in which $R^1$ is ethyl, Z is NH and $R^3$ is 3,3-dibromoprop-2-enyl and $R^2$ for a compound corresponds in each case to a group in Table A.

Table 2764

Compounds of the formula I.A, in which $R^1$ is isopropyl, Z is oxygen and $R^3$ is 3,3-dibromoprop-2-enyl and $R^2$ for a compound corresponds in each case to a group in Table A.

Table 2765

Compounds of the formula I.B, in which $R^1$ is isopropyl, Z is oxygen and $R^3$ is 3,3-dibromoprop-2-enyl and $R^2$ for a compound corresponds in each case to a group in Table A.

Table 2766

Compounds of the formula I.A, in which $R^1$ is isopropyl, Z is sulfur and $R^3$ is 3,3-dibromoprop-2-enyl and $R^2$ for a compound corresponds in each case to a group in Table A.

Table 2767

Compounds of the formula I.B, in which $R^1$ is isopropyl, Z is sulfur and $R^3$ is 3,3-dibromoprop-2-enyl and $R^2$ for a compound corresponds in each case to a group in Table A.

Table 2768

Compounds of the formula I.A, in which $R^1$ is isopropyl, Z is NH and $R^3$ is 3,3-dibromoprop-2-enyl and $R^2$ for a compound corresponds in each case to a group in Table A.

Table 2769

Compounds of the formula I.B, in which $R^1$ is isopropyl, Z is NH and $R^3$ is 3,3-dibromoprop-2-enyl and $R^2$ for a compound corresponds in each case to a group in Table A.

Table 2770

Compounds of the formula I.A, in which $R^1$ is hydrogen, Z is oxygen and $R^3$ is 2,3,3,-tribromoprop-2-enyl and $R^2$ for a compound corresponds in each case to a group in Table A.

Table 2771

Compounds of the formula I.B, in which $R^1$ is hydrogen, Z is oxygen and $R^3$ is 2,3,3,-tribromoprop-2-enyl and $R^2$ for a compound corresponds in each case to a group in Table A.

Table 2772

Compounds of the formula I.A, in which $R^1$ is hydrogen, Z is sulfur and $R^3$ is 2,3,3,-tribromoprop-2-enyl and $R^2$ for a compound corresponds in each case to a group in Table A.

Table 2773

Compounds of the formula I.B, in which $R^1$ is hydrogen, Z is sulfur and $R^3$ is 2,3,3,-tribromoprop-2-enyl and $R^2$ for a compound corresponds in each case to a group in Table A.

Table 2774

Compounds of the formula I.A, in which $R^1$ is hydrogen, Z is NH and $R^3$ is 2,3,3,-tribromoprop-2-enyl and $R^2$ for a compound corresponds in each case to a group in Table A.

Table 2775

Compounds of the formula I.B, in which $R^1$ is hydrogen, Z is NH and $R^3$ is 2,3,3,-tribromoprop-2-enyl and $R^2$ for a compound corresponds in each case to a group in Table A.

Table 2776

Compounds of the formula I.A, in which $R^1$ is methyl, Z is oxygen and $R^3$ is 2,3,3,-tribromoprop-2-enyl and $R^2$ for a compound corresponds in each case to a group in Table A.

Table 2777

Compounds of the formula I.B, in which $R^1$ is methyl, Z is oxygen and $R^3$ is 2,3,3,-tribromoprop-2-enyl and $R^2$ for a compound corresponds in each case to a group in Table A.

Table 2778

Compounds of the formula I.A, in which $R^1$ is methyl, Z is sulfur and $R^3$ is 2,3,3,-tribromoprop-2-enyl and $R^2$ for a compound corresponds in each case to a group in Table A.

Table 2779

Compounds of the formula I.B, in which $R^1$ is methyl, Z is sulfur and $R^3$ is 2,3,3,-tribromoprop-2-enyl and $R^2$ for a compound corresponds in each case to a group in Table A.

Table 2780

Compounds of the formula I.A, in which $R^1$ is methyl, Z is NH and $R^3$ is 2,3,3,-tribromoprop-2-enyl and $R^2$ for a compound corresponds in each case to a group in Table A.

Table 2781

Compounds of the formula I.B, in which $R^1$ is methyl, Z is NH and $R^3$ is 2,3,3,-tribromoprop-2-enyl and $R^2$ for a compound corresponds in each case to a group in Table A.

Table 2782

Compounds of the formula I.A, in which $R^1$ is ethyl, Z is oxygen and $R^3$ is 2,3,3,-tribromoprop-2-enyl and $R^2$ for a compound corresponds in each case to a group in Table A.

Table 2783

Compounds of the formula I.B, in which $R^1$ is ethyl, Z is oxygen and $R^3$ is 2,3,3,-tribromoprop-2-enyl and $R^2$ for a compound corresponds in each case to a group in Table A.

Table 2784

Compounds of the formula I.A, in which $R^1$ is ethyl, Z is sulfur and $R^3$ is 2,3,3,-tribromoprop-2-enyl and $R^2$ for a compound corresponds in each case to a group in Table A.

Table 2785

Compounds of the formula I.B, in which $R^1$ is ethyl, Z is sulfur and $R^3$ is 2,3,3,-tribromoprop-2-enyl and $R^2$ for a compound corresponds in each case to a group in Table A.

Table 2786

Compounds of the formula I.A, in which $R^1$ is ethyl, Z is NH and $R^3$ is 2,3,3,-tribromoprop-2-enyl and $R^2$ for a compound corresponds in each case to a group in Table A.

Table 2787

Compounds of the formula I.B, in which $R^1$ is ethyl, Z is NH and $R^3$ is 2,3,3,-tribromoprop-2-enyl and $R^2$ for a compound corresponds in each case to a group in Table A.

Table 2788

Compounds of the formula I.A, in which $R^1$ is isopropyl, Z is oxygen and $R^3$ is 2,3,3,-tribromoprop-2-enyl and $R^2$ for a compound corresponds in each case to a group in Table A.

Table 2789

Compounds of the formula I.B, in which $R^1$ is isopropyl, Z is oxygen and $R^3$ is 2,3,3,-tribromoprop-2-enyl and $R^2$ for a compound corresponds in each case to a group in Table A.

Table 2790

Compounds of the formula I.A, in which $R^1$ is isopropyl, Z is sulfur and $R^3$ is 2,3,3,-tribromoprop-2-enyl and $R^2$ for a compound corresponds in each case to a group in Table A.

Table 2791

Compounds of the formula I.B, in which $R^1$ is isopropyl, Z is sulfur and $R^3$ is 2,3,3,-tribromoprop-2-enyl and $R^2$ for a compound corresponds in each case to a group in Table A.

Table 2792

Compounds of the formula I.A, in which $R^1$ is isopropyl, Z is NH and $R^3$ is 2,3,3,-tribromoprop-2-enyl and $R^2$ for a compound corresponds in each case to a group in Table A.

Table 2793

Compounds of the formula I.B, in which $R^1$ is isopropyl, Z is NH and $R^3$ is 2,3,3,-tribromoprop-2-enyl and $R^2$ for a compound corresponds in each case to a group in Table A.

Table 2794

Compounds of the formula I.A, in which $R^1$ is hydrogen, Z is oxygen and $R^3$ is cis-2,3-dibromoprop-2-enyl and $R^2$ for a compound corresponds in each case to a group in Table A.

Table 2795

Compounds of the formula I.B, in which $R^1$ is hydrogen, Z is oxygen and $R^3$ is cis-2,3-dibromoprop-2-enyl and $R^2$ for a compound corresponds in each case to a group in Table A.

Table 2796

Compounds of the formula I.A, in which $R^1$ is hydrogen, Z is sulfur and $R^3$ is cis-2,3-dibromoprop-2-enyl and $R^2$ for a compound corresponds in each case to a group in Table A.

Table 2797

Compounds of the formula I.B, in which $R^1$ is hydrogen, Z is sulfur and $R^3$ is cis-2,3-dibromoprop-2-enyl and $R^2$ for a compound corresponds in each case to a group in Table A.

Table 2798

Compounds of the formula I.A, in which $R^1$ is hydrogen, Z is NH and $R^3$ is cis-2,3-dibromoprop-2-enyl and $R^2$ for a compound corresponds in each case to a group in Table A.

Table 2799

Compounds of the formula I.B, in which $R^1$ is hydrogen, Z is NH and $R^3$ is cis-2,3-dibromoprop-2-enyl and $R^2$ for a compound corresponds in each case to a group in Table A.

Table 2800

Compounds of the formula I.A, in which $R^1$ is methyl, Z is oxygen and $R^3$ is cis-2,3-dibromoprop-2-enyl and $R^2$ for a compound corresponds in each case to a group in Table A.

Table 2801

Compounds of the formula I.B, in which $R^1$ is methyl, Z is oxygen and $R^3$ is cis-2,3-dibromoprop-2-enyl and $R^2$ for a compound corresponds in each case to a group in Table A.

Table 2802

Compounds of the formula I.A, in which $R^1$ is methyl, Z is sulfur and $R^3$ is cis-2,3-dibromoprop-2-enyl and $R^2$ for a compound corresponds in each case to a group in Table A.

Table 2803

Compounds of the formula I.B, in which $R^1$ is methyl, Z is sulfur and $R^3$ is cis-2,3-dibromoprop-2-enyl and $R^2$ for a compound corresponds in each case to a group in Table A.

Table 2804

Compounds of the formula I.A, in which $R^1$ is methyl, Z is NH and $R^3$ is cis-2,3-dibromoprop-2-enyl and $R^2$ for a compound corresponds in each case to a group in Table A.

Table 2805

Compounds of the formula I.B, in which $R^1$ is methyl, Z is NH and $R^3$ is cis-2,3-dibromoprop-2-enyl and $R^2$ for a compound corresponds in each case to a group in Table A.

Table 2806

Compounds of the formula I.A, in which $R^1$ is ethyl, Z is oxygen and $R^3$ is cis-2,3-dibromoprop-2-enyl and $R^2$ for a compound corresponds in each case to a group in Table A.

Table 2807

Compounds of the formula I.B, in which $R^1$ is ethyl, Z is oxygen and $R^3$ is cis-2,3-dibromoprop-2-enyl and $R^2$ for a compound corresponds in each case to a group in Table A.

Table 2808

Compounds of the formula I.A, in which $R^1$ is ethyl, Z is sulfur and $R^3$ is cis-2,3-dibromoprop-2-enyl and $R^2$ for a compound corresponds in each case to a group in Table A.

Table 2809

Compounds of the formula I.B, in which $R^1$ is ethyl, Z is sulfur and $R^3$ is cis-2,3-dibromoprop-2-enyl and $R^2$ for a compound corresponds in each case to a group in Table A.

Table 2810

Compounds of the formula I.A, in which $R^1$ is ethyl, Z is NH and $R^3$ is cis-2,3-dibromoprop-2-enyl and $R^2$ for a compound corresponds in each case to a group in Table A.

Table 2811

Compounds of the formula I.B, in which $R^1$ is ethyl, Z is NH and $R^3$ is cis-2,3-dibromoprop-2-enyl and $R^2$ for a compound corresponds in each case to a group in Table A.

Table 2812

Compounds of the formula I.A, in which $R^1$ is isopropyl, Z is oxygen and $R^3$ is cis-2,3-dibromoprop-2-enyl and $R^2$ for a compound corresponds in each case to a group in Table A.

Table 2813

Compounds of the formula I.B, in which $R^1$ is isopropyl, Z is oxygen and $R^3$ is cis-2,3-dibromoprop-2-enyl and $R^2$ for a compound corresponds in each case to a group in Table A.

Table 2814

Compounds of the formula I.A, in which $R^1$ is isopropyl, Z is sulfur and $R^3$ is cis-2,3-dibromoprop-2-enyl and $R^2$ for a compound corresponds in each case to a group in Table A.

Table 2815

Compounds of the formula I.B, in which $R^1$ is isopropyl, Z is sulfur and $R^3$ is cis-2,3-dibromoprop-2-enyl and $R^2$ for a compound corresponds in each case to a group in Table A.

Table 2816

Compounds of the formula I.A, in which $R^1$ is isopropyl, Z is NH and $R^3$ is cis-2,3-dibromoprop-2-enyl and $R^2$ for a compound corresponds in each case to a group in Table A.

Table 2817

Compounds of the formula I.B, in which $R^1$ is isopropyl, Z is NH and $R^3$ is cis-2,3-dibromoprop-2-enyl and $R^2$ for a compound corresponds in each case to a group in Table A.

Table 2818

Compounds of the formula I.A, in which $R^1$ is hydrogen, Z is oxygen and $R^3$ is trans-2,3-dibromoprop-2-enyl and $R^2$ for a compound corresponds in each case to a group in Table A.

Table 2819

Compounds of the formula I.B, in which $R^1$ is hydrogen, Z is oxygen and $R^3$ is trans-2,3-dibromoprop-2-enyl and $R^2$ for a compound corresponds in each case to a group in Table A.

Table 2820

Compounds of the formula I.A, in which $R^1$ is hydrogen, Z is sulfur and $R^3$ is trans-2,3-dibromoprop-2-enyl and $R^2$ for a compound corresponds in each case to a group in Table A.

Table 2821

Compounds of the formula I.B, in which $R^1$ is hydrogen, Z is sulfur and $R^3$ is trans-2,3-dibromoprop-2-enyl and $R^2$ for a compound corresponds in each case to a group in Table A.

Table 2822

Compounds of the formula I.A, in which $R^1$ is hydrogen, Z is NH and $R^3$ is trans-2,3-dibromoprop-2-enyl and $R^2$ for a compound corresponds in each case to a group in Table A.

Table 2823

Compounds of the formula I.B, in which $R^1$ is hydrogen, Z is NH and $R^3$ is trans-2,3-dibromoprop-2-enyl and $R^2$ for a compound corresponds in each case to a group in Table A.

Table 2824

Compounds of the formula I.A, in which $R^1$ is methyl, Z is oxygen and $R^3$ is trans-2,3-dibromoprop-2-enyl and $R^2$ for a compound corresponds in each case to a group in Table A.

Table 2825

Compounds of the formula I.B, in which $R^1$ is methyl, Z is oxygen and $R^3$ is trans-2,3-dibromoprop-2-enyl and $R^2$ for a compound corresponds in each case to a group in Table A.

Table 2826

Compounds of the formula I.A, in which $R^1$ is methyl, Z is sulfur and $R^3$ is trans-2,3-dibromoprop-2-enyl and $R^2$ for a compound corresponds in each case to a group in Table A.

Table 2827

Compounds of the formula I.B, in which $R^1$ is methyl, Z is sulfur and $R^3$ is trans-2,3-dibromoprop-2-enyl and $R^2$ for a compound corresponds in each case to a group in Table A.

Table 2828

Compounds of the formula I.A, in which $R^1$ is methyl, Z is NH and $R^3$ is trans-2,3-dibromoprop-2-enyl and $R^2$ for a compound corresponds in each case to a group in Table A.

Table 2829

Compounds of the formula I.B, in which $R^1$ is methyl, Z is NH and $R^3$ is trans-2,3-dibromoprop-2-enyl and $R^2$ for a compound corresponds in each case to a group in Table A.

Table 2830

Compounds of the formula I.A, in which $R^1$ is ethyl, Z is oxygen and $R^3$ is trans-2,3-dibromoprop-2-enyl and $R^2$ for a compound corresponds in each case to a group in Table A.

Table 2831

Compounds of the formula I.B, in which $R^1$ is ethyl, Z is oxygen and $R^3$ is trans-2,3-dibromoprop-2-enyl and $R^2$ for a compound corresponds in each case to a group in Table A.

Table 2832

Compounds of the formula I.A, in which $R^1$ is ethyl, Z is sulfur and $R^3$ is trans-2,3-dibromoprop-2-enyl and $R^2$ for a compound corresponds in each case to a group in Table A.

Table 2833

Compounds of the formula I.B, in which $R^1$ is ethyl, Z is sulfur and $R^3$ is trans-2,3-dibromoprop-2-enyl and $R^2$ for a compound corresponds in each case to a group in Table A.

Table 2834

Compounds of the formula I.A, in which $R^1$ is ethyl, Z is NH and $R^3$ is trans-2,3-dibromoprop-2-enyl and $R^2$ for a compound corresponds in each case to a group in Table A.

Table 2835

Compounds of the formula I.B, in which $R^1$ is ethyl, Z is NH and $R^3$ is trans-2,3-dibromoprop-2-enyl and $R^2$ for a compound corresponds in each case to a group in Table A.

Table 2836

Compounds of the formula I.A, in which $R^1$ is isopropyl, Z is oxygen and $R^3$ is trans-2,3-dibromoprop-2-enyl and $R^2$ for a compound corresponds in each case to a group in Table A.

Table 2837

Compounds of the formula I.B, in which $R^1$ is isopropyl, Z is oxygen and $R^3$ is trans-2,3-dibromoprop-2-enyl and $R^2$ for a compound corresponds in each case to a group in Table A.

Table 2838

Compounds of the formula I.A, in which $R^1$ is isopropyl, Z is sulfur and $R^3$ is trans-2,3-dibromoprop-2-enyl and $R^2$ for a compound corresponds in each case to a group in Table A.

Table 2839

Compounds of the formula I.B, in which $R^1$ is isopropyl, Z is sulfur and $R^3$ is trans-2,3-dibromoprop-2-enyl and $R^2$ for a compound corresponds in each case to a group in Table A.

Table 2840

Compounds of the formula I.A, in which $R^1$ is isopropyl, Z is NH and $R^3$ is trans-2,3-dibromoprop-2-enyl and $R^2$ for a compound corresponds in each case to a group in Table A.

Table 2841

Compounds of the formula I.B, in which $R^1$ is isopropyl, Z is NH and $R^3$ is trans-2,3-dibromoprop-2-enyl and $R^2$ for a compound corresponds in each case to a group in Table A.

Table 2842

Compounds of the formula I.A, in which $R^1$ is hydrogen, Z is oxygen and $R^3$ is trans-2-chlorobut-2-enyl and $R^2$ for a compound corresponds in each case to a group in Table A.

Table 2843

Compounds of the formula I.B, in which $R^1$ is hydrogen, Z is oxygen and $R^3$ is trans-2-chlorobut-2-enyl and $R^2$ for a compound corresponds in each case to a group in Table A.

Table 2844

Compounds of the formula I.A, in which $R^1$ is hydrogen, Z is sulfur and $R^3$ is trans-2-chlorobut-2-enyl and $R^2$ for a compound corresponds in each case to a group in Table A.

Table 2845

Compounds of the formula I.B, in which $R^1$ is hydrogen, Z is sulfur and $R^3$ is trans-2-chlorobut-2-enyl and $R^2$ for a compound corresponds in each case to a group in Table A.

Table 2846

Compounds of the formula I.A, in which $R^1$ is hydrogen, Z is NH and $R^3$ is trans-2-chlorobut-2-enyl and $R^2$ for a compound corresponds in each case to a group in Table A.

Table 2847

Compounds of the formula I.B, in which $R^1$ is hydrogen, Z is NH and $R^3$ is trans-2-chlorobut-2-enyl and $R^2$ for a compound corresponds in each case to a group in Table A.

Table 2848

Compounds of the formula I.A, in which $R^1$ is methyl, Z is oxygen and $R^3$ is trans-2-chlorobut-2-enyl and $R^2$ for a compound corresponds in each case to a group in Table A.

Table 2849

Compounds of the formula I.B, in which $R^1$ is methyl, Z is oxygen and $R^3$ is trans-2-chlorobut-2-enyl and $R^2$ for a compound corresponds in each case to a group in Table A.

Table 2850

Compounds of the formula I.A, in which $R^1$ is methyl, Z is sulfur and $R^3$ is trans-2-chlorobut-2-enyl and $R^2$ for a compound corresponds in each case to a group in Table A.

Table 2851

Compounds of the formula I.B, in which $R^1$ is methyl, Z is sulfur and $R^3$ is trans-2-chlorobut-2-enyl and $R^2$ for a compound corresponds in each case to a group in Table A.

Table 2852

Compounds of the formula I.A, in which $R^1$ is methyl, Z is NH and $R^3$ is trans-2-chlorobut-2-enyl and $R^2$ for a compound corresponds in each case to a group in Table A.

Table 2853

Compounds of the formula I.B, in which $R^1$ is methyl, Z is NH and $R^3$ is trans-2-chlorobut-2-enyl and $R^2$ for a compound corresponds in each case to a group in Table A.

Table 2854

Compounds of the formula I.A, in which $R^1$ is ethyl, Z is oxygen and $R^3$ is trans-2-chlorobut-2-enyl and $R^2$ for a compound corresponds in each case to a group in Table A.

Table 2855

Compounds of the formula I.B, in which $R^1$ is ethyl, Z is oxygen and $R^3$ is trans-2-chlorobut-2-enyl and $R^2$ for a compound corresponds in each case to a group in Table A.

Table 2856

Compounds of the formula I.A, in which $R^1$ is ethyl, Z is sulfur and $R^3$ is trans-2-chlorobut-2-enyl and $R^2$ for a compound corresponds in each case to a group in Table A.

Table 2857

Compounds of the formula I.B, in which $R^1$ is ethyl, Z is sulfur and $R^3$ is trans-2-chlorobut-2-enyl and $R^2$ for a compound corresponds in each case to a group in Table A.

Table 2858

Compounds of the formula I.A, in which $R^1$ is ethyl, Z is NH and $R^3$ is trans-2-chlorobut-2-enyl and $R^2$ for a compound corresponds in each case to a group in Table A.

Table 2859

Compounds of the formula I.B, in which $R^1$ is ethyl, Z is NH and $R^3$ is trans-2-chlorobut-2-enyl and $R^2$ for a compound corresponds in each case to a group in Table A.

Table 2860

Compounds of the formula I.A, in which $R^1$ is isopropyl, Z is oxygen and $R^3$ is trans-2-chlorobut-2-enyl and $R^2$ for a compound corresponds in each case to a group in Table A.

Table 2861

Compounds of the formula I.B, in which $R^1$ is isopropyl, Z is oxygen and $R^3$ is trans-2-chlorobut-2-enyl and $R^2$ for a compound corresponds in each case to a group in Table A.

Table 2862

Compounds of the formula I.A, in which $R^1$ is isopropyl, Z is sulfur and $R^3$ is trans-2-chlorobut-2-enyl and $R^2$ for a compound corresponds in each case to a group in Table A.

Table 2863

Compounds of the formula I.B, in which $R^1$ is isopropyl, Z is sulfur and $R^3$ is trans-2-chlorobut-2-enyl and $R^2$ for a compound corresponds in each case to a group in Table A.

Table 2864

Compounds of the formula I.A, in which $R^1$ is isopropyl, Z is NH and $R^3$ is trans-2-chlorobut-2-enyl and $R^2$ for a compound corresponds in each case to a group in Table A.

Table 2865

Compounds of the formula I.B, in which $R^1$ is isopropyl, Z is NH and $R^3$ is trans-2-chlorobut-2-enyl and $R^2$ for a compound corresponds in each case to a group in Table A.

Table 2866

Compounds of the formula I.A, in which $R^1$ is hydrogen, Z is oxygen and $R^3$ is cis-2-chlorobut-2-enyl and $R^2$ for a compound corresponds in each case to a group in Table A.

Table 2867

Compounds of the formula I.B, in which $R^1$ is hydrogen, Z is oxygen and $R^3$ is cis-2-chlorobut-2-enyl and $R^2$ for a compound corresponds in each case to a group in Table A.

Table 2868

Compounds of the formula I.A, in which $R^1$ is hydrogen, Z is sulfur and $R^3$ is cis-2-chlorobut-2-enyl and $R^2$ for a compound corresponds in each case to a group in Table A.

Table 2869

Compounds of the formula I.B, in which $R^1$ is hydrogen, Z is sulfur and $R^3$ is cis-2-chlorobut-2-enyl and $R^2$ for a compound corresponds in each case to a group in Table A.

Table 2870

Compounds of the formula I.A, in which $R^1$ is hydrogen, Z is NH and $R^3$ is cis-2-chlorobut-2-enyl and $R^2$ for a compound corresponds in each case to a group in Table A.

Table 2871

Compounds of the formula I.B, in which $R^1$ is hydrogen, Z is NH and $R^3$ is cis-2-chlorobut-2-enyl and $R^2$ for a compound corresponds in each case to a group in Table A.

Table 2872

Compounds of the formula I.A, in which $R^1$ is methyl, Z is oxygen and $R^3$ is cis-2-chlorobut-2-enyl and $R^2$ for a compound corresponds in each case to a group in Table A.

Table 2873

Compounds of the formula I.B, in which $R^1$ is methyl, Z is oxygen and $R^3$ is cis-2-chlorobut-2-enyl and $R^2$ for a compound corresponds in each case to a group in Table A.

Table 2874

Compounds of the formula I.A, in which $R^1$ is methyl, Z is sulfur and $R^3$ is cis-2-chlorobut-2-enyl and $R^2$ for a compound corresponds in each case to a group in Table A.

Table 2875

Compounds of the formula I.B, in which $R^1$ is methyl, Z is sulfur and $R^3$ is cis-2-chlorobut-2-enyl and $R^2$ for a compound corresponds in each case to a group in Table A.

Table 2876

Compounds of the formula I.A, in which $R^1$ is methyl, Z is NH and $R^3$ is cis-2-chlorobut-2-enyl and $R^2$ for a compound corresponds in each case to a group in Table A.

Table 2877

Compounds of the formula I.B, in which $R^1$ is methyl, Z is NH and $R^3$ is cis-2-chlorobut-2-enyl and $R^2$ for a compound corresponds in each case to a group in Table A.

Table 2878

Compounds of the formula I.A, in which $R^1$ is ethyl, Z is oxygen and $R^3$ is cis-2-chlorobut-2-enyl and $R^2$ for a compound corresponds in each case to a group in Table A.

Table 2879

Compounds of the formula I.B, in which $R^1$ is ethyl, Z is oxygen and $R^3$ is cis-2-chlorobut-2-enyl and $R^2$ for a compound corresponds in each case to a group in Table A.

Table 2880

Compounds of the formula I.A, in which $R^1$ is ethyl, Z is sulfur and $R^3$ is cis-2-chlorobut-2-enyl and $R^2$ for a compound corresponds in each case to a group in Table A.

Table 2881

Compounds of the formula I.B, in which $R^1$ is ethyl, Z is sulfur and $R^3$ is cis-2-chlorobut-2-enyl and $R^2$ for a compound corresponds in each case to a group in Table A.

Table 2882

Compounds of the formula I.A, in which $R^1$ is ethyl, Z is NH and $R^3$ is cis-2-chlorobut-2-enyl and $R^2$ for a compound corresponds in each case to a group in Table A.

Table 2883

Compounds of the formula I.B, in which $R^1$ is ethyl, Z is NH and $R^3$ is cis-2-chlorobut-2-enyl and $R^2$ for a compound corresponds in each case to a group in Table A.

Table 2884

Compounds of the formula I.A, in which $R^1$ is isopropyl, Z is oxygen and $R^3$ is cis-2-chlorobut-2-enyl and $R^2$ for a compound corresponds in each case to a group in Table A.

Table 2885

Compounds of the formula I.B, in which $R^1$ is isopropyl, Z is oxygen and $R^3$ is cis-2-chlorobut-2-enyl and $R^2$ for a compound corresponds in each case to a group in Table A.

Table 2886

Compounds of the formula I.A, in which $R^1$ is isopropyl, Z is sulfur and $R^3$ is cis-2-chlorobut-2-enyl and $R^2$ for a compound corresponds in each case to a group in Table A.

Table 2887

Compounds of the formula I.B, in which $R^1$ is isopropyl, Z is sulfur and $R^3$ is cis-2-chlorobut-2-enyl and $R^2$ for a compound corresponds in each case to a group in Table A.

Table 2888

Compounds of the formula I.A, in which $R^1$ is isopropyl, Z is NH and $R^3$ is cis-2-chlorobut-2-enyl and $R^2$ for a compound corresponds in each case to a group in Table A.

Table 2889

Compounds of the formula I.B, in which $R^1$ is isopropyl, Z is NH and $R^3$ is cis-2-chlorobut-2-enyl and $R^2$ for a compound corresponds in each case to a group in Table A.

Table 2890

Compounds of the formula I.A, in which $R^1$ is hydrogen, Z is oxygen and $R^3$ is trans-3-chlorobut-2-enyl and $R^2$ for a compound corresponds in each case to a group in Table A.

Table 2891

Compounds of the formula I.B, in which $R^1$ is hydrogen, Z is oxygen and $R^3$ is trans-3-chlorobut-2-enyl and $R^2$ for a compound corresponds in each case to a group in Table A.

Table 2892

Compounds of the formula I.A, in which $R^1$ is hydrogen, Z is sulfur and $R^3$ is trans-3-chlorobut-2-enyl and $R^2$ for a compound corresponds in each case to a group in Table A.

Table 2893

Compounds of the formula I.B, in which $R^1$ is hydrogen, Z is sulfur and $R^3$ is trans-3-chlorobut-2-enyl and $R^2$ for a compound corresponds in each case to a group in Table A.

Table 2894

Compounds of the formula I.A, in which $R^1$ is hydrogen, Z is NH and $R^3$ is trans-3-chlorobut-2-enyl and $R^2$ for a compound corresponds in each case to a group in Table A.

Table 2895

Compounds of the formula I.B, in which $R^1$ is hydrogen, Z is NH and $R^3$ is trans-3-chlorobut-2-enyl and $R^2$ for a compound corresponds in each case to a group in Table A.

Table 2896

Compounds of the formula I.A, in which $R^1$ is methyl, Z is oxygen and $R^3$ is trans-3-chlorobut-2-enyl and $R^2$ for a compound corresponds in each case to a group in Table A.

Table 2897

Compounds of the formula I.B, in which $R^1$ is methyl, Z is oxygen and $R^3$ is trans-3-chlorobut-2-enyl and $R^2$ for a compound corresponds in each case to a group in Table A.

Table 2898

Compounds of the formula I.A, in which $R^1$ is methyl, Z is sulfur and $R^3$ is trans-3-chlorobut-2-enyl and $R^2$ for a compound corresponds in each case to a group in Table A.

Table 2899

Compounds of the formula I.B, in which $R^1$ is methyl, Z is sulfur and $R^3$ is trans-3-chlorobut-2-enyl and $R^2$ for a compound corresponds in each case to a group in Table A.

Table 2900

Compounds of the formula I.A, in which $R^1$ is methyl, Z is NH and $R^3$ is trans-3-chlorobut-2-enyl and $R^2$ for a compound corresponds in each case to a group in Table A.

Table 2901

Compounds of the formula I.B, in which $R^1$ is methyl, Z is NH and $R^3$ is trans-3-chlorobut-2-enyl and $R^2$ for a compound corresponds in each case to a group in Table A.

Table 2902

Compounds of the formula I.A, in which $R^1$ is ethyl, Z is oxygen and $R^3$ is trans-3-chlorobut-2-enyl and $R^2$ for a compound corresponds in each case to a group in Table A.

Table 2903

Compounds of the formula I.B, in which $R^1$ is ethyl, Z is oxygen and $R^3$ is trans-3-chlorobut-2-enyl and $R^2$ for a compound corresponds in each case to a group in Table A.

Table 2904

Compounds of the formula I.A, in which $R^1$ is ethyl, Z is sulfur and $R^3$ is trans-3-chlorobut-2-enyl and $R^2$ for a compound corresponds in each case to a group in Table A.

Table 2905

Compounds of the formula I.B, in which $R^1$ is ethyl, Z is sulfur and $R^3$ is trans-3-chlorobut-2-enyl and $R^2$ for a compound corresponds in each case to a group in Table A.

Table 2906

Compounds of the formula I.A, in which $R^1$ is ethyl, Z is NH and $R^3$ is trans-3-chlorobut-2-enyl and $R^2$ for a compound corresponds in each case to a group in Table A.

Table 2907

Compounds of the formula I.B, in which $R^1$ is ethyl, Z is NH and $R^3$ is trans-3-chlorobut-2-enyl and $R^2$ for a compound corresponds in each case to a group in Table A.

Table 2908

Compounds of the formula I.A, in which $R^1$ is isopropyl, Z is oxygen and $R^3$ is trans-3-chlorobut-2-enyl and $R^2$ for a compound corresponds in each case to a group in Table A.

Table 2909

Compounds of the formula I.B, in which $R^1$ is isopropyl, Z is oxygen and $R^3$ is trans-3-chlorobut-2-enyl and $R^2$ for a compound corresponds in each case to a group in Table A.

Table 2910

Compounds of the formula I.A, in which $R^1$ is isopropyl, Z is sulfur and $R^3$ is trans-3-chlorobut-2-enyl and $R^2$ for a compound corresponds in each case to a group in Table A.

Table 2911

Compounds of the formula I.B, in which $R^1$ is isopropyl, Z is sulfur and $R^3$ is trans-3-chlorobut-2-enyl and $R^2$ for a compound corresponds in each case to a group in Table A.

Table 2912

Compounds of the formula I.A, in which $R^1$ is isopropyl, Z is NH and $R^3$ is trans-3-chlorobut-2-enyl and $R^2$ for a compound corresponds in each case to a group in Table A.

Table 2913

Compounds of the formula I.B, in which $R^1$ is isopropyl, Z is NH and $R^3$ is trans-3-chlorobut-2-enyl and $R^2$ for a compound corresponds in each case to a group in Table A.

Table 2914

Compounds of the formula I.A, in which $R^1$ is hydrogen, Z is oxygen and $R^3$ is cis-3-chlorobut-2-enyl and $R^2$ for a compound corresponds in each case to a group in Table A.

Table 2915

Compounds of the formula I.B, in which $R^1$ is hydrogen, Z is oxygen and $R^3$ is cis-3-chlorobut-2-enyl and $R^2$ for a compound corresponds in each case to a group in Table A.

Table 2916

Compounds of the formula I.A, in which $R^1$ is hydrogen, Z is sulfur and $R^3$ is cis-3-chlorobut-2-enyl and $R^2$ for a compound corresponds in each case to a group in Table A.

Table 2917

Compounds of the formula I.B, in which $R^1$ is hydrogen, Z is sulfur and $R^3$ is cis-3-chlorobut-2-enyl and $R^2$ for a compound corresponds in each case to a group in Table A.

Table 2918

Compounds of the formula I.A, in which $R^1$ is hydrogen, Z is NH and $R^3$ is cis-3-chlorobut-2-enyl and $R^2$ for a compound corresponds in each case to a group in Table A.

Table 2919

Compounds of the formula I.B, in which $R^1$ is hydrogen, Z is NH and $R^3$ is cis-3-chlorobut-2-enyl and $R^2$ for a compound corresponds in each case to a group in Table A.

Table 2920

Compounds of the formula I.A, in which $R^1$ is methyl, Z is oxygen and $R^3$ is cis-3-chlorobut-2-enyl and $R^2$ for a compound corresponds in each case to a group in Table A.

Table 2921

Compounds of the formula I.B, in which $R^1$ is methyl, Z is oxygen and $R^3$ is cis-3-chlorobut-2-enyl and $R^2$ for a compound corresponds in each case to a group in Table A.

Table 2922

Compounds of the formula I.A, in which $R^1$ is methyl, Z is sulfur and $R^3$ is cis-3-chlorobut-2-enyl and $R^2$ for a compound corresponds in each case to a group in Table A.

Table 2923

Compounds of the formula I.B, in which $R^1$ is methyl, Z is sulfur and $R^3$ is cis-3-chlorobut-2-enyl and $R^2$ for a compound corresponds in each case to a group in Table A.

Table 2924

Compounds of the formula I.A, in which $R^1$ is methyl, Z is NH and $R^3$ is cis-3-chlorobut-2-enyl and $R^2$ for a compound corresponds in each case to a group in Table A.

Table 2925

Compounds of the formula I.B, in which $R^1$ is methyl, Z is NH and $R^3$ is cis-3-chlorobut-2-enyl and $R^2$ for a compound corresponds in each case to a group in Table A.

Table 2926

Compounds of the formula I.A, in which $R^1$ is ethyl, Z is oxygen and $R^3$ is cis-3-chlorobut-2-enyl and $R^2$ for a compound corresponds in each case to a group in Table A.

Table 2927

Compounds of the formula I.B, in which $R^1$ is ethyl, Z is oxygen and $R^3$ is cis-3-chlorobut-2-enyl and $R^2$ for a compound corresponds in each case to a group in Table A.

Table 2928

Compounds of the formula I.A, in which $R^1$ is ethyl, Z is sulfur and $R^3$ is cis-3-chlorobut-2-enyl and $R^2$ for a compound corresponds in each case to a group in Table A.

Table 2929

Compounds of the formula I.B, in which $R^1$ is ethyl, Z is sulfur and $R^3$ is cis-3-chlorobut-2-enyl and $R^2$ for a compound corresponds in each case to a group in Table A.

Table 2930

Compounds of the formula I.A, in which $R^1$ is ethyl, Z is NH and $R^3$ is cis-3-chlorobut-2-enyl and $R^2$ for a compound corresponds in each case to a group in Table A.

Table 2931

Compounds of the formula I.B, in which $R^1$ is ethyl, Z is NH and $R^3$ is cis-3-chlorobut-2-enyl and $R^2$ for a compound corresponds in each case to a group in Table A.

Table 2932

Compounds of the formula I.A, in which $R^1$ is isopropyl, Z is oxygen and $R^3$ is cis-3-chlorobut-2-enyl and $R^2$ for a compound corresponds in each case to a group in Table A.

Table 2933

Compounds of the formula I.B, in which $R^1$ is isopropyl, Z is oxygen and $R^3$ is cis-3-chlorobut-2-enyl and $R^2$ for a compound corresponds in each case to a group in Table A.

Table 2934

Compounds of the formula I.A, in which $R^1$ is isopropyl, Z is sulfur and $R^3$ is cis-3-chlorobut-2-enyl and $R^2$ for a compound corresponds in each case to a group in Table A.

Table 2935

Compounds of the formula I.B, in which $R^1$ is isopropyl, Z is sulfur and $R^3$ is cis-3-chlorobut-2-enyl and $R^2$ for a compound corresponds in each case to a group in Table A.

Table 2936

Compounds of the formula I.A, in which $R^1$ is isopropyl, Z is NH and $R^3$ is cis-3-chlorobut-2-enyl and $R^2$ for a compound corresponds in each case to a group in Table A.

Table 2937

Compounds of the formula I.B, in which $R^1$ is isopropyl, Z is NH and $R^3$ is cis-3-chlorobut-2-enyl and $R^2$ for a compound corresponds in each case to a group in Table A.

Table 2938

Compounds of the formula I.A, in which $R^1$ is hydrogen, Z is oxygen and $R^3$ is trans-2-bromobut-2-enyl and $R^2$ for a compound corresponds in each case to a group in Table A.

Table 2939

Compounds of the formula I.B, in which $R^1$ is hydrogen, Z is oxygen and $R^3$ is trans-2-bromobut-2-enyl and $R^2$ for a compound corresponds in each case to a group in Table A.

Table 2940

Compounds of the formula I.A, in which $R^1$ is hydrogen, Z is sulfur and $R^3$ is trans-2-bromobut-2-enyl and $R^2$ for a compound corresponds in each case to a group in Table A.

Table 2941

Compounds of the formula I.B, in which $R^1$ is hydrogen, Z is sulfur and $R^3$ is trans-2-bromobut-2-enyl and $R^2$ for a compound corresponds in each case to a group in Table A.

Table 2942

Compounds of the formula I.A, in which $R^1$ is hydrogen, Z is NH and $R^3$ is trans-2-bromobut-2-enyl and $R^2$ for a compound corresponds in each case to a group in Table A.

Table 2943

Compounds of the formula I.B, in which $R^1$ is hydrogen, Z is NH and $R^3$ is trans-2-bromobut-2-enyl and $R^2$ for a compound corresponds in each case to a group in Table A.

Table 2944

Compounds of the formula I.A, in which $R^1$ is methyl, Z is oxygen and $R^3$ is trans-2-bromobut-2-enyl and $R^2$ for a compound corresponds in each case to a group in Table A.

Table 2945

Compounds of the formula I.B, in which $R^1$ is methyl, Z is oxygen and $R^3$ is trans-2-bromobut-2-enyl and $R^2$ for a compound corresponds in each case to a group in Table A.

Table 2946

Compounds of the formula I.A, in which $R^1$ is methyl, Z is sulfur and $R^3$ is trans-2-bromobut-2-enyl and $R^2$ for a compound corresponds in each case to a group in Table A.

Table 2947

Compounds of the formula I.B, in which $R^1$ is methyl, Z is sulfur and $R^3$ is trans-2-bromobut-2-enyl and $R^2$ for a compound corresponds in each case to a group in Table A.

Table 2948

Compounds of the formula I.A, in which $R^1$ is methyl, Z is NH and $R^3$ is trans-2-bromobut-2-enyl and $R^2$ for a compound corresponds in each case to a group in Table A.

Table 2949

Compounds of the formula I.B, in which $R^1$ is methyl, Z is NH and $R^3$ is trans-2-bromobut-2-enyl and $R^2$ for a compound corresponds in each case to a group in Table A.

Table 2950

Compounds of the formula I.A, in which $R^1$ is ethyl, Z is oxygen and $R^3$ is trans-2-bromobut-2-enyl and $R^2$ for a compound corresponds in each case to a group in Table A.

Table 2951

Compounds of the formula I.B, in which $R^1$ is ethyl, Z is oxygen and $R^3$ is trans-2-bromobut-2-enyl and $R^2$ for a compound corresponds in each case to a group in Table A.

Table 2952

Compounds of the formula I.A, in which $R^1$ is ethyl, Z is sulfur and $R^3$ is trans-2-bromobut-2-enyl and $R^2$ for a compound corresponds in each case to a group in Table A.

Table 2953

Compounds of the formula I.B, in which $R^1$ is ethyl, Z is sulfur and $R^3$ is trans-2-bromobut-2-enyl and $R^2$ for a compound corresponds in each case to a group in Table A.

Table 2954

Compounds of the formula I.A, in which $R^1$ is ethyl, Z is NH and $R^3$ is trans-2-bromobut-2-enyl and $R^2$ for a compound corresponds in each case to a group in Table A.

Table 2955

Compounds of the formula I.B, in which $R^1$ is ethyl, Z is NH and $R^3$ is trans-2-bromobut-2-enyl and $R^2$ for a compound corresponds in each case to a group in Table A.

Table 2956

Compounds of the formula I.A, in which $R^1$ is isopropyl, Z is oxygen and $R^3$ is trans-2-bromobut-2-enyl and $R^2$ for a compound corresponds in each case to a group in Table A.

Table 2957

Compounds of the formula I.B, in which $R^1$ is isopropyl, Z is oxygen and $R^3$ is trans-2-bromobut-2-enyl and $R^2$ for a compound corresponds in each case to a group in Table A.

Table 2958

Compounds of the formula I.A, in which $R^1$ is isopropyl, Z is sulfur and $R^3$ is trans-2-bromobut-2-enyl and $R^2$ for a compound corresponds in each case to a group in Table A.

Table 2959

Compounds of the formula I.B, in which $R^1$ is isopropyl, Z is sulfur and $R^3$ is trans-2-bromobut-2-enyl and $R^2$ for a compound corresponds in each case to a group in Table A.

Table 2960

Compounds of the formula I.A, in which $R^1$ is isopropyl, Z is NH and $R^3$ is trans-2-bromobut-2-enyl and $R^2$ for a compound corresponds in each case to a group in Table A.

Table 2961

Compounds of the formula I.B, in which $R^1$ is isopropyl, Z is NH and $R^3$ is trans-2-bromobut-2-enyl and $R^2$ for a compound corresponds in each case to a group in Table A.

Table 2962

Compounds of the formula I.A, in which $R^1$ is hydrogen, Z is oxygen and $R^3$ is cis-2-bromobut-2-enyl and $R^2$ for a compound corresponds in each case to a group in Table A.

Table 2963

Compounds of the formula I.B, in which $R^1$ is hydrogen, Z is oxygen and $R^3$ is cis-2-bromobut-2-enyl and $R^2$ for a compound corresponds in each case to a group in Table A.

Table 2964

Compounds of the formula I.A, in which $R^1$ is hydrogen, Z is sulfur and $R^3$ is cis-2-bromobut-2-enyl and $R^2$ for a compound corresponds in each case to a group in Table A.

Table 2965

Compounds of the formula I.B, in which $R^1$ is hydrogen, Z is sulfur and $R^3$ is cis-2-bromobut-2-enyl and $R^2$ for a compound corresponds in each case to a group in Table A.

Table 2966

Compounds of the formula I.A, in which $R^1$ is hydrogen, Z is NH and $R^3$ is cis-2-bromobut-2-enyl and $R^2$ for a compound corresponds in each case to a group in Table A.

Table 2967

Compounds of the formula I.B, in which $R^1$ is hydrogen, Z is NH and $R^3$ is cis-2-bromobut-2-enyl and $R^2$ for a compound corresponds in each case to a group in Table A.

Table 2968

Compounds of the formula I.A, in which $R^1$ is methyl, Z is oxygen and $R^3$ is cis-2-bromobut-2-enyl and $R^2$ for a compound corresponds in each case to a group in Table A.

Table 2969

Compounds of the formula I.B, in which $R^1$ is methyl, Z is oxygen and $R^3$ is cis-2-bromobut-2-enyl and $R^2$ for a compound corresponds in each case to a group in Table A.

Table 2970

Compounds of the formula I.A, in which $R^1$ is methyl, Z is sulfur and $R^3$ is cis-2-bromobut-2-enyl and $R^2$ for a compound corresponds in each case to a group in Table A.

Table 2971

Compounds of the formula I.B, in which $R^1$ is methyl, Z is sulfur and $R^3$ is cis-2-bromobut-2-enyl and $R^2$ for a compound corresponds in each case to a group in Table A.

Table 2972

Compounds of the formula I.A, in which $R^1$ is methyl, Z is NH and $R^3$ is cis-2-bromobut-2-enyl and $R^2$ for a compound corresponds in each case to a group in Table A.

Table 2973

Compounds of the formula I.B, in which $R^1$ is methyl, Z is NH and $R^3$ is cis-2-bromobut-2-enyl and $R^2$ for a compound corresponds in each case to a group in Table A.

Table 2974

Compounds of the formula I.A, in which $R^1$ is ethyl, Z is oxygen and $R^3$ is cis-2-bromobut-2-enyl and $R^2$ for a compound corresponds in each case to a group in Table A.

Table 2975

Compounds of the formula I.B, in which $R^1$ is ethyl, Z is oxygen and $R^3$ is cis-2-bromobut-2-enyl and $R^2$ for a compound corresponds in each case to a group in Table A.

Table 2976

Compounds of the formula I.A, in which $R^1$ is ethyl, Z is sulfur and $R^3$ is cis-2-bromobut-2-enyl and $R^2$ for a compound corresponds in each case to a group in Table A.

Table 2977

Compounds of the formula I.B, in which $R^1$ is ethyl, Z is sulfur and $R^3$ is cis-2-bromobut-2-enyl and $R^2$ for a compound corresponds in each case to a group in Table A.

Table 2978

Compounds of the formula I.A, in which $R^1$ is ethyl, Z is NH and $R^3$ is cis-2-bromobut-2-enyl and $R^2$ for a compound corresponds in each case to a group in Table A.

Table 2979

Compounds of the formula I.B, in which $R^1$ is ethyl, Z is NH and $R^3$ is cis-2-bromobut-2-enyl and $R^2$ for a compound corresponds in each case to a group in Table A.

Table 2980

Compounds of the formula I.A, in which $R^1$ is isopropyl, Z is oxygen and $R^3$ is cis-2-bromobut-2-enyl and $R^2$ for a compound corresponds in each case to a group in Table A.

Table 2981

Compounds of the formula I.B, in which $R^1$ is isopropyl, Z is oxygen and $R^3$ is cis-2-bromobut-2-enyl and $R^2$ for a compound corresponds in each case to a group in Table A.

Table 2982

Compounds of the formula I.A, in which $R^1$ is isopropyl, Z is sulfur and $R^3$ is cis-2-bromobut-2-enyl and $R^2$ for a compound corresponds in each case to a group in Table A.

Table 2983

Compounds of the formula I.B, in which $R^1$ is isopropyl, Z is sulfur and $R^3$ is cis-2-bromobut-2-enyl and $R^2$ for a compound corresponds in each case to a group in Table A.

Table 2984

Compounds of the formula I.A, in which $R^1$ is isopropyl, Z is NH and $R^3$ is cis-2-bromobut-2-enyl and $R^2$ for a compound corresponds in each case to a group in Table A.

Table 2985

Compounds of the formula I.B, in which $R^1$ is isopropyl, Z is NH and $R^3$ is cis-2-bromobut-2-enyl and $R^2$ for a compound corresponds in each case to a group in Table A.

Table 2986

Compounds of the formula I.A, in which $R^1$ is hydrogen, Z is oxygen and $R^3$ is cis-3-bromobut-2-enyl and $R^2$ for a compound corresponds in each case to a group in Table A.

Table 2987

Compounds of the formula I.B, in which $R^1$ is hydrogen, Z is oxygen and $R^3$ is cis-3-bromobut-2-enyl and $R^2$ for a compound corresponds in each case to a group in Table A.

Table 2988

Compounds of the formula I.A, in which $R^1$ is hydrogen, Z is sulfur and $R^3$ is cis-3-bromobut-2-enyl and $R^2$ for a compound corresponds in each case to a group in Table A.

Table 2989

Compounds of the formula I.B, in which $R^1$ is hydrogen, Z is sulfur and $R^3$ is cis-3-bromobut-2-enyl and $R^2$ for a compound corresponds in each case to a group in Table A.

Table 2990

Compounds of the formula I.A, in which $R^1$ is hydrogen, Z is NH and $R^3$ is cis-3-bromobut-2-enyl and $R^2$ for a compound corresponds in each case to a group in Table A.

Table 2991

Compounds of the formula I.B, in which $R^1$ is hydrogen, Z is NH and $R^3$ is cis-3-bromobut-2-enyl and $R^2$ for a compound corresponds in each case to a group in Table A.

Table 2992

Compounds of the formula I.A, in which $R^1$ is methyl, Z is oxygen and $R^3$ is cis-3-bromobut-2-enyl and $R^2$ for a compound corresponds in each case to a group in Table A.

Table 2993

Compounds of the formula I.B, in which $R^1$ is methyl, Z is oxygen and $R^3$ is cis-3-bromobut-2-enyl and $R^2$ for a compound corresponds in each case to a group in Table A.

Table 2994

Compounds of the formula I.A, in which $R^1$ is methyl, Z is sulfur and $R^3$ is cis-3-bromobut-2-enyl and $R^2$ for a compound corresponds in each case to a group in Table A.

Table 2995

Compounds of the formula I.B, in which $R^1$ is methyl, Z is sulfur and $R^3$ is cis-3-bromobut-2-enyl and $R^2$ for a compound corresponds in each case to a group in Table A.

Table 2996

Compounds of the formula I.A, in which $R^1$ is methyl, Z is NH and $R^3$ is cis-3-bromobut-2-enyl and $R^2$ for a compound corresponds in each case to a group in Table A.

Table 2997

Compounds of the formula I.B, in which $R^1$ is methyl, Z is NH and $R^3$ is cis-3-bromobut-2-enyl and $R^2$ for a compound corresponds in each case to a group in Table A.

Table 2998

Compounds of the formula I.A, in which $R^1$ is ethyl, Z is oxygen and $R^3$ is cis-3-bromobut-2-enyl and $R^2$ for a compound corresponds in each case to a group in Table A.

Table 2999

Compounds of the formula I.B, in which $R^1$ is ethyl, Z is oxygen and $R^3$ is cis-3-bromobut-2-enyl and $R^2$ for a compound corresponds in each case to a group in Table A.

Table 3000

Compounds of the formula I.A, in which $R^1$ is ethyl, Z is sulfur and $R^3$ is cis-3-bromobut-2-enyl and $R^2$ for a compound corresponds in each case to a group in Table A.

Table 3001

Compounds of the formula I.B, in which $R^1$ is ethyl, Z is sulfur and $R^3$ is cis-3-bromobut-2-enyl and $R^2$ for a compound corresponds in each case to a group in Table A.

Table 3002

Compounds of the formula I.A, in which $R^1$ is ethyl, Z is NH and $R^3$ is cis-3-bromobut-2-enyl and $R^2$ for a compound corresponds in each case to a group in Table A.

Table 3003

Compounds of the formula I.B, in which $R^1$ is ethyl, Z is NH and $R^3$ is cis-3-bromobut-2-enyl and $R^2$ for a compound corresponds in each case to a group in Table A.

Table 3004

Compounds of the formula I.A, in which $R^1$ is isopropyl, Z is oxygen and $R^3$ is cis-3-bromobut-2-enyl and $R^2$ for a compound corresponds in each case to a group in Table A.

Table 3005

Compounds of the formula I.B, in which $R^1$ is isopropyl, Z is oxygen and $R^3$ is cis-3-bromobut-2-enyl and $R^2$ for a compound corresponds in each case to a group in Table A.

Table 3006

Compounds of the formula I.A, in which $R^1$ is isopropyl, Z is sulfur and $R^3$ is cis-3-bromobut-2-enyl and $R^2$ for a compound corresponds in each case to a group in Table A.

Table 3007

Compounds of the formula I.B, in which $R^1$ is isopropyl, Z is sulfur and $R^3$ is cis-3-bromobut-2-enyl and $R^2$ for a compound corresponds in each case to a group in Table A.

Table 3008

Compounds of the formula I.A, in which $R^1$ is isopropyl, Z is NH and $R^3$ is cis-3-bromobut-2-enyl and $R^2$ for a compound corresponds in each case to a group in Table A.

Table 3009

Compounds of the formula I.B, in which $R^1$ is isopropyl, Z is NH and $R^3$ is cis-3-bromobut-2-enyl and $R^2$ for a compound corresponds in each case to a group in Table A.

Table 3010

Compounds of the formula I.A, in which $R^1$ is hydrogen, Z is oxygen and $R^3$ is trans-3-bromobut-2-enyl and $R^2$ for a compound corresponds in each case to a group in Table A.

Table 3011

Compounds of the formula I.B, in which $R^1$ is hydrogen, Z is oxygen and $R^3$ is trans-3-bromobut-2-enyl and $R^2$ for a compound corresponds in each case to a group in Table A.

Table 3012

Compounds of the formula I.A, in which $R^1$ is hydrogen, Z is sulfur and $R^3$ is trans-3-bromobut-2-enyl and $R^2$ for a compound corresponds in each case to a group in Table A.

Table 3013

Compounds of the formula I.B, in which $R^1$ is hydrogen, Z is sulfur and $R^3$ is trans-3-bromobut-2-enyl and $R^2$ for a compound corresponds in each case to a group in Table A.

Table 3014

Compounds of the formula I.A, in which $R^1$ is hydrogen, Z is NH and $R^3$ is trans-3-bromobut-2-enyl and $R^2$ for a compound corresponds in each case to a group in Table A.

Table 3015

Compounds of the formula I.B, in which $R^1$ is hydrogen, Z is NH and $R^3$ is trans-3-bromobut-2-enyl and $R^2$ for a compound corresponds in each case to a group in Table A.

Table 3016

Compounds of the formula I.A, in which $R^1$ is methyl, Z is oxygen and $R^3$ is trans-3-bromobut-2-enyl and $R^2$ for a compound corresponds in each case to a group in Table A.

Table 3017

Compounds of the formula I.B, in which $R^1$ is methyl, Z is oxygen and $R^3$ is trans-3-bromobut-2-enyl and $R^2$ for a compound corresponds in each case to a group in Table A.

Table 3018

Compounds of the formula I.A, in which $R^1$ is methyl, Z is sulfur and $R^3$ is trans-3-bromobut-2-enyl and $R^2$ for a compound corresponds in each case to a group in Table A.

Table 3019

Compounds of the formula I.B, in which $R^1$ is methyl, Z is sulfur and $R^3$ is trans-3-bromobut-2-enyl and $R^2$ for a compound corresponds in each case to a group in Table A.

Table 3020

Compounds of the formula I.A, in which $R^1$ is methyl, Z is NH and $R^3$ is trans-3-bromobut-2-enyl and $R^2$ for a compound corresponds in each case to a group in Table A.

Table 3021

Compounds of the formula I.B, in which $R^1$ is methyl, Z is NH and $R^3$ is trans-3-bromobut-2-enyl and $R^2$ for a compound corresponds in each case to a group in Table A.

Table 3022

Compounds of the formula I.A, in which $R^1$ is ethyl, Z is oxygen and $R^3$ is trans-3-bromobut-2-enyl and $R^2$ for a compound corresponds in each case to a group in Table A.

Table 3023

Compounds of the formula I.B, in which $R^1$ is ethyl, Z is oxygen and $R^3$ is trans-3-bromobut-2-enyl and $R^2$ for a compound corresponds in each case to a group in Table A.

Table 3024

Compounds of the formula I.A, in which $R^1$ is ethyl, Z is sulfur and $R^3$ is trans-3-bromobut-2-enyl and $R^2$ for a compound corresponds in each case to a group in Table A.

Table 3025

Compounds of the formula I.B, in which $R^1$ is ethyl, Z is sulfur and $R^3$ is trans-3-bromobut-2-enyl and $R^2$ for a compound corresponds in each case to a group in Table A.

Table 3026

Compounds of the formula I.A, in which $R^1$ is ethyl, Z is NH and $R^3$ is trans-3-bromobut-2-enyl and $R^2$ for a compound corresponds in each case to a group in Table A.

Table 3027

Compounds of the formula I.B, in which $R^1$ is ethyl, Z is NH and $R^3$ is trans-3-bromobut-2-enyl and $R^2$ for a compound corresponds in each case to a group in Table A.

Table 3028

Compounds of the formula I.A, in which $R^1$ is isopropyl, Z is oxygen and $R^3$ is trans-3-bromobut-2-enyl and $R^2$ for a compound corresponds in each case to a group in Table A.

Table 3029

Compounds of the formula I.B, in which $R^1$ is isopropyl, Z is oxygen and $R^3$ is trans-3-bromobut-2-enyl and $R^2$ for a compound corresponds in each case to a group in Table A.

Table 3030

Compounds of the formula I.A, in which $R^1$ is isopropyl, Z is sulfur and $R^3$ is trans-3-bromobut-2-enyl and $R^2$ for a compound corresponds in each case to a group in Table A.

Table 3031

Compounds of the formula I.B, in which $R^1$ is isopropyl, Z is sulfur and $R^3$ is trans-3-bromobut-2-enyl and $R^2$ for a compound corresponds in each case to a group in Table A.

Table 3032

Compounds of the formula I.A, in which $R^1$ is isopropyl, Z is NH and $R^3$ is trans-3-bromobut-2-enyl and $R^2$ for a compound corresponds in each case to a group in Table A.

Table 3033

Compounds of the formula I.B, in which $R^1$ is isopropyl, Z is NH and $R^3$ is trans-3-bromobut-2-enyl and $R^2$ for a compound corresponds in each case to a group in Table A.

Table 3034

Compounds of the formula I.A, in which $R^1$ is hydrogen, Z is oxygen and $R^3$ is prop-2-ynyl and $R^2$ for a compound corresponds in each case to a group in Table A.

Table 3035

Compounds of the formula I.B, in which $R^1$ is hydrogen, Z is oxygen and $R^3$ is prop-2-ynyl and $R^2$ for a compound corresponds in each case to a group in Table A.

Table 3036

Compounds of the formula I.A, in which $R^1$ is hydrogen, Z is sulfur and $R^3$ is prop-2-ynyl and $R^2$ for a compound corresponds in each case to a group in Table A.

Table 3037

Compounds of the formula I.B, in which $R^1$ is hydrogen, Z is sulfur and $R^3$ is prop-2-ynyl and $R^2$ for a compound corresponds in each case to a group in Table A.

Table 3038

Compounds of the formula I.A, in which $R^1$ is hydrogen, Z is NH and $R^3$ is prop-2-ynyl and $R^2$ for a compound corresponds in each case to a group in Table A.

Table 3039

Compounds of the formula I.B, in which $R^1$ is hydrogen, Z is NH and $R^3$ is prop-2-ynyl and $R^2$ for a compound corresponds in each case to a group in Table A.

Table 3040

Compounds of the formula I.A, in which $R^1$ is methyl, Z is oxygen and $R^3$ is prop-2-ynyl and $R^2$ for a compound corresponds in each case to a group in Table A.

Table 3041

Compounds of the formula I.B, in which $R^1$ is methyl, Z is oxygen and $R^3$ is prop-2-ynyl and $R^2$ for a compound corresponds in each case to a group in Table A.

Table 3042

Compounds of the formula I.A, in which $R^1$ is methyl, Z is sulfur and $R^3$ is prop-2-ynyl and $R^2$ for a compound corresponds in each case to a group in Table A.

Table 3043

Compounds of the formula I.B, in which $R^1$ is methyl, Z is sulfur and $R^3$ is prop-2-ynyl and $R^2$ for a compound corresponds in each case to a group in Table A.

Table 3044

Compounds of the formula I.A, in which $R^1$ is methyl, Z is NH and $R^3$ is prop-2-ynyl and $R^2$ for a compound corresponds in each case to a group in Table A.

Table 3045

Compounds of the formula I.B, in which $R^1$ is methyl, Z is NH and $R^3$ is prop-2-ynyl and $R^2$ for a compound corresponds in each case to a group in Table A.

Table 3046

Compounds of the formula I.A, in which $R^1$ is ethyl, Z is oxygen and $R^3$ is prop-2-ynyl and $R^2$ for a compound corresponds in each case to a group in Table A.

Table 3047

Compounds of the formula I.B, in which $R^1$ is ethyl, Z is oxygen and $R^3$ is prop-2-ynyl and $R^2$ for a compound corresponds in each case to a group in Table A.

Table 3048

Compounds of the formula I.A, in which $R^1$ is ethyl, Z is sulfur and $R^3$ is prop-2-ynyl and $R^2$ for a compound corresponds in each case to a group in Table A.

Table 3049

Compounds of the formula I.B, in which $R^1$ is ethyl, Z is sulfur and $R^3$ is prop-2-ynyl and $R^2$ for a compound corresponds in each case to a group in Table A.

Table 3050

Compounds of the formula I.A, in which $R^1$ is ethyl, Z is NH and $R^3$ is prop-2-ynyl and $R^2$ for a compound corresponds in each case to a group in Table A.

Table 3051

Compounds of the formula I.B, in which $R^1$ is ethyl, Z is NH and $R^3$ is prop-2-ynyl and $R^2$ for a compound corresponds in each case to a group in Table A.

Table 3052

Compounds of the formula I.A, in which $R^1$ is isopropyl, Z is oxygen and $R^3$ is prop-2-ynyl and $R^2$ for a compound corresponds in each case to a group in Table A.

Table 3053

Compounds of the formula I.B, in which $R^1$ is isopropyl, Z is oxygen and $R^3$ is prop-2-ynyl and $R^2$ for a compound corresponds in each case to a group in Table A.

Table 3054

Compounds of the formula I.A, in which $R^1$ is isopropyl, Z is sulfur and $R^3$ is prop-2-ynyl and $R^2$ for a compound corresponds in each case to a group in Table A.

Table 3055

Compounds of the formula I.B, in which $R^1$ is isopropyl, Z is sulfur and $R^3$ is prop-2-ynyl and $R^2$ for a compound corresponds in each case to a group in Table A.

Table 3056

Compounds of the formula I.A, in which $R^1$ is isopropyl, Z is NH and $R^3$ is prop-2-ynyl and $R^2$ for a compound corresponds in each case to a group in Table A.

Table 3057

Compounds of the formula I.B, in which $R^1$ is isopropyl, Z is NH and $R^3$ is prop-2-ynyl and $R^2$ for a compound corresponds in each case to a group in Table A.

Table 3058

Compounds of the formula I.A, in which $R^1$ is hydrogen, Z is oxygen and $R^3$ is 3-chloroprop-2-ynyl and $R^2$ for a compound corresponds in each case to a group in Table A.

Table 3059

Compounds of the formula I.B, in which $R^1$ is hydrogen, Z is oxygen and $R^3$ is 3-chloroprop-2-ynyl and $R^2$ for a compound corresponds in each case to a group in Table A.

Table 3060

Compounds of the formula I.A, in which $R^1$ is hydrogen, Z is sulfur and $R^3$ is 3-chloroprop-2-ynyl and $R^2$ for a compound corresponds in each case to a group in Table A.

Table 3061

Compounds of the formula I.B, in which $R^1$ is hydrogen, Z is sulfur and $R^3$ is 3-chloroprop-2-ynyl and $R^2$ for a compound corresponds in each case to a group in Table A.

Table 3062

Compounds of the formula I.A, in which $R^1$ is hydrogen, Z is NH and $R^3$ is 3-chloroprop-2-ynyl and $R^2$ for a compound corresponds in each case to a group in Table A.

Table 3063

Compounds of the formula I.B, in which $R^1$ is hydrogen, Z is NH and $R^3$ is 3-chloroprop-2-ynyl and $R^2$ for a compound corresponds in each case to a group in Table A.

Table 3064

Compounds of the formula I.A, in which $R^1$ is methyl, Z is oxygen and $R^3$ is 3-chloroprop-2-ynyl and $R^2$ for a compound corresponds in each case to a group in Table A.

Table 3065

Compounds of the formula I.B, in which $R^1$ is methyl, Z is oxygen and $R^3$ is 3-chloroprop-2-ynyl and $R^2$ for a compound corresponds in each case to a group in Table A.

Table 3066

Compounds of the formula I.A, in which $R^1$ is methyl, Z is sulfur and $R^3$ is 3-chloroprop-2-ynyl and $R^2$ for a compound corresponds in each case to a group in Table A.

Table 3067

Compounds of the formula I.B, in which $R^1$ is methyl, Z is sulfur and $R^3$ is 3-chloroprop-2-ynyl and $R^2$ for a compound corresponds in each case to a group in Table A.

Table 3068

Compounds of the formula I.A, in which $R^1$ is methyl, Z is NH and $R^3$ is 3-chloroprop-2-ynyl and $R^2$ for a compound corresponds in each case to a group in Table A.

Table 3069

Compounds of the formula I.B, in which $R^1$ is methyl, Z is NH and $R^3$ is 3-chloroprop-2-ynyl and $R^2$ for a compound corresponds in each case to a group in Table A.

Table 3070

Compounds of the formula I.A, in which $R^1$ is ethyl, Z is oxygen and $R^3$ is 3-chloroprop-2-ynyl and $R^2$ for a compound corresponds in each case to a group in Table A.

Table 3071

Compounds of the formula I.B, in which $R^1$ is ethyl, Z is oxygen and $R^3$ is 3-chloroprop-2-ynyl and $R^2$ for a compound corresponds in each case to a group in Table A.

Table 3072

Compounds of the formula I.A, in which $R^1$ is ethyl, Z is sulfur and $R^3$ is 3-chloroprop-2-ynyl and $R^2$ for a compound corresponds in each case to a group in Table A.

Table 3073

Compounds of the formula I.B, in which $R^1$ is ethyl, Z is sulfur and $R^3$ is 3-chloroprop-2-ynyl and $R^2$ for a compound corresponds in each case to a group in Table A.

Table 3074

Compounds of the formula I.A, in which $R^1$ is ethyl, Z is NH and $R^3$ is 3-chloroprop-2-ynyl and $R^2$ for a compound corresponds in each case to a group in Table A.

Table 3075

Compounds of the formula I.B, in which $R^1$ is ethyl, Z is NH and $R^3$ is 3-chloroprop-2-ynyl and $R^2$ for a compound corresponds in each case to a group in Table A.

Table 3076

Compounds of the formula I.A, in which $R^1$ is isopropyl, Z is oxygen and $R^3$ is 3-chloroprop-2-ynyl and $R^2$ for a compound corresponds in each case to a group in Table A.

Table 3077

Compounds of the formula I.B, in which $R^1$ is isopropyl, Z is oxygen and $R^3$ is 3-chloroprop-2-ynyl and $R^2$ for a compound corresponds in each case to a group in Table A.

Table 3078

Compounds of the formula I.A, in which $R^1$ is isopropyl, Z is sulfur and $R^3$ is 3-chloroprop-2-ynyl and $R^2$ for a compound corresponds in each case to a group in Table A.

Table 3079

Compounds of the formula I.B, in which $R^1$ is isopropyl, Z is sulfur and $R^3$ is 3-chloroprop-2-ynyl and $R^2$ for a compound corresponds in each case to a group in Table A.

Table 3080

Compounds of the formula I.A, in which $R^1$ is isopropyl, Z is NH and $R^3$ is 3-chloroprop-2-ynyl and $R^2$ for a compound corresponds in each case to a group in Table A.

Table 3081

Compounds of the formula I.B, in which $R^1$ is isopropyl, Z is NH and $R^3$ is 3-chloroprop-2-ynyl and $R^2$ for a compound corresponds in each case to a group in Table A.

Table 3082

Compounds of the formula I.A, in which $R^1$ is hydrogen, Z is oxygen and $R^3$ is 3-bromoprop-2-ynyl and $R^2$ for a compound corresponds in each case to a group in Table A.

Table 3083

Compounds of the formula I.B, in which $R^1$ is hydrogen, Z is oxygen and $R^3$ is 3-bromoprop-2-ynyl and $R^2$ for a compound corresponds in each case to a group in Table A.

Table 3084

Compounds of the formula I.A, in which $R^1$ is hydrogen, Z is sulfur and $R^3$ is 3-bromoprop-2-ynyl and $R^2$ for a compound corresponds in each case to a group in Table A.

Table 3085

Compounds of the formula I.B, in which $R^1$ is hydrogen, Z is sulfur and $R^3$ is 3-bromoprop-2-ynyl and $R^2$ for a compound corresponds in each case to a group in Table A.

Table 3086

Compounds of the formula I.A, in which $R^1$ is hydrogen, Z is NH and $R^3$ is 3-bromoprop-2-ynyl and $R^2$ for a compound corresponds in each case to a group in Table A.

Table 3087

Compounds of the formula I.B, in which $R^1$ is hydrogen, Z is NH and $R^3$ is 3-bromoprop-2-ynyl and $R^2$ for a compound corresponds in each case to a group in Table A.

Table 3088

Compounds of the formula I.A, in which $R^1$ is methyl, Z is oxygen and $R^3$ is 3-bromoprop-2-ynyl and $R^2$ for a compound corresponds in each case to a group in Table A.

Table 3089

Compounds of the formula I.B, in which $R^1$ is methyl, Z is oxygen and $R^3$ is 3-bromoprop-2-ynyl and $R^2$ for a compound corresponds in each case to a group in Table A.

Table 3090

Compounds of the formula I.A, in which $R^1$ is methyl, Z is sulfur and $R^3$ is 3-bromoprop-2-ynyl and $R^2$ for a compound corresponds in each case to a group in Table A.

Table 3091

Compounds of the formula I.B, in which $R^1$ is methyl, Z is sulfur and $R^3$ is 3-bromoprop-2-ynyl and $R^2$ for a compound corresponds in each case to a group in Table A.

Table 3092

Compounds of the formula I.A, in which $R^1$ is methyl, Z is NH and $R^3$ is 3-bromoprop-2-ynyl and $R^2$ for a compound corresponds in each case to a group in Table A.

Table 3093

Compounds of the formula I.B, in which $R^1$ is methyl, Z is NH and $R^3$ is 3-bromoprop-2-ynyl and $R^2$ for a compound corresponds in each case to a group in Table A.

Table 3094

Compounds of the formula I.A, in which $R^1$ is ethyl, Z is oxygen and $R^3$ is 3-bromoprop-2-ynyl and $R^2$ for a compound corresponds in each case to a group in Table A.

Table 3095

Compounds of the formula I.B, in which $R^1$ is ethyl, Z is oxygen and $R^3$ is 3-bromoprop-2-ynyl and $R^2$ for a compound corresponds in each case to a group in Table A.

Table 3096

Compounds of the formula I.A, in which $R^1$ is ethyl, Z is sulfur and $R^3$ is 3-bromoprop-2-ynyl and $R^2$ for a compound corresponds in each case to a group in Table A.

Table 3097

Compounds of the formula I.B, in which $R^1$ is ethyl, Z is sulfur and $R^3$ is 3-bromoprop-2-ynyl and $R^2$ for a compound corresponds in each case to a group in Table A.

Table 3098

Compounds of the formula I.A, in which $R^1$ is ethyl, Z is NH and $R^3$ is 3-bromoprop-2-ynyl and $R^2$ for a compound corresponds in each case to a group in Table A.

Table 3099

Compounds of the formula I.B, in which $R^1$ is ethyl, Z is NH and $R^3$ is 3-bromoprop-2-ynyl and $R^2$ for a compound corresponds in each case to a group in Table A.

Table 3100

Compounds of the formula I.A, in which $R^1$ is isopropyl, Z is oxygen and $R^3$ is 3-bromoprop-2-ynyl and $R^2$ for a compound corresponds in each case to a group in Table A.

Table 3101

Compounds of the formula I.B, in which $R^1$ is isopropyl, Z is oxygen and $R^3$ is 3-bromoprop-2-ynyl and $R^2$ for a compound corresponds in each case to a group in Table A.

Table 3102

Compounds of the formula I.A, in which $R^1$ is isopropyl, Z is sulfur and $R^3$ is 3-bromoprop-2-ynyl and $R^2$ for a compound corresponds in each case to a group in Table A.

Table 3103

Compounds of the formula I.B, in which $R^1$ is isopropyl, Z is sulfur and $R^3$ is 3-bromoprop-2-ynyl and $R^2$ for a compound corresponds in each case to a group in Table A.

Table 3104

Compounds of the formula I.A, in which $R^1$ is isopropyl, Z is NH and $R^3$ is 3-bromoprop-2-ynyl and $R^2$ for a compound corresponds in each case to a group in Table A.

Table 3105

Compounds of the formula I.B, in which $R^1$ is isopropyl, Z is NH and $R^3$ is 3-bromoprop-2-ynyl and $R^2$ for a compound corresponds in each case to a group in Table A.

Table 3106

Compounds of the formula I.A, in which $R^1$ is hydrogen, Z is oxygen and $R^3$ is 3-iodoprop-2-ynyl and $R^2$ for a compound corresponds in each case to a group in Table A.

Table 3107

Compounds of the formula I.B, in which $R^1$ is hydrogen, Z is oxygen and $R^3$ is 3-iodoprop-2-ynyl and $R^2$ for a compound corresponds in each case to a group in Table A.

Table 3108

Compounds of the formula I.A, in which $R^1$ is hydrogen, Z is sulfur and $R^3$ is 3-iodoprop-2-ynyl and $R^2$ for a compound corresponds in each case to a group in Table A.

Table 3109

Compounds of the formula I.B, in which $R^1$ is hydrogen, Z is sulfur and $R^3$ is 3-iodoprop-2-ynyl and $R^2$ for a compound corresponds in each case to a group in Table A.

Table 3110

Compounds of the formula I.A, in which $R^1$ is hydrogen, Z is NH and $R^3$ is 3-iodoprop-2-ynyl and $R^2$ for a compound corresponds in each case to a group in Table A.

Table 3111

Compounds of the formula I.B, in which $R^1$ is hydrogen, Z is NH and $R^3$ is 3-iodoprop-2-ynyl and $R^2$ for a compound corresponds in each case to a group in Table A.

Table 3112

Compounds of the formula I.A, in which $R^1$ is methyl, Z is oxygen and $R^3$ is 3-iodoprop-2-ynyl and $R^2$ for a compound corresponds in each case to a group in Table A.

Table 3113

Compounds of the formula I.B, in which $R^1$ is methyl, Z is oxygen and $R^3$ is 3-iodoprop-2-ynyl and $R^2$ for a compound corresponds in each case to a group in Table A.

Table 3114

Compounds of the formula I.A, in which $R^1$ is methyl, Z is sulfur and $R^3$ is 3-iodoprop-2-ynyl and $R^2$ for a compound corresponds in each case to a group in Table A.

Table 3115

Compounds of the formula I.B, in which $R^1$ is methyl, Z is sulfur and $R^3$ is 3-iodoprop-2-ynyl and $R^2$ for a compound corresponds in each case to a group in Table A.

Table 3116

Compounds of the formula I.A, in which $R^1$ is methyl, Z is NH and $R^3$ is 3-iodoprop-2-ynyl and $R^2$ for a compound corresponds in each case to a group in Table A.

Table 3117

Compounds of the formula I.B, in which $R^1$ is methyl, Z is NH and $R^3$ is 3-iodoprop-2-ynyl and $R^2$ for a compound corresponds in each case to a group in Table A.

Table 3118

Compounds of the formula I.A, in which $R^1$ is ethyl, Z is oxygen and $R^3$ is 3-iodoprop-2-ynyl and $R^2$ for a compound corresponds in each case to a group in Table A.

Table 3119

Compounds of the formula I.B, in which $R^1$ is ethyl, Z is oxygen and $R^3$ is 3-iodoprop-2-ynyl and $R^2$ for a compound corresponds in each case to a group in Table A.

Table 3120

Compounds of the formula I.A, in which $R^1$ is ethyl, Z is sulfur and $R^3$ is 3-iodoprop-2-ynyl and $R^2$ for a compound corresponds in each case to a group in Table A.

Table 3121

Compounds of the formula I.B, in which $R^1$ is ethyl, Z is sulfur and $R^3$ is 3-iodoprop-2-ynyl and $R^2$ for a compound corresponds in each case to a group in Table A.

Table 3122

Compounds of the formula I.A, in which $R^1$ is ethyl, Z is NH and $R^3$ is 3-iodoprop-2-ynyl and $R^2$ for a compound corresponds in each case to a group in Table A.

Table 3123

Compounds of the formula I.B, in which $R^1$ is ethyl, Z is NH and $R^3$ is 3-iodoprop-2-ynyl and $R^2$ for a compound corresponds in each case to a group in Table A.

Table 3124

Compounds of the formula I.A, in which $R^1$ is isopropyl, Z is oxygen and $R^3$ is 3-iodoprop-2-ynyl and $R^2$ for a compound corresponds in each case to a group in Table A.

Table 3125

Compounds of the formula I.B, in which $R^1$ is isopropyl, Z is oxygen and $R^3$ is 3-iodoprop-2-ynyl and $R^2$ for a compound corresponds in each case to a group in Table A.

Table 3126

Compounds of the formula I.A, in which $R^1$ is isopropyl, Z is sulfur and $R^3$ is 3-iodoprop-2-ynyl and $R^2$ for a compound corresponds in each case to a group in Table A.

Table 3127

Compounds of the formula I.B, in which $R^1$ is isopropyl, Z is sulfur and $R^3$ is 3-iodoprop-2-ynyl and $R^2$ for a compound corresponds in each case to a group in Table A.

Table 3128

Compounds of the formula I.A, in which $R^1$ is isopropyl, Z is NH and $R^3$ is 3-iodoprop-2-ynyl and $R^2$ for a compound corresponds in each case to a group in Table A.

Table 3129

Compounds of the formula I.B, in which $R^1$ is isopropyl, Z is NH and $R^3$ is 3-iodoprop-2-ynyl and $R^2$ for a compound corresponds in each case to a group in Table A.

Table 3130

Compounds of the formula I.A, in which $R^1$ is hydrogen, Z is oxygen and $R^3$ is but-2-ynyl and $R^2$ for a compound corresponds in each case to a group in Table A.

Table 3131

Compounds of the formula I.B, in which $R^1$ is hydrogen, Z is oxygen and $R^3$ is but-2-ynyl and $R^2$ for a compound corresponds in each case to a group in Table A.

Table 3132

Compounds of the formula I.A, in which $R^1$ is hydrogen, Z is sulfur and $R^3$ is but-2-ynyl and $R^2$ for a compound corresponds in each case to a group in Table A.

Table 3133

Compounds of the formula I.B, in which $R^1$ is hydrogen, Z is sulfur and $R^3$ is but-2-ynyl and $R^2$ for a compound corresponds in each case to a group in Table A.

Table 3134

Compounds of the formula I.A, in which $R^1$ is hydrogen, Z is NH and $R^3$ is but-2-ynyl and $R^2$ for a compound corresponds in each case to a group in Table A.

Table 3135

Compounds of the formula I.B, in which $R^1$ is hydrogen, Z is NH and $R^3$ is but-2-ynyl and $R^2$ for a compound corresponds in each case to a group in Table A.

Table 3136

Compounds of the formula I.A, in which $R^1$ is methyl, Z is oxygen and $R^3$ is but-2-ynyl and $R^2$ for a compound corresponds in each case to a group in Table A.

Table 3137

Compounds of the formula I.B, in which $R^1$ is methyl, Z is oxygen and $R^3$ is but-2-ynyl and $R^2$ for a compound corresponds in each case to a group in Table A.

Table 3138

Compounds of the formula I.A, in which $R^1$ is methyl, Z is sulfur and $R^3$ is but-2-ynyl and $R^2$ for a compound corresponds in each case to a group in Table A.

Table 3139

Compounds of the formula I.B, in which $R^1$ is methyl, Z is sulfur and $R^3$ is but-2-ynyl and $R^2$ for a compound corresponds in each case to a group in Table A.

Table 3140

Compounds of the formula I.A, in which $R^1$ is methyl, Z is NH and $R^3$ is but-2-ynyl and $R^2$ for a compound corresponds in each case to a group in Table A.

Table 3141

Compounds of the formula I.B, in which $R^1$ is methyl, Z is NH and $R^3$ is but-2-ynyl and $R^2$ for a compound corresponds in each case to a group in Table A.

Table 3142

Compounds of the formula I.A, in which $R^1$ is ethyl, Z is oxygen and $R^3$ is but-2-ynyl and $R^2$ for a compound corresponds in each case to a group in Table A.

Table 3143

Compounds of the formula I.B, in which $R^1$ is ethyl, Z is oxygen and $R^3$ is but-2-ynyl and $R^2$ for a compound corresponds in each case to a group in Table A.

Table 3144

Compounds of the formula I.A, in which $R^1$ is ethyl, Z is sulfur and $R^3$ is but-2-ynyl and $R^2$ for a compound corresponds in each case to a group in Table A.

Table 3145

Compounds of the formula I.B, in which $R^1$ is ethyl, Z is sulfur and $R^3$ is but-2-ynyl and $R^2$ for a compound corresponds in each case to a group in Table A.

Table 3146

Compounds of the formula I.A, in which $R^1$ is ethyl, Z is NH and $R^3$ is but-2-ynyl and $R^2$ for a compound corresponds in each case to a group in Table A.

Table 3147

Compounds of the formula I.B, in which $R^1$ is ethyl, Z is NH and $R^3$ is but-2-ynyl and $R^2$ for a compound corresponds in each case to a group in Table A.

Table 3148

Compounds of the formula I.A, in which $R^1$ is isopropyl, Z is oxygen and $R^3$ is but-2-ynyl and $R^2$ for a compound corresponds in each case to a group in Table A.

Table 3149

Compounds of the formula I.B, in which $R^1$ is isopropyl, Z is oxygen and $R^3$ is but-2-ynyl and $R^2$ for a compound corresponds in each case to a group in Table A.

Table 3150

Compounds of the formula I.A, in which $R^1$ is isopropyl, Z is sulfur and $R^3$ is but-2-ynyl and $R^2$ for a compound corresponds in each case to a group in Table A.

Table 3151

Compounds of the formula I.B, in which $R^1$ is isopropyl, Z is sulfur and $R^3$ is but-2-ynyl and $R^2$ for a compound corresponds in each case to a group in Table A.

Table 3152

Compounds of the formula I.A, in which $R^1$ is isopropyl, Z is NH and $R^3$ is but-2-ynyl and $R^2$ for a compound corresponds in each case to a group in Table A.

Table 3153

Compounds of the formula I.B, in which $R^1$ is isopropyl, Z is NH and $R^3$ is but-2-ynyl and $R^2$ for a compound corresponds in each case to a group in Table A.

Table 3154

Compounds of the formula I.A, in which $R^1$ is hydrogen, Z is oxygen and $R^3$ is but-3-ynyl and $R^2$ for a compound corresponds in each case to a group in Table A.

Table 3155

Compounds of the formula I.B, in which $R^1$ is hydrogen, Z is oxygen and $R^3$ is but-3-ynyl and $R^2$ for a compound corresponds in each case to a group in Table A.

Table 3156

Compounds of the formula I.A, in which $R^1$ is hydrogen, Z is sulfur and $R^3$ is but-3-ynyl and $R^2$ for a compound corresponds in each case to a group in Table A.

Table 3157

Compounds of the formula I.B, in which $R^1$ is hydrogen, Z is sulfur and $R^3$ is but-3-ynyl and $R^2$ for a compound corresponds in each case to a group in Table A.

Table 3158

Compounds of the formula I.A, in which $R^1$ is hydrogen, Z is NH and $R^3$ is but-3-ynyl and $R^2$ for a compound corresponds in each case to a group in Table A.

Table 3159

Compounds of the formula I.B, in which $R^1$ is hydrogen, Z is NH and $R^3$ is but-3-ynyl and $R^2$ for a compound corresponds in each case to a group in Table A.

Table 3160

Compounds of the formula I.A, in which $R^1$ is methyl, Z is oxygen and $R^3$ is but-3-ynyl and $R^2$ for a compound corresponds in each case to a group in Table A.

Table 3161

Compounds of the formula I.B, in which $R^1$ is methyl, Z is oxygen and $R^3$ is but-3-ynyl and $R^2$ for a compound corresponds in each case to a group in Table A.

Table 3162

Compounds of the formula I.A, in which $R^1$ is methyl, Z is sulfur and $R^3$ is but-3-ynyl and $R^2$ for a compound corresponds in each case to a group in Table A.

Table 3163

Compounds of the formula I.B, in which $R^1$ is methyl, Z is sulfur and $R^3$ is but-3-ynyl and $R^2$ for a compound corresponds in each case to a group in Table A.

Table 3164

Compounds of the formula I.A, in which $R^1$ is methyl, Z is NH and $R^3$ is but-3-ynyl and $R^2$ for a compound corresponds in each case to a group in Table A.

Table 3165

Compounds of the formula I.B, in which $R^1$ is methyl, Z is NH and $R^3$ is but-3-ynyl and $R^2$ for a compound corresponds in each case to a group in Table A.

Table 3166

Compounds of the formula I.A, in which $R^1$ is ethyl, Z is oxygen and $R^3$ is but-3-ynyl and $R^2$ for a compound corresponds in each case to a group in Table A.

Table 3167

Compounds of the formula I.B, in which $R^1$ is ethyl, Z is oxygen and $R^3$ is but-3-ynyl and $R^2$ for a compound corresponds in each case to a group in Table A.

Table 3168

Compounds of the formula I.A, in which $R^1$ is ethyl, Z is sulfur and $R^3$ is but-3-ynyl and $R^2$ for a compound corresponds in each case to a group in Table A.

Table 3169

Compounds of the formula I.B, in which $R^1$ is ethyl, Z is sulfur and $R^3$ is but-3-ynyl and $R^2$ for a compound corresponds in each case to a group in Table A.

Table 3170

Compounds of the formula I.A, in which $R^1$ is ethyl, Z is NH and $R^3$ is but-3-ynyl and $R^2$ for a compound corresponds in each case to a group in Table A.

Table 3171

Compounds of the formula I.B, in which $R^1$ is ethyl, Z is NH and $R^3$ is but-3-ynyl and $R^2$ for a compound corresponds in each case to a group in Table A.

Table 3172

Compounds of the formula I.A, in which $R^1$ is isopropyl, Z is oxygen and $R^3$ is but-3-ynyl and $R^2$ for a compound corresponds in each case to a group in Table A.

Table 3173

Compounds of the formula I.B, in which $R^1$ is isopropyl, Z is oxygen and $R^3$ is but-3-ynyl and $R^2$ for a compound corresponds in each case to a group in Table A.

Table 3174

Compounds of the formula I.A, in which $R^1$ is isopropyl, Z is sulfur and $R^3$ is but-3-ynyl and $R^2$ for a compound corresponds in each case to a group in Table A.

Table 3175

Compounds of the formula I.B, in which $R^1$ is isopropyl, Z is sulfur and $R^3$ is but-3-ynyl and $R^2$ for a compound corresponds in each case to a group in Table A.

Table 3176

Compounds of the formula I.A, in which $R^1$ is isopropyl, Z is NH and $R^3$ is but-3-ynyl and $R^2$ for a compound corresponds in each case to a group in Table A.

Table 3177

Compounds of the formula I.B, in which $R^1$ is isopropyl, Z is NH and $R^3$ is but-3-ynyl and $R^2$ for a compound corresponds in each case to a group in Table A.

Table 3178

Compounds of the formula I.A, in which $R^1$ is hydrogen, Z is oxygen and $R^3$ is but-3-yn-2-yl and $R^2$ for a compound corresponds in each case to a group in Table A.

Table 3179

Compounds of the formula I.B, in which $R^1$ is hydrogen, Z is oxygen and $R^3$ is but-3-yn-2-yl and $R^2$ for a compound corresponds in each case to a group in Table A.

Table 3180

Compounds of the formula I.A, in which $R^1$ is hydrogen, Z is sulfur and $R^3$ is but-3-yn-2-yl and $R^2$ for a compound corresponds in each case to a group in Table A.

Table 3181

Compounds of the formula I.B, in which $R^1$ is hydrogen, Z is sulfur and $R^3$ is but-3-yn-2-yl and $R^2$ for a compound corresponds in each case to a group in Table A.

Table 3182

Compounds of the formula I.A, in which $R^1$ is hydrogen, Z is NH and $R^3$ is but-3-yn-2-yl and $R^2$ for a compound corresponds in each case to a group in Table A.

Table 3183

Compounds of the formula I.B, in which $R^1$ is hydrogen, Z is NH and $R^3$ is but-3-yn-2-yl and $R^2$ for a compound corresponds in each case to a group in Table A.

Table 3184

Compounds of the formula I.A, in which $R^1$ is methyl, Z is oxygen and $R^3$ is but-3-yn-2-yl and $R^2$ for a compound corresponds in each case to a group in Table A.

Table 3185

Compounds of the formula I.B, in which $R^1$ is methyl, Z is oxygen and $R^3$ is but-3-yn-2-yl and $R^2$ for a compound corresponds in each case to a group in Table A.

Table 3186

Compounds of the formula I.A, in which $R^1$ is methyl, Z is sulfur and $R^3$ is but-3-yn-2-yl and $R^2$ for a compound corresponds in each case to a group in Table A.

Table 3187

Compounds of the formula I.B, in which $R^1$ is methyl, Z is sulfur and $R^3$ is but-3-yn-2-yl and $R^2$ for a compound corresponds in each case to a group in Table A.

Table 3188

Compounds of the formula I.A, in which $R^1$ is methyl, Z is NH and $R^3$ is but-3-yn-2-yl and $R^2$ for a compound corresponds in each case to a group in Table A.

Table 3189

Compounds of the formula I.B, in which $R^1$ is methyl, Z is NH and $R^3$ is but-3-yn-2-yl and $R^2$ for a compound corresponds in each case to a group in Table A.

Table 3190

Compounds of the formula I.A, in which $R^1$ is ethyl, Z is oxygen and $R^3$ is but-3-yn-2-yl and $R^2$ for a compound corresponds in each case to a group in Table A.

Table 3191

Compounds of the formula I.B, in which $R^1$ is ethyl, Z is oxygen and $R^3$ is but-3-yn-2-yl and $R^2$ for a compound corresponds in each case to a group in Table A.

Table 3192

Compounds of the formula I.A, in which $R^1$ is ethyl, Z is sulfur and $R^3$ is but-3-yn-2-yl and $R^2$ for a compound corresponds in each case to a group in Table A.

Table 3193

Compounds of the formula I.B, in which $R^1$ is ethyl, Z is sulfur and $R^3$ is but-3-yn-2-yl and $R^2$ for a compound corresponds in each case to a group in Table A.

Table 3194

Compounds of the formula I.A, in which $R^1$ is ethyl, Z is NH and $R^3$ is but-3-yn-2-yl and $R^2$ for a compound corresponds in each case to a group in Table A.

Table 3195

Compounds of the formula I.B, in which $R^1$ is ethyl, Z is NH and $R^3$ is but-3-yn-2-yl and $R^2$ for a compound corresponds in each case to a group in Table A.

Table 3196

Compounds of the formula I.A, in which $R^1$ is isopropyl, Z is oxygen and $R^3$ is but-3-yn-2-yl and $R^2$ for a compound corresponds in each case to a group in Table A.

Table 3197

Compounds of the formula I.B, in which $R^1$ is isopropyl, Z is oxygen and $R^3$ is but-3-yn-2-yl and $R^2$ for a compound corresponds in each case to a group in Table A.

Table 3198

Compounds of the formula I.A, in which $R^1$ is isopropyl, Z is sulfur and $R^3$ is but-3-yn-2-yl and $R^2$ for a compound corresponds in each case to a group in Table A.

Table 3199

Compounds of the formula I.B, in which $R^1$ is isopropyl, Z is sulfur and $R^3$ is but-3-yn-2-yl and $R^2$ for a compound corresponds in each case to a group in Table A.

Table 3200

Compounds of the formula I.A, in which $R^1$ is isopropyl, Z is NH and $R^3$ is but-3-yn-2-yl and $R^2$ for a compound corresponds in each case to a group in Table A.

Table 3201

Compounds of the formula I.B, in which $R^1$ is isopropyl, Z is NH and $R^3$ is but-3-yn-2-yl and $R^2$ for a compound corresponds in each case to a group in Table A.

Table 3202

Compounds of the formula I.A, in which $R^1$ is hydrogen, Z is oxygen and $R^3$ is pent-4-ynyl and $R^2$ for a compound corresponds in each case to a group in Table A.

Table 3203

Compounds of the formula I.B, in which $R^1$ is hydrogen, Z is oxygen and $R^3$ is pent-4-ynyl and $R^2$ for a compound corresponds in each case to a group in Table A.

Table 3204

Compounds of the formula I.A, in which $R^1$ is hydrogen, Z is sulfur and $R^3$ is pent-4-ynyl and $R^2$ for a compound corresponds in each case to a group in Table A.

Table 3205

Compounds of the formula I.B, in which $R^1$ is hydrogen, Z is sulfur and $R^3$ is pent-4-ynyl and $R^2$ for a compound corresponds in each case to a group in Table A.

Table 3206

Compounds of the formula I.A, in which $R^1$ is hydrogen, Z is NH and $R^3$ is pent-4-ynyl and $R^2$ for a compound corresponds in each case to a group in Table A.

Table 3207

Compounds of the formula I.B, in which $R^1$ is hydrogen, Z is NH and $R^3$ is pent-4-ynyl and $R^2$ for a compound corresponds in each case to a group in Table A.

Table 3208

Compounds of the formula I.A, in which $R^1$ is methyl, Z is oxygen and $R^3$ is pent-4-ynyl and $R^2$ for a compound corresponds in each case to a group in Table A.

Table 3209

Compounds of the formula I.B, in which $R^1$ is methyl, Z is oxygen and $R^3$ is pent-4-ynyl and $R^2$ for a compound corresponds in each case to a group in Table A.

Table 3210

Compounds of the formula I.A, in which $R^1$ is methyl, Z is sulfur and $R^3$ is pent-4-ynyl and $R^2$ for a compound corresponds in each case to a group in Table A.

Table 3211

Compounds of the formula I.B, in which $R^1$ is methyl, Z is sulfur and $R^3$ is pent-4-ynyl and $R^2$ for a compound corresponds in each case to a group in Table A.

Table 3212

Compounds of the formula I.A, in which $R^1$ is methyl, Z is NH and $R^3$ is pent-4-ynyl and $R^2$ for a compound corresponds in each case to a group in Table A.

Table 3213

Compounds of the formula I.B, in which $R^1$ is methyl, Z is NH and $R^3$ is pent-4-ynyl and $R^2$ for a compound corresponds in each case to a group in Table A.

Table 3214

Compounds of the formula I.A, in which $R^1$ is ethyl, Z is oxygen and $R^3$ is pent-4-ynyl and $R^2$ for a compound corresponds in each case to a group in Table A.

Table 3215

Compounds of the formula I.B, in which $R^1$ is ethyl, Z is oxygen and $R^3$ is pent-4-ynyl and $R^2$ for a compound corresponds in each case to a group in Table A.

Table 3216

Compounds of the formula I.A, in which $R^1$ is ethyl, Z is sulfur and $R^3$ is pent-4-ynyl and $R^2$ for a compound corresponds in each case to a group in Table A.

Table 3217

Compounds of the formula I.B, in which $R^1$ is ethyl, Z is sulfur and $R^3$ is pent-4-ynyl and $R^2$ for a compound corresponds in each case to a group in Table A.

Table 3218

Compounds of the formula I.A, in which $R^1$ is ethyl, Z is NH and $R^3$ is pent-4-ynyl and $R^2$ for a compound corresponds in each case to a group in Table A.

Table 3219

Compounds of the formula I.B, in which $R^1$ is ethyl, Z is NH and $R^3$ is pent-4-ynyl and $R^2$ for a compound corresponds in each case to a group in Table A.

Table 3220

Compounds of the formula I.A, in which $R^1$ is isopropyl, Z is oxygen and $R^3$ is pent-4-ynyl and $R^2$ for a compound corresponds in each case to a group in Table A.

Table 3221

Compounds of the formula I.B, in which $R^1$ is isopropyl, Z is oxygen and $R^3$ is pent-4-ynyl and $R^2$ for a compound corresponds in each case to a group in Table A.

Table 3222

Compounds of the formula I.A, in which $R^1$ is isopropyl, Z is sulfur and $R^3$ is pent-4-ynyl and $R^2$ for a compound corresponds in each case to a group in Table A.

Table 3223

Compounds of the formula I.B, in which $R^1$ is isopropyl, Z is sulfur and $R^3$ is pent-4-ynyl and $R^2$ for a compound corresponds in each case to a group in Table A.

Table 3224

Compounds of the formula I.A, in which $R^1$ is isopropyl, Z is NH and $R^3$ is pent-4-ynyl and $R^2$ for a compound corresponds in each case to a group in Table A.

Table 3225

Compounds of the formula I.B, in which $R^1$ is isopropyl, Z is NH and $R^3$ is pent-4-ynyl and $R^2$ for a compound corresponds in each case to a group in Table A.

Table 3226

Compounds of the formula I.A, in which $R^1$ is hydrogen, Z is oxygen and $R^3$ is pent-3-ynyl and $R^2$ for a compound corresponds in each case to a group in Table A.

Table 3227

Compounds of the formula I.B, in which $R^1$ is hydrogen, Z is oxygen and $R^3$ is pent-3-ynyl and $R^2$ for a compound corresponds in each case to a group in Table A.

Table 3228

Compounds of the formula I.A, in which $R^1$ is hydrogen, Z is sulfur and $R^3$ is pent-3-ynyl and $R^2$ for a compound corresponds in each case to a group in Table A.

Table 3229

Compounds of the formula I.B, in which $R^1$ is hydrogen, Z is sulfur and $R^3$ is pent-3-ynyl and $R^2$ for a compound corresponds in each case to a group in Table A.

Table 3230

Compounds of the formula I.A, in which $R^1$ is hydrogen, Z is NH and $R^3$ is pent-3-ynyl and $R^2$ for a compound corresponds in each case to a group in Table A.

Table 3231

Compounds of the formula I.B, in which $R^1$ is hydrogen, Z is NH and $R^3$ is pent-3-ynyl and $R^2$ for a compound corresponds in each case to a group in Table A.

Table 3232

Compounds of the formula I.A, in which $R^1$ is methyl, Z is oxygen and $R^3$ is pent-3-ynyl and $R^2$ for a compound corresponds in each case to a group in Table A.

Table 3233

Compounds of the formula I.B, in which $R^1$ is methyl, Z is oxygen and $R^3$ is pent-3-ynyl and $R^2$ for a compound corresponds in each case to a group in Table A.

Table 3234

Compounds of the formula I.A, in which $R^1$ is methyl, Z is sulfur and $R^3$ is pent-3-ynyl and $R^2$ for a compound corresponds in each case to a group in Table A.

Table 3235

Compounds of the formula I.B, in which $R^1$ is methyl, Z is sulfur and $R^3$ is pent-3-ynyl and $R^2$ for a compound corresponds in each case to a group in Table A.

Table 3236

Compounds of the formula I.A, in which $R^1$ is methyl, Z is NH and $R^3$ is pent-3-ynyl and $R^2$ for a compound corresponds in each case to a group in Table A.

Table 3237

Compounds of the formula I.B, in which $R^1$ is methyl, Z is NH and $R^3$ is pent-3-ynyl and $R^2$ for a compound corresponds in each case to a group in Table A.

Table 3238

Compounds of the formula I.A, in which $R^1$ is ethyl, Z is oxygen and $R^3$ is pent-3-ynyl and $R^2$ for a compound corresponds in each case to a group in Table A.

Table 3239

Compounds of the formula I.B, in which $R^1$ is ethyl, Z is oxygen and $R^3$ is pent-3-ynyl and $R^2$ for a compound corresponds in each case to a group in Table A.

Table 3240

Compounds of the formula I.A, in which $R^1$ is ethyl, Z is sulfur and $R^3$ is pent-3-ynyl and $R^2$ for a compound corresponds in each case to a group in Table A.

Table 3241

Compounds of the formula I.B, in which $R^1$ is ethyl, Z is sulfur and $R^3$ is pent-3-ynyl and $R^2$ for a compound corresponds in each case to a group in Table A.

Table 3242

Compounds of the formula I.A, in which $R^1$ is ethyl, Z is NH and $R^3$ is pent-3-ynyl and $R^2$ for a compound corresponds in each case to a group in Table A.

Table 3243

Compounds of the formula I.B, in which $R^1$ is ethyl, Z is NH and $R^3$ is pent-3-ynyl and $R^2$ for a compound corresponds in each case to a group in Table A.

Table 3244

Compounds of the formula I.A, in which $R^1$ is isopropyl, Z is oxygen and $R^3$ is pent-3-ynyl and $R^2$ for a compound corresponds in each case to a group in Table A.

Table 3245

Compounds of the formula I.B, in which $R^1$ is isopropyl, Z is oxygen and $R^3$ is pent-3-ynyl and $R^2$ for a compound corresponds in each case to a group in Table A.

Table 3246

Compounds of the formula I.A, in which $R^1$ is isopropyl, Z is sulfur and $R^3$ is pent-3-ynyl and $R^2$ for a compound corresponds in each case to a group in Table A.

Table 3247

Compounds of the formula I.B, in which $R^1$ is isopropyl, Z is sulfur and $R^3$ is pent-3-ynyl and $R^2$ for a compound corresponds in each case to a group in Table A.

Table 3248

Compounds of the formula I.A, in which $R^1$ is isopropyl, Z is NH and $R^3$ is pent-3-ynyl and $R^2$ for a compound corresponds in each case to a group in Table A.

Table 3249

Compounds of the formula I.B, in which $R^1$ is isopropyl, Z is NH and $R^3$ is pent-3-ynyl and $R^2$ for a compound corresponds in each case to a group in Table A.

Table 3250

Compounds of the formula I.A, in which $R^1$ is hydrogen, Z is oxygen and $R^3$ is pent-3-yn-2-yl and $R^2$ for a compound corresponds in each case to a group in Table A.

Table 3251

Compounds of the formula I.B, in which $R^1$ is hydrogen, Z is oxygen and $R^3$ is pent-3-yn-2-yl and $R^2$ for a compound corresponds in each case to a group in Table A.

Table 3252

Compounds of the formula I.A, in which $R^1$ is hydrogen, Z is sulfur and $R^3$ is pent-3-yn-2-yl and $R^2$ for a compound corresponds in each case to a group in Table A.

Table 3253

Compounds of the formula I.B, in which $R^1$ is hydrogen, Z is sulfur and $R^3$ is pent-3-yn-2-yl and $R^2$ for a compound corresponds in each case to a group in Table A.

Table 3254

Compounds of the formula I.A, in which $R^1$ is hydrogen, Z is NH and $R^3$ is pent-3-yn-2-yl and $R^2$ for a compound corresponds in each case to a group in Table A.

Table 3255

Compounds the formula I.B, in which $R^1$ is hydrogen, Z is NH and $R^3$ is pent-3-yn-2-yl and $R^2$ for a compound case to a group in Table A.

Table 3256

Compounds of the formula I.A, in which $R^1$ is methyl, Z is oxygen and $R^3$ is pent-3-yn-2-yl and $R^2$ for a compound corresponds in each case to a group in Table A.

Table 3257

Compounds of the formula I.B, in which $R^1$ is methyl, Z is oxygen and $R^3$ is pent-3-yn-2-yl and $R^2$ for a compound corresponds in each case to a group in Table A.

Table 3258

Compounds of the formula I.A, in which $R^1$ is methyl, Z is sulfur and $R^3$ is pent-3-yn-2-yl and $R^2$ for a compound corresponds in each case to a group in Table A.

Table 3259

Compounds of the formula I.B, in which $R^1$ is methyl, Z is sulfur and $R^3$ is pent-3-yn-2-yl and $R^2$ for a compound corresponds in each case to a group in Table A.

Table 3260

Compounds of the formula I.A, in which $R^1$ is methyl, Z is NH and $R^3$ is pent-3-yn-2-yl and $R^2$ for a compound corresponds in each case to a group in Table A.

Table 3261

Compounds of the formula I.B, in which $R^1$ is methyl, Z is NH and $R^3$ is pent-3-yn-2-yl and $R^2$ for a compound corresponds in each case to a group in Table A.

Table 3262

Compounds of the formula I.A, in which $R^1$ is ethyl, Z is oxygen and $R^3$ is pent-3-yn-2-yl and $R^2$ for a compound corresponds in each case to a group in Table A.

Table 3263

Compounds of the formula I.B, in which $R^1$ is ethyl, Z is oxygen and $R^3$ is pent-3-yn-2-yl and $R^2$ for a compound corresponds in each case to a group in Table A.

Table 3264
Compounds of the formula I.A, in which $R^1$ is ethyl, Z is sulfur and $R^3$ is pent-3-yn-2-yl and $R^2$ for a compound corresponds in each case to a group in Table A.

Table 3265
Compounds of the formula I.B, in which $R^1$ is ethyl, Z is sulfur and $R^3$ is pent-3-yn-2-yl and $R^2$ for a compound corresponds in each case to a group in Table A.

Table 3266
Compounds of the formula I.A, in which $R^1$ is ethyl, Z is NH and $R^3$ is pent-3-yn-2-yl and $R^2$ for a compound corresponds in each case to a group in Table A.

Table 3267
Compounds of the formula I.B, in which $R^1$ is ethyl, Z is NH and $R^3$ is pent-3-yn-2-yl and $R^2$ for a compound corresponds in each case to a group in Table A.

Table 3268
Compounds of the formula I.A, in which $R^1$ is isopropyl, Z is oxygen and $R^3$ is pent-3-yn-2-yl and $R^2$ for a compound corresponds in each case to a group in Table A.

Table 3269
Compounds of the formula I.B, in which $R^1$ is isopropyl, Z is oxygen and $R^3$ is pent-3-yn-2-yl and $R^2$ for a compound corresponds in each case to a group in Table A.

Table 3270
Compounds of the formula I.A, in which $R^1$ is isopropyl, Z is sulfur and $R^3$ is pent-3-yn-2-yl and $R^2$ for a compound corresponds in each case to a group in Table A.

Table 3271
Compounds of the formula I.B, in which $R^1$ is isopropyl, Z is sulfur and $R^3$ is pent-3-yn-2-yl and $R^2$ for a compound corresponds in each case to a group in Table A.

Table 3272
Compounds of the formula I.A, in which $R^1$ is isopropyl, Z is NH and $R^3$ is pent-3-yn-2-yl and $R^2$ for a compound corresponds in each case to a group in Table A.

Table 3273
Compounds of the formula I.B, in which $R^1$ is isopropyl, Z is NH and $R^3$ is pent-3-yn-2-yl and $R^2$ for a compound corresponds in each case to a group in Table A.

Table 3274
Compounds of the formula I.A, in which $R^1$ is trifluoromethyl, Z is oxygen and $R^3$ is methyl and $R^2$ for a compound corresponds in each case to a group in Table A.

Table 3275
Compounds of the formula I.B, in which $R^1$ is trifluoromethyl, Z is oxygen and $R^3$ is methyl and $R^2$ for a compound corresponds in each case to a group in Table A.

Table 3276
Compounds of the formula I.A, in which $R^1$ is trifluoromethyl, Z is sulfur and $R^3$ is methyl and $R^2$ for a compound corresponds in each case to a group in Table A.

Table 3277
Compounds of the formula I.B, in which $R^1$ is trifluoromethyl, Z is sulfur and $R^3$ is methyl and $R^2$ for a compound corresponds in each case to a group in Table A.

Table 3278
Compounds of the formula I.A, in which $R^1$ is trifluoromethyl, Z is NH and $R^3$ is methyl and $R^2$ for a compound corresponds in each case to a group in Table A.

Table 3279
Compounds of the formula I.B, in which $R^1$ is trifluoromethyl, Z is NH and $R^3$ is methyl and $R^2$ for a compound corresponds in each case to a group in Table A.

Table 3280
Compounds of the formula I.A, in which $R^1$ is trifluoromethyl, Z is $NCH_3$ and $R^3$ is methyl and $R^2$ for a compound corresponds in each case to a group in Table A.

Table 3281
Compounds of the formula I.B, in which $R^1$ is trifluoromethyl, Z is $NCH_3$ and $R^3$ is methyl and $R^2$ for a compound corresponds in each case to a group in Table A.

Table 3282
Compounds of the formula I.A, in which $R^1$ is trifluoromethyl, Z is oxygen and $R^3$ is prop-2-ynyl and $R^2$ for a compound corresponds in each case to a group in Table A.

Table 3283
Compounds of the formula I.B, in which $R^1$ is trifluoromethyl, Z is oxygen and $R^3$ is prop-2-ynyl and $R^2$ for a compound corresponds in each case to a group in Table A.

Table 3284
Compounds of the formula I.A, in which $R^1$ is trifluoromethyl, Z is sulfur and $R^3$ is prop-2-ynyl and $R^2$ for a compound corresponds in each case to a group in Table A.

Table 3285
Compounds of the formula I.B, in which $R^1$ is trifluoromethyl, Z is sulfur and $R^3$ is prop-2-ynyl and $R^2$ for a compound corresponds in each case to a group in Table A.

Table 3286
Compounds of the formula I.A, in which $R^1$ is trifluoromethyl, Z is NH and $R^3$ is prop-2-ynyl and $R^2$ for a compound corresponds in each case to a group in Table A.

Table 3287
Compounds of the formula I.B, in which $R^1$ is trifluoromethyl, Z is NH and $R^3$ is prop-2-ynyl and $R^2$ for a compound corresponds in each case to a group in Table A.

Table 3288
Compounds of the formula I.A, in which $R^1$ is trifluoromethyl, Z is $NCH_3$ and $R^3$ is prop-2-ynyl and $R^2$ for a compound corresponds in each case to a group in Table A.

Table 3289

Compounds of the formula I.B, in which $R^1$ is trifluoromethyl, Z is $NCH_3$ and $R^3$ is prop-2-ynyl and $R^2$ for a compound corresponds in each case to a group in Table A.

Table 3290

Compounds of the formula I.A, in which $R^1$ is methyl, Z is $NCH_3$ and $R^3$ is methyl and $R^2$ for a compound corresponds in each case to a group in Table A.

Table 3291

Compounds of the formula I.B, in which $R^1$ is methyl, Z is $NCH_3$ and $R^3$ is methyl and $R^2$ for a compound corresponds in each case to a group in Table A.

Table 3292

Compounds of the formula I.A, in which $R^1$ is methyl, Z is $NCH_3$ and $R^3$ is ethyl and $R^2$ for a compound corresponds in each case to a group in Table A.

Table 3293

Compounds of the formula I.B, in which $R^1$ is methyl, Z is $NCH_3$ and $R^3$ is ethyl and $R^2$ for a compound corresponds in each case to a group in Table A.

Table 3294

Compounds of the formula I.A, in which $R^1$ is methyl, Z is $NCH_3$ and $R^3$ is prop-2-enyl and $R^2$ for a compound corresponds in each case to a group in Table A.

Table 3295

Compounds of the formula I.B, in which $R^1$ is methyl, Z is $NCH_3$ and $R^3$ is prop-2-enyl and $R^2$ for a compound corresponds in each case to a group in Table A.

Table 3296

Compounds of the formula I.A, in which $R^1$ is methyl, Z is $NCH_3$ and $R^3$ is prop-2-ynyl and $R^2$ for a compound corresponds in each case to a group in Table A.

Table 3297

Compounds of the formula I.B, in which $R^1$ is methyl, Z is $NCH_3$ and $R^3$ is prop-2-ynyl and $R^2$ for a compound corresponds in each case to a group in Table A.

Table 3298

Compounds of the formula I.A, in which $R^1$ is methyl, $R^3$ is methyl and $ZR^2$ for a compound corresponds in each case to a group in Table B.

Table 3299

Compounds of the formula I.B, in which $R^1$ is methyl, $R^3$ is methyl and $ZR^2$ for a compound corresponds in each case to a group in Table B.

Table 3300

Compounds of the formula I.A, in which $R^1$ is methyl, $R^3$ is ethyl and $ZR^2$ for a compound corresponds in each case to a group in Table B.

Table 3301

Compounds of the formula I.B, in which $R^1$ is methyl, $R^3$ is ethyl and $ZR^2$ for a compound corresponds in each case to a group in Table B.

Table 3302

Compounds of the formula I.A, in which $R^1$ is methyl, $R^3$ is prop-2-enyl and $ZR^2$ for a compound corresponds in each case to a group in Table B.

Table 3303

Compounds of the formula I.B, in which $R^1$ is methyl, $R^3$ is prop-2-enyl and $ZR^2$ for a compound corresponds in each case to a group in Table B.

Table 3304

Compounds of the formula I.A, in which $R^1$ is methyl, $R^3$ is prop-2-ynyl and $ZR^2$ for a compound corresponds in each case to a group in Table B.

Table 3305

Compounds of the formula I.B, in which $R^1$ is methyl, $R^3$ is prop-2-ynyl and $ZR^2$ for a compound corresponds in each case to a group in Table B.

TABLE A

| No. | $R^2$ |
|---|---|
| 1 | $CH_2CH_3$ |
| 2 | $CH_2CH_2CH_3$ |
| 3 | $CH(CH_3)_2$ |
| 4 | cyclopropyl |
| 5 | $(CH_2)_3CH_3$ |
| 6 | $CH(CH_3)CH_2CH_3$ |
| 7 | $CH_2CH(CH_3)_2$ |
| 8 | $C(CH_3)_3$ |
| 9 | cyclobutyl |
| 10 | $(CH_2)_4CH_3$ |
| 11 | $CH(CH_3)(CH_2)_2CH_3$ |
| 12 | $CH_2CH(CH_3)CH_2CH_3$ |
| 13 | $(CH_2)_2CH(CH_3)_2$ |
| 14 | $CH_2C(CH_3)_3$ |
| 15 | $CH(CH_2CH_3)_2$ |
| 16 | $C(CH_3)_2CH_2CH_3$ |
| 17 | $CH(CH_3)CH(CH_3)_2$ |
| 18 | cyclopentyl |
| 19 | $(CH_2)_5CH_3$ |
| 20 | $CH(CH_3)(CH_2)_3CH_3$ |
| 21 | $CH(CH_2CH_3)(CH_2)_2CH_3$ |
| 22 | $CH_2CH(CH_3)(CH_2)_2CH_3$ |
| 23 | $(CH_2)_2CH(CH_3)CH_2CH_3$ |
| 24 | $(CH_2)_3CH(CH_3)_2$ |
| 25 | $(CH_2)_2C(CH_3)_3$ |
| 26 | $CH_2CH(CH_2CH_3)_2$ |
| 27 | $CH(CH_3)CH(CH_3)CH_2CH_3$ |
| 28 | $CH(CH_3)CH_2CH(CH_3)_2$ |
| 29 | $CH_2CH(CH_3)CH(CH_3)_2$ |
| 30 | $CH(CH_3)C(CH_3)_3$ |
| 31 | $CH(CH_2CH_3)CH(CH_3)_2$ |
| 32 | $C(CH_3)_2CH_2CH_2CH_3$ |
| 33 | $CH_2C(CH_3)_2CH_2CH_3$ |
| 34 | $C(CH_3)_2CH(CH_3)_2$ |
| 35 | cyclohexyl |
| 36 | $CH_2CN$ |
| 37 | $(CH_2)_2CN$ |
| 38 | $(CH_2)_3CN$ |
| 39 | $(CH_2)_4CN$ |
| 40 | $CH_2NO_2$ |
| 41 | $(CH_2)_2NO_2$ |
| 42 | $(CH_2)_3NO_2$ |
| 43 | $(CH_2)_4NO_2$ |
| 44 | $(CH_2)_2OH$ |
| 45 | $(CH_2)_3OH$ |
| 46 | $(CH_2)_4OH$ |
| 47 | $(CH_2)_2NH_2$ |
| 48 | $(CH_2)_3NH_2$ |
| 49 | $(CH_2)_4NH_2$ |
| 50 | $(CH_2)_2NHCH_3$ |

TABLE A-continued

| No. | $R^2$ |
|---|---|
| 51 | $(CH_2)_3NHCH_3$ |
| 52 | $(CH_2)_4NHCH_3$ |
| 53 | $(CH_2)_2N(CH_3)_2$ |
| 54 | $(CH_2)_3N(CH_3)_2$ |
| 55 | $(CH_2)_4N(CH_3)_2$ |
| 56 | $(CH_2)_2N(CH_2CH_3)_2$ |
| 57 | $(CH_2)_3N(CH_2CH_3)_2$ |
| 58 | $(CH_2)_4N(CH_2CH_3)_2$ |
| 59 | $(CH_2)_2OCH_3$ |
| 60 | $(CH_2)_3OCH_3$ |
| 61 | $(CH_2)_4OCH_3$ |
| 62 | $(CH_2)_2OCH_2CH_3$ |
| 63 | $(CH_2)_3OCH_2CH_3$ |
| 64 | $(CH_2)_4OCH_2CH_3$ |
| 65 | $(CH_2)_2O(CH_2)_2CH_3$ |
| 66 | $(CH_2)_3O(CH_2)_2CH_3$ |
| 67 | $(CH_2)_4O(CH_2)_2CH_3$ |
| 68 | $(CH_2)_2OCH(CH_3)_2$ |
| 69 | $(CH_2)_3OCH(CH_3)_2$ |
| 70 | $(CH_2)_4OCH(CH_3)_2$ |
| 71 | $(CH_2)_2OC(CH_3)_3$ |
| 72 | $(CH_2)_3OC(CH_3)_3$ |
| 73 | $(CH_2)_4OC(CH_3)_3$ |
| 74 | $(CH_2)_2OCF_3$ |
| 75 | $(CH_2)_3OCF_3$ |
| 76 | $(CH_2)_4OCF_3$ |
| 77 | $(CH_2)_2SCH_3$ |
| 78 | $(CH_2)_3SCH_3$ |
| 79 | $(CH_2)_4SCH_3$ |
| 80 | $(CH_2)_2SOCH_3$ |
| 81 | $(CH_2)_3SOCH_3$ |
| 82 | $(CH_2)_4SOCH_3$ |
| 83 | $(CH_2)_2SO_2CH_3$ |
| 84 | $(CH_2)_3SO_2CH_3$ |
| 85 | $(CH_2)_4SO_2CH_3$ |
| 86 | $CH_2$-cyclopropyl |
| 87 | $(CH_2)_2$-cyclopropyl |
| 88 | $(CH_2)_3$-cyclopropyl |
| 89 | $(CH_2)_4$-cyclopropyl |
| 90 | $CH_2$-cyclopentyl |
| 91 | $(CH_2)_2$-cyclopentyl |
| 92 | $(CH_2)_3$-cyclopentyl |
| 93 | $(CH_2)_4$-cyclopentyl |
| 94 | $CH_2$-cyclohexyl |
| 95 | $(CH_2)_2$-cyclohexyl |
| 96 | $(CH_2)_3$-cyclohexyl |
| 97 | $(CH_2)_4$-cyclohexyl |
| 98 | $CHF_2$ |
| 99 | $CF_3$ |
| 100 | $CH_2CHF_2$ |
| 101 | $CH_2CF_3$ |
| 102 | $CHFCHF_2$ |
| 103 | $CH_2CH_2F$ |
| 104 | $CHFCH_3$ |
| 105 | $CHFCF_3$ |
| 106 | $CF_2CHF_2$ |
| 107 | $CF_2CHFCF_3$ |
| 108 | $CH_2CCl_3$ |
| 109 | $CF_2CHCl_2$ |
| 110 | $CF_2CHFCl$ |
| 111 | $CF_2CHFBr$ |
| 112 | $CH(CF_3)_2$ |
| 113 | $CH(CF_3)CH_3$ |
| 114 | $CH_2CH_2CF_3$ |
| 115 | $CH_2CHFCH_3$ |
| 116 | $CH_2CF_2CF_3$ |
| 117 | $CH_2CH_2CH_2F$ |
| 118 | $CH_2CF_2CF_2CF_3$ |
| 119 | $CH_2CH_2CHFCH_3$ |
| 120 | $CH_2CH_2CH_2CH_2F$ |
| 121 | $CH_2CH_2Cl$ |
| 122 | $CH_2CHClCH_3$ |
| 123 | $CH_2CH_2CH_2Cl$ |
| 124 | $CH_2CH_2CHClCH_3$ |
| 125 | $CH_2CH_2CH_2CH_2Cl$ |
| 126 | $CH_2CH_2Br$ |
| 127 | $CH_2CHBrCH_3$ |
| 128 | $CH_2CH_2CH_2Br$ |
| 129 | $CH_2CH_2CHBrCH_3$ |
| 130 | $CH_2CH_2CH_2CH_2Br$ |
| 131 | $CH_2—C_6H_5$ |
| 132 | $CH(CH_3)CN$ |
| 133 | $CH(CH_3)CH_2CN$ |
| 134 | $CH_2CH(CH_3)CN$ |
| 135 | $CH(CH_3)CH(CH_3)CN$ |
| 136 | $CH(CH_3)(CH_2)_2CN$ |
| 137 | $CH_2CH(CH_3)CH_2CN$ |
| 138 | $(CH_2)_2CH(CH_3)CN$ |
| 139 | $CH(CH_3)CH(CH_3)CH_2CN$ |
| 140 | $CH(CH_3)CH_2CH(CH_3)CN$ |
| 141 | $CH_2CH(CH_3)CH(CH_3)CN$ |
| 142 | $CH(CH_3)CH(CH_3)CH(CH_3)CN$ |
| 143 | $CH(CH_3)(CH_2)_3CN$ |
| 144 | $CH(CH_3)NO_2$ |
| 145 | $CH(CH_3)CH_2NO_2$ |
| 146 | $CH_2CH(CH_3)NO_2$ |
| 147 | $CH(CH_3)CH(CH_3)NO_2$ |
| 148 | $CH(CH_3)(CH_2)_2NO_2$ |
| 149 | $CH_2CH(CH_3)CH_2NO_2$ |
| 150 | $(CH_2)_2CH(CH_3)NO_2$ |
| 151 | $CH(CH_3)CH(CH_3)CH_2NO_2$ |
| 152 | $CH(CH_3)CH_2CH(CH_3)NO_2$ |
| 153 | $CH_2CH(CH_3)CH(CH_3)NO_2$ |
| 154 | $CH(CH_3)CH(CH_3)CH(CH_3)NO_2$ |
| 155 | $CH(CH_3)(CH_2)_3NO_2$ |
| 156 | $CH(CH_3)CH_2OH$ |
| 157 | $CH_2CH(CH_3)OH$ |
| 158 | $CH(CH_3)CH(CH_3)OH$ |
| 159 | $CH(CH_3)(CH_2)_2OH$ |
| 160 | $CH_2CH(CH_3)CH_2OH$ |
| 161 | $(CH_2)_2CH(CH_3)OH$ |
| 162 | $CH(CH_3)CH(CH_3)CH_2OH$ |
| 163 | $CH(CH_3)CH_2CH(CH_3)OH$ |
| 164 | $CH_2CH(CH_3)CH(CH_3)OH$ |
| 165 | $CH(CH_3)CH(CH_3)CH(CH_3)OH$ |
| 166 | $CH(CH_3)(CH_2)_3OH$ |
| 167 | $CH(CH_3)CH_2OCH_3$ |
| 168 | $CH_2CH(CH_3)OCH_3$ |
| 169 | $CH(CH_3)CH(CH_3)OCH_3$ |
| 170 | $CH(CH_3)(CH_2)_2OCH_3$ |
| 171 | $CH_2CH(CH_3)CH_2OCH_3$ |
| 172 | $(CH_2)_2CH(CH_3)OCH_3$ |
| 173 | $CH(CH_3)CH(CH_3)CH_2OCH_3$ |
| 174 | $CH(CH_3)CH_2CH(CH_3)OCH_3$ |
| 175 | $CH_2CH(CH_3)CH(CH_3)OCH_3$ |
| 176 | $CH(CH_3)CH(CH_3)CH(CH_3)OCH_3$ |
| 177 | $CH(CH_3)(CH_2)_3OCH_3$ |
| 178 | $CH(CH_3)CH_2OCH_2CH_3$ |
| 179 | $CH_2CH(CH_3)OCH_2CH_3$ |
| 180 | $CH(CH_3)CH(CH_3)OCH_2CH_3$ |
| 181 | $CH(CH_3)(CH_2)_2OCH_2CH_3$ |
| 182 | $CH_2CH(CH_3)CH_2OCH_2CH_3$ |
| 183 | $(CH_2)_2CH(CH_3)OCH_2CH_3$ |
| 184 | $CH(CH_3)CH(CH_3)CH_2OCH_2CH_3$ |
| 185 | $CH(CH_3)CH_2CH(CH_3)OCH_2CH_3$ |
| 186 | $CH_2CH(CH_3)CH(CH_3)OCH_2CH_3$ |
| 187 | $CH(CH_3)CH(CH_3)CH(CH_3)OCH_2CH_3$ |
| 188 | $CH(CH_3)(CH_2)_3OCH_2CH_3$ |
| 189 | $CH(CH_3)CH_2O(CH_2)_2CH_3$ |
| 190 | $CH_2CH(CH_3)O(CH_2)_2CH_3$ |
| 191 | $CH(CH_3)CH(CH_3)O(CH_2)_2CH_3$ |
| 192 | $CH(CH_3)(CH_2)_2O(CH_2)_2CH_3$ |
| 193 | $CH_2CH(CH_3)CH_2O(CH_2)_2CH_3$ |
| 194 | $(CH_2)_2CH(CH_3)O(CH_2)_2CH_3$ |
| 195 | $CH(CH_3)CH(CH_3)CH_2O(CH_2)_2CH_3$ |
| 196 | $CH(CH_3)CH_2CH(CH_3)O(CH_2)_2CH_3$ |
| 197 | $CH_2CH(CH_3)CH(CH_3)O(CH_2)_2CH_3$ |
| 198 | $CH(CH_3)CH(CH_3)CH(CH_3)O(CH_2)_2CH_3$ |
| 199 | $CH(CH_3)(CH_2)_3O(CH_2)_2CH_3$ |
| 200 | $CH(CH_3)CH_2OCH(CH_3)_2$ |
| 201 | $CH_2CH(CH_3)OCH(CH_3)_2$ |
| 202 | $CH(CH_3)CH(CH_3)OCH(CH_3)_2$ |
| 203 | $CH(CH_3)(CH_2)_2OCH(CH_3)_2$ |
| 204 | $CH_2CH(CH_3)CH_2OCH(CH_3)_2$ |

TABLE A-continued

| No. | R² |
|---|---|
| 205 | (CH₂)₂CH(CH₃)OCH(CH₃)₂ |
| 206 | CH(CH₃)CH(CH₃)CH₂OCH(CH₃)₂ |
| 207 | CH(CH₃)CH₂CH(CH₃)OCH(CH₃)₂ |
| 208 | CH₂CH(CH₃)CH(CH₃)OCH(CH₃)₂ |
| 209 | CH(CH₃)CH(CH₃)CH(CH₃)OCH(CH₃)₂ |
| 210 | CH(CH₃)(CH₂)₃OCH(CH₃)₂ |
| 211 | CH(CH₃)CH₂OC(CH₃)₃ |
| 212 | CH₂CH(CH₃)OC(CH₃)₃ |
| 213 | CH(CH₃)CH(CH₃)OC(CH₃)₃ |
| 214 | CH(CH₃)(CH₂)₂OC(CH₃)₃ |
| 215 | CH₂CH(CH₃)CH₂OC(CH₃)₃ |
| 216 | (CH₂)₂CH(CH₃)OC(CH₃)₃ |
| 217 | CH(CH₃)CH(CH₃)CH₂OC(CH₃)₃ |
| 218 | CH(CH₃)CH₂CH(CH₃)OC(CH₃)₃ |
| 219 | CH₂CH(CH₃)CH(CH₃)OC(CH₃)₃ |
| 220 | CH(CH₃)CH(CH₃)CH(CH₃)OC(CH₃)₃ |
| 221 | CH(CH₃)(CH₂)₃OC(CH₃)₃ |
| 222 | CH(CH₃)CH₂OCF₃ |
| 223 | CH₂CH(CH₃)OCF₃ |
| 224 | CH(CH₃)CH(CH₃)OCF₃ |
| 225 | CH(CH₃)CH₂OCF₃ |
| 226 | CH₂CH(CH₃)CH₂OCF₃ |
| 227 | (CH₂)₂CH(CH₃)OCF₃ |
| 228 | CH(CH₃)CH(CH₃)CH₂OCF₃ |
| 229 | CH(CH₃)CH₂CH(CH₃)OCF₃ |
| 230 | CH₂CH(CH₃)CH(CH₃)OCF₃ |
| 231 | CH(CH₃)CH(CH₃)CH(CH₃)OCF₃ |
| 232 | CH(CH₃)(CH₂)₃OCF₃ |
| 233 | CH(CH₃)CH₂SCH₃ |
| 234 | CH₂CH(CH₃)SCH₃ |
| 235 | CH(CH₃)CH(CH₃)SCH₃ |
| 236 | CH(CH₃)(CH₂)₂SCH₃ |
| 237 | CH₂CH(CH₃)CH₂SCH₃ |
| 238 | (CH₂)₂CH(CH₃)SCH₃ |
| 239 | CH(CH₃)CH(CH₃)CH₂SCH₃ |
| 240 | CH(CH₃)CH₂CH(CH₃)SCH₃ |
| 241 | CH₂CH(CH₃)CH(CH₃)SCH₃ |
| 242 | CH(CH₃)CH(CH₃)CH(CH₃)SCH₃ |
| 243 | CH(CH₃)(CH₂)₃SCH₃ |
| 244 | CH(CH₃)CH₂SOCH₃ |
| 245 | CH₂CH(CH₃)SOCH₃ |
| 246 | CH(CH₃)CH(CH₃)SOCH₃ |
| 247 | CH(CH₃)(CH₂)₂SOCH₃ |
| 248 | CH₂CH(CH₃)CH₂SOCH₃ |
| 249 | (CH₂)₂CH(CH₃)SOCH₃ |
| 250 | CH(CH₃)CH(CH₃)CH₂SOCH₃ |
| 251 | CH(CH₃)CH₂CH(CH₃)SOCH₃ |
| 252 | CH₂CH(CH₃)CH(CH₃)SOCH₃ |
| 253 | CH(CH₃)CH(CH₃)CH(CH₃)SOCH₃ |
| 254 | CH(CH₃)(CH₂)₃SOCH₃ |
| 255 | CH(CH₃)CH₂SO₂CH₃ |
| 256 | CH₂CH(CH₃)SO₂CH₃ |
| 257 | CH(CH₃)CH(CH₃)SO₂CH₃ |
| 258 | CH(CH₃)(CH₂)₂SO₂CH₃ |
| 259 | CH₂CH(CH₃)CH₂SO₂CH₃ |
| 260 | (CH₂)₂CH(CH₃)SO₂CH₃ |
| 261 | CH(CH₃)CH(CH₃)CH₂SO₂CH₃ |
| 262 | CH(CH₃)CH₂CH(CH₃)SO₂CH₃ |
| 263 | CH(CH₃)CH(CH₃)SO₂CH₃ |
| 264 | CH(CH₃)CH(CH₃)CH(CH₃)SO₂CH₃ |
| 265 | CH(CH₃)(CH₂)₃SO₂CH₃ |
| 266 | CH(CH₃)-cyclopropyl |
| 267 | CH(CH₃)CH₂-cyclopropyl |
| 268 | CH₂CH(CH₃)-cyclopropyl |
| 269 | CH(CH₃)CH(CH₃)-cyclopropyl |
| 270 | CH(CH₃)(CH₂)₂-cyclopropyl |
| 271 | CH₂CH(CH₃)CH₂-cyclopropyl |
| 272 | (CH₂)₂CH(CH₃)-cyclopropyl |
| 273 | CH(CH₃)CH(CH₃)CH₂-cyclopropyl |
| 274 | CH(CH₃)CH₂CH(CH₃)-cyclopropyl |
| 275 | CH₂CH(CH₃)CH(CH₃)-cyclopropyl |
| 276 | CH(CH₃)CH(CH₃)CH(CH₃)-cyclopropyl |
| 277 | CH(CH₃)(CH₂)₃-cyclopropyl |
| 278 | CH(CH₃)-cyclopentyl |
| 279 | CH(CH₃)CH₂-cyclopentyl |
| 280 | CH₂CH(CH₃)-cyclopentyl |
| 281 | CH(CH₃)CH(CH₃)-cyclopentyl |
| 282 | CH(CH₃)(CH₂)₂-cyclopentyl |
| 283 | CH₂CH(CH₃)CH₂-cyclopentyl |
| 284 | (CH₂)₂CH(CH₃)-cyclopentyl |
| 285 | CH(CH₃)CH(CH₃)CH₂-cyclopentyl |
| 286 | CH(CH₃)CH₂CH(CH₃)-cyclopentyl |
| 287 | CH₂CH(CH₃)CH(CH₃)-cyclopentyl |
| 288 | CH(CH₃)CH(CH₃)CH(CH₃)-cyclopentyl |
| 289 | CH(CH₃)(CH₂)₃-cyclopentyl |
| 290 | CH(CH₃)-cyclohexyl |
| 291 | CH(CH₃)CH₂-cyclohexyl |
| 292 | CH₂CH(CH₃)-cyclohexyl |
| 293 | CH(CH₃)CH(CH₃)cyclohexyl |
| 294 | CH(CH₃)(CH₂)₂-cyclohexyl |
| 295 | CH₂CH(CH₃)CH₂-cyclohexyl |
| 296 | (CH₂)₂CH(CH₃)-cyclohexyl |
| 297 | CH(CH₃)CH(CH₃)CH₂-cyclohexyl |
| 298 | CH(CH₃)CH₂CH(CH₃)-cyclohexyl |
| 299 | CH₂CH(CH₃)CH(CH₃)-cyclohexyl |
| 300 | CH(CH₃)CH(CH₃)CH(CH₃)-cyclohexyl |
| 301 | CH(CH₃)(CH₂)₃-cyclohexyl |
| 302 | CH(CH₃)CHF₂ |
| 303 | CF(CH₃)CHF₂ |
| 304 | CH(CH₃)CH₂F |
| 305 | CF(CH₃)CH₃ |
| 306 | CF(CH₃)CF₃ |
| 307 | CH(CH₃)CCl₃ |
| 308 | CH(CH₃)CH₂CF₃ |
| 309 | CH₂CH(CH₃)CF₃ |
| 310 | CH(CH₃)CH(CH₃)CF₃ |
| 311 | CH(CH₃)CF₂CF₃ |
| 312 | CH(CH₃)-phenyl |
| 313 | CH(CH₃)CH₂-phenyl |
| 314 | CH₂CH(CH₃)-phenyl |
| 315 | CH(CH₃)CH(CH₃)-phenyl |
| 316 | CH(CH₃)(CH₂)₂-phenyl |
| 317 | CH₂CH(CH₃)CH₂-phenyl |
| 318 | (CH₂)₂CH(CH₃)-phenyl |
| 319 | CH(CH₃)CH(CH₃)CH₂-phenyl |
| 320 | CH(CH₃)CH₂CH(CH₃)-phenyl |
| 321 | CH₂CH(CH₃)CH(CH₃)-phenyl |
| 322 | CH(CH₃)CH(CH₃)CH(CH₃)-phenyl |
| 323 | CH(CH₃)(CH₂)₃-phenyl |
| 324 | 2-F—C₆H₄—CH₂ |
| 325 | 3-F—C₆H₄—CH₂ |
| 326 | 4-F—C₆H₄—CH₂ |
| 327 | 2,3-F₂—C₆H₃—CH₂ |
| 328 | 2,4-F₂—C₆H₃—CH₂ |
| 329 | 2,5-F₂—C₆H₃—CH₂ |
| 330 | 2,6-F₂—C₆H₃—CH₂ |
| 331 | 3,4-F₂—C₆H₃—CH₂ |
| 332 | 3,5-F₂—C₆H₃—CH₂ |
| 333 | 2-Cl—C₆H₄—CH₂ |
| 334 | 3-Cl—C₆H₄—CH₂ |
| 335 | 4-Cl—C₆H₄—CH₂ |
| 336 | 2,3-Cl₂—C₆H₃—CH₂ |
| 337 | 2,4-Cl₂—C₆H₃—CH₂ |
| 338 | 2,5-Cl₂—C₆H₃—CH₂ |
| 339 | 2,6-Cl₂—C₆H₃—CH₂ |
| 340 | 3,4-Cl₂—C₆H₃—CH₂ |
| 341 | 3,5-Cl₂—C₆H₃—CH₂ |
| 342 | 2,3,4-Cl₃—C₆H₂—CH₂ |
| 343 | 2,3,5-Cl₃—C₆H₂—CH₂ |
| 344 | 2,3,6-Cl₃—C₆H₂—CH₂ |
| 345 | 2,4,5-Cl₃—C₆H₂—CH₂ |
| 346 | 2,4,6-Cl₃—C₆H₂—CH₂ |
| 347 | 3,4,5-Cl₃—C₆H₂—CH₂ |
| 348 | 2-Br—C₆H₄—CH₂ |
| 349 | 3-Br—C₆H₄—CH₂ |
| 350 | 4-Br—C₆H₄—CH₂ |
| 351 | 2,3-Br₂—C₆H₃—CH₂ |
| 352 | 2,4-Br₂—C₆H₃—CH₂ |
| 353 | 2,5-Br₂—C₆H₃—CH₂ |
| 354 | 2,6-Br₂—C₆H₃—CH₂ |
| 355 | 3,4-Br₂—C₆H₃—CH₂ |
| 356 | 3,5-Br₂—C₆H₃—CH₂ |
| 357 | 2-F, 3-Cl—C₆H₃—CH₂ |
| 358 | 2-F, 4-Cl—C₆H₃—CH₂ |

TABLE A-continued

| No. | R² |
|---|---|
| 359 | 2-F, 5-Cl—C$_6$H$_3$—CH$_2$ |
| 360 | 2-F, 3-Br—C$_6$H$_3$—CH$_2$ |
| 361 | 2-F, 4-Br—C$_6$H$_3$—CH$_2$ |
| 362 | 2-F, 5-Br—C$_6$H$_3$—CH$_2$ |
| 363 | 2-Cl, 3-F—C$_6$H$_3$—CH$_2$ |
| 364 | 2-Cl, 4-F—C$_6$H$_3$—CH$_2$ |
| 365 | 2-Cl, 5-F—C$_6$H$_3$—CH$_2$ |
| 366 | 2-Cl, 3-Br—C$_6$H$_3$—CH$_2$ |
| 367 | 2-Cl, 4-Br—C$_6$H$_3$—CH$_2$ |
| 368 | 2-Cl, 5-Br—C$_6$H$_3$—CH$_2$ |
| 369 | 2-Br, 3-F—C$_6$H$_3$—CH$_2$ |
| 370 | 2-Br, 4-F—C$_6$H$_3$—CH$_2$ |
| 371 | 2-Br, 5-F—C$_6$H$_3$—CH$_2$ |
| 372 | 2-Br, 3-Cl—C$_6$H$_3$—CH$_2$ |
| 373 | 2-Br, 4-Cl—C$_6$H$_3$—CH$_2$ |
| 374 | 2-Br, 5-Cl—C$_6$H$_3$—CH$_2$ |
| 375 | 4-Cl, 3,5-Br$_2$—C$_6$H$_2$—CH$_2$ |
| 376 | 2-CN—C$_6$H$_4$—CH$_2$ |
| 377 | 3-CN—C$_6$H$_4$—CH$_2$ |
| 378 | 4-CN—C$_6$H$_4$—CH$_2$ |
| 379 | 2-NO$_2$—C$_6$H$_4$—CH$_2$ |
| 380 | 3-NO$_2$—C$_6$H$_4$—CH$_2$ |
| 381 | 4-NO$_2$—C$_6$H$_4$—CH$_2$ |
| 382 | 2-CH$_3$—C$_6$H$_4$—CH$_2$ |
| 383 | 3-CH$_3$—C$_6$H$_4$—CH$_2$ |
| 384 | 4-CH$_3$—C$_6$H$_4$—CH$_2$ |
| 385 | 2,3-(CH$_3$)$_2$—C$_6$H$_3$—CH$_2$ |
| 386 | 2,4-(CH$_3$)$_2$—C$_6$H$_3$—CH$_2$ |
| 387 | 2,5-(CH$_3$)$_2$—C$_6$H$_3$—CH$_2$ |
| 388 | 2,6-(CH$_3$)$_2$—C$_6$H$_3$—CH$_2$ |
| 389 | 3,4-(CH$_3$)$_2$—C$_6$H$_3$—CH$_2$ |
| 390 | 3,5-(CH$_3$)$_2$—C$_6$H$_3$—CH$_2$ |
| 391 | 2-CH$_2$CH$_3$—C$_6$H$_4$—CH$_2$ |
| 392 | 3-CH$_2$CH$_3$—C$_6$H$_4$—CH$_2$ |
| 393 | 4-CH$_2$CH$_3$—C$_6$H$_4$—CH$_2$ |
| 394 | 2-CH(CH$_3$)$_2$—C$_6$H$_4$—CH$_2$ |
| 395 | 3-CH(CH$_3$)$_2$—C$_6$H$_4$—CH$_2$ |
| 396 | 4-CH(CH$_3$)$_2$—C$_6$H$_4$—CH$_2$ |
| 397 | 3-C(CH$_3$)$_3$—C$_6$H$_4$—CH$_2$ |
| 398 | 4-C(CH$_3$)$_3$—C$_6$H$_4$—CH$_2$ |
| 399 | 2-C$_6$H$_5$—C$_6$H$_4$—CH$_2$ |
| 400 | 3-C$_6$H$_5$—C$_6$H$_4$—CH$_2$ |
| 401 | 4-C$_6$H$_5$—C$_6$H$_4$—CH$_2$ |
| 402 | 2-OCH$_3$—C$_6$H$_4$—CH$_2$ |
| 403 | 3-OCH$_3$—C$_6$H$_4$—CH$_2$ |
| 404 | 4-OCH$_3$—C$_6$H$_4$—CH$_2$ |
| 405 | 2,3-(OCH$_3$)$_2$—C$_6$H$_3$—CH$_2$ |
| 406 | 2,4-(OCH$_3$)$_2$—C$_6$H$_3$—CH$_2$ |
| 407 | 2,5-(OCH$_3$)$_2$—C$_6$H$_3$—CH$_2$ |
| 408 | 2,6-(OCH$_3$)$_2$—C$_6$H$_3$—CH$_2$ |
| 409 | 3,4-(OCH$_3$)$_2$—C$_6$H$_3$—CH$_2$ |
| 410 | 3,5-(OCH$_3$)$_2$—C$_6$H$_3$—CH$_2$ |
| 411 | 3,4,5-(OCH$_3$)$_3$—C$_6$H$_2$—CH$_2$ |
| 412 | 2-OCH$_2$CH$_3$—C$_6$H$_4$—CH$_2$ |
| 413 | 3-OCH$_2$CH$_3$—C$_6$H$_4$—CH$_2$ |
| 414 | 4-OCH$_2$CH$_3$—C$_6$H$_4$—CH$_2$ |
| 415 | 2-O(CH$_2$)$_2$CH$_3$—C$_6$H$_4$—CH$_2$ |
| 416 | 3-O(CH$_2$)$_2$CH$_3$—C$_6$H$_4$—CH$_2$ |
| 417 | 4-O(CH$_2$)$_2$CH$_3$—C$_6$H$_4$—CH$_2$ |
| 418 | 2-OCH(CH$_3$)$_2$—C$_6$H$_4$—CH$_2$ |
| 419 | 3-OCH(CH$_3$)$_2$—C$_6$H$_4$—CH$_2$ |
| 420 | 4-OCH(CH$_3$)$_2$—C$_6$H$_4$—CH$_2$ |
| 421 | 3-OC(CH$_3$)$_3$—C$_6$H$_4$—CH$_2$ |
| 422 | 4-OC(CH$_3$)$_3$—C$_6$H$_4$—CH$_2$ |
| 423 | 2-OCH$_2$CH═CH$_2$—C$_6$H$_4$—CH$_2$ |
| 424 | 3-OCH$_2$CH═CH$_2$—C$_6$H$_4$—CH$_2$ |
| 425 | 4-OCH$_2$CH═CH$_2$—C$_6$H$_4$—CH$_2$ |
| 426 | 2-CF$_3$—C$_6$H$_4$—CH$_2$ |
| 427 | 3-CF$_3$—C$_6$H$_4$—CH$_2$ |
| 428 | 4-CF$_3$—C$_6$H$_4$—CH$_2$ |
| 429 | 2-CO$_2$CH$_3$—C$_6$H$_4$—CH$_2$ |
| 430 | 3-CO$_2$CH$_3$—C$_6$H$_4$—CH$_2$ |
| 431 | 4-CO$_2$CH$_3$—C$_6$H$_4$—CH$_2$ |
| 432 | 2-CO$_2$CH$_2$CH$_3$—C$_6$H$_4$—CH$_2$ |
| 433 | 3-CO$_2$CH$_2$CH$_3$—C$_6$H$_4$—CH$_2$ |
| 434 | 4-CO$_2$CH$_2$CH$_3$—C$_6$H$_4$—CH$_2$ |
| 435 | 2-CONH$_2$—C$_6$H$_4$—CH$_2$ |
| 436 | 3-CONH$_2$—C$_6$H$_4$—CH$_2$ |
| 437 | 4-CONH$_2$—C$_6$H$_4$—CH$_2$ |
| 438 | 2-CON(CH$_3$)$_2$—C$_6$H$_4$—CH$_2$ |
| 439 | 3-CON(CH$_3$)$_2$—C$_6$H$_4$—CH$_2$ |
| 440 | 4-CON(CH$_3$)$_2$—C$_6$H$_4$—CH$_2$ |
| 441 | 2-CONHCH$_3$—C$_6$H$_4$—CH$_2$ |
| 442 | 3-CONHCH$_3$—C$_6$H$_4$—CH$_2$ |
| 443 | 4-CONHCH$_3$—C$_6$H$_4$—CH$_2$ |
| 444 | 2-NH$_2$—C$_6$H$_4$—CH$_2$ |
| 445 | 3-NH$_2$—C$_6$H$_4$—CH$_2$ |
| 446 | 4-NH$_2$—C$_6$H$_4$—CH$_2$ |
| 447 | 2-N(CH$_3$)$_2$—C$_6$H$_4$—CH$_2$ |
| 448 | 3-N(CH$_3$)$_2$—C$_6$H$_4$—CH$_2$ |
| 449 | 4-N(CH$_3$)$_2$—C$_6$H$_4$—CH$_2$ |
| 450 | 2-NHCH$_3$—C$_6$H$_4$—CH$_2$ |
| 451 | 3-NHCH$_3$—C$_6$H$_4$—CH$_2$ |
| 452 | 4-NHCH$_3$—C$_6$H$_4$—CH$_2$ |
| 453 | 2-CSNH$_2$—C$_6$H$_4$—CH$_2$ |
| 454 | 3-CSNH$_2$—C$_6$H$_4$—CH$_2$ |
| 455 | 4-CSNH$_2$—C$_6$H$_4$—CH$_2$ |
| 456 | 2-SCH$_3$—C$_6$H$_4$—CH$_2$ |
| 457 | 3-SCH$_3$—C$_6$H$_4$—CH$_2$ |
| 458 | 4-SCH$_3$—C$_6$H$_4$—CH$_2$ |
| 459 | 2-SOCH$_3$—C$_6$H$_4$—CH$_2$ |
| 460 | 3-SOCH$_3$—C$_6$H$_4$—CH$_2$ |
| 461 | 4-SOCH$_3$—C$_6$H$_4$—CH$_2$ |
| 462 | 2-SO$_2$CH$_3$—C$_6$H$_4$—CH$_2$ |
| 463 | 3-SO$_2$CH$_3$—C$_6$H$_4$—CH$_2$ |
| 464 | 4-SO$_2$CH$_3$—C$_6$H$_4$—CH$_2$ |
| 465 | 2-OCF$_3$—C$_6$H$_4$—CH$_2$ |
| 466 | 3-OCF$_3$—C$_6$H$_4$—CH$_2$ |
| 467 | 4-OCF$_3$—C$_6$H$_4$—CH$_2$ |
| 468 | 2-OCHF$_2$—C$_6$H$_4$—CH$_2$ |
| 469 | 3-OCHF$_2$—C$_6$H$_4$—CH$_2$ |
| 470 | 4-OCHF$_2$—C$_6$H$_4$—CH$_2$ |
| 471 | 3-CF$_3$, 4-OCF$_3$—C$_6$H$_3$—CH$_2$ |
| 472 | 2-CH$_2$CH$_2$F—C$_6$H$_4$—CH$_2$ |
| 473 | 3-CH$_2$CH$_2$F—C$_6$H$_4$—CH$_2$ |
| 474 | 4-CH$_2$CH$_2$F—C$_6$H$_4$—CH$_2$ |
| 475 | 2-CH$_2$CF$_3$—C$_6$H$_4$—CH$_2$ |
| 476 | 3-CH$_2$CF$_3$—C$_6$H$_4$—CH$_2$ |
| 477 | 4-CH$_2$CF$_3$—C$_6$H$_4$—CH$_2$ |
| 478 | 2-CF$_2$CHF$_2$—C$_6$H$_4$—CH$_2$ |
| 479 | 3-CF$_2$CHF$_2$—C$_6$H$_4$—CH$_2$ |
| 480 | 4-CF$_2$CHF$_2$—C$_6$H$_4$—CH$_2$ |
| 481 | 2-CHF$_2$—C$_6$H$_4$—CH$_2$ |
| 482 | 3-CHF$_2$—C$_6$H$_4$—CH$_2$ |
| 483 | 4-CHF$_2$—C$_6$H$_4$—CH$_2$ |
| 484 | naphthalen-1-yl-CH$_2$ |
| 485 | naphthalen-2-yl-CH$_2$ |
| 486 | pyrid-2-yl-CH$_2$ |
| 487 | pyrid-3-yl-CH$_2$ |
| 488 | pyrid-4-yl-CH$_2$ |
| 489 | 5-CH$_3$-pyrid-2-yl-CH$_2$ |
| 490 | 6-CH$_3$-pyrid-2-yl-CH$_2$ |
| 491 | 5-CH$_3$-pyrid-3-yl-CH$_2$ |
| 492 | 6-CH$_3$-pyrid-3-yl-CH$_2$ |
| 493 | 5-OCH$_3$-pyrid-2-yl-CH$_2$ |
| 494 | 6-OCH$_3$-pyrid-2-yl-CH$_2$ |
| 495 | 5-OCH$_3$-pyrid-3-yl-CH$_2$ |
| 496 | 6-OCH$_3$-pyrid-3-yl-CH$_2$ |
| 497 | 4-Cl-pyrid-2-yl-CH$_2$ |
| 498 | 5-Cl-pyrid-2-yl-CH$_2$ |
| 499 | 6-Cl-pyrid-2-yl-CH$_2$ |
| 500 | 2-Cl-pyrid-3-yl-CH$_2$ |
| 501 | 5-Cl-pyrid-3-yl-CH$_2$ |
| 502 | 6-Cl-pyrid-3-yl-CH$_2$ |
| 503 | 2-Cl-pyrid-4-yl-CH$_2$ |
| 504 | 3,5-Cl-pyrid-2-yl-CH$_2$ |
| 505 | pyrimidin-2-yl-CH$_2$ |
| 506 | 4-Cl-pyrimidin-2-yl-CH$_2$ |
| 507 | 5-Cl-pyrimidin-2-yl-CH$_2$ |
| 508 | 4-CH$_3$-pyrimidin-2-yl-CH$_2$ |
| 509 | 5-CH$_3$-pyrimidin-2-yl-CH$_2$ |
| 510 | 4-OCH$_3$-pyrimidin-2-yl-CH$_2$ |
| 511 | 5-OCH$_3$-pyrimidin-2-yl-CH$_2$ |
| 512 | 4-OCH$_2$CH$_3$-pyrimidin-2-yl-CH$_2$ |

TABLE A-continued

| No. | R² |
|---|---|
| 513 | 5-OCH₂CH₃-pyrimidin-2-yl-CH₂ |
| 514 | pyrimidin-4-yl-CH₂ |
| 515 | 2-Cl-pyrimidin-4-yl-CH₂ |
| 516 | 6-Cl-pyrimidin-4-yl-CH₂ |
| 517 | 2,6-Cl₂-pyrimidin-4-yl-CH₂ |
| 518 | 2-CH₃-pyrimidin-4-yl-CH₂ |
| 519 | 6-CH₃-pyrimidin-4-yl-CH₂ |
| 520 | 2-OCH₃-pyrimidin-4-yl-CH₂ |
| 521 | 6-OCH₃-pyrimidin-4-yl-CH₂ |
| 522 | 2-OCH₂CH₃-pyrimidin-4-yl-CH₂ |
| 523 | 6-OCH₂CH₃-pyrimidin-4-yl-CH₂ |
| 524 | pyrimidin-5-yl-CH₂ |
| 525 | 2-Cl-pyrimidin-5-yl-CH₂ |
| 526 | 2-CH₃-pyrimidin-5-yl-CH₂ |
| 527 | 2-OCH₃-pyrimidin-5-yl-CH₂ |
| 528 | 2-OCH₂CH₃-pyrimidin-5-yl-CH₂ |
| 529 | furan-2-yl-CH₂ |
| 530 | 4-Br-furan-2-yl-CH₂ |
| 531 | 4-Cl-furan-2-yl-CH₂ |
| 532 | 4-CN-furan-2-yl-CH₂ |
| 533 | 4-CH₃-furan-2-yl-CH₂ |
| 534 | 5-Br-furan-2-yl-CH₂ |
| 535 | 5-Cl-furan-2-yl-CH₂ |
| 536 | 5-CN-furan-2-yl-CH₂ |
| 537 | 5-CH₃-furan-2-yl-CH₂ |
| 538 | furan-3-yl-CH₂ |
| 539 | 5-Br-furan-3-yl-CH₂ |
| 540 | 5-Cl-furan-3-yl-CH₂ |
| 541 | 5-CN-furan-3-yl-CH₂ |
| 542 | 5-CH₃-furan-3-yl-CH₂ |
| 543 | thien-2-yl-CH₂ |
| 544 | 4-Br-thien-2-yl-CH₂ |
| 545 | 4-Cl-thien-2-yl-CH₂ |
| 546 | 4-CN-thien-2-yl-CH₂ |
| 547 | 4-CH₃-thien-2-yl-CH₂ |
| 548 | 5-Br-thien-2-yl-CH₂ |
| 549 | 5-Cl-thien-2-yl-CH₂ |
| 550 | 5-CN-thien-2-yl-CH₂ |
| 551 | 5-CH₃-thien-2-yl-CH₂ |
| 552 | thien-3-yl-CH₂ |
| 553 | 5-Br-thien-3-yl-CH₂ |
| 554 | 5-Cl-thien-3-yl-CH₂ |
| 555 | 5-CN-thien-3-yl-CH₂ |
| 556 | 5-CH₃-thien-3-yl-CH₂ |
| 557 | oxazol-2-yl-CH₂ |
| 558 | 4-Br-oxazol-2-yl-CH₂ |
| 559 | 4-Cl-oxazol-2-yl-CH₂ |
| 560 | 4-CN-oxazol-2-yl-CH₂ |
| 561 | 4-CH₃-oxazol-2-yl-CH₂ |
| 562 | 5-Br-oxazol-2-yl-CH₂ |
| 563 | 5-Cl-oxazol-2-yl-CH₂ |
| 564 | 5-CN-oxazol-2-yl-CH₂ |
| 565 | 5-CH₃-oxazol-2-yl-CH₂ |
| 566 | oxazol-4-yl-CH₂ |
| 567 | 2-Br-oxazol-4-yl-CH₂ |
| 568 | 2-Cl-oxazol-4-yl-CH₂ |
| 569 | 2-CN-oxazol-4-yl-CH₂ |
| 570 | 2-CH₃-oxazol-4-yl-CH₂ |
| 571 | 2-C₆H₅-oxazol-4-yl-CH₂ |
| 572 | 5-Br-oxazol-4-yl-CH₂ |
| 573 | 5-Cl-oxazol-4-yl-CH₂ |
| 574 | 5-CN-oxazol-4-yl-CH₂ |
| 575 | 5-CH₃-oxazol-4-yl-CH₂ |
| 576 | oxazol-5-yl-CH₂ |
| 577 | 4-Br-oxazol-5-yl-CH₂ |
| 578 | 4-Cl-oxazol-5-yl-CH₂ |
| 579 | 4-CN-oxazol-5-yl-CH₂ |
| 580 | 4-CH₃-oxazol-5-yl-CH₂ |
| 581 | 2-Br-oxazol-5-yl-CH₂ |
| 582 | 2-Cl-oxazol-5-yl-CH₂ |
| 583 | 2-CN-oxazol-5-yl-CH₂ |
| 584 | 2-CH₃-oxazol-5-yl-CH₂ |
| 585 | isoxazol-3-yl-CH₂ |
| 586 | 4-Br-isoxazol-3-yl-CH₂ |
| 587 | 4-Cl-isoxazol-3-yl-CH₂ |
| 588 | 4-CN-isoxazol-3-yl-CH₂ |
| 589 | 4-CH₃-isoxazol-3-yl-CH₂ |
| 590 | 5-Br-isoxazol-3-yl-CH₂ |
| 591 | 5-Cl-isoxazol-3-yl-CH₂ |
| 592 | 5-CN-isoxazol-3-yl-CH₂ |
| 593 | 5-CH₃-isoxazol-3-yl-CH₂ |
| 594 | isoxazol-4-yl-CH₂ |
| 595 | 3-Br-isoxazol-4-yl-CH₂ |
| 596 | 3-Cl-isoxazol-4-yl-CH₂ |
| 597 | 3-CN-isoxazol-4-yl-CH₂ |
| 598 | 3-CH₃-isoxazol-4-yl-CH₂ |
| 599 | 5-Br-isoxazol-4-yl-CH₂ |
| 600 | 5-Cl-isoxazol-4-yl-CH₂ |
| 601 | 5-CN-isoxazol-4-yl-CH₂ |
| 602 | 5-CH₃-isoxazol-4-yl-CH₂ |
| 603 | 3,5-(CH₃)₂-isoxazol-4-yl-CH₂ |
| 604 | isoxazol-5-yl-CH₂ |
| 605 | 3-Br-isoxazol-5-yl-CH₂ |
| 606 | 3-Cl-isoxazol-5-yl-CH₂ |
| 607 | 3-CN-isoxazol-5-yl-CH₂ |
| 608 | 3-CH₃-isoxazol-5-yl-CH₂ |
| 609 | 3-C₆H₅-isoxazol-5-yl-CH₂ |
| 610 | 4-Cl, 3-C₆H₅-isoxazol-5-yl-CH₂ |
| 611 | 4-Br, 3-C₆H₅-isoxazol-5-yl-CH₂ |
| 612 | 4-Br-isoxazol-5-yl-CH₂ |
| 613 | 4-Cl-isoxazol-5-yl-CH₂ |
| 614 | 4-CN-isoxazol-5-yl-CH₂ |
| 615 | 4-CH₃-isoxazol-5-yl-CH₂ |
| 616 | thiazol-2-yl-CH₂ |
| 617 | 4-Br-thiazol-2-yl-CH₂ |
| 618 | 4-Cl-thiazol-2-yl-CH₂ |
| 619 | 4-CN-thiazol-2-yl-CH₂ |
| 620 | 4-CH₃-thiazol-2-yl-CH₂ |
| 621 | 5-Br-thiazol-2-yl-CH₂ |
| 622 | 5-Cl-thiazol-2-yl-CH₂ |
| 623 | 5-CN-thiazol-2-yl-CH₂ |
| 624 | 5-CH₃-thiazol-2-yl-CH₂ |
| 625 | thiazol-4-yl-CH₂ |
| 626 | 2-Br-thiazol-4-yl-CH₂ |
| 627 | 2-Cl-thiazol-4-yl-CH₂ |
| 628 | 2-CN-thiazol-4-yl-CH₂ |
| 629 | 2-CH₃-thiazol-4-yl-CH₂ |
| 630 | 5-Br-thiazol-4-yl-CH₂ |
| 631 | 5-Cl-thiazol-4-yl-CH₂ |
| 632 | 5-CN-thiazol-4-yl-CH₂ |
| 633 | 5-CH₃-thiazol-4-yl-CH₂ |
| 634 | thiazol-5-yl-CH₂ |
| 635 | 4-Br-thiazol-5-yl-CH₂ |
| 636 | 4-Cl-thiazol-5-yl-CH₂ |
| 637 | 4-CN-thiazol-5-yl-CH₂ |
| 638 | 4-CH₃-thiazol-5-yl-CH₂ |
| 639 | 2-Br-thiazol-5-yl-CH₂ |
| 640 | 2-Cl-thiazol-5-yl-CH₂ |
| 641 | 2-CN-thiazol-5-yl-CH₂ |
| 642 | 2-CH₃-thiazol-5-yl-CH₂ |
| 643 | isothiazol-3-yl-CH₂ |
| 644 | 4-Br-isothiazol-3-yl-CH₂ |
| 645 | 4-Cl-isothiazol-3-yl-CH₂ |
| 646 | 4-CN-isothiazol-3-yl-CH₂ |
| 647 | 4-CH₃-isothiazol-3-yl-CH₂ |
| 648 | 5-Br-isothiazol-3-yl-CH₂ |
| 649 | 5-Cl-isothiazol-3-yl-CH₂ |
| 650 | 5-CN-isothiazol-3-yl-CH₂ |
| 651 | 5-CH₃-isothiazol-3-yl-CH₂ |
| 652 | isothiazol-4-yl-CH₂ |
| 653 | 3-Br-isothiazol-4-yl-CH₂ |
| 654 | 3-Cl-isothiazol-4-yl-CH₂ |
| 655 | 3-CN-isothiazol-4-yl-CH₂ |
| 656 | 3-CH₃-isothiazol-4-yl-CH₂ |
| 657 | 5-Br-isothiazol-4-yl-CH₂ |
| 658 | 5-Cl-isothiazol-4-yl-CH₂ |
| 659 | 5-CN-isothiazol-4-yl-CH₂ |
| 660 | 5-CH₃-isothiazol-4-yl-CH₂ |
| 661 | 3,5-(CH₃)₂-isothiazol-4-yl-CH₂ |
| 662 | isothiazol-5-yl-CH₂ |
| 663 | 3-Br-isothiazol-5-yl-CH₂ |
| 664 | 3-Cl-isothiazol-5-yl-CH₂ |
| 665 | 3-CN-isothiazol-5-yl-CH₂ |
| 666 | 3-CH₃-isothiazol-5-yl-CH₂ |

TABLE A-continued

| No. | R² |
|---|---|
| 667 | 4-Br-isothiazol-5-yl-CH₂ |
| 668 | 4-Cl-isothiazol-5-yl-CH₂ |
| 669 | 4-CN-isothiazol-5-yl-CH₂ |
| 670 | 4-CH₃-isothiazol-5-yl-CH₂ |
| 671 | imidazol-2-yl-CH₂ |
| 672 | 1-Cl-imidazol-2-yl-CH₂ |
| 673 | 1-Br-imidazol-2-yl-CH₂ |
| 674 | 1-CN-imidazol-2-yl-CH₂ |
| 675 | 1-CH₃-imidazol-2-yl-CH₂ |
| 676 | 4-Cl-imidazol-2-yl-CH₂ |
| 677 | 4-Br-imidazol-2-yl-CH₂ |
| 678 | 4-CN-imidazol-2-yl-CH₂ |
| 679 | 4-CH₃-imidazol-2-yl-CH₂ |
| 680 | 1-CH₃, 5-Cl-imidazol-2-yl-CH₂ |
| 681 | 1,4-(CH₃)₂-imidazol-2-yl-CH₂ |
| 682 | 1,5-(CH₃)₂-imidazol-2-yl-CH₂ |
| 683 | imidazol-4-yl-CH₂ |
| 684 | 2-Cl-imidazol-4-yl-CH₂ |
| 685 | 2-Br-imidazol-4-yl-CH₂ |
| 686 | 2-CN-imidazol-4-yl-CH₂ |
| 687 | 1-CH₃-imidazol-4-yl-CH₂ |
| 688 | 2-CH₃-imidazol-4-yl-CH₂ |
| 689 | 5-Cl-imidazol-4-yl-CH₂ |
| 690 | 5-Br-imidazol-4-yl-CH₂ |
| 691 | 5-CN-imidazol-4-yl-CH₂ |
| 692 | 5-CH₃-imidazol-4-yl-CH₂ |
| 693 | 1-CH₃, 5-Cl-imidazol-4-yl-CH₂ |
| 694 | 1,2-(CH₃)₂-imidazol-4-yl-CH₂ |
| 695 | 1,5-(CH₃)₂-imidazol-4-yl-CH₂ |
| 696 | pyrazol-3-yl-CH₂ |
| 697 | 5-Br-pyrazol-3-yl-CH₂ |
| 698 | 5-Cl-pyrazol-3-yl-CH₂ |
| 699 | 5-CN-pyrazol-3-yl-CH₂ |
| 700 | 5-CH₃-pyrazol-3-yl-CH₂ |
| 701 | 1-C₆H₅-pyrazol-3-yl-CH₂ |
| 702 | 4-Br-pyrazol-3-yl-CH₂ |
| 703 | 4-Cl-pyrazol-3-yl-CH₂ |
| 704 | 4-CN-pyrazol-3-yl-CH₂ |
| 705 | 4-CH₃-pyrazol-3-yl-CH₂ |
| 706 | 1-CH₃-pyrazol-3-yl-CH₂ |
| 707 | 1,4-(CH₃)₂-pyrazol-3-yl-CH₂ |
| 708 | 1,5-(CH₃)₂-pyrazol-3-yl-CH₂ |
| 709 | 1-CH₃, 4-Cl-pyrazol-3-yl-CH₂ |
| 710 | 1-CH₃, 5-Cl-pyrazol-3-yl-CH₂ |
| 711 | pyrazol-4-yl-CH₂ |
| 712 | 3-Br-pyrazol-4-yl-CH₂ |
| 713 | 3-Cl-pyrazol-4-yl-CH₂ |
| 714 | 3-CN-pyrazol-4-yl-CH₂ |
| 715 | 3-CH₃-pyrazol-4-yl-CH₂ |
| 716 | 1-CH₃-pyrazol-4-yl-CH₂ |
| 717 | 1,5-(CH₃)₂-pyrazol-4-yl-CH₂ |
| 718 | 1,3-(CH₃)₂-pyrazol-4-yl-CH₂ |
| 719 | 1-CH₃, 3-Cl-pyrazol-4-yl-CH₂ |
| 720 | 1-CH₃, 5-Cl-pyrazol-4-yl-CH₂ |
| 721 | pyrazol-5-yl-CH₂ |
| 722 | 3-Br-pyrazol-5-yl-CH₂ |
| 723 | 3-Cl-pyrazol-5-yl-CH₂ |
| 724 | 3-CN-pyrazol-5-yl-CH₂ |
| 725 | 3-CH₃-pyrazol-5-yl-CH₂ |
| 726 | 1-CH₃-pyrazol-5-yl-CH₂ |
| 727 | 4-Br-pyrazol-5-yl-CH₂ |
| 728 | 4-Cl-pyrazol-5-yl-CH₂ |
| 729 | 4-CN-pyrazol-5-yl-CH₂ |
| 730 | 4-CH₃-pyrazol-5-yl-CH₂ |
| 731 | 1,3-(CH₃)₂-pyrazol-5-yl-CH₂ |
| 732 | 1,4-(CH₃)₂-pyrazol-5-yl-CH₂ |
| 733 | 1-CH₃, 3-Cl-pyrazol-5-yl-CH₂ |
| 734 | 1-CH₃, 4-Cl-pyrazol-5-yl-CH₂ |
| 735 | 1,3,4-oxadiazol-5-yl-CH₂ |
| 736 | 2-CH₃-1,3,4-oxadiazol-5-yl-CH₂ |
| 737 | 2-CF₃-1,3,4-oxadiazol-5-yl-CH₂ |
| 738 | 2-OCH₃-1,3,4-oxadiazol-5-yl-CH₂ |
| 739 | 2-Cl-1,3,4-oxadiazol-5-yl-CH₂ |
| 740 | 2-CH(CH₃)₂-1,3,4-oxadiazol-5-yl-CH₂ |
| 741 | 1,3,4-oxadiazol-2-yl-CH₂ |
| 742 | 5-CH₃-1,3,4-oxadiazol-2-yl-CH₂ |
| 743 | 5-CF₃-1,3,4-oxadiazol-2-yl-CH₂ |
| 744 | 5-OCH₃-1,3,4-oxadiazol-2-yl-CH₂ |
| 745 | 5-Cl-1,3,4-oxadiazol-2-yl-CH₂ |
| 746 | 5-CH(CH₃)₂-1,3,4-oxadiazol-2-yl-CH₂ |
| 745 | 5-C₆H₅-1,3,4-oxadiazol-2-yl-CH₂ |
| 748 | 1,2,4-oxadiazol-3-yl-CH₂ |
| 749 | 5-CH₃-1,2,4-oxadiazol-3-yl-CH₂ |
| 750 | 5-CF₃-1,2,4-oxadiazol-3-yl-CH₂ |
| 751 | 5-OCH₃-1,2,4-oxadiazol-3-yl-CH₂ |
| 752 | 5-Cl-1,2,4-oxadiazol-3-yl-CH₂ |
| 753 | 5-CH(CH₃)₂-1,2,4-oxadiazol-3-yl-CH₂ |
| 754 | 1,2,4-triazol-3-yl-CH₂ |
| 755 | 1-CH₃-1,2,4-triazol-3-yl-CH₂ |
| 756 | 5-CH₃-1,2,4-triazol-3-yl-CH₂ |
| 757 | 5-CF₃-1,2,4-triazol-3-yl-CH₂ |
| 758 | 5-OCH₃-1,2,4-triazol-3-yl-CH₂ |
| 759 | 5-Cl-1,2,4-triazol-3-yl-CH₂ |
| 760 | 5-CH(CH₃)₂-1,2,4-triazol-3-yl-CH₂ |
| 761 | 1-C₆H₅-1,2,4-triazol-3-yl-CH₂ |
| 762 | 1,3,4-thiadiazol-5-yl-CH₂ |
| 763 | 2-CH₃-1,3,4-thiadiazol-5-yl-CH₂ |
| 764 | 2-CF₃-1,3,4-thiadiazol-5-yl-CH₂ |
| 765 | 2-OCH₃-1,3,4-thiadiazol-5-yl-CH₂ |
| 766 | 2-CH₂OCH₃-1,3,4-thiadiazol-5-yl-CH₂ |
| 767 | 2-Cl-1,3,4-thiadiazol-5-yl-CH₂ |
| 768 | 2-CH(CH₃)₂-1,3,4-thiadiazol-5-yl-CH₂ |
| 769 | 1,3,4-thiadiazol-2-yl-CH₂ |
| 770 | 5-CH₃-1,3,4-thiadiazol-2-yl-CH₂ |
| 77i | 5-CF₃-1,3,4-thiadiazol-2-yl-CH₂ |
| 772 | 5-OCH₃-1,3,4-thiadiazol-2-yl-CH₂ |
| 773 | 5-Cl-1,3,4-thiadiazol-2-yl-CH₂ |
| 774 | 5-CH(CH₃)₂-1,3,4-thiadiazol-2-yl-CH₂ |
| 775 | 5-C₆H₅-1,3,4-thiadiazol-2-yl-CH₂ |
| 776 | 1,2,4-thiadiazol-3-yl-CH₂ |
| 777 | 5-CH₃-1,2,4-thiadiazol-3-yl-CH₂ |
| 778 | 5-CF₃-1,2,4-thiadiazol-3-yl-CH₂ |
| 779 | 5-OCH₃-1,2,4-thiadiazol-3-yl-CH₂ |
| 780 | 5-Cl-1,2,4-thiadiazol-3-yl-CH₂ |
| 781 | 5-CH(CH₃)₂-1,2,4-thiadiazol-3-yl-CH₂ |
| 782 | pyrrol-2-yl-CH₂ |
| 783 | 4-Cl-pyrrol-2-yl-CH₂ |
| 784 | 4-Br-pyrrol-2-yl-CH₂ |
| 785 | 4-CH₃-pyrrol-2-yl-CH₂ |
| 786 | 4-C₆H₅-pyrrol-2-yl-CH₂ |
| 787 | benzimidazol-2-yl-CH₂ |
| 788 | quinolin-2-yl-CH₂ |
| 789 | oxiranyl-CH₂ |
| 790 | 2-CH₃-oxiran-2-yl-CH₂ |
| 791 | 2-CH₃-oxiran-3-yl-CH₂ |
| 792 | 2,2-(CH₃)₂-oxiran-3-yl-CH₂ |
| 793 | 2,3-(CH₃)₂-oxiran-3-yl-CH₂ |
| 794 | 2,3,3-(CH₃)₃-oxiran-2-yl-CH₂ |
| 795 | oxiranyl-CH(CH₃) |
| 796 | 2-CH₃-oxiran-2-yl-CH(CH₃) |
| 797 | 2-CH₃-oxiran-3-yl-CH(CH₃) |
| 798 | 2,2-(CH₃)₂-oxiran-3-yl-CH(CH₃) |
| 799 | 2,3-(CH₃)₂-oxiran-3-yl-CH(CH₃) |
| 800 | 2,3,3-(CH₃)₃-oxiran-2-yl-CH(CH₃) |
| 801 | 1,1-Cl₂-cyclopropan-2-yl-CH₂ |
| 802 | 2-CH₃, 1,1-Cl₂-cyclopropan-2-yl-CH₂ |
| 803 | 2-CH₃, 1,1-Cl₂-cyclopropan-3-yl-CH₂ |
| 804 | 2,2-(CH₃)₂, 1,1-Cl₂-cyclopropan-3-yl-CH₂ |
| 805 | 2,3-(CH₃)₂, 1,1-Cl₂-cyclopropan-3-yl-CH₂ |
| 806 | 2,3,3-(CH₃)₃, 1,1-Cl₂-cyclopropan-2-yl-CH₂ |
| 807 | 1,1-Cl₂-cyclopropan-2-yl-CH(CH₃) |
| 808 | 2-CH₃, 1,1-Cl₂-cyclopropan-2-yl-CH(CH₃) |
| 809 | 2-CH₃, 1,1-Cl₂-cyclopropan-3-yl-CH(CH₃) |
| 810 | 2,2-(CH₃)₂, 1,1-Cl₂-cyclopropan-3-yl-CH(CH₃) |
| 811 | 2,3-(CH₃)₂, 1,1-Cl₂-cyclopropan-3-yl-CH(CH₃) |
| 812 | 2,3,3-(CH₃)₃, 1,1-Cl₂-cyclopropan-2-yl-CH(CH₃) |
| 813 | 1,1-Br₂-cyclopropan-2-yl-CH₂ |
| 814 | 2-CH₃, 1,1-Br₂-cyclopropan-2-yl-CH₂ |
| 815 | 2-CH₃, 1,1-Br₂-cyclopropan-3-yl-CH₂ |
| 816 | 2,2-(CH₃)₂, 1,1-Br₂-cyclopropan-3-yl-CH₂ |
| 817 | 2,3-(CH₃)₂, 1,1-Br₂-cyclopropan-3-yl-CH₂ |
| 818 | 2,3,3-(CH₃)₃, 1,1-Br₂-cyclopropan-2-yl-CH₂ |
| 819 | 1,1-Br₂-cyclopropan-2-yl-CH(CH₃) |
| 820 | 2-CH₃, 1,1-Br₂-cyclopropan-2-yl-CH(CH₃) |

TABLE A-continued

| No. | R² |
| --- | --- |
| 821 | 2-CH₃, 1,1-Br₂-cyclopropan-3-yl-CH(CH₃) |
| 822 | 2,2-(CH₃)₂, 1,1-Br₂-cyclopropan-3-yl-CH(CH₃) |
| 823 | 2,3-(CH₃)₂, 1,1-Br₂-cyclopropan-3-yl-CH(CH₃) |
| 824 | 2,3,3-(CH₃)₃, 1,1-Br₂-cyclopropan-2-yl-CH(CH₃) |
| 825 | CH₂CH=CH₂ |
| 826 | CH₂CCl=CH₂ |
| 827 | CH₂CH=CHCl (E) |
| 828 | CH₂CH=CHCl (Z) |
| 829 | CH₂CCl=CHCl (E) |
| 830 | CH₂CCl=CHCl (Z) |
| 831 | CH₂CH=CCl₂ |
| 832 | CH₂CCl=CCl₂ |
| 833 | CH₂CBr=CH₂ |
| 834 | CH₂CH=CHBr (E) |
| 835 | CH₂CH=CHBr (Z) |
| 836 | CH₂CBr=CHBr (E) |
| 837 | CH₂CBr=CHBr (Z) |
| 838 | CH₂CH=CBr₂ |
| 839 | CH₂CBr=CBr₂ |
| 840 | CH₂C(CH₃)=CH₂ |
| 841 | CH₂CH=CHCH₃ (E) |
| 842 | CH₂CH=CHCH₃ (Z) |
| 843 | CH₂C(CH₃)=CHCH₃ (E) |
| 844 | CH₂C(CH₃)=CHCH₃ (Z) |
| 845 | CH₂CH=C(CH₃)₂ |
| 846 | CH₂CH₂CH=CH₂ |
| 847 | CH₂CCl=CHCH₃ (E) |
| 848 | CH₂CCl=CHCH₃ (Z) |
| 849 | CH₂CH=CClCH₃ (E) |
| 850 | CH₂CH=CClCH₃ (Z) |
| 851 | CH₂C(CH₃)=C(CH₃)₂ |
| 852 | CH₂CBr=CHCH₃ (E) |
| 853 | CH₂CBr=CHCH₃ (Z) |
| 854 | CH₂CH=CBrCH₃ (E) |
| 855 | CH₂CH=CBrCH₃ (Z) |
| 856 | CH₂CH=CHCH₂Cl (E) |
| 857 | CH₂CH=CHCH₂Cl (Z) |
| 858 | CH₂CH=CHCH₂CH₃ (E) |
| 859 | CH₂CH=CHCH₂CH₃ (Z) |
| 860 | CH₂CH=CHCH₂Br (E) |
| 861 | CH₂CH=CHCH₂Br (Z) |
| 862 | CH₂CCl=CClCH₂Cl (E) |
| 863 | CH₂CCl=CClCH₂Cl (Z) |
| 864 | CH₂CF=CH₂ |
| 865 | CH₂CH=CHF (E) |
| 866 | CH₂CH=CHF (Z) |
| 867 | CH₂CH=CF₂ |
| 868 | CH₂CF=CHF (E) |
| 869 | CH₂CF=CHF (Z) |
| 870 | CH(CH₃)CH=CH₂ |
| 871 | CH(CH₃)CCl=CH₂ |
| 872 | CH(CH₃)CH=CHCl (E) |
| 873 | CH(CH₃)CH=CHCl (Z) |
| 874 | CH(CH₃)CCl=CHCl (E) |
| 875 | CH(CH₃)CCl=CHCl (Z) |
| 876 | CH(CH₃)CH=CCl₂ |
| 877 | CH(CH₃)CCl=CCl₂ |
| 878 | CH(CH₃)CBr=CH₂ |
| 879 | CH(CH₃)CH=CHBr (E) |
| 880 | CH(CH₃)CH=CHBr (Z) |
| 881 | CH(CH₃)CBr=CHBr (E) |
| 882 | CH(CH₃)CBr=CHBr (Z) |
| 883 | CH(CH₃)CH=CBr₂ |
| 884 | CH(CH₃)CBr=CBr₂ |
| 885 | CH(CH₃)C(CH₃)=CH₂ |
| 886 | CH(CH₃)CH=CHCH₃ (E) |
| 887 | CH(CH₃)CH=CHCH₃ (Z) |
| 888 | CH(CH₃)C(CH₃)=CHCH₃ (E) |
| 889 | CH(CH₃)C(CH₃)=CHCH₃ (Z) |
| 890 | CH(CH₃)CH=C(CH₃)₂ |
| 891 | CH(CH₃)CCl=CHCH₃ (E) |
| 892 | CH(CH₃)CCl=CHCH₃ (Z) |
| 893 | CH(CH₃)CH=CClCH₃ (E) |
| 894 | CH(CH₃)CH=CClCH₃ (Z) |
| 895 | CH(CH₃)CBr=CHCH₃ (E) |
| 896 | CH(CH₃)CBr=CHCH₃ (Z) |
| 897 | CH(CH₃)CH=CBrCH₃ (E) |
| 898 | CH(CH₃)CH=CBrCH₃ (Z) |
| 899 | CH(CH₃)CH=CHCH₂Cl (E) |
| 900 | CH(CH₃)CH=CHCH₂Cl (Z) |
| 901 | CH(CH₃)CH=CHCH₂CH₃ (E) |
| 902 | CH(CH₃)CH=CHCH₂CH₃ (Z) |
| 903 | CH(CH₃)CH=CHCH₂Br (E) |
| 904 | CH(CH₃)CH=CHCH₂Br (Z) |
| 905 | CH(CH₃)CCl=CClCH₂Cl (E) |
| 906 | CH(CH₃)CCl=CClCH₂Cl (Z) |
| 907 | CH(CH₃)CF=CH₂ |
| 908 | CH(CH₃)CH=CHF (E) |
| 909 | CH(CH₃)CH=CHF (Z) |
| 910 | CH(CH₃)CH=CF₂ |
| 911 | CH(CH₃)CF=CHF (E) |
| 912 | CH(CH₃)CF=CHF (Z) |
| 913 | CH₂CHClCH=CH₂ |
| 914 | CH₂CH₂CH=C(CH₃)₂ |
| 915 | CH₂CH₂C(CH₃)=CHCH₃ (E) |
| 916 | CH₂CH₂C(CH₃)=CHCH₃ (Z) |
| 917 | CH₂C≡CH |
| 918 | CH₂C≡CCl |
| 919 | CH₂C≡CBr |
| 920 | CH₂C≡CI |
| 921 | CH₂C≡CCH₃ |
| 922 | CH₂C≡CCH₂CH₃ |
| 923 | CH₂C≡CCH₂OH |
| 924 | CH₂C≡CCH₂NH₂ |
| 925 | CH₂C≡CCH₂Cl |
| 926 | CH₂C≡CCH₂OCH₃ |
| 927 | CH₂C≡CCH₂OCH₂CH₃ |
| 928 | CH₂C≡CCH₂SCH₃ |
| 929 | CH₂C≡CCH₂N(CH₃)₂ |
| 930 | CH₂C≡CC₆H₅ |
| 931 | CH₂CH₂C≡CH |
| 932 | CH₂CH₂C≡CCl |
| 933 | CH₂CH₂C≡CBr |
| 934 | CH₂CH₂C≡CI |
| 935 | CH₂CH₂C≡CCH₃ |
| 936 | CH₂CH₂C≡CCH₂CH₃ |
| 937 | CH₂CH₂C≡CCH₂OH |
| 938 | CH₂CH₂C≡CCH₂NH₂ |
| 939 | CH₂CH₂C≡CCH₂Cl |
| 940 | CH₂CH₂C≡CCH₂OCH₃ |
| 941 | CH₂CH₂C≡CCH₂OCH₂CH₃ |
| 942 | CH₂CH₂C≡CCH₂SCH₃ |
| 943 | CH₂CH₂C≡CCH₂N(CH₃)₂ |
| 944 | CH₂CH₂C≡CC₆H₅ |
| 945 | CH₂CH₂CH₂C≡CH |
| 946 | CH₂CH₂CH₂C≡CCl |
| 947 | CH₂CH₂CH₂C≡CBr |
| 948 | CH₂CH₂CH₂C≡CI |
| 949 | CH₂CH₂CH₂C≡CCH₃ |
| 950 | CH₂CH₂CH₂C≡CCH₂CH₃ |
| 951 | CH₂CH₂CH₂C≡CCH₂OH |
| 952 | CH₂CH₂CH₂C≡CCH₂NH₂ |
| 953 | CH₂CH₂CH₂C≡CCH₂Cl |
| 954 | CH₂CH₂CH₂C≡CCH₂OCH₃ |
| 955 | CH₂CH₂CH₂C≡CCH₂OCH₂CH₃ |
| 956 | CH₂CH₂CH₂C≡CCH₂SCH₃ |
| 957 | CH₂CH₂CH₂C≡CCH₂N(CH₃)₂ |
| 958 | CH₂CH₂CH₂C≡CC₆H₅ |
| 959 | CH(CH₃)C≡CH |
| 960 | CH(CH₃)C≡CCl |
| 961 | CH(CH₃)C≡CBr |
| 962 | CH(CH₃)C≡CI |
| 963 | CH(CH₃)C≡CCH₃ |
| 964 | CH(CH₃)C≡CCH₂CH₃ |
| 965 | CH(CH₃)C≡CCH₂OH |
| 966 | CH(CH₃)C≡CCH₂NH₂ |
| 967 | CH(CH₃)C≡CCH₂Cl |
| 968 | CH(CH₃)C≡CCH₂OCH₃ |
| 969 | CH(CH₃)C≡CCH₂OCH₂CH₃ |
| 970 | CH(CH₃)C≡CCH₂SCH₃ |
| 971 | CH(CH₃)C≡CCH₂N(CH₃)₂ |
| 972 | CH(CH₃)C≡CC₆H₅ |

TABLE B

| No. | ZR$^2$ |
|---|---|
| 1 | N(CH$_2$CH$_3$)$_2$ |
| 2 | N(CH$_2$CH$_2$CH$_3$)$_2$ |
| 3 | N[CH(CH$_3$)$_2$]$_2$ |
| 4 | N[cyclopropyl]$_2$ |
| 5 | N(CH$_2$CH$_2$CH$_2$CH$_3$)$_2$ |
| 6 | N[CH(CH$_3$)CH$_2$CH$_3$]$_2$ |
| 7 | N[CH$_2$CH(CH$_3$)$_2$]$_2$ |
| 8 | N[C(CH$_3$)$_3$]2 |
| 9 | N(CH$_2$CH$_2$CH$_2$CH$_2$CH$_3$)$_2$ |
| 10 | N(CH$_2$CH$_2$CH$_2$CH$_2$CH$_2$CH$_3$)$_2$ |
| 11 | N(CH$_2$CH$_3$)(CH$_2$CH$_2$CH$_3$) |
| 12 | N(CH$_2$CH$_3$)[CH(CH$_3$)$_2$] |
| 13 | N(CH$_2$CH$_3$)[cyclopropyl] |
| 14 | N(CH$_2$CH$_3$)(CH$_2$CH$_2$CH$_2$CH$_3$) |
| 15 | N(CH$_2$CH$_3$)[CH(CH$_3$)CH$_2$CH$_3$] |
| 16 | N(CH$_2$CH$_3$)[CH$_2$CH(CH$_3$)$_2$] |
| 17 | N(CH$_2$CH$_3$)[C(CH$_3$)$_3$] |
| 18 | N(CH$_2$CH$_3$)(CH$_2$CH$_2$CH$_2$CH$_2$CH$_3$) |
| 19 | N(CH$_2$CH$_3$)(CH$_2$CH$_2$CH$_2$CH$_2$CH$_2$CH$_3$) |
| 20 | N(CH$_2$CH$_2$CH$_3$)[CH(CH$_3$)$_2$] |
| 21 | N(CH$_2$CH$_2$CH$_3$)[cyclopropyl] |
| 22 | N(CH$_2$CH$_2$CH$_3$)(CH$_2$CH$_2$CH$_2$CH$_3$) |
| 23 | N(CH$_2$CH$_2$CH$_3$)[CH(CH$_3$)CH$_2$CH$_3$] |
| 24 | N(CH$_2$CH$_2$CH$_3$)[CH$_2$CH(CH$_3$)$_2$] |
| 25 | N(CH$_2$CH$_2$CH$_3$)[C(CH$_3$)$_3$] |
| 26 | N(CH$_2$CH$_2$CH$_3$)(CH$_2$CH$_2$CH$_2$CH$_2$CH$_3$) |
| 27 | N(CH$_2$CH$_2$CH$_3$)(CH$_2$CH$_2$CH$_2$CH$_2$CH$_2$CH$_3$) |
| 28 | N[CH(CH$_3$)$_2$][cyclopropyl] |
| 29 | N[CH(CH$_3$)$_2$](CH$_2$CH$_2$CH$_2$CH$_3$) |
| 30 | N[CH(CH$_3$)$_2$][CH(CH$_3$)CH$_2$CH$_3$] |
| 31 | N[CH(CH$_3$)$_2$][CH$_2$CH(CH$_3$)$_2$] |
| 32 | N[CH(CH$_3$)$_2$][C(CH$_3$)$_3$] |
| 33 | N[CH(CH$_3$)$_2$](CH$_2$CH$_2$CH$_2$CH$_2$CH$_3$) |
| 34 | N[CH(CH$_3$)$_2$](CH$_2$CH$_2$CH$_2$CH$_2$CH$_2$CH$_3$) |
| 35 | N(CH$_2$CH$_2$CH$_2$CH$_3$)[CH(CH$_3$)CH$_2$CH$_3$] |
| 36 | N(CH$_2$CH$_2$CH$_2$CH$_3$)[CH$_2$CH(CH$_3$)$_2$] |
| 37 | N(CH$_2$CH$_2$CH$_2$CH$_3$)[C(CH$_3$)$_3$] |
| 38 | N(CH$_2$CH$_2$CH$_2$CH$_3$)(CH$_2$CH$_2$CH$_2$CH$_2$CH$_3$) |
| 39 | N(CH$_2$CH$_2$CH$_2$CH$_3$)(CH$_2$CH$_2$CH$_2$CH$_2$CH$_2$CH$_3$) |
| 40 | N[CH(CH$_3$)CH$_2$CH$_3$][CH$_2$CH(CH$_3$)$_2$] |
| 41 | N[CH(CH$_3$)CH$_2$CH$_3$][C(CH$_3$)$_3$] |
| 42 | N[CH(CH$_3$)CH$_2$CH$_3$](CH$_2$CH$_2$CH$_2$CH$_2$CH$_3$) |
| 43 | N[CH(CH$_3$)CH$_2$CH$_3$](CH$_2$CH$_2$CH$_2$CH$_2$CH$_2$CH$_3$) |
| 44 | N[CH$_2$CH(CH$_3$)$_2$][C(CH$_3$)$_3$] |
| 45 | N[CH$_2$CH(CH$_3$)$_2$](CH$_2$CH$_2$CH$_2$CH$_2$CH$_3$) |
| 46 | N[CH$_2$CH(CH$_3$)$_2$](CH$_2$CH$_2$CH$_2$CH$_2$CH$_2$CH$_3$) |
| 47 | N[C(CH$_3$)$_3$](CH$_2$CH$_2$CH$_2$CH$_3$) |
| 48 | N[C(CH$_3$)$_3$](CH$_2$CH$_2$CH$_2$CH$_2$CH$_2$CH$_3$) |
| 49 | N[(CH$_2$)$_4$CH$_3$][(CH$_2$)$_5$CH$_3$] |
| 50 | N(CH$_2$CH=CH$_2$)$_2$ |
| 51 | N(CH$_2$CH$_3$)(CH$_2$CH=CH$_2$) |
| 52 | N(CH$_2$CH$_2$CH$_3$)(CH$_2$CH=CH$_2$) |
| 53 | N[(CH$_2$)$_5$CH$_3$](CH$_2$CH=CH$_2$) |
| 54 | N(CH$_2$CH$_2$OH)(CH$_2$CH=CH$_2$) |
| 55 | N(CH$_2$CH$_2$CN)(CH$_2$CH=CH$_2$) |
| 56 | N(CH$_2$CH$_2$CH$_3$)(CH$_2$CCl=CH$_2$) |
| 57 | N[CH$_2$C(CH$_3$)=CH$_2$]$_2$ |
| 58 | N(CH$_2$CH$_3$)[CH$_2$C(CH$_3$)=CH$_2$] |
| 59 | N(CH$_2$C=CH)$_2$ |
| 60 | N(CH$_2$CH$_3$)(CH$_2$C≡CH) |
| 61 | N[CH(CH$_3$)$_2$](CH$_2$C≡CH) |
| 62 | N(CH$_2$CH=CH$_2$)(CH$_2$C≡CH) |

The compounds I are suitable as fungicides.

The compounds I are distinguished by excellent activity against a broad spectrum of phytopathogenic fungi, in particular from the class consisting of the Ascomycetes, Deuteromycetes, Phycomycetes and Basidiomycetes. Some of them have systemic activity and can be used as foliar and soil fungicides.

They are particularly important for controlling a large number of fungi on various crops, such as wheat, rye, barley, oats, rice, corn, grass, cotton, soybeans, coffee, sugar cane, grapevines, fruit, trees, ornamentals and vegetable plants, such as cucumbers, beans and Cucurbitaceae, and on the seeds of these plants.

They are particularly suitable for controlling the following plant diseases: *Erysiphe graminis* (powdery mildew) in cereals, *Erysiphe cichoracearum* and *Sphaerotheca fuliginea* on cucurbitacaea, *Podosphaera leucotricha* on apples, *Uncinula necator* on grapevines, Puccinia species on cereals, Rhizoctonia species on cotton, rice and lawns, Ustilago species on cereals and sugar cane, *Venturia inaequalis* (scab) on apples, Helminthosporium species on cereals, Septoria nodorum on wheat, *Botrytis cinerea* (gray mold) on strawberries, vegetables, ornamentals and grape vines, *Cercospora arachidicola* on peanuts, *Pseudocercosporella herpotrichoides* on wheat and barley, *Pyricularia oryzae* on rice, *Phytophthora infestans* on potatoes and tomatoes, Fusarium and Verticillium species on various plants, *Plasmopara viticola* on grapevines and Alternaria species on vegetables and fruit.

The compounds are used by treating the fungi or the plants, seeds and materials or the soil to be protected from fungal attack with a fungicidal amount of the active ingredients. Application is effected before or after the infection of the materials, plants or seeds with fungi.

They may be converted into the conventional formulations, such as solutions, emulsions or suspensions, dusts, powders, pastes and granules. The application form depends on the particular intended use; it should in any case ensure a fine and uniform distribution of the compound I. The formulations are prepared in a known manner, for example by extending the active ingredient with solvents and/or carriers, if desired with the use of emulsifiers and dispersants, and other organic solvents may also be used as auxiliary solvents when water is used as diluent. Suitable systems for this purpose are essentially solvents, such as aromatics (e.g. xylene), chlorinated aromatics (e.g. chlorobenzenes), paraffins (e.g. mineral oil fractions), alcohols (e.g. methanol, butanol), ketones (e.g. cyclohexanone), amines (e.g. ethanolamine, dimethylformamide) and water; carriers such as crushed natural minerals (e.g. kaolins, aluminas, talc, chalk) and crushed synthetic minerals (e.g. finely divided silica, silicates); emulsifiers, such as nonionic and anionic emulsifiers (e.g. polyoxyethylene fatty alcohol ethers, alkanesulfonates and arylsulfonates) and dispersants, such as ligninsulfite waste liquors and methylcellulose.

The fungicides contain in general from 0.1 to 95, preferably from 0.5 to 90, % by weight of active ingredient.

The application rates are from 0.01 to 2.0 kg of active ingredient per ha, depending on the type of effect desired.

In the seed treatment, from 0.001 to 0.1, preferably from 0.01 to 0.05, g per kilogram of seed is generally required.

In the application form as fungicides, the novel agents may also be present together with other active ingredients, for example with herbicides, insecticides, growth regulators or fungicides or else with fertilizers.

When mixed with fungicides, the fungicidal action spectrum is broadened in many cases.

The following list of fungicides together with which the novel compounds may be applied is intended to illustrate the possible combinations but not to impose any restriction: sulfur, dithiocarbamates and derivatives thereof, such as ferric dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc N,N- ethylenebisdithiocarbamate, ammonia complex of zinc N,N'-propylenebisdithiocarbamate, zinc N,N'-propylenebisdithiocarbamate, N,N'-polypropylenebisthiocarbamoyl disulfide;

nitro derivatives, such as dinitro(1-methylheptyl)phenyl crotonate, 2-sec-butyl-4,6-dinitrophenyl 3,3-dimethylacrylate, 2-sec-butyl-4,6-dinitrophenyl isopropyl carbonate, diisopropyl 5-nitro-isophthalate;

heterocyclic substances, such as 2-heptadecyl-2-imidazoline acetate, 2,4-dichloro-6-(o-chloroanilino)-s-triazine, O,O-diethyl-phthalimidophosphonothioate, 5-amino-1-[bis(dimethylamino)phos-phinyl]-3-phenyl-1,2,4-triazole, 2,3-dicyano-1,4-dithioanthraquinone, 2-thio-1,3-dithiolo-[4,5-b]-quinoxaline, methyl 1-(butylcarbamoyl)-2-benzimidazolecarbamate, 2-methoxycarbonylaminobenzimidazole, 2-fur-2-ylbenzimidazole, 2-thiazol-4-ylbenzimidazole, N-(1,1,2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenylsulfuric acid diamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, 2-thiopyridine 1-oxide, 8-hydroxyquinoline and its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diylbis(1-(2,2,2-trichloroethyl)formamide), 1-(3,4-dichloroanilino)-1-formylamino-2,2,2-trichloroethane, 2,6-dimethyl-N-tridecylmorpholine and its salts, 2,6-dimethyl-N-cyclododecylmorpholine and its salts, N-[3-(p-tert-butylphenyl)-2-methylpropyl]-cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-ylethyl]-1H-1,2,4-triazole, 1-[2-(2,4-dichlorophenyl)-4-n-propyl-1,3-dioxolan-2-yl-ethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, (2-chlorophenyl)-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, [2-(4-chlorophenyl)ethyl]-(1,1-dimethylethyl)-1H-1,2,4-triazole-1-ethanol, -1-[3-(2-chlorophenyl)-1-(4-fluorophenyl)oxiran-2-ylmethyl]-1H-1,2,4-triazole and various fungicides, such as dodecylguanidine acetate, 3-[3-(3,5-dimethyl-2-oxycyclohexyl)-2-hydroxyethyl]glutarimide, hexachlorobenzene, methyl DL-N-(2,6-dimethylphenyl)-N-2-furoylalaninate, methyl DL-N-(2,6-dimethylphenyl)-N-(2'-methoxyacetyl)alaninate, N-(2,6-dimethylphenyl)-N-chloroacetyl-D,L-2-aminobutyrolactone, methyl DL-N-(2,6-dimethylphenyl)-N-(phenylacetyl)alaninate, 5-methyl-5-vinyl-3-(3,5-dichlorophenyl)-2,4-dioxo-1,3-oxazolidine, 3-(3,5-dichlorophenyl)-5-methyl-5-methoxymethyl-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4-dichlorophenyl)pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine, 1-((bis(4-fluorophenyl)methylsilyl)methyl)-1H-1,2,4-triazole.

Strobilurines such as methyl E-methoximino-[α-(o-tolyloxy)-o-tolyl]acetate, methyl E-2-{2-[6-(2-cyanophenoxy)pyrimidin-4-yloxy]phenyl}-3-methoxyacrylate, N-methyl-E-methoximi-no-[α-(2-phenoxyphenyl)]acetamide, N-methyl-E-methoximino-[α-(2,5-dimethylphenoxy)-o-tolyl]acetamide.

Anilinopyrimidines, such as N-(4,6-dimethylpyrimidin-2-yl)aniline, N-[4-methyl-6-(1-propynyl)pyrimidin-2-yl]aniline, N-(4-methyl-6-cyclopropylpyrimidin-2-yl)aniline.

Phenylpyrroles, such as 4-(2,2-difluoro-1,3-benzodioxol-4-yl)pyrrole-3-carbonitrile.

Cinnamides, such as the morpholide of 3-(4-chlorophenyl)-3-(3,4-dimethoxyphenyl)acrylic acid.

(2RS,3SR)-1-[3-(2-chlorophenyl)-2-[4-fluorophenyl]oxiran-2-ylmethyl]-1H-1,2,4-triazole.

The compounds of the formula I are also suitable for effectively controlling pests from the classes consisting of the insects, arachnids and nematodes. They can be used as pesticides in crop protection and in the hygiene, material protection and veterinary sector.

The insect pests include, from the order of the butterflies (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni, Zeiraphera canadensis;* from the order of the beetles (Coleoptera), for example *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus* vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Otiorrhynchus sulcatus, Otiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus, Sitophilus granaria;

from the order of the Diptera, for example Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea, Tipula paludosa;

from the order of the Thysanoptera, for example Frankliniella fusca, Frankliniella occidentalis, Frankliniella tritici, Scirtothrips citri, Thrips oryzae, Thrips palmi, Thrips tabaci;

from the order of the Hymenoptera, for example Athalia rosae, Atta cephalotes, Atta sexdens, Atta texana, Hoplocampa minuta, Hoplocampa testudinea, Monomorium pharaonis, Solenopsis geminata, Solenopsis invicta;

from the order of the Heteroptera, for example Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis, Thyanta perditor;

from the order of the Homoptera, for example Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dysaphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum, Viteus vitifolii;

from the order of the Isoptera, for example Calotermes flavicollis, Leucotermes flavipes, Reticulitermes lucifugus, Termes natalensis;

from the order of the Orthoptera, for example Acheta domestica, Blatta orientalis, Blattella germanica, Forficula auricularia, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus, Tachycines asynamorus;

from the class of the Arachnoidea, for example Acarina, such as Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobius megnini, Paratetranychus pilosus, Dermanyssus gallinae, Phyllocoptruta oleivora, Polyphagotarsonemus latus, Psoroptes ovis, Rhipicephalus appendiculatus, Rhipicephalus evertsi, Sarcoptes scabiei, Tetranychus cinnabarinus, Tetranychus kanzawai, Tetranychus pacificus, Tetranychus telarius, Tetranychus urticae;

from the class of the nematodes, for example root gall nematodes, e.g. Meloidogyne hapla, Meloidogyne incognita, Meloidogyne javanica, cyst-forming nematodes, e.g. Globodera rostochiensis, Heterodera avenae, Heterodera glycines, Heterodera schachtii, Heteroder trifolii, stem and leaf nematodes, eg. Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus, Pratylenchus goodeyi.

The active ingredients can be used as such, in the form of their formulations or in the application forms prepared therefrom, for example in the form of directly sprayable solutions, powders, suspensions or dispersions, emulsions, oil dispersions, pastes, dusting agents, broadcasting agents or granules, by spraying, nebulizing, dusting, broadcasting or pouring. The application forms depend entirely on the intended uses; they should in any case ensure a very fine distribution of the novel active ingredients.

The active ingredient concentrations in the ready-to-use formulations may be varied within relatively wide ranges.

In general, they are from 0.0001 to 10%, preferably from 0.01 to 1%.

The active ingredients may also successfully be used in the ultra low volume (ULV) method, it being possible to apply formulations containing more than 95% by weight of active ingredient or even the active ingredient without additives.

The application rate of active ingredient for controlling pests is from 0.1 to 2.0, preferably from 0.2 to 1.0, kg/ha under outdoor conditions.

Mineral oil fractions having a medium to high boiling point, such as kerosene or diesel oil, and coal tar oils and oils of vegetable or animal origin, aliphatic, cyclic and aromatic hydrocarbons, e.g. benzene, toluene, xylene, paraffin, tetrahydronaphthalene, alkylated naphthalenes or derivatives thereof, methanol, ethanol, propanol, butanol, chloroform, carbon tetrachloride, cyclohexanol, cyclohexanone, chlorobenzene, isophorone and strongly polar solvents, e.g. dimethyl formamide, dimethyl sulfoxide, N-methylpyrrolidone or water, are suitable for the preparation of directly sprayable solutions, emulsions, pastes or oil dispersions.

Aqueous application forms can be prepared from emulsion concentrates, pastes or wettable powders (spray powders, oil dispersions) by adding water. For the preparation of emulsions, pastes or oil dispersions, the substances, as such or dissolved in an oil or solvent, can be homogenized in water by means of wetting agents, adherents, dispersants or emulsifiers. However, it is also possible to prepare concentrates which consist of active ingredient, wetting agents, adherents, dispersants or emulsifiers and possibly solvents or oil and which are suitable for dilution with water.

Suitable surfactants are alkali metal, alkaline earth metal and ammonium salts of ligninsulfonic acid, naphthalenesulfonic acid, phenolsulfonic acid, dibutylnaphthalenesulfonic acid, alkylarylsulfonates, alkylsulfates, alkanesulfonates, fatty alcohol sulfates and fatty acids and alkali metal and alkaline earth metal salts thereof, salts of sulfated fatty alcohol glycol ethers, condensates of sulfonated naphthalene and naphthalene derivatives with formaldehyde, condensates of naphthalene or of naphthalenesulfonic acid with phenol and formaldehyde, polyoxyethylene octylphenol ethers, ethoxylated isooctylphenol, octylphenol, nonylphenol, alkylphenol polyglycol ether, tributylphenyl polyglycol ethers, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, ligninsulfite waste liquors and methylcellulose.

Powders, broadcasting agents and dusting agents can be prepared by mixing or milling the active ingredients together with a solid carrier.

The formulations contained in general from 0.01 to 95, preferably from 0.1 to 90, % by weight of the active ingredient. The active ingredients are used in a purity of from 90 to 100%, preferably from 95 to 100% (according to NMR spectrum).

Examples of formulations are:

I. 5 parts by weight of a novel compound are thoroughly mixed with 95 parts by weight of finely divided kaolin. A dusting agent which contains 5% by weight of the active ingredient is obtained in this manner.

II. 30 parts by weight of a novel compound are thoroughly mixed with a mixture of 92 parts by weight of silica gel powder and 8 parts by weight of liquid paraffin, which were sprayed onto the surface of the silica gel. A formulation of the active ingredient having good adhesion is obtained in this manner (active ingredient content 23% by weight).

III. 10 parts by weight of a novel compound are dissolved in a mixture which consists of 90 parts by weight of xylene, 6 parts by weight of the adduct of from 8 to 10 mol of ethylene oxide with 1 mol of N-monoethanololeamide, 2 parts by weight of the calcium salt of dodecylbenzenesulfonic acid and 2 parts by weight of the adduct of 40 mol of ethylene oxide with 1 mol of castor oil (active ingredient content 9% by weight).

IV. 20 parts by weight of a novel compound are dissolved in a mixture which consists of 60 parts by weight of cyclohexanone, 30 parts by weight of isobutanol, 5 parts by weight of the adduct of 7 mol of ethylene oxide with 1 mol of isooctylphenol and 5 parts by weight of the adduct of 40 mol of ethylene oxide with 1 mol of castor oil (active ingredient content 16% by weight).

V. 80 parts by weight of a novel compound are thoroughly mixed with 3 parts by weight of the sodium salt of diisobutylnaphthalene-alpha-sulfonic acid, 10 parts by weight of the sodium salt of a ligninsulfonic acid obtained from a sulfite waste liquor and 7 parts by weight of silica gel powder, and the mixture is milled in a hammer mill (active ingredient content 80% by weight).

VI. 90 parts by weight of a novel compound are mixed with 10 parts by weight of N-methyl-α-pyrrolidone, and a solution which is suitable for use in the form of very small drops is obtained (active ingredient content 90% by weight).

VII. 20 parts by weight of a novel compound are dissolved in a mixture which consists of 40 parts by weight of cyclohexanone, 30 parts by weight of isobutanol, 20 parts by weight of the adduct of 7 mol of ethylene oxide with 1 mol of isooctylphenol and 10 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

VIII. 20 parts by weight of a novel compound are thoroughly mixed with 3 parts by weight of the sodium salt of diisobutylnaphthalene-α-sulfonic acid, 17 parts by weight of the sodium salt of a ligninsulfonic acid obtained from a sulfite waste liquor and 60 parts by weight of silica gel powder, and the mixture is milled in a hammer mill. By finely distributing the mixture in 20,000 parts by weight of water, a spray liquor which contains 0.1% by weight of active ingredient is obtained.

Granules, for example coated, impregnated and homogeneous granules, can be prepared by binding the active ingredients to solid carriers. Solid carriers are, for example, mineral earths such as silica gel, silicas, silicates, talc, kaolin, attaclay, limestone, lime, chalk, bole, loess, clay, dolomite, kieselguhr, calcium sulfate, magnesium sulfate, magnesium oxide, milled plastics, fertilizers, e.g. ammonium sulfate, ammonium phosphate, ammonium nitrate and ureas, and vegetable products, such as grain flour, bark meal, wood meal and nutshell meal, cellulosic powders and other solid carriers.

Oils of various types, herbicides, fungicides, other pesticides and bactericides may be added to the active ingredients, if necessary not until immediately before application (tankmix). These agents may be mixed with the novel agents in a ratio of from 1:10 to 10:1.

SYNTHESIS EXAMPLES

The methods stated in the synthesis examples below were used, with appropriate modification of the starting compounds, for obtaining further compounds I. The compounds thus obtained are shown in the table below, together with physical data.

Example 1

Preparation of methyl (E)-N-methoxy-N-{2-[(1'-methyl, 1'-methoxycarbonyl)iminooxymethyl]phenyl}carbamate A solution of 8.5 g (0.073 mol) of methyl E-2-hydroximinopropionate in 30 ml of dimethylformamide was added to a mixture of 2.4 g (0.08 mol) of sodium hydride (80%) in 50 ml of dimethylformamide at about 25° C. (heating to 35° C.). The mixture was cooled to about 25° C. and a solution of 20 g (0.073 mol) of methyl N-(2-bromomethylphenyl)-N-methoxycarbamate in 50 ml of dimethylformamide was then added. After 60 hours at about 25° C., the reaction mixture was poured onto water and extracted with tert-butyl methyl ether. The organic phase was washed with water, and dried and evaporated down under reduced pressure. The crude product thus obtained was purified by column chromatography (silica gel, tert-butyl methyl ethyl/N-hexane). 15 g of the title compound were obtained as a colorless oil.

¹H-NMR (CDCl₃; δ in ppm): 2.10 (s, 3H); 3.73 (s, 3H); 3.77 (s, 3H); 3.83 (s, 3H); 5.35 (s, 2H); 7.32–7.51 (m,4H)

Example 2

Preparation of methyl (E)-N-methoxy-N-{2-[('-methyl, 1'-hydroxycarbonyl)iminoxymethyl]phenyl}carbamate 48 ml of a 1M potassium hydroxide solution was added to a solution of 15 g (48.4 mmol) of the compound from example 1) and 30 ml of methanol while cooling with ice. After 60 hours at about 25° C., the reaction mixture was extracted with tert-butyl methyl ether. The aqueous phase was acidified with dilute HCl and then extracted with tert-butyl methyl ether. The organic phase thus obtained was dried and was evaporated down under reduced pressure. 9.5 g of the title compound were obtained in this manner as a pale yellow oil.

¹H-NMR (CDCl₃; δ in ppm): 2.07 (s, 3H); 3.74 (s, 3H); 3.83 (s, 3H); 5.29 (s, 2H); 7.33–7.52 (m, 4H)

Example 3

Preparation of methyl (E)-N-methoxy-N-{2-[(1'-methyl, 1'-methoxyaminocarbonyl)iminoxymethyl]phenyl}carbamate 4.9 g (30.4 mmol) of carbonyldiimidazole were added to a solution of 9.0 g (30.4 mmol) of the compound from Example 2) in 80 ml of tetrahydrofuran. After the end of gas evolution, 5.1 g (61 mmol) of methoxyammonium hydrochloride were added to the mixture obtained. After 16 hours at about 25° C., the reaction mixture was poured onto water and extracted with tert-butyl methyl ether. The organic phase was washed with water, dried and evaporated down under reduced pressure. 7.5 g of the title compound were obtained in this manner as a beige powder of melting point 79–82° C.

¹H-NMR (CDCl₃; δ in ppm): 2.04 (s, 3H); 3.72 (s, 3H); 3.77 (s, 3H); 3.82 (s, 3H); 5.20 (s, 2H); 7.28–7.47 (m, 4H); 9.40 (s, br, 1H)

Example 4

Preparation of methyl (E,Z)-N-methoxy-N-{2-[(1'-methyl, 1'-(1"-ethoxy, 1"-methoxyiminomethyl))iminooxymethyl]phenyl}carbamate (Table I, No. I.1)

A mixture of 1.3 g (4.4 mmol) of the compound from Example 3 and 1.2 g (8.8 mmol) of potassium carbonate in 50 ml of dimethylformamide were stirred for 20 minutes at about 25° C., and 0.95 g (8.8 mmol) of bromoethane was then added. After 60 hours at about 25° C., the reaction mixture was poured onto water and extracted several times with tert-butyl methyl ether. The combined organic phases were washed with water, dried and evaporated down under reduced pressure. The crude product thus obtained was purified by column chromatography (silica gel, tert-butyl methyl ether/n-hexane). 0.6 g of the title compound was obtained in this manner as a yellowish oil.

¹H-NMR (CDCl₃; δ in ppm): 1.24 (t, 3H); 2.06 (s, 3H); 3.74 (s, 3H); 3.79 (s, 3H); 3.88 (s, 3H); 4.14 (q, 2H); 5.27 (s, 2H); 7.32–7.52 (m, 4H)

Example 5

Preparation of methyl (E,Z)-N-methoxy-N-{2-[(1'-methyl, 1'-(1"-bromo-1"-methoxyiminomethyl))iminooxymethyl]phenyl}carbamate A mixture of 10 g (31 mmol) of the compound from Example 3 and 40 g (0.15 mol) of triphenylphosphine in 350 ml acetonitrile was treated with 51 g (0.15 mol) of tetrabromomethane, a little at a time. The resulting mixture was refluxed for 72 hours. The reaction mixture was filtered at about 25° C. The filtrate was concentrated and the residue obtained was purified by column chromatography (silica gel; tert-butyl methyl ether/hexane). 7 g of the title compound were obtained in this manner as an orange oil.

¹H-NMR (CDCl₃; δ in ppm): 2.17 (s, 3H); 3.74 (s, 3H); 3.78 (s, 3H); 4.08 (s, 3H); 5.30 (s, 2H); 7.32–7.88 (m, 4H)

Example 6

Preparation of methyl (E,Z)-N-methoxy-N-methoxy-N-{2-[(1'-methyl, 1'-(1"-ethylthio, 1"-methoxyiminomethyl))iminooxymethyl]phenyl}carbamate (Table I, No. I.19)

0.7 g (8.6 mmol) of sodium ethanethiolate were added to a solution of 1.5 g (3.9 mmol) of the compound from Example 5 in 50 ml of dimethylformamide, and stirring was continued for 16 hours at room temperature. The reaction mixture was poured onto water and extracted with methyl tert-butyl ether. The organic phase was washed with water and concentrated. After purification by column chromatography (silica gel; methyl tert-butyl ether/hexane), 0.5 g of the title compound was obtained as a yellow oil.

¹H-NMR (CDCl₃; δ in ppm): 1.07 (t, 3H); 2.14 (s, 3H); 2.73 (q, 2H); 3.74 (s, 3H); 3.77 (s, 3H); 3.99 (s, 3H); 5.24 (s, 2H); 7.32–7.53 (m, 4H)

TABLE I

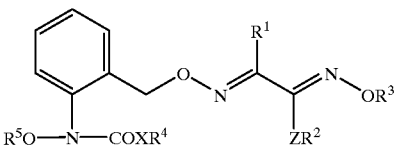

(I)

| No. | R¹ | Z | R² | R³ | XR⁴ | R⁵ | physical data* |
|---|---|---|---|---|---|---|---|
| I.1 | CH₃ | O | CH₂CH₃ | CH₃ | OCH₃ | CH₃ | 2937, 1740, 1456, 1441, 1366, 1344, 1151, 1104, 1059, 1018 cm⁻¹ |
| I.2 | CH₃ | O | CH₂CH₂CH₃ | CH₃ | OCH₃ | CH₃ | 2958, 2925, 2854, 1742, 1457, 1441, 1353, 1340, 1062, 1031 cm⁻¹ |
| I.3 | CH₃ | O | CH(CH₃)₂ | CH₃ | OCH₃ | CH₃ | 2930, 1741, 1709, 1456, 1441, 1362, 1339, 1154, 1103, 1058, 1031 cm⁻¹ |
| I.4 | CH₃ | O | CH₂CH=CH₂ | CH₃ | OCH₃ | CH₃ | 2929, 1743, 1456, 1441, 1364, 1342, 1253, 1058, 1032, 1015 cm⁻¹ |

TABLE I-continued

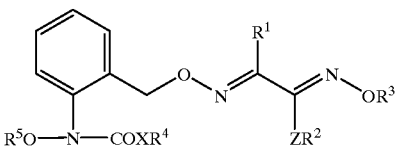

(I)

| No. | R¹ | Z | R² | R³ | XR⁴ | R⁵ | physical data* |
|---|---|---|---|---|---|---|---|
| I.5 | $CH_3$ | O | $CH(CH_3)CH_2CH_3$ | $CH_3$ | $OCH_3$ | $CH_3$ | 2937, 1741, 1456, 1441, 1341, 1337, 1153, 1108, 1058, 1031 $cm^{-1}$ |
| I.6 | $CH_3$ | O | $(CH_2)_3CH_3$ | $CH_3$ | $OCH_3$ | $CH_3$ | 2959, 2937, 1741, 1456, 1440, 1348, 1155, 1059, 1031, 1017 $cm^{-1}$ |
| I.7 | $CH_3$ | O | $CH_2CH(CH_3)_2$ | $CH_3$ | $OCH_3$ | $CH_3$ | 2959, 1741, 1722, 1456, 1440, 1367, 1351, 1059, 1031, 1016 $cm^{-1}$ |
| I.8 | $CH_3$ | O | $CH_2$-cyclo-propyl | $CH_3$ | $OCH_3$ | $CH_3$ | 2940, 1740, 1456, 1440, 1360, 1334, 1145, 1102, 1058, 1022, 855 $cm^{-1}$ |
| I.9 | $CH_3$ | O | $CH_2CH=CHCl$ (E) | $CH_3$ | $OCH_3$ | $CH_3$ | 2935, 1739, 1712, 1456, 1441, 1345, 1146, 1098, 1056, 1032, 765 $cm^{-1}$ |
| I.10 | $CH_3$ | O | $CH_2CH=CCl_2$ | $CH_3$ | $OCH_3$ | $CH_3$ | 2957, 1740, 1456, 1441, 1366, 1346, 1147, 1057, 1035, 990 $cm^{-1}$ |
| I.11 | $CH_3$ | O | $CH_2CCl=CCl_2$ | $CH_3$ | $OCH_3$ | $CH_3$ | 2940, 2920, 1730, 1456, 1441, 1366, 1343, 1147, 1058, 1033, 991, 923 $cm^{-1}$ |
| I.12 | $CH_3$ | O | $CH_2CCl=CH_2$ | $CH_3$ | $OCH_3$ | $CH_3$ | 2937, 1739, 1456, 1441, 1364, 1347, 1143, 1100, 1061, 1016, 900 $cm^{-1}$ |
| I.13 | $CH_3$ | O | $CH_2C(CH_3)=CH_2$ | $CH_3$ | $OCH_3$ | $CH_3$ | 2930, 1740, 1456, 1441, 1344, 1150, 1100, 1055, 1031, 1017, 904 $cm^{-1}$ |
| I.14 | $CH_3$ | O | $CH_2C\equiv CH$ | $CH_3$ | $OCH_3$ | $CH_3$ | 3285, 2940, 1733, 1456, 1442, 1366, 1343, 1143, 1107, 1058, 1034, 1016 $cm^{-1}$ |
| I.15 | $CH_3$ | O | $CH_2C\equiv C-CH_3$ | $CH_3$ | $OCH_3$ | $CH_3$ | 2940, 1739, 1456, 1441, 1365, 1341, 1152, 1101, 1057, 1032, 1017 $cm^{-1}$ |
| I.16 | $CH_3$ | O | $CH_2-C_6H_5$ | $CH_3$ | $OCH_3$ | $CH_3$ | 2938, 1739, 1710, 1455, 1440, 1347, 1261, 1147, 1057, 1029, 1016 $cm^{-1}$ |
| I.17 | $CH_3$ | O | $CH_2-(4-F-C_6H_4)$ | $CH_3$ | $OCH_3$ | $CH_3$ | 2940, 1739, 1710, 1512, 1441, 1346, 1224, 1146, 1058, 1032, 1017 $cm^{-1}$ |
| I.18 | $CH_3$ | O | $CH_2CH_2CH=CH_2$ | $CH_3$ | $OCH_3$ | $CH_3$ | 2935, 1741, 1456, 1441, 1348, 1252, 1152, 1100, 1059, 1031, 1017 $cm^{-1}$ |
| I.19 | $CH_3$ | S | $CH_2CH_3$ | $CH_3$ | $OCH_3$ | $CH_3$ | 2934, 1740, 1712, 1456, 1441, 1364, 1338, 1081, 1040, 1017 $cm^{-1}$ |

*: m.p. (° C.); IR ($cm^{-1}$); ¹H-NMR (δ in ppm/$CDCl_3$)

Examples of the action against harmful fungi

The fungicidal action of the compounds of the formula I was demonstrated by the following experiments:

The active ingredients were prepared as a 20% strength emulsion in a mixture of 70% by weight of cyclohexanone, 20% by weight of Nekanil® LN (Lutensol®) AP6, wetting agent having an emulsifying and dispersing effect and based on ethoxylated alkylphenols) and 10% by weight of Emulphor® EL (Emulan® EL, emulsifier based on ethoxylated fatty alcohols) and were diluted with water to give the desired concentration.

Compounds A (compound No. 12, WO-A 96/16, 030) and B (compound No. 6, WO-A 96/16, 030) were used as comparative compounds.

Action against Erysiphe graminis var. tritici (Wheat mildew) Leaves of wheat seedlings ("Frühgold" variety) were first treated with the aqueous preparation of the active ingredients (application rate: 4 ppm). After about 24 hours, the plants were dusted with spores of wheat mildew (Erysiphe graminis var. tritici). The plants treated in this manner were then incubated for 7 days at 20–22° C. and a relative humidity of 75–80%. The extent of fungal development was then determined.

In this test, the plants treated with the novel compounds 1, 2, 3, 4, 5, 6, 7, 8 and 9 showed an infestation of 15% or less. The plants treated with the comparative compounds exhibited an infestation of 40% (A) or 65% (B), while the untreated (control) plants showed an infestation of 80%.

Action against *Plasmopara viticola* (Grape vine perenospora) Potted vines ("Müller Thurgau" variety) were sprayed to run-off with the active ingredient formulation (application rate: 250 ppm). After 8 days, the plants were sprayed with a zoospore suspension of the fungus *Plasmopara viticola* and kept for 5 days at 20–30° C. and high relative humidity. Before the evaluation, the plants were then kept for 16 hours at high relative humidity. The evaluation was carried out visually.

In this test, the plants treated with the novel compounds 1, 2, 3, 4, 5, 6, 7, 8, 9, 10, 11, 12, 13, 14, 15, 16, 17, 18 and 19 showed an infestation of 5% or less. The plants treated with the comparative compound A exhibited an infestation of 40%, while the untreated (control) plants showed an infestation of 70%.

Action against *Puccinia recondita* (Brown rust of wheat) Leaves of wheat seedlings ("Kanzler" variety) were dusted with spores of brown rust (*Puccinia recondita*). The plants thus treated were incubated for 24 hours at 20–22° C. and 90–95% relative humidity and then treated with the aqueous active ingredient formulation (application rate: 250 ppm). After a further 8 days at 20–22° C. and 65–70% relative humidity, the extent of fungal development was determined. The evaluation was carried out visually.

In this test, the plants treated with the novel compounds 1, 2, 3, 4, 5, 6, 7, 8, 9, 10, 11, 12, 13, 14, 16, 17, 18 and 19 showed an infestation of from 0 to 5%. The plants treated with the comparative compound B exhibited an infestation of 40%, while the untreated (control) plants showed an infestation of 70%.

Examples of the action against animal pests

The action of the compounds of the general formula I against animal pests was demonstrated by the following experiments The active ingredients were prepared a) as a 0.1% strength solution in acetone or b) as 10% strength emulsion in a mixture of 70% by weight of cyclohexanone, 20% by weight of Nekanil® LN (Lutensol® AP6, wetting agent having an emulsifying and dispersing action and based on ethoxylated alkylphenols) and 10% by weight of Emulphor® EL (Emulan® EL, emulsifier based on ethoxylated fatty alcohols)

and were diluted with acetone in the case of a) and with water in the case of b) to give the desired concentration.

After completion of the experiments, the lowest concentration in each case at which the compounds caused 80–100% inhibition or mortality compared with untreated control experiments was determined (action threshold or minimum concentration).

Action against Nephotettix cincticeps, green rice leafhopper (contact experiment)

Round filters (Ø9 cm) were treated with 1 cm³ of the aqueous preparation of active ingredient and placed into a plastic Petri dish provided with projections (Ø94 mm). Then, 5 adult rice leafhoppers were introduced, and the Petri dish was sealed.

The mortality was scored after 24 hours.

In this test, compounds 8, 9 and 16 showed an action threshold of 200 ppm.

We claim:
1. A phenylcarbamate of the formula I

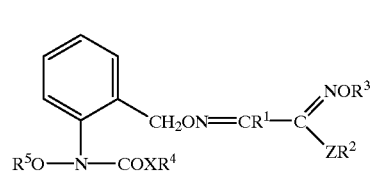

(I)

where

X is a direct bond, O or $NR^a$;

$R^a$ is hydrogen or alkyl;

Z is O, S or $NR^b$;

$R^b$ is hydrogen, $C_1$–$C_6$-alkyl, $C_3$–$C_6$-alkenyl or $C_3$–$C_6$-alkynyl;

$R^1$ is hydrogen, $C_1$–$C_6$-alkyl or $C_1$–$C_4$-haloalkyl; and $R^2$ is $C_2$–$C_6$-alkyl, $C_3$–$C_6$-alkenyl or $C_3$–$C_6$-alkynyl, where these groups may be partially or completely halogenated or may carry from one to three of the following radicals:

cyano, nitro, amino, hydroxyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfonyl, $C_1$–$C_6$-alkylsulfoxyl, $C_1$–$C_6$-alkylamino, di-$C_1$–$C_6$-alkylamino, $C_3$–$C_6$-cycloalkyl, aryl, hetaryl or oxiranyl, where the cyclic radicals in turn may be partially or completely halogenated or may carry from one to three of the following groups: cyano, nitro, amino, aminocarbonyl, aminothiocarbonyl, $C_1$–$C_4$-alkyl, $C_1$–$C_4$-haloalkyl, $C_1$–$C_4$-alkylcarbonyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-haloalkylthio, $C_1$–$C_6$-alkylsulfonyl, $C_1$–$C_6$-alkylsulfoxyl, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_2$–$C_6$-alkenyloxy and phenyl;

methyl, which carries from one to three halogen atoms or carries one of the following radicals:

cyano, nitro, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfonyl, $C_1$–$C_6$-alkylsulfoxyl, $C_1$–$C_6$-alkylamino, di-$C_1$–$C_6$-alkylamino, $C_3$–$C_6$-cycloalkyl, aryl, hetaryl or oxiranyl, where the cyclic radicals in turn may be partially or completely halogenated or may carry from one to three of the following groups: cyano, nitro, amino, aminocarbonyl, aminothiocarbonyl, $C_1$–$C_4$-alkyl, $C_1$–$C_4$-haloalkyl, $C_1$–$C_4$-alkylcarbonyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-haloalkylthio, $C_1$–$C_6$-alkylsulfonyl, $C_1$–$C_6$-alkylsulfoxyl, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_2$–$C_6$-alkenyloxy and phenyl;

$C_3$–$C_6$-cycloalkyl, where these groups may be partially or completely halogenated or may carry from one to three of the following radicals:

cyano, nitro, amino, hydroxyl, $C_1$–$C_4$-alkyl, $C_1$–$C_4$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfonyl, $C_1$–$C_6$-alkylsulfoxyl, $C_1$–$C_6$-alkylamino, di-$C_1$–$C_6$-alkylamino, $R^3$ is $C_1$–$C_6$-alkyl, $C_2$–$C_6$-alkenyl or $C_2$–$C_6$-alkynyl, where these groups may be partially or completely halogenated or may carry from one to three of the following radicals:

cyano, $C_1$–$C_3$-alkoxy, oxiranyl or $C_3$–$C_6$-cycloalkyl, where the cyclic radicals in turn may be partially or completely halogenated or may carry from one to three $C_1$–$C_4$-alkyl groups; and $R^4$ is alkyl, alkenyl or alkynyl, and, where X is $NR^a$, additionally hydrogen; and $R^5$ is hydrogen or unsubstituted or substituted alkyl, alkenyl, alkynyl, alkylcarbonyl or alkoxycarbonyl.

2. The phenylcarbamate of formula I as defined claim 1, in which $R^2$ has the following meanings $C_2$–$C_6$-alkyl, $C_3$–$C_6$-alkenyl or $C_3$–$C_6$-alkynyl, where these groups may be partially or completely halogenated or may carry from one to three of the following radicals:

$C_3$–$C_6$-cycloalkyl, phenyl or oxiranyl, where the cyclic radicals in turn may be completely or partially halogenated or may carry from 1 to 3 of the following groups: cyano, $C_1$–$C_4$-alkyl, $C_1$–$C_4$-haloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-haloalkylthio and phenyl;

methyl, which carries from one to three halogen atoms or carries one of the following radicals:

cyano, nitro, $C_3$–$C_6$-cycloalkyl, aryl, hetaryl or oxiranyl, where the cyclic radicals in turn may be partially or completely halogenated or may carry from one to three of the following groups: cyano, nitro, amino, aminocarbonyl, aminothiocarbonyl, $C_1$–$C_4$-alkyl, $C_1$–$C_4$-haloalkyl, $C_1$–$C_4$-alkylcarbonyl, $C_1$–$C_4$-alkoxy, $C_1$–$C_4$-haloalkoxy, $C_1$–$C_4$-alkoxycarbonyl, $C_1$–$C_4$-alkylthio, $C_1$–$C_4$-haloalkylthio, $C_1$–$C_4$-alkylsulfonyl, $C_1$–$C_4$-alkylsulfoxyl, $C_1$–$C_4$-alkylamino, di-$C_1$–$C_4$-alkylamino, $C_1$–$C_4$-alkylaminocarbonyl, di-$C_1$–$C_4$-alkylaminocarbonyl, $C_2$–$C_4$-alkenyloxy and phenyl;

$C_3$–$C_6$-cycloalkyl, where these groups may be partially or completely halogenated or may carry from one to three of the following radicals:

cyano, $C_1$–$C_4$-alkyl, $C_1$–$C_4$-haloalkyl, $C_1$–$C_6$-alkoxy, $C_1$–$C_6$-haloalkoxy, $C_1$–$C_6$-alkylthio and $C_1$–$C_6$-haloalkylthio.

3. The phenylcarbamate of the formula I as defined in claim 1, in which Z is oxygen or sulfur.

4. A process for the preparation of a compound of the formula I as defined in claim 1, wherein a benzyl derivative of the formula II

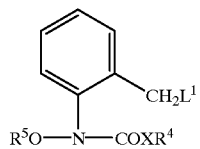

(II)

where $L^1$ is a nucleophilically substitutable leaving group, is reacted with a dihydroxyimine of the formula III

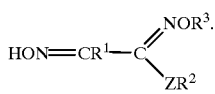

(III)

5. A process for the preparation of a compound of the formula I as defined in claim 1, wherein a benzyl derivative of the formula II

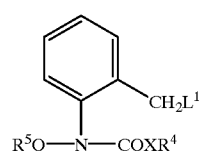

(II)

where $L^1$ is a nucleophilically substitutable leaving group, is reacted with a dihydroxyimine of the formula IV

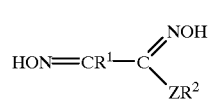

(IV)

to give a compound of the formula V

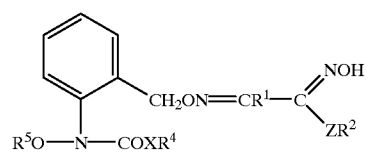

(V)

and V is then reacted with a compound of the formula VIa $$R^3\text{—}L^2 \qquad (VIa)$$

where $L^2$ is a nucleophilically substitutable leaving group, to give I.

6. A process for the preparation of a compound I as defined in claim 1, in which $R^5$ is hydrogen, wherein a nitrobenzene of the formula VII

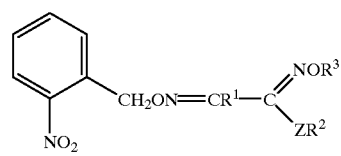

(VII)

is reduced to the corresponding hydroxylamine VIII

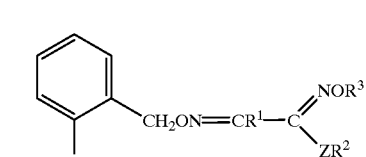

(VIII)

and VIII is reacted with an acylating agent of the formula VIb $$L^3\text{—}COXR^4 \qquad (VIb)$$

where $L^3$ is halogen or aryloxy.

7. A process for the preparation of a compound I as defined in claim 1, in which $R^5$ is unsubstituted or substituted alkyl, alkenyl, alkynyl, alkylcarbonyl or alkoxycarbonyl, wherein a compound of the formula I

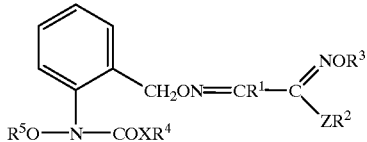
(I)

$R^5$ is hydrogen, is reacted with a compound of the formula VIc

 (VIc)

where $L^4$ is halogen, mesylate, tosylate, carboxylate or sulfate.

8. An agent suitable for controlling animal pests or harmful fungi, and containing a solid or liquid carrier and a compound of the formula I as defined in claim 1.

9. A method for controlling harmful fungi, wherein the fungi or the materials, plants, soil or seeds to be protected from fungal attack are treated with an effective amount of a compound of the formula I as defined in claim 1.

10. A method for controlling animal pests, wherein the pests or the materials, plants soil or seeds to be protected from them are treated with an effective amount of a compound of the formula I as defined in claim 1.

11. A compound of the formula Xa

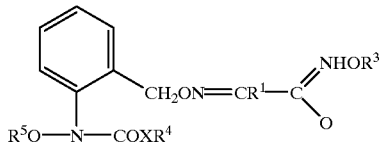
Xa where
- X is a direct bond, O or $NR^a$;
- $R^a$ is hydrogen or alkyl;
- Z is O, S or $NR^b$;
- $R^b$ is hydrogen, $C_1$–$C_6$-alkyl, $C_3$–$C_6$-alkenyl or $C_3$–$C_6$-alkynyl;
- $R^1$ is hydrogen, $C_1$–$C_6$-alkyl or $C_1$–$C_4$-haloalkyl; and
- $R^3$ is $C_1$–$C_6$-alkyl, $C_2$–$C_6$-alkenyl or $C_2$–$C_6$-alkynyl, where these groups may be partially or completely halogenated or may carry from one to three of the following radicals:
  cyano, $C_1$–$C_3$alkoxy,
  oxiranyl or $C_1$–$C_3$-cycloalkyl, where the cyclic radicals in turn may be partially or completely halogenated or may carry from one to three $C_1$–$C_4$-alkyl groups; and
- $R^4$ is alkyl, alkenyl or alkynyl, and, where X is $NR^a$, additionally hydrogen, and
- $R^5$ is hydrogen or unsubstituted or substituted alkyl, alkenyl, alkynyl, alkylcarbonyl or alkoxycarbonyl.

* * * * *

UNITED STATES PATENT AND TRADEMARK OFFICE
CERTIFICATE OF CORRECTION

PATENT NO.: 6,130,247

DATED: October 10, 2000

INVENTOR(S): BAYER et al.

It is certified that error appears in the above-identified patent and that said Letters Patent is hereby corrected as shown below:

On the title page insert item,

--[73] Assignee: BASF Aktiengesellschaft, Ludwigshafen, Germany--

In the abstract, line 3, "alkyl halide" should be --haloalkyl--.

In the abstract, lines 4, 6 and 8, "alkinyl" should be --alkynyl--.

Col. 213, claim 2, line 10, "of formula I as defined" should be --of the formula I defined in--.

Col. 215, claim 10, line 29, "plants soil" should be --plants, soil--.

Signed and Sealed this

Twenty-fourth Day of April, 2001

NICHOLAS P. GODICI

Attest:

Attesting Officer

Acting Director of the United States Patent and Trademark Office